United States Patent [19]

Schneiderman

[11] Patent Number: 5,508,912
[45] Date of Patent: Apr. 16, 1996

[54] CLINICAL DATABASE OF CLASSIFIED OUT-PATIENTS FOR TRACKING PRIMARY CARE OUTCOME

[75] Inventor: Barry Schneiderman, P.O. Box 53, Rye, N.H. 03870

[73] Assignee: Barry Schneiderman, Rye, N.H.

[21] Appl. No.: 542,752

[22] Filed: Jun. 25, 1990

Related U.S. Application Data

[63] Continuation of Ser. No. 276,414, Jan. 23, 1989, abandoned.

[51] Int. Cl.$^6$ ..................................................... G06F 15/42
[52] U.S. Cl. ............................................................ 364/401
[58] Field of Search ........................................ 364/413.02

[56] References Cited

U.S. PATENT DOCUMENTS

| | | | |
|---|---|---|---|
| 3,872,448 | 3/1975 | Mitchell, Jr. | 364/200 |
| 4,491,225 | 1/1985 | Pritchard | 235/380 |
| 4,667,292 | 5/1987 | Mohlenbrock et al. | 364/406 |
| 4,764,870 | 8/1988 | Haskin | 364/413.22 |
| 4,893,270 | 1/1990 | Beck et al. | 364/900 |
| 5,018,067 | 5/1991 | Mohlenbrock et al. | 364/413.02 |

OTHER PUBLICATIONS

Mowry, Michele M. et al., "Automated Information Systems In Quality Assurance", Nursing Economics 1987.

Young, Wanda W., "Incorporating Severity of Illness and Comorbidity In Case–Mix Measurement", *Health Care Financing Review*, Nov. 1984 pp. 23–31.

Kreitzer et al., "Severity of Illness: The DRG's Missing Link?", *QRB/Quality Rev. Bulletin*, May 1982 pp. 21–34.

Horn et al., "Measuring Severity of Illness to Predict Patient Resource Use With DRG", *Inquiry*, vol. XX Winter 1983, pp. 314–321.

Mendenhall, "DRG's must be changed to take patient's illness severity into account", *Modern Health Care*, Nov. 15 1984, pp. 86 and 88.

Young, "Incorporating Severity of Illness and Comorbidity in case–mix measurements", *Health Care Financing Review* Nov., 1984, pp. 23–31.

Panniers et al., "The ICD–9–CM DRGs: Increase Homogeneity Through Use of As–Score", *QRB*, Feb. 1985, pp. 47–52.

Medicine and Health Perspectives, McGraw–Hill, Mar. 11, 1985 4 page report.

(List continued on next page.)

*Primary Examiner*—Gail O. Hayes

[57] ABSTRACT

A computerized medical database system for the standardized recording and tracking of out-patient care by the simulation through existing software of multiple facets of a typical primary care clinical environment.

Central to the system's data processing are office visit records as the primary vehicle for encoded data input and a chronic diagnosis classification table for ranking out-patients into separate, prioritized diagnostic categories. Integrated with both in a relational database are other files storing distinct but related clinical attributes of both the transactional and inventory type. The former, as event-based, include emergency room, medicine activity, specialist, lab tests and an office visit-derived or intermediary file while the latter type, as a fixed pool of clinically descriptive data elements, include long and short-term diagnosis, physical signs and symptoms and a generic medication list.

The data processing is of three kinds; data entry of office visit, one master medical for each out-patient and lab test result records, data query for obtaining summary-type, narrowly focused information for a single or group of related out-patients and, thirdly, the compilation of data from office visits for reporting various clinical results.

Some of the latter type processing, using sets of clinical criteria including diagnostic category for specific record selection, include detecting and justifying excessive office visits, determining lab test overusage, monitoring physician activity during episodes of protracted illnesses of differing severity and the printing of physical, medication and lab test results from the same office visit.

11 Claims, 152 Drawing Sheets

OTHER PUBLICATIONS

Brewster et al., "MEDISGRPS: A Clinically Based Approach to Classifying Hospital Patient at Admission", Inquiry, vol. XXII, Winter 1985, pp. 377–387.

Horn et al, "Severity of Illness Within DRGs—Homogeneity Study", *Medical Care,* Mar. 1986, vol. 24, No. 3 pp. 225–235.

Young, "ICD–9–CM Code and Coding Practices", *American Med. Res. Ass. Jrl* Mar. 1986, pp. 29–33.

Horn et al., "Profiles of Physician Practice and Patient Severity of Illness", *Amer. Jrl of Pub. Health,* May 1986, pp. 532–535.

Horn, "Measuring severity: How sick is sick? How well is well?", *Healthcare Financial Management,* Oct. 1986, pp. 21–32.

"Patient Care Information Systems; Looking to the Future", Ralph Korpman.

Mowry et al. "Evaluating Automated Information Systems", Nursing Economics, vol. 5, No. 1, Jan./Feb. 1987.

"Ultrcare, a bedside patient care information system", Product Literature from Health Data Sciences Corp. 1984.

"PDMS Clinical User's Guide", Product Manual from Hewlett Packard, Jan. 1982 Manual Part No. 78707–91996.

"Patient Data Management System", Product Manual from Hewlett Packard, Jan. 1982, Manual Part No. 78707–91996.

Principi et al., "Better care shorter stays, thanks to networking", Data Communications, Nov. 1986.

Mowry et al., "Automated Information System in Quality Assurance", Nursing Economics, Sep./Oct. 1987.

Brimm, "Computers in Critical Care", Critical Care Nursing Quarterly, 1987.

Korpman, "Patient Care Information Systems: Looking to the Future", Software in Healthcare.

Childs, "William Beaumont Hospital and Its New Generation System", U.S. Healthcare, vol. 6, No. 3, Mar. 1989.

"Primary Care Clinic in Ofice Practice", Zimmer, vol. 12 No. 3 pp. 429–442.

| RECORD# | CODETYPE | CODE | DESCRIPT |
|---:|:---:|:---:|:---|
| 1 | AH | 0000 | ACUTE ANGINA, UNSTABLE, CHF |
| 2 | AH | 0001 | ACUTE ANGINA, UNSTABLE |
| 3 | AR | 0002 | SYST. LUPUS + NEPHRITIS |
| 4 | AR | 0003 | PROB.SYST.SCLEROSIS,UREMI |
| 5 | AV | 0007 | MALIGNT.HYPERTENS. (SYMPT) |
| 6 | AL | 0010 | COPD, SEVERE HYPERCAPNIA |
| 7 | AV | 0006 | CLAUDICATION, REST, CALF |
| 8 | AN | 0009 | HYPERTENSIVE TIA |
| 9 | AP | 0004 | ACUTE BLASTOCYT. LEUKEMIA |
| 10 | AC | 0005 | METASTIC CA + CHEMOTH. |
| 11 | AI | 0008 | AUTOIMM. DEFICIENCY SYNDROME |
| 12 | BG | 0013 | ULCERATIVE COLITIS |
| 13 | BH | 0011 | CHRONIC ANGINA |
| 14 | BH | 0012 | CHF, CHR. VENT. HYPERTROPHY |
| 15 | BN | 0015 | CVA, RECENT |
| 16 | BK | 0016 | ACUTE GLOMERULONEPHRITIS |
| 17 | BE | 0019 | DIABETES MELLITUS |
| 18 | BL | 0018 | COPD, MILD HYPERCAPNIA |
| 19 | BV | 0017 | CHRONIC CLAUDICATION |
| 20 | BP | 0014 | MULTIPLE MYELOMA |
| 21 | BR | 0020 | ACUTE GOUTY ARTHRITIS |
| 22 | BR | 0022 | ACUTE RHEUMATOID ARTH. |
| 23 | BG | 0023 | CHR. PANCREATITIS |
| 24 | CH | 0024 | CARDIOMEGALY, ASYMPT. RHD. |
| 25 | BK | 0021 | CHRONIC PYELONEPHRITIS |
| 26 | CP | 0025 | PERNICIOUS ANEMIA |
| 27 | CP | 0026 | IRON DEF. ANEMIA |
| 28 | CK | 0027 | CHRONIC RENAL STONES |
| 29 | CR | 0028 | OSTEOARTH., SEVERE |
| 30 | CG | 0029 | CHRONIC PEPTIC ULCER |
| 31 | CL | 0030 | CHRONIC BRONCHITIS |

FIG. 3

STRUCTURE FOR DATABASE:MEDICAL.DBF

| FIELD NAME | TYPE | WIDTH |
| --- | --- | --- |
| DOCTOR | CHARACTER | 20 |
| PT_ID | CHARACTER | 11 |
| DOB | CHARACTER | 6 |
| LNAME | DATE | 8 |
| FNAME | CHARACTER | 1 |
| SEX | CHARACTER | 1 |
| DIAGNOSIS1 | CHARACTER | 6 |
| CODE1 | CHARACTER | 6 |
| DURATION1 | CHARACTER | 6 |
| MEDFLAG1 | LOGICAL | 1 |
| MEDINV1 | LOGICAL | 1 |
| DIAGNOSIS2 | LOGICAL | 1 |
| CODE2 | LOGICAL | 1 |
| DURATION2 | LOGICAL | 1 |
| MEDFLAG2 | LOGICAL | 1 |
| MEDINV2 | CHARACTER | 6 |
| DIAGNOSIS3 | NUMERIC | 3 |
| CODE3 | CHARACTER | 3 |
| DURATION3 | CHARACTER | 3 |
| MEDFLAG3 | CHARACTER | 5 |
| MEDINV3 | CHARACTER | 5 |
| DESCRIPONE | CHARACTER | 5 |
| AMTONE | CHARACTER | 5 |
| MEDONE | | |
| MEDTWO | | |
| DESCRIPTWO | | |
| AMTTWO | | |
| MEDTHREE | | |
| DESCRIPTHR | | |
| AMTTHREE | | |
| MAJORSURG | | |
| PRIOR_SURG | | |
| TREATMENT | | |
| LAST_HOSP | | |
| ALLERGIES | | |
| WEIGHT | | |
| SYSTOLIC | | |
| DIASTOLIC | | |
| DATE | | |

FIG. 4

STRUCTURE FOR DATABASE: NOTIFY.DBF

| FIELD NAME | TYPE | WIDTH |
| --- | --- | --- |
| DOCTOR | CHARACTER | 20 |
| PT_ID | CHARACTER | 11 |
| INVOICE | CHARACTER | 6 |
| CATEGORY | CHARACTER | 7 |
| CODE | CHARACTER | 1 |
| DATE | DATE | 8 |
| HINVOICE | CHARACTER | 6 |
| EINVOICE | CHARACTER | 6 |
| TINVOICE | CHARACTER | 6 |
| LINVOICE | CHARACTER | 6 |
| SINVOICE | CHARACTER | 6 |
| CONDITION | CHARACTER | 6 |
| COMPLAINT1 | CHARACTER | 5 |
| FINDING1 | CHARACTER | 5 |
| COMPLAINT2 | CHARACTER | 5 |
| FINDING2 | CHARACTER | 5 |
| KINVOICE | CHARACTER | 6 |

FIG. 5

STRUCTURE FOR DATABASE:MEDICAL.DBF

| FIELD NAME | TYPE | WIDTH |
|---|---|---|
| DOCTOR | CHARACTER | 20 |
| PT_ID | CHARACTER | 11 |
| DOB | DATE | 8 |
| LNAME | CHARACTER | 12 |
| FNAME | CHARACTER | 8 |
| SEX | CHARACTER | 1 |
| DIAGNOSIS1 | CHARACTER | 25 |
| CODE1 | CHARACTER | 6 |
| DURATION1 | NUMERIC | 2 |
| MEDFLAG1 | LOGICAL | 1 |
| MEDINV1 | CHARACTER | 6 |
| DIAGNOSIS2 | CHARACTER | 25 |
| CODE2 | CHARACTER | 6 |
| DURATION2 | NUMERIC | 2 |
| MEDFLAG2 | LOGICAL | 1 |
| MEDINV2 | CHARACTER | 6 |
| DIAGNOSIS3 | CHARACTER | 25 |
| CODE3 | CHARACTER | 6 |
| DURATION3 | NUMBERIC | 2 |
| MEDFLAG3 | LOGICAL | 1 |
| MEDINV3 | CHARACTER | 6 |
| DESCRIPONE | CHARACTER | 12 |
| AMTONE | CHARACTER | 5 |
| MEDONE | CHARACTER | 5 |
| MEDTWO | CHARACTER | 5 |
| DESCRIPTWO | CHARACTER | 12 |
| AMTTWO | CHARACTER | 5 |
| MEDTHREE | CHARACTER | 5 |
| DESCRIPTHR | CHARACTER | 12 |
| AMTTHREE | CHARACTER | 5 |
| MAJORSURG | LOGICAL | 1 |
| PRIOR_HOSP | NUMERIC | 2 |
| TREATMENT | LOGICAL | 1 |
| LAST_HOSP | DATE | 8 |
| ALLERGIES | CHARACTER | 30 |
| WEIGHT | NUMERIC | 3 |
| SYSTOLIC | CHARACTER | 3 |
| DIASTOLIC | CHARACTER | 3 |
| DATE | DATE | 8 |

FIG. 6

STRUCTURE FOR DATABASE:ABN_LAB.DBF

| FIELD NAME | TYPE | WIDTH |
|---|---|---|
| DOCTOR | CHARACTER | 20 |
| PT_ID | CHARACTER | 11 |
| DATE | DATE | 8 |
| INVOICE | CHARACTER | 6 |
| INVOICEFRM | CHARACTER | 6 |
| BUN | CHARACTER | 7 |
| CR | CHARACTER | 7 |
| HG | CHARACTER | 7 |
| HCT | CHARACTER | 7 |
| SED_RATE | CHARACTER | 7 |
| POTASSIUM | CHARACTER | 7 |
| BLD_SUG | CHARACTER | 7 |
| PH | CHARACTER | 7 |
| PO2 | CHARACTER | 7 |
| PCO2 | CHARACTER | 7 |
| WBC | CHARACTER | 7 |
| CALCIUM | CHARACTER | 7 |
| EKG | CHARACTER | 7 |
| CXR | CHARACTER | 7 |

FIG. 7

| RECORD# | CODETYPE | CODE | DESCRIPT |
|---|---|---|---|
| 1 | H1 | 0000 | ACUTE MI |
| 2 | H1 | 0002 | CHF, ACUTE |
| 3 | H1 | 0003 | ANGINA, NO ISCHEMIA |
| 4 | H2 | 0014 | CHRONIC CHF |
| 5 | V1 | 0004 | ACUTE THROMBOSIS, LEGS |
| 6 | R3 | 0030 | ACUTE LOW BACK PAIN |
| 7 | G1 | 0005 | ACUTE ABDOMEN, REBOUND TND |
| 8 | N1 | 0009 | ACUTE CVA |
| 9 | N2 | 0011 | TIA, INTERMITTENT |
| 10 | V2 | 0013 | MALIGNANT HYPERTENSION |
| 11 | V3 | 0019 | MIGRAINOUS HEADACHE |
| 12 | L1 | 0006 | R/O ACUTE PULM EMBOLUS |
| 13 | L1 | 0007 | ACUTE PULM INSUFFICIENCY |
| 14 | L3 | 0023 | CHRONIC BRONCHITIS |
| 15 | L2 | 0016 | ACUTE ASTHMA |
| 16 | E2 | 0012 | KETOSIS + HYPERGLYCEMIA |
| 17 | K2 | 0015 | PYLONEPHRITIS, ACUTE |
| 18 | L2 | 0017 | PNEUMONIA |
| 19 | I1 | 0010 | SEPTICEMIA, HYPOTENSION |
| 20 | I2 | 0018 | BACTEREMIA |
| 21 | N1 | 0001 | DEEP OBTUNDATION |
| 22 | G2 | 0020 | VOMITING, DIARRHEA |
| 23 | L3 | 0028 | URI, NO SPUTUM |
| 24 | G2 | 0022 | GI BLEEDING |
| 25 | G3 | 0026 | GASTRITIS, MILD |
| 26 | K1 | 0008 | ACUTE URINARY OBSTRUCTION |
| 27 | K3 | 0027 | BACTEURIA, HEAVY |
| 28 | K3 | 0025 | WEAK URINARY STREAM |
| 29 | I2 | 0021 | FEVER, MALAISE, ANOREXIA |
| 30 | R2 | 0024 | ACUTE POLYARTHRITIS |
| 31 | I3 | 0029 | FUNCTIONAL DISORDER |

FIG. 8

STRUCTURE FOR DATABASE:MEDICINE.DBF

| FIELD NAME | TYPE | WIDTH |
|---|---|---|
| PT_ID | CHARACTER | 11 |
| INVOICE | CHARACTER | 6 |
| MED1 | CHARACTER | 5 |
| AMOUNT1 | CHARACTER | 4 |
| ACTION1 | CHARACTER | 1 |
| LENGTH1 | CHARACTER | 2 |
| MED2 | CHARACTER | 5 |
| AMOUNT2 | CHARACTER | 4 |
| ACTION2 | CHARACTER | 1 |
| LENGTH2 | CHARACTER | 2 |
| MED3 | CHARACTER | 5 |
| AMOUNT3 | CHARACTER | 4 |
| ACTION3 | CHARACTER | 1 |
| LENGTH3 | CHARACTER | 2 |

FIG. 9

| RECORD# | CODETYPE | CODE | DESCRIPT |
|---|---|---|---|
| 1 | HA | 000 | RALES, S3, LOW B/P, PVC'S |
| 2 | HA | 001 | TACHYCARDIA, S3 |
| 3 | HB | 002 | S3, THIRD HEART SOUND |
| 4 | HC | 003 | SINUS TACHYCARDIA |
| 5 | HB | 004 | ELEVATED CVP, LOW B/P |
| 6 | HB | 005 | CARDIOMEGALY, BILATERAL |
| 7 | HC | 006 | LEFT VENT.HYPERTROPHY |
| 8 | NA | 007 | APHASIC, LOSS OF FUNCTION |
| 9 | NA | 008 | SLURRY SPEECH, WEAKNESS |
| 10 | VA | 009 | LOSS OF PULSE, POPLITEAL |
| 11 | VA | 010 | LOSS OF PULSE, FOOT |
| 12 | LA | 011 | HYPERCAPNIA, PCO2>55 |
| 13 | LB | 012 | HYPERCAPNIA, PCO2<55 |
| 14 | LB | 013 | LUNG CONSOLIDATION |
| 15 | LB | 014 | INCREASED BREATHSOUNDS |
| 16 | VA | 015 | ABSENT PULSE, CALF |
| 17 | VB | 016 | WEAK PULSE CALF,BILATERAL |
| 18 | IC | 017 | ACUTE ANXIETY, DIAPHORETIC |
| 19 | IB | 018 | CACHECTIC, ANORECTIC |
| 20 | GA | 019 | RUQ TENDERNESS, MASS |
| 21 | GB | 020 | MILD ABD TENDERNESS |
| 22 | NA | 021 | OBTUNDED, SOMNOLENT |
| 23 | RA | 022 | JOINTS TENDER + SWOLLEN |
| 24 | LC | 023 | DRY HACKING COUGH |
| 25 | IA | 024 | FEVER >102 |
| 26 | IB | 025 | FEVER <=102 |
| 27 | KB | 026 | CLOUDY URINE |
| 28 | KA | 027 | SEVERE FLANK TENDERNESS |
| 29 | VA | 028 | HYPOVOLEMIA, LOW B/P |
| 30 | IA | 029 | SEPTICEMIA |
| 31 | IB | 030 | BACTEREMIA |

FIG. 10

| RECORD# | CODETYPE | CODE | DESCRIPT |
|---|---|---|---|
| 1 | HA | 000 | CRUSHING CHEST PAIN |
| 2 | HA | 001 | HEAVY CHEST PAIN, EXERCISE |
| 3 | HA | 002 | PND, ORTHOPNEA, SOB AT REST |
| 4 | HB | 003 | EASY FATIGUE, SOB, EXERCISE |
| 5 | HB | 004 | WEIGHT GAIN, ANKLE SWELL |
| 6 | VA | 005 | ACUTE CLAUDICATION, REST |
| 7 | RB | 025 | MILD JT PAIN, NO SWELLING |
| 8 | IB | 023 | LOSS OF APPETITE, MALAISE |
| 9 | IB | 022 | FATIGUE, WEAKNESS |
| 10 | IB | 030 | ANXIETY, HEADACHE |
| 11 | RB | 017 | INTERMITT. JT. SWELLING |
| 12 | GA | 006 | ACUTE ABD.PAIN, VOMIT, WEAK |
| 13 | GB | 011 | BLOODY STOOLS, INTERMITTEN |
| 14 | GA | 010 | UGI BLEED, VOMIT, WEAKNESS |
| 15 | GC | 024 | CHRONIC ABD PAIN, NO VOMIT |
| 16 | GC | 020 | DIARRHEA, MILD |
| 17 | NA | 009 | SEVERE HEADACHE, VOMITING |
| 18 | KA | 008 | FLANK PAIN, VOMITING, FEVER |
| 19 | KB | 013 | POLYURIA, POLYDIPSIA |
| 20 | KA | 012 | CLD.URINE, FREQUENCY, CHILL |
| 21 | RB | 014 | ACUTE JT. SWELL, PAIN, FEVER |
| 22 | NA | 007 | SLURRY SPEECH, HAND WEAK |
| 23 | HB | 026 | CHR. CHEST PAIN, EXERCISE |
| 24 | LA | 016 | SPUTUM, CHST. PAIN, FEVER |
| 25 | VB | 015 | CHR. NUMBNESS CALF, EXERC. |
| 26 | VB | 018 | INT. NUMBNESS, FEET |
| 27 | LA | 019 | SUDDEN CHEST PAIN, DYSPNEA |
| 28 | LC | 021 | COUGH, MILD, SPUTUM |
| 29 | KB | 028 | WEAK STREAM, FREQUENCY |
| 30 | IB | 029 | SHAKING CHILLS, FEVER, WEAK |
| 31 | GA | 027 | RUQ PAIN, COLICKY, VOMITING |

FIG. 11

| RECORD# | CODENAME | DESCRIPT | TOXI1 | TOXI2 |
|---|---|---|---|---|
| 1 | M0000 | DIGOXIN | POTASSIUM | EKG |
| 2 | M0001 | LASIX | POTASSIUM | BUN |
| 3 | M0002 | INDERAL | | |
| 4 | M0003 | NITROGLYCERI | | |
| 5 | M0004 | ISORDIL | | |
| 6 | M0005 | PREDNISONE | BUN | POTASSIUM |
| 7 | M0006 | CHEMOTHERAPY | WBC | HG |
| 8 | M0007 | NALFON | | |
| 9 | M0008 | KEFLIN | HG | HCT |
| 10 | M0009 | LOW SALT | BUN | POTASSIUM |
| 11 | M0010 | LOW PROTEIN | BUN | |
| 12 | M0011 | PENICILLIN | HCT | BUN |
| 13 | M0012 | HYDRODIURIL | POTASSIUM | BUN |
| 14 | M0013 | MAALOX | HCT | |
| 15 | M0014 | INDERIDE | | |
| 16 | M0015 | KCL | POTASSIUM | |
| 17 | M0016 | LIBRIUM | | |
| 18 | M0017 | INSULIN | BLD SUGAR | POTASSIUM |
| 19 | M0018 | AMINOPHYLLIN | | |
| 20 | M0019 | ASPIRIN | HCT | |
| 21 | M0020 | IPPB, EPI | | |
| 22 | M0021 | DILANTIN | | |
| 23 | M0022 | VASODILAN | | |
| 24 | M0023 | CALCIUM | CALCIUM | |
| 25 | M0024 | CYTOXAN | WBC | |
| 26 | M0025 | ALDOMET | HG | HCT |

FIG. 12

| RECORD# | CODETYPE | CODE | DESCRIPT |
|---|---|---|---|
| 1 | AH | 000 | CORONARY ARTERY BYPASS |
| 2 | AH | 001 | AORTIC ANUERYSECTOMY |
| 3 | AN | 002 | CAROTID ENDARTERECTOMY |
| 4 | AN | 003 | DECOMPRESSIVE CRANIOTOMY |
| 5 | AV | 004 | AORTIC POPLITEAL BYPASS |
| 6 | BL | 005 | LOBECTOMY, CA |
| 7 | BG | 006 | WHIPPLES PROCEDURE |
| 8 | BG | 007 | COLECTOMY, CA |
| 9 | BG | 008 | GASTRECTOMY, CA |
| 10 | BG | 009 | GASTRECTOMY, ULCER |
| 11 | BV | 010 | POPLITEAL-FEMORAL BYPASS |
| 12 | CG | 011 | VAGOTOMY + PYLOROPLASTY |
| 13 | CG | 012 | POST TRAUM. SPLENECTOMY |
| 14 | CR | 013 | HIP REPLACEMENT |
| 15 | CR | 014 | FX'S + OPEN REDUCTION |

FIG. 13

STRUCTURE FOR DATABASE:SURGLINK.DBF

| FIELD NAME | TYPE | WIDTH |
|---|---|---|
| PT_ID | CHARACTER | 11 |
| SURGCODE | CHARACTER | 5 |
| DATE | DATE | 8 |
| INVOICE | CHARACTER | 6 |

STRUCTURE FOR DATABASE:TREATMEN.DBF

| FIELD NAME | TYPE | WIDTH |
|---|---|---|
| DOCTOR | CHARACTER | 20 |
| PT_ID | CHARACTER | 11 |
| INVOICE | CHARACTER | 6 |
| DATE | DATE | 8 |
| RX | CHARACTER | 20 |
| STATUS | CHARACTER | 1 |
| REASON | CHARACTER | 6 |

FIG. 14

STRUCTURE FOR DATABASE:ER_ROOM.DBF

| FIELD NAME | TYPE | WIDTH |
| --- | --- | --- |
| DOCTOR | CHARACTER | 20 |
| PT_ID | CHARACTER | 11 |
| INVOICE | CHARACTER | 6 |
| DATE | DATE | 8 |
| DIAGNOSIS | CHARACTER | 6 |
| CONDITION | CHARACTER | 1 |
| MEDICATION | CHARACTER | 5 |
| STATUS | CHARACTER | 1 |
| COMPLAINT1 | CHARACTER | 5 |
| COMPLAINT2 | CHARACTER | 5 |
| FINDING1 | CHARACTER | 5 |
| FINDING2 | CHARACTER | 5 |

FIG. 15

STRUCTURE FOR DATABASE:PT_HOSP.DBF

| FIELD NAME | TYPE | WIDTH |
|---|---|---|
| DOCTOR | CHARACTER | 20 |
| PT_ID | CHARACTER | 11 |
| INVOICE | CHARACTER | 6 |
| DAT_ADM | DATE | 8 |
| ADM_DX | CHARACTER | 6 |
| DURATION | NUMERIC | 2 |
| DISCH_DX | CHARACTER | 6 |
| MAJ_SURG | LOGICAL | 1 |
| BLD_TRANS | NUMERIC | 2 |
| ICU | LOGICAL | 1 |
| NARRATIVE | MEMO | 10 |

FIG. 16

PATIENT I.D. NUMBER _ _ _ (3401) _ _ _ _ _ _ _   NEW PROBLEM (3402) _   STATUS (3403) _
                       (SOCIAL SEC. #)           (Y/N)      (1,2,3,4,5)

MCODE 1 _ _ _ _ (3404)    MCODE 2 _ _ _ _ (3405)    MCODE 3 _ _ _ _ (3406)

CONDITION CODE _ _ _ _ (3407)

COMPLAINTS (SYMPTOMS)

MCOMP 1 _ _ _ (3408)
MCOMP 2 _ _ _ (3409)   } FIRST METHOD

MLET1 (3410) _
MLET1 DESC. _ _ _ _ _ _ _ _ (3411) _ _ _ _ _ _ _ _ _ _
MLET2 (3412) _                                               } SECOND METHOD
MLET2 DESC. _ _ _ _ _ _ _ _ (3413) _ _ _ _ _ _ _ _ _ _

FINDINGS (SIGNS)

MFIND 1 _ _ _
MFIND 2 _ _ _   } FIRST METHOD (3414)

MLET3 (3415) _
MLET3 DESC. _ _ _ _ _ _ _ _ (3416) _ _ _ _ _ _ _ _ _ _
MLET4 (3417) _                                               } SECOND METHOD
MLET4 DESC. _ _ _ _ _ _ _ _ (3418) _ _ _ _ _ _ _ _ _ _

FIG 50

```
Record # DOCTOR                PT_ID      INVOICE  DATE     TYPE STATUS PRIM_DX S
EC_DX TERT_DX MED_CHANGE NEW_MED LAB_WORK CONSULT NEWPROBLEM INJECTION CONDITION
WEIGHT SYSTOLIC DIASTOLIC  COMPLAINT1  COMPLAINT2  FINDING1  FINDING2
       1    abbott            011-35-3777  O00005   01/24/87   S    1    AA0015
                    .F.          .F.       .F.       .F.       .F.        .F.     AA0015
       0  135      95
       2    abbott            011-35-3777  O00019   02/05/87   S    1    AA0015
                    .F.          .F.       .F.       .F.       .F.        .F.     mc0002
       0  135      95
       3    abbott            013-32-5312  O00000   01/12/87   U    1    AA0012 B
A0015 CR0029  .F.    .F.          .F.       .F.       .F.       .F.     BA0015
       0
       4    abbott            013-32-5312  O00011   02/14/87   S    1    AA0012 B
A0015 CR0029  .F.    .F.          .F.       .F.       .F.       .F.     mc0003
       0
       5    abbott            013-32-5312  O00015   02/19/87   S    1    AA0012 B
A0015 CR0029  .F.    .F.          .T.       .F.       .F.       .F.     CR0029
       0
       6    abbott            112-23-3145  O00007   01/11/87   U    1    AB0024 C
K0026          .F.    .F.          .F.       .F.       .F.       .F.     CK0026
       0
       7    abbott            112-23-3145  O00014   02/01/87   S    1    AB0024 C
K0026          .F.    .F.          .F.       .F.       .F.       .F.     CK0026
       0
       8    abbott            114-24-3145  O00002   01/02/87   S    1    BA0012 B
A0015 BB0001  .F.    .F.          .F.       .F.       .F.       .F.     BA0015
       0
       9    abbott            114-24-3145  O00009   01/24/87   S    1    BA0012 B
A0015 BA0001  .F.    .F.          .F.       .F.       .F.       .F.     BG0012
       0
      10    abbott            131-25-6721  O00012   01/20/87   S    1    AB0006
                    .F.          .F.       .F.       .F.       .F.        .F.     AB0006
       0  160      90
      11    abbott            131-25-6721  O00027   01/27/87   S    1    AB0006
                    .F.          .F.       .F.       .F.       .F.        .F.     AB0006
       0  169      90
      12    abbott            131-25-6721  O00031   02/03/87   S    1    AB0006
                    .F.          .F.       .F.       .F.       .T.        .F.     AB0006
       0  160      95
      13    abbott            212-32-5487  O00008   01/02/87   U    1    AA0005
                    .T.          .F.       .F.       .F.       .F.        .F.     AA0005
       0
      14    abbott            212-32-5487  O00024   01/17/87   U    1    AA0005
                    .F.          .F.       .F.       .F.       .F.        .F.     AA0005
       0
      15    abbott            212-32-5487  O00029   02/05/87   S    1    AA0005
                    .F.          .F.       .F.       .F.       .F.        .F.     AA0005
       0
      16    abbott            212-32-5487  O00032   02/09/87   S    1    AA0005
                    .F.          .F.       .F.       .F.       .F.        .F.     AA0005

17    costello          152-43-2916  O00003   01/13/87   S    1    AA0001 A
H0010          .F.    .F.          .F.       .F.       .F.       .F.     AA0001
       0  140      90
      18    costello          152-43-2916  O00010   01/17/87   U    1    AA0001 A
H0010          .F.    .F.          .F.       .F.       .T.       .F.     AH0010
       0  140      90
      19    costello          152-43-2916  O00016   02/02/87   S    1    AA0001 A
H0010          .F.    .F.          .F.       .F.       .F.       .F.     AH0010
       0  140      90
      20    hampton           010-53-6677  O00001   01/02/87   U    1    AH0018 C
C0024          .F.    .F.          .F.       .F.       .F.       .F.     CC0024
       0  150      90
```

FIG. 56

| | | | | | | | | |
|---|---|---|---|---|---|---|---|---|
| 21 | hampton .F. | | 010-53-6677 .F. | O00030 .F. | 01/27/87 .F. | S .F. | 2 | AH0028 C CC0024 |
| C0024 | 0 150 | 90 | | | | | | |
| 22 | hampton .F. | | 324-53-0764 .F. | O00004 .F. | 01/10/87 .F. | S .F. | 1 | AA0005 AA0005 |
| 0 | | | | | | | | |
| 23 | hampton .F. | | 324-53-0764 .F. | O00033 .F. | 01/19/87 .F. | U .F. | 1 | AA0005 AA0005 |
| 0 | | | | | | | | |
| 24 | hampton .F. | | 324-53-0764 .F. | O00036 .F. | 03/19/87 .F. | S .F. | 1 | AA0005 |
| 25 | hampton .F. | | 324-53-0764 .F. | O00038 .F. | 03/26/87 .F. | S .F. | 1 | AA0005 AH0002 |
| 26 | hampton .F. | | 324-53-0764 .F. | O00041 .F. | 04/01/87 .F. | S .F. | 1 | AA0005 |
| | 160 | 90 | | | | | | |
| 27 | hampton .F. | | 324-53-0764 .F. | O00044 .F. | 04/08/87 .F. | U .F. | 1 | AA0005 AA0005 |
| | 160 | 90 | | | | | | |
| 28 | hampton A0015 BG0020 .F. | | 454-12-3621 .T. | O00006 .F. | 01/23/87 .F. | S .F. | 1 | BA0012 B mb0000 |
| | 0 150 | 89 | | | | | | |
| 29 | hampton A0015 BG0020 .F. | | 454-12-3621 .F. | O00029 .F. | 02/04/87 .F. | S .F. | 1 | BA0012 B mb0000 |
| | 0 150 | 89 | | | | | | |
| 30 | hampton .F. | | 324-53-0764 .F. AB003 | O00046 .F. BB006 | 04/14/87 .F. AB007 | U .F. | 2 | AA0005 BB0017 |
| 31 | costello .F. | | 152-43-2916 .F. BB002 | O00019 .F. | 02-28-87 .F. | S .F. | 2 | cA0001 AA0001 |

FIG. 57

| Record # | DOCTOR | PT_ID | INVOICE | CATEGORY | CODE | DATE | HINVOICE |
|---|---|---|---|---|---|---|---|
| E | EINVOICE | TINVOICE | LINVOICE | SINVOICE | CONDITION | COMPLAINT1 | FINDING1 | COMPLAINT2 | F |
| INDING2 | KINVOICE | | | | | | | | |
| 1 | abbott | 011-35-3777 | O00019 | | SA | t | 02/05/87 |
| E00002 | | L00002 | | mc0002 | | | |
| 2 | abbott | 114-24-3145 | O00009 | | SA | t | 01/24/87 |
| | | L00023 | | BG0012 | | | |
| K00003 | | | | | | | |
| 3 | abbott | 131-25-6721 | O00027 | | SA | t | 01/27/87 |
| | | | | AB0006 | | | |
| K00000 | | | | | | | |
| 4 | abbott | 212-32-5487 | O00032 | | SA | f | 02/09/87 |
| | | L00016 | | AA0005 | | | |
| 5 | hampton | 324-53-0764 | O00038 | | SA | t | 03/26/87 |
| E00003 | | L00020 | | AH0002 | | | |
| K00002 | | | | | | | |
| 6 | hampton | 324-53-0764 | O00041 | | SA | t | 04/01/87 |
| | | L00022 | | | | | |
| K00002 | | | | | | | |

FIG. 58

| Record # | DOCTOR | HG | HCT | PT_ID | DATE | INVOICE | INVOICEFRM | BUN | CR |
|---|---|---|---|---|---|---|---|---|---|
| | | SED_RATE | POTTASIUM | BLD_SUG | PH | P02 | PC02 | WBC | |
| | CALCIUM | EKG | | CXR | | | | | |
| 1 | hampton | | | 010-53-6677 | 01/04/87 | I00000 | O00015 | | C2U29.6 |
| 2 | abbott | S3U10.2 | C4U32.5 | 112-23-3145 | 01/18/87 | L00001 | O00007 | | |
| 3 | abbott | | | 011-35-3777 | 01/25/87 | L00002 | O00005 | | C2 |
| | U56 | | | A1W45 | | | | | |
| 4 | | | | 112-23-3145 | 01/14/87 | L00003 | O00013 | | S3 |
| | W40 | | C2U30.5 | | | | | | |
| 5 | | T B | T B | 112-23-3145 | 01/17/87 | L00004 | O00014 | | A1P16X3 |
| | | | | T C | A1N432 | | | | |
| 6 | | | A2N28.5 | 010-53-6677 | 01/08/87 | L00005 | O00021 | T B | T |
| | C | | | | | | | | |
| 7 | | | A2I28 | 011-35-3777 | 02/06/87 | L00006 | O00019 | | C2 |
| | 136.5 | | | | | | | | |
| 8 | | S4U10.6 | | 131-25-6721 | 01/04/87 | L00008 | O00012 | | |
| | | | | A1N6.2 | A2W206 | | | | |
| 9 | | | | 131-25-6721 | 01/13/87 | L00009 | O00027 | | S2I28.7 |
| | | S2U | S1W | | | | | | |
| 10 | | | A2I24 | 454-12-3621 | 01/24/87 | L00010 | O00006 | | |
| | | | | | A3W6.9 | | S2I55 | | |
| 11 | | | S3W27.4 | 454-12-3621 | 02/04/87 | L00011 | O00029 | | |
| | A2W14.8 | | | A4N2.9 | | | | | |
| 12 | | | S2I30.5 | 152-43-2916 | 01/13/87 | L00012 | O00003 | | A2 |
| | N8.6 | | | | | | | | C2W15.3 |
| 13 | | | A2U22.9 | 152-43-2916 | 01/17/87 | L00013 | O00010 | | |
| | | | | C3W6.9 | | | | | |
| 14 | | | C4U30.2 | 212-32-5487 | 01/07/87 | L00013 | O00008 | | A2W42.6 |
| 15 | | | | 212-32-5487 | 01/18/87 | L00015 | O00024 | | S1 |
| | W14.6 | | | A4U151 | | | | | |
| 16 | | | | 212-32-5487 | 02/07/87 | L00016 | O00029 | | C4U25.5 |
| | | | | T A | | | | | |
| 17 | | | A2N20.5 | 324-53-0764 | 01/11/87 | L00029 | O00004 | | T C |
| 18 | | T C | | 324-53-0764 | 03/19/87 | L00020 | O00036 | | T A |
| | A1P15.0 | | | T B | | | | | S1W23x3 |
| 19 | | T A | A2P21.5 | 324-53-0764 | 03/26/87 | L00022 | O00038 | | |
| 20 | | | | 114-24-3145 | 01/03/87 | L00023 | O00002 | | |
| | | | | A4W3.0 | | | C3W50.0 | C1W52.0 | |

| Record# | DOCTOR STATUS | COMPLAINT1 | EDICATION | PT_ID | INVOICE | DATE | DIAGNOSIS | CONDITION | M |
|---|---|---|---|---|---|---|---|---|---|
| | | | | COMPLAINT2 | FINDING1 | FINDING2 | | | |
| 1 | hampton 1 | nc011 | | 454-12-3621 nz026 | E00000 | 01/26/87 | mb0000 | b | |
| 2 | costello 1 | np009 | | 152-43-2916 nc015 | E00001 | 02/01/87 | mc0002 | b | |
| 3 | abbott 1 | np009 | | 011-35-3777 | E00002 | 02/04/87 | mc0002 | b | |
| 4 | 1 | | | 324-53-0764 | E00003 | 03/25/87 | AH0002 | | |

B

| Record# | PT_ID | SURGCODE | DATE | INVOICE |
|---|---|---|---|---|
| 1 | 131-25-6721 | AN002 | 01/22/87 | K00000 |
| 2 | 212-32-5487 | CG001 | 11/01/86 | K00001 |
| 3 | 324-53-0764 | CR004 | 02/19/87 | K00002 |
| 4 | 114-24-3145 | CG001 | 11/24/86 | K00003 |
| 5 | 013-32-5312 | CR013 | 12/29/86 | K00004 |

C

| Record# | DOCTOR | _DX | MAJ_SURG | BLD_TRANS | ICU | PT_ID NARRATIVE | INVOICE | DAT_ADM | ADM_DX | DURATION | DISCH |
|---|---|---|---|---|---|---|---|---|---|---|---|
| 1 | hampton | 4 | .F. | 2 | .F. Memo | 010-53-6677 | H00000 | 01/10/87 | mc0001 | 8 | CC002 |
| 2 | abbott | 2 | .F. | | .F. Memo | 112-23-3145 | H00001 | 03/04/87 | mb0002 | 7 | CB002 |
| 3 | abbott | 2 | .F. | | .F. Memo | 013-32-5312 | H00002 | 01/04/87 | mc0003 | 6 | AB001 |

D

| Record# | DOCTOR STATUS | REASON | PT_ID | INVOICE | DATE | RX |
|---|---|---|---|---|---|---|
| 1 | abbott 2 | BP0008 | 112-23-3145 | T00000 | 01/28/87 | inhalation therapy |
| 2 | abbott 1 | CR0008 | 013-32-5312 | T00001 | 02/15/87 | heat,P.T. |
| 3 | abbott 1 | AA0005 | 212-32-5487 | T00002 | 02/08/87 | cardiac exercise |

FIG. 60

```
Record # DOCTOR                PT_ID    INVOICE DATE   TYPE STATUS PRIM_DX S
EC_DX TERT_DX MED_CHANGE NEW_MED LAB_WORK CONSULT NEWPROBLEM INJECTION CONDITION
WEIGHT  SYSTOLIC DIASTOLIC COMPLAINT1 COMPLAINT2 FINDING1 FINDING2
       1    abbott          011-35-3777  O00005  01/24/87  S    1    AA0015
            .F.        .F.     .F.     .F.     .F.          .F.      AA0015
      0  135      95
       2    abbott          011-35-3777  O00019  02/05/87  S    1    AA0015
            .F.        .F.     .F.     .F.     .F.          .F.      mc0002
      0  135      95
       3    abbott          013-32-5312  O00000  01/12/87  U    1    AA0012 B
A0015 CR0029  .F.     .F.     .F.     .F.     .F.          .F.      BA0015
      0
       4    abbott          013-32-5312  O00011  02/14/87  S    1    AA0012 B
A0015 CR0029  .F.     .F.     .F.     .F.     .F.          .F.      mc0003
      0
       5    abbott          013-32-5312  O00015  02/19/87  S    1    AA0012 B
A0015 CR0029  .F.     .F.     .T.     .F.     .F.          .F.      CR0029
      0
       6    abbott          112-23-3145  O00007  01/11/87  U    1    AB0024 C
K0026         .F.     .F.     .F.     .F.     .F.          .F.      CK0026
      0
       7    abbott          112-23-3145  O00014  02/01/87  S    1    AB0024 C
K0026         .F.     .F.     .F.     .F.     .F.          .F.      CK0026
      0
       8    abbott          114-24-3145  O00002  01/02/87  U    1    BA0012 B
A0015 BB0001  .T.     .F.     .F.     .F.     .F.          .F.      BA0015
      0
       9    abbott          114-24-3145  O00009  01/24/87  S    1    BA0012 B
A0015 BA0001  .F.     .F.     .F.     .F.     .F.          .F.      BA0012
      0
      10    abbott          131-25-6721  O00012  01/20/87  S    1    AB0006
              .F.     .F.     .F.     .F.     .F.          .F.      AB0006
      0  160      90
      11    abbott          131-25-6721  O00027  01/27/87  U    1    AB0006
              .F.     .F.     .F.     .F.     .F.          .F.      AB0006
      0  169      90
      12    abbott          131-25-6721  O00031  02/03/87  S    1    AB0006
              .F.     .F.     .F.     .F.     .T.          .F.      AB0006
      0  160      95
      13    abbott          212-32-5487  O00008  01/02/87  U    1    AA0005
              .T.     .F.     .F.     .F.     .F.          .F.      AA0005
      0
      14    abbott          212-32-5487  O00024  01/17/87  U    1    AA0005
              .F.     .F.     .F.     .F.     .F.          .F.      AA0005
      0
      15    abbott          212-32-5487  O00029  02/05/87  U    1    AA0005
              .F.     .F.     .F.     .F.     .F.          .F.      AA0005
      0
      16    abbott          212-32-5487  O00032  02/09/87  S    1    AA0005
              .F.     .F.     .F.     .F.     .F.          .F.      AA0005

17    costello        152-43-2916  O00003  01/13/87  S    1    AA0001 A
H0010         .F.     .F.     .F.     .F.     .F.          .F.      AA0001
      0  140      90
      18    costello        152-43-2916  O00010  01/17/87  U    1    AA0001 A
H0010         .F.     .F.     .F.     .F.     .T.          .F.      AH0010
      0  140      90
      19    costello        152-43-2916  O00016  02/02/87  S    1    AA0001 A
H0010         .F.     .F.     .F.     .F.     .F.          .F.      AH0010
      0  140      90
      20    hampton         010-53-6677  O00001  01/02/87  U    1    AH0018 C
C0024         .F.     .F.     .F.     .F.     .F.          .F.      CC0024
      0  150      90
```

FIG. 61

| | | | | | | | | |
|---|---|---|---|---|---|---|---|---|
| 21 | hampton | | 010-53-6677 | O00030 | 01/27/87 | S | 2 | AH0018 C |
| C0024 | .F. | .F. | .F. | .F. | .F. | | .F. | CC0024 |
| 0 150 | | 90 | | | | | | |
| 22 | hampton | | 324-53-0764 | O00004 | 01/10/87 | S | 1 | AA0005 |
| | .F. | .F. | .F. | .F. | .F. | | .F. | AA0005 |
| 0 | | | | | | | | |
| 23 | hampton | | 324-53-0764 | O00033 | 01/19/87 | U | 1 | AA0005 |
| | .F. | .F. | .F. | .F. | .F. | | .F. | AA0005 |
| 0 | | | | | | | | |
| 24 | hampton | | 324-53-0764 | O00036 | 03/19/87 | U | 2 | AA0005 |
| | .F. | .F. | .F. | .F. | .F. | | .F. | |
| 25 | hampton | | 324-53-0764 | O00038 | 03/26/87 | S | 1 | AA0005 |
| | .F. | .F. | .F. | .F. | .F. | | .F. | |
| 26 | hampton | | 324-53-0764 | O00041 | 04/01/87 | S | 1 | AA0005 |
| | .F. | .F. | .F. | .F. | .F. | | .F. | |
| 160 | | 90 | | | | | | |
| 27 | hampton | | 324-53-0764 | O00044 | 04/08/87 | U | 1 | AA0005 |
| | .F. | .F. | .F. | .F. | .F. | | .F. | AA0005 |
| 160 | | 90 | | | | | | |
| 28 | hampton | | 454-12-3621 | O00006 | 01/23/87 | U | 1 | BA0012 B |
| A0015 BG0020 | .F. | .T. | .F. | .F. | .F. | | .F. | mb0000 |
| 0 150 | | 89 | | | | | | |
| 29 | hampton | | 454-12-3621 | O00029 | 02/04/87 | S | 1 | BA0012 B |
| A0015 BG0020 | .F. | .F. | .F. | .F. | .F. | | .F. | mb0000 |
| 0 150 | | 89 | | | | | | |
| 30 | hampton | | 324-53-0764 | O00046 | 04/14/87 | U | 2 | AA0005 |
| | .F. | .F. | .F. | .F. | .F. | | .F. | BB0017 |
| | | AB003 | BB006 | AB007 | | | | |
| 31 | costello | | 152-43-2916 | O00019 | 02-28-87 | S | 2 | cA0001 |
| | .F. | .F. | .F. | .F. | .F. | | .F. | AA0001 |
| | | BB002 | | | | | | |

FIG. 62

| Record # | DOCTOR | PT_ID | INVOICE | CATEGORY | CODE | DATE | HINVOICE |
|---|---|---|---|---|---|---|---|
| EINVOICE | TINVOICE | LINVOICE | SINVOICE | CONDITION | COMPLAINT1 | FINDING1 | COMPLAINT2 FINDING2 KINVOICE |
| 1 | abbott | 112-23-3145 | O00014 | AU | | t | 02/01/87 |
| | T00000 | L00001 | CK0026 | | | | |
| 2 | abbott | 212-32-5487 | O00024 | AU2 | C | | 01/17/87 |
| | | AA0005 | | | | | |
| 3 | abbott | 212-32-5487 | O00029 | AU3 | C | | 02/05/87 |
| | | AA0005 | | | | | |
| 4 | abbott | 212-32-5487 | O00032 | AU | | | 02/09/87 |
| | | AA0005 | | | | | |
| 5 | hampton | 324-53-0764 | O00036 | AU2 | C | | 03/19/87 |
| 6 | hampton | 324-53-0764 | O00046 | AU2 | C | | 04/14/87 |
| | | BB0017 | | | | | |
| 7 | hampton | 454-12-3621 | O00029 | AU | | t | 02/04/87 |
| E00000 | | mb0000 | | | | | |

FIG. 63

| Record # | DOCTOR | PT_ID | INVOICE | DATE | TYPE | STATUS | PRIM_DX | S | EC_DX | TERT_DX | MED_CHANGE | NEW_MED | LAB_WORK | CONSULT | NEWPROBLEM | INJECTION | CONDITION | WEIGHT | SYSTOLIC | DIASTOLIC | COMPLAINT1 | COMPLAINT2 | FINDING1 | FINDING2 |
|---|---|---|---|---|---|---|---|---|---|---|---|---|---|---|---|---|---|---|---|---|---|---|---|---|
| 1 | abbott | 011-35-3777 | O00005 | 01/24/87 | S | 1 | AA0015 | | | | .F. | .F. | .F. | .F. | .F. | .F. | AA0015 | 0 | 135 | 95 | | | | |
| 2 | abbott | 011-35-3777 | O00019 | 02/05/87 | S | 1 | AA0015 | | | | .F. | .F. | .F. | .F. | .F. | .F. | mc0002 | 0 | 135 | 95 | | | | |
| 3 | abbott | 013-32-5312 | O00000 | 01/12/87 | U | 2 | AA0012 | B | A0015 | CR0029 | .F. | .F. | .F. | .F. | .F. | .F. | AA0015 | 0 | | | | | | |
| 4 | abbott | 013-32-5312 | O00011 | 02/14/87 | S | 4 | AA0012 | B | A0015 | CR0029 | .F. | .F. | .F. | .F. | .F. | .F. | AA0012 | 0 | | | | | | |
| 5 | abbott | 013-32-5312 | O00015 | 02/19/87 | S | 2 | AA0012 | B | A0015 | CR0029 | .F. | .T. | .F. | .F. | .F. | .F. | AA0012 | 0 | | | | | | |
| 6 | abbott | 112-23-3145 | O00007 | 01/11/87 | U | 1 | AB0024 | C | K0026 | | .F. | .F. | .F. | .F. | .F. | .F. | CK0026 | 0 | | | | | | |
| 7 | abbott | 112-23-3145 | O00014 | 02/01/87 | S | 1 | AB0024 | C | K0026 | | .F. | .F. | .F. | .F. | .F. | .F. | CK0026 | 0 | | | | | | |
| 8 | abbott | 114-24-3145 | O00002 | 01/02/87 | U | 1 | BA0012 | B | A0015 | BB0001 | .T. | .F. | .F. | .F. | .F. | .F. | BA0015 | 0 | | | | | | |
| 9 | abbott | 114-24-3145 | O00009 | 01/24/87 | S | 1 | BA0012 | B | A0015 | BA0001 | .F. | .F. | .F. | .F. | .F. | .F. | BA0012 | 0 | | | | | | |
| 10 | abbott | 131-25-6721 | O00012 | 01/20/87 | S | 2 | AB0006 | | | | .F. | .F. | .F. | .F. | .F. | .F. | AB0006 | 0 | 160 | 90 | | | | |
| 11 | abbott | 131-25-6721 | O00027 | 01/27/87 | U | 2 | AB0006 | | | | .F. | .F. | .F. | .F. | .F. | .F. | AB0006 | 0 | 169 | 90 | | | | |
| 12 | abbott | 131-25-6721 | O00031 | 02/03/87 | S | 4 | AB0006 | | | | .F. | .F. | .F. | .F. | .T. | .F. | AB0006 | 0 | 160 | 95 | | | | |
| 13 | abbott | 212-32-5487 | O00008 | 01/02/87 | U | 2 | AA0005 | | | | .T. | .F. | .F. | .F. | .F. | .F. | AA0005 | 0 | | | | | | |
| 14 | abbott | 212-32-5487 | O00024 | 01/17/87 | U | 2 | AA0005 | | | | .F. | .F. | .F. | .F. | .F. | .F. | AA0005 | 0 | | | | | | |
| 15 | abbott | 212-32-5487 | O00029 | 02/05/87 | S | 2 | AA0005 | | | | .F. | .F. | .F. | .F. | .F. | .F. | AA0005 | 0 | | | | | | |
| 16 | abbott | 212-32-5487 | O00032 | 02/09/87 | S | 3 | AA0005 | | | | .F. | .F. | .F. | .F. | .F. | .F. | AA0005 | | | | | | | |
| 17 | costello | 152-43-2916 | O00003 | 01/13/87 | S | 2 | AA0001 | A | H0010 | | .F. | .F. | .F. | .F. | .F. | .F. | AA0001 | 0 | 140 | 90 | | | | |
| 18 | costello | 152-43-2916 | O00010 | 01/17/87 | U | 2 | AA0001 | A | H0010 | | .F. | .F. | .F. | .F. | .T. | .F. | AA0010 | 0 | 140 | 90 | | | | |
| 19 | costello | 152-43-2916 | O00016 | 02/02/87 | S | 4 | AA0001 | A | H0010 | | .F. | .F. | .F. | .F. | .F. | .F. | AA0010 | 0 | 140 | 90 | | | | |
| 20 | hampton | 010-53-6677 | O00001 | 01/02/87 | U | 1 | AH0018 | C | C0024 | | .F. | .F. | .F. | .F. | .F. | .F. | CC0024 | 0 | 150 | 90 | | | | |

FIG. 64

| | | | | | | | | |
|---|---|---|---|---|---|---|---|---|
| 21 | hampton .F. | | 010-53-6677 .F. | O00030 .F. | 01/27/87 .F. | S | 2 .F. | AH0018 C CC0024 |
| C0024 | 0 150 | 90 | | | | | | |
| 22 | hampton .F. | .F. | 324-53-0764 .F. | O00004 .F. | 01/10/87 .F. | S | 2 .F. | AA0005 AA0005 |
| 0 | | | | | | | | |
| 23 | hampton .F. | .F. | 324-53-0764 .F. | O00033 .F. | 01/19/87 .F. | U | 2 .F. | AA0005 AA0005 |
| 0 | | | | | | | | |
| 24 | hampton .F. | .F. | 324-53-0764 .F. | O00036 .F. | 03/19/87 .F. | S | 1 .F. | AA0005 |
| 25 | hampton .F. | .F. | 324-53-0764 .F. | O00038 .F. | 03/26/87 .F. | S | 1 .F. | AA0005 |
| 26 | hampton .F. | .F. | 324-53-0764 .F. | O00041 .F. | 04/01/87 .F. | S | 1 .F. | AA0005 |
| | 160 | 90 | | | | | | |
| 27 | hampton .F. | .F. | 324-53-0764 .F. | O00044 .F. | 04/08/87 .F. | U | 1 .F. | AA0005 AA0005 |
| | 160 | 90 | | | | | | |
| 28 | hampton .F. | .T. | 454-12-3621 .F. | O00006 .F. | 01/23/87 .F. | S | 1 .F. | BA0012 B mb0000 |
| A0015 BG0020 | 0 150 | 89 | | | | | | |
| 29 | hampton .F. | .F. | 454-12-3621 .F. | O00029 .F. | 02/04/87 .F. | S | 1 .F. | BA0012 B mb0000 |
| A0015 BG0020 | 0 150 | 89 | | | | | | |
| 30 | hampton .F. | .F. | 324-53-0764 .F. | O00046 .F. | 04/14/87 .F. | U | 2 .F. | BA0005 BB0017 |
| | AB003 | BB006 | | AB007 | | | | |
| 31 | costello .F. | .F. | 152-43-2916 .F. | O00019 .F. | 02-28-87 .F. | S | 2 .F. | AA0001 AA0002 |
| | | BB002 | | | | | | |

FIG. 65

| Record # | DOCTOR | PT_ID | INVOICE | CATEGORY CONDITION | CODE COMPLAINT1 | DATE FINDING1 | HINVOICE COMPLAINT2 | FINDING2 | EINVOICE | TINVOICE | LINVOICE | SINVOICE | KINVOICE |
|---|---|---|---|---|---|---|---|---|---|---|---|---|---|
| 1 | abbott | 013-32-5312 | O00000 | AB2U | A | f | 01/12/87 | | | | | | AA0012 |
| 2 | abbott | 013-32-5312 | O00011 | AB4S | A | f | | | 02/14/87 | | | | AA0012 |
| 3 | abbott | 031-32-5312 | O00015 | AB2S | A | f | | | | 02/19/87 | | | AA0012 |
| 4 | abbott | 131-25-6721 | O00012 | AB2S | A | f | | | | 01/20/87 | | | AB0006 |
| 5 | abbott | 131-25-6721 | O00027 | AB2U | A | f | | | | 01/27/87 | | | AB0006 |
| 6 | abbott | 131-25-6721 | O00031 | AB4S | A | t | | | | 02/03/87 | | | AB0006 |
| 7 | abbott | 212-32-5487 | O00008 | AB2U | B | f | 01/02/87 | | | | | | AA0005 |
| 8 | abbott | 212-32-5487 | O00024 | AB2U | A | f | 01/17/87 | | | | | | AA0005 |
| 9 | abbott | 212-32-5487 | O00029 | AB2S | A | f | 02/05/87 | | | | | | AA0005 |
| 10 | costello | 152-43-2916 | O00003 | AB2S | A | f | 01/13/87 | | | | | | AA0001 |
| 11 | costello | 152-43-2916 | O00010 | AB2U | A | t | 01/17/87 | | | | | | AA0001 |
| 12 | costello | 152-43-2916 | O00016 | AB4S | A | f | 02/02/87 | | | | | | AA0001 |

FIG. 66

```
A =  0, NOTHING DONE
B =  1, MED_CHANGE ONLY
C =  2, NEW_MED ONLY
D =  3, MED_CHANGE AND NEW_MED
E =  4, LAB_WORK ONLY
F =  5, LAB_WORK AND MED_CHANGE
G =  6, NEW_MED AND LAB_WORK
H =  7, MED_CHANGE AND CONSULT
I =  8, CONSULT ONLY
J =  9, MED_CHANGE AND CONSULT
K = 10, NEW_MED AND CONSULT
L = 11, MED_CHANGE, NEW_MED AND CONSULT
M = 12, LAB_WORK AND CONSULT
N = 13, MED_CHANGE, LAB_WORK, CONSULT
O = 14, NEW_MED, LAB_WORK, AND CONSULT
P = 15, MED_CHANGE, NEW_MED, LAB_WORK, CONSULT
```

FIG. 66a

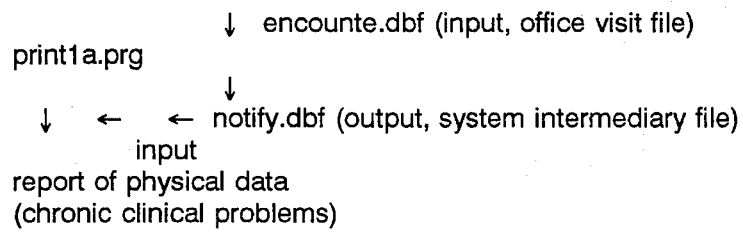
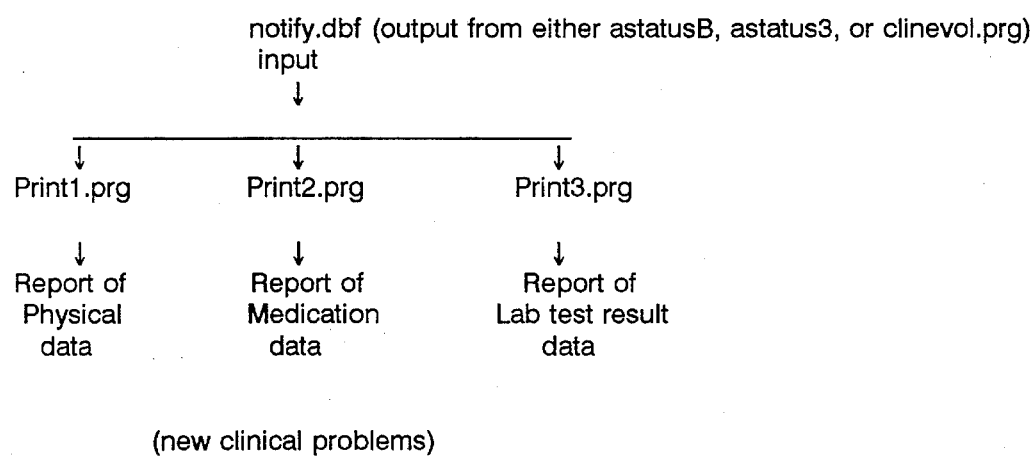
(new clinical problems)
FIG. 67

| Record# | PT_ID | INVOICE | MED1 | AMOUNT1 | ACTION1 | LENGTH1 | MED2 | AMOUNT2 | ACTION2 | LENGTH2 | MED3 | AMOUNT3 | ACTION3 | LENGTH3 |
|---|---|---|---|---|---|---|---|---|---|---|---|---|---|---|
| 1 | 454-12-3621 | O00004 | m0000 | 25 | A | | m0001 | 40 | A | | m009 | 1000 | A | |
| 2 | 011-35-3777 | O00006 | m0001 | 40 | C | | m0009 | 500 | C | | | | | |
| 3 | 010-53-6677 | O00009 | m0001 | 80 | C | | | | | | | | | |
| 4 | 011-35-3777 | O00012 | m0001 | 80 | C | | m0009 | 1000 | C | | | | | |
| 5 | 023-15-1643 | O00023 | m0010 | 4 | | 0. | m0001 | 4 | | | | | | |
| 6 | 024-31-1357 | O00023 | m0019 | 1 | | 0. | m0007 | | | | | | | |
| 7 | 112-23-3145 | O00007 | m0018 | 1600 | C | | | | | | | | | |
| 8 | 131-25-6721 | O00031 | m0001 | 80 | A | | m0014 | 60 | M | | | | | |
| 9 | 112-23-3145 | O00013 | m0005 | 60 | C | | m00180 | 800 | C | | | | | |
| 10 | 010-53-6677 | O00005 | m0001 | 60 | A | | m0010 | 40 | A | | | | | |
| 11 | 454-12-3621 | O00016 | m0009 | 750 | C | | | | | | | | | |
| 12 | 015-21-2341 | O00034 | m0005 | 60g | | | | | | | | | | |
| 13 | 030-12-3126 | O00035 | m0018 | 1.0g | | | m0020 | 4q.d | | | | | | |
| 14 | 041-23-1515 | O00036 | m0006 | 2.0g | | | m0001 | 40qd | | | | | | |
| 15 | 131-25-6721 | O00008 | m0001 | 40 | C | | m0014 | 100 | C | | | | | |
| 16 | 321-12-5432 | O00037 | m0001 | 4 | | | m0010 | 40q | | | | | | |
| 17 | 414-42-4116 | O00038 | m0023 | 4qd | | | | | | | | | | |
| 18 | 454-12-3621 | O00039 | m0022 | 120M | A | | | | | | | | | |
| 19 | 915-32-6167 | O00040 | m0001 | 80mg | | | m0004 | 4qd | | | | | | |
| 20 | 010-53-6677 | O00015 | m0001 | 120 | C | | | | | | | | | |
| 21 | 071-12-5431 | O00041 | m0002 | 40mg | | | m0009 | 500m | | | | | | |
| 22 | 131-25-6721 | O00014 | m0001 | 80 | C | | m0014 | 120 | C | | | | | |
| 23 | 131-25-6721 | O00020 | m0015 | 40 | A | | | | | | | | | |
| 24 | 324-53-0764 | O00004 | m0000 | 25mg | | | m0001 | 40mg | | | | | | |
| 25 | 010-53-6677 | O00021 | m0010 | 60 C | | | | | | | | | | |
| 26 | 454-12-3621 | O00010 | m0001 | 120m | C | | m0009 | 500 | C | | | | | |
| 27 | 112-23-3145 | O00001 | m0018 | 1200 | A | | m0005 | 20 | A | | | | | |
| 28 | 152-43-2916 | O00011 | m0023 | 120 | C | | m0021 | 400 | C | | | | | |
| 29 | 152-43-2916 | O00017 | m0023 | 120 | C | | | | | | | | | |
| 30 | 152-43-2916 | O00003 | m0021 | 200 | I | | m0023 | 80 | A | | | | | |
| 31 | 011-35-3777 | O00000 | m0001 | 100m | A | | m0009 | 1000 | A | | | | | |

FIG. 68

| Record # | DOCTOR | PT_ID | INVOICE | DATE | TYPE | STATUS | PRIM_DX | SEC_DX | TERT_DX | MED_CHANGE | NEW_MED | LAB_WORK | CONSULT | NEWPROBLEM | INJECTION | CONDITION | WEIGHT | SYSTOLIC | DIASTOLIC | COMPLAINT1 | COMPLAINT2 | FINDING1 | FINDING2 |
|---|---|---|---|---|---|---|---|---|---|---|---|---|---|---|---|---|---|---|---|---|---|---|---|
| 1 | abbott | 011-35-3777 | O00006 | 01/24/87 | S | 1 | AA0015 | | | .F. | .F. | .F. | .F. | .F. | .F. | AA0015 | 0 | 135 | 95 | | | | |
| 2 | abbott | 011-35-3777 | O00019 | 02/05/87 | S | 1 | AA0015 | | | .F. | .F. | .F. | .F. | .F. | .F. | mc0002 | 0 | 135 | 95 | | | | |
| 3 | abbott | 013-32-5312 | O00000 | 01/12/87 | U | 1 | AA0012 | BA0015 | CR0029 | .F. | .F. | .F. | .F. | .F. | .F. | BA0015 | 0 | | | | | | |
| 4 | abbott | 013-32-5312 | O00011 | 02/14/87 | S | 1 | AA0012 | BA0015 | CR0029 | .F. | .F. | .F. | .F. | .F. | .F. | mc0003 | 0 | | | | | | |
| 5 | abbott | 013-32-5312 | O00015 | 02/19/87 | S | 1 | AA0012 | BA0015 | CR0029 | .F. | .F. | .T. | .F. | .F. | .F. | CR0029 | 0 | | | | | | |
| 6 | abbott | 112-23-3145 | O00007 | 01/11/87 | U | 1 | AB0024 | CK0026 | | .F. | .F. | .F. | .F. | .F. | .F. | CK0026 | 0 | | | | | | |
| 7 | abbott | 112-23-3145 | O00014 | 02/01/87 | S | 1 | AB0024 | CK0026 | | .F. | .F. | .F. | .F. | .F. | .F. | CK0026 | 0 | | | | | | |
| 8 | abbott | 114-24-3145 | O00002 | 01/02/87 | U | 1 | BA0012 | BA0015 | BB0001 | .T. | .F. | .F. | .F. | .F. | .F. | BA0015 | 0 | | | | | | |
| 9 | abbott | 114-24-3145 | O00009 | 01/24/87 | S | 1 | BA0012 | BA0015 | BA0001 | .F. | .F. | .F. | .F. | .F. | .F. | BA0012 | 0 | | | | | | |
| 10 | abbott | 131-25-6721 | O00012 | 01/20/87 | S | 1 | AB0006 | | | .F. | .F. | .F. | .F. | .F. | .F. | AB0006 | 0 | 160 | 90 | | | | |
| 11 | abbott | 131-25-6721 | O00027 | 01/27/87 | U | 2 | AB0006 | | | .F. | .F. | .F. | .F. | .F. | .F. | AB0006 | 0 | 169 | 90 | | | | |
| 12 | abbott | 131-25-6721 | O00031 | 02/03/87 | S | 3 | AB0006 | | | .F. | .F. | .F. | .F. | .T. | .T. | AB0006 | 0 | 160 | 95 | | | | |
| 13 | abbott | 212-32-5487 | O00008 | 01/02/87 | U | 1 | AA0005 | | | .T. | .F. | .F. | .F. | .F. | .F. | AA0005 | 0 | | | | | | |
| 14 | abbott | 212-32-5487 | O00024 | 01/17/87 | U | 2 | AA0005 | | | .F. | .F. | .F. | .F. | .F. | .F. | AA0005 | 0 | | | | | | |
| 15 | abbott | 212-32-5487 | O00029 | 02/05/87 | S | 1 | AA0005 | | | .F. | .F. | .F. | .F. | .F. | .F. | AA0005 | 0 | | | | | | |
| 16 | abbott | 212-32-5487 | O00032 | 02/09/87 | S | 3 | AA0005 | | | .F. | .F. | .F. | .F. | .F. | .F. | AA0005 | 0 | | | | | | |
| 17 | costello | 152-43-2916 | O00003 | 01/13/87 | S | 2 | AA0001 | AH0010 | | .F. | .F. | .F. | .F. | .F. | .T. | AA0001 | 0 | 140 | 90 | | | | |
| 18 | costello | 152-43-2916 | O00010 | 01/17/87 | U | 2 | AA0001 | AH0010 | | .F. | .F. | .F. | .F. | .T. | .F. | AH0010 | 0 | 140 | 90 | | | | |
| 19 | costello | 152-43-2916 | O00016 | 02/02/87 | S | 3 | AA0001 | AH0010 | | .F. | .F. | .F. | .F. | .F. | .F. | AH0010 | 0 | 140 | 90 | | | | |
| 20 | hampton | 010-53-6677 | O00001 | 01/02/87 | U | 1 | CH0018 | CC0024 | | .F. | .F. | .F. | .F. | .F. | .F. | CC0024 | 0 | 150 | 90 | | | | |

FIG. 69

| | | | | | | | | |
|---|---|---|---|---|---|---|---|---|
| 21 | hampton .F. C0024 0 150 90 | | 010-53-0764 .F. | O00030 .F. | 01/27/87 .F. | S .F. | 1 | AH0018 C CC0024 |
| 22 | hampton .F. 0 | .F. | 324-53-0764 .F. | O00004 .F. | 01/10/87 .F. | S .F. | 1 | AA0005 AA0005 |
| 23 | hampton .F. 0 | .F. | 324-53-0764 .F. | O00033 .F. | 01/19/87 .F. | U .F. | 2 | AA0005 AA0005 |
| 24 | hampton .F. | .F. | 324-53-0764 .F. | O00036 .F. | 03/19/87 .F. | S .F. | 1 | AA0005 |
| 25 | hampton .F. | .F. | 324-53-0764 .F. | O00038 .F. | 03/26/87 .F. | S .F. | 2 | AA0005 |
| 26 | hampton .F. 160 90 | .F. | 324-53-0764 .F. | O00041 .F. | 04/01/87 .F. | S .F. | 2 | AA0005 |
| 27 | hampton .F. 160 90 | .F. | 324-53-0764 .F. | O00044 .F. | 04/08/87 .F. | U .F. | 2 | AA0005 AA0005 |
| 28 | hampton A0015 BG0020 .F. 0 150 89 | .T. | 454-12-3621 .F. | O00006 .F. | 01/23/87 .F. | S .F. | 2 | BA0012 B mb0000 |
| 29 | hampton A0015 BG0020 .F. 0 150 89 | .F. | 454-12-3621 .F. | O00029 .F. | 02/04/87 .F. | S .F. | 1 | BA0012 B mb0000 |
| 30 | hampton .F. | .F. AB003 | 324-53-0764 .F. BB006 | O00046 .F. AB007 | 04/14/87 .F. | U .F. | 3 | AA0005 BB0017 |
| 31 | costello .F. | .F. BB002 | 152-43-2916 .F. | O00019 .F. | 02-28-87 .F. | S .F. | 3 | AA0001 AA0001 |

FIG. 70

| Record # | DOCTOR | PT_ID | INVOICE | CATEGORY | CODE | DATE | HINVOICE | COMPLAINT2 | FINDING2 | KINVOICE |
|---|---|---|---|---|---|---|---|---|---|---|
| | EINVOICE | TINVOICE | LINVOICE | SINVOICE | CONDITION | COMPLAINT1 | FINDING1 | | | |
| 1 | abbott | | | 131-25-6721 | O00031 | A33S M A | t | 02/03/87 | | |
| | | | | AB0006 | | | | | | |
| 2 | abbott | | | 131-25-6721 | O00027 | A32U A | f | 01/27/87 | | |
| | | | | AB0006 | | | | | | |
| 3 | costello | | | 152-43-2916 | O00016 | A33S A | f | 02/02/87 | | |
| | | | | AH0010 | | | | | | |
| 4 | costello | | | 152-43-2916 | O00010 | A32U A | t | 01/17/87 | | |
| | | | | AH0010 | | | | | | |
| 5 | costello | | | 152-43-2916 | O00003 | A32SI A | f | 01/13/87 | | |
| | | | | AH0010 | | | | | | |
| 6 | costello | | | 152-43-2916 | O00019 | A33S A | f | 02/28/87 | | |
| | | | | AA0001 | BB002 | | | | | |
| 7 | abbott | | | 212-32-5487 | O00032 | A33S A | f | 02/09/87 | | |
| | | | | AA0005 | | | | | | |
| 8 | hampton | | | 324-53-0764 | O00046 | A33U A | f | 04/14/87 | | |
| | | | | BB0017 | AB003 | | AB007 | BB006 | | |
| 9 | hampton | | | 324-53-0764 | O00044 | A32U A | f | 04/08/87 | | |
| | | | | BB0017 | | | | | | |
| 10 | hampton | | | 324-53-0764 | O00041 | A32S A | f | 04/01/87 | | |
| | | | | BB0017 | | | | | | |
| 11 | hampton | | | 324-53-0764 | O00038 | A32S A | f | 03/26/87 | | |
| | | | | BB0017 | | | | | | |

FIG. 71

| Record # | CODETYPE | CODE | DESCRIPT |
|---|---|---|---|
| 1 | HA | 000 | rales,s3,low b/p,pvc's |
| 2 | HA | 001 | tachycardia,s3 |
| 3 | HA | 002 | s3,third heart sound |
| 4 | HC | 003 | sinus tachycardia |
| 5 | HB | 004 | elevated cvp,low b/p |
| 6 | HB | 005 | cardiomegaly,bilateral |
| 7 | HC | 006 | left vent.hypertrophy |
| 8 | NA | 007 | aphasic,loss of function |
| 9 | NA | 008 | slurry speech,weakness |
| 10 | VA | 009 | loss of pulse,popliteal |
| 11 | VA | 010 | loss of pulse,foot |
| 12 | LA | 011 | hypercapnia,pco2>55 |
| 13 | LB | 012 | hypercapnia,pco2<55 |
| 14 | LB | 013 | lung consolidation |
| 15 | LB | 014 | increased breathsounds |
| 16 | VA | 015 | absent pulse,calf |
| 17 | VB | 016 | weak pulse calf,bilateral |
| 18 | IC | 017 | acute anxiety,diaphoretic |
| 19 | IB | 018 | cachectic,anorectic |
| 20 | GA | 019 | ruq tenderness,mass |
| 21 | GB | 020 | mild abd tenderness |
| 22 | NA | 021 | obtunded,somnolent |
| 23 | RA | 022 | joints tender + swollen |
| 24 | LC | 023 | dry hacking cough |
| 25 | IA | 024 | fever >102 |
| 26 | IB | 025 | fever <=102 |
| 27 | KB | 026 | cloudy urine |
| 28 | KA | 027 | severe flank tenderness |
| 29 | VA | 028 | hypovolemia,low b/p |
| 30 | IA | 029 | septicemia |
| 31 | IB | 030 | bacteremia |

FIG. 72

```
Record # DOCTOR                    PT_ID        INVOICE   DATE      TYPE  STATUS  PRIM_DX   S
EC_DX  TERT_DX  MED_CHANGE  NEW_MED  LAB_WORK  CONSULT  NEWPROBLEM  INJECTION  CONDITION
WEIGHT  SYSTOLIC  DIASTOLIC  COMPLAINT1  COMPLAINT2  FINDING1  FINDING2
         1    abbott              011-35-3777   O00005   01/24/87    S      1       AH0001
                  .T.        .F.       .F.       .T.      .F.          .F.        AH0001
       0   135      95
         2    abbott              011-35-3777   O00019   02/05/87    S      2       AH0001
                  .F.        .T.       .F.       .F.      .F.          .F.        AH0001
       0   175     100       HA002       HA001      HA001     HA002
         3    abbott              013-32-5312   O00000   01/12/87    U      5       AI0008  B
H0012  CR0028    .F.        .F.       .T.       .F.      .F.          .F.        AI0008
       0                              IB029       IB023      IB013     IB018
         4    abbott              013-32-5312   O00011   02/14/87    S      2       AI0008  B
H0012  CR0028    .F.        .F.       .F.       .F.      .F.          .T.        AI0008
       0                              IB022                  LC023
         5    abbott              013-32-5312   O00015   02/19/87    S      1       AI0008  B
H0012  CR0028    .F.        .F.       .T.       .F.      .F.          .F.        AI0008
       0
         6    abbott              112-23-3145   O00007   01/11/87    U      1       AR0002  C
K0027            .F.        .F.       .F.       .T.      .F.          .F.        AR0002
       0
         7    abbott              112-23-3145   O00014   02/01/87    S      5       AR0002  C
K0027            .F.        .F.       .F.       .F.      .F.          .F.        AR0002
       0                              RB014                  RA022     IB025
         8    abbott              114-24-3145   O00002   01/02/87    U      5       AL0010  B
H0012  BB0001    .F.        .T.       .F.       .F.      .F.          .F.        AL0010
       0                              LA016                  LA011
         9    abbott              114-24-3145   O00009   01/24/87    S      1       AL0010  B
H0012  BA0001    .F.        .T.       .F.       .F.      .F.          .F.        AL0010
       0                              LC021
        10    abbott              131-25-6721   O00012   01/20/87    S      1       BG0013  B
V0017  BR0020    .F.        .F.       .T.       .F.      .F.          .F.        BG0013
       0   160      90
        11    abbott              131-25-6721   O00027   01/27/87    U      2       BG0013  B
V0017  BR0020    .T.        .F.       .F.       .F.      .F.          .F.        BG0013
       0   169      90                GC020                  GB020
        12    abbott              131-25-6721   O00031   02/03/87    S      1       BG0013  B
V0017  BR0020    .F.        .F.       .F.       .F.      .T.          .F.        BG0013
       0   160      95
        13    abbott              212-32-5487   O00008   01/02/87    U      1       AR0002
                  .F.        .T.       .F.       .F.      .F.          .F.        AR0002
       0
        14    abbott              212-32-5487   O00024   01/17/87    U      2       AR0002
                  .T.        .F.       .F.       .F.      .F.          .F.        AR0002
       0                              HA002                  HA002
        15    abbott              212-32-5487   O00029   02/05/87    S      3       AR0002
                  .F.        .T.       .F.       .F.      .F.          .F.        AR0002
       0                              RB014       IB022      RA022     IA024
        16    abbott              212-32-5487   O00032   02/09/87    S      1       AR0002
                  .F.        .F.       .F.       .T.      .F.          .F.        AR0002
       0
        17    costello            152-43-2916   O00003   01/13/87    S      5       BN0015  B
E0019  BK0021    .F.        .F.       .F.       .F.      .F.          .F.        BN0015
       0   140      90       NA007                  NA007
        18    costello            152-43-2916   O00010   01/17/87    U      3       BN0015  B
E0019  BK0021    .F.        .F.       .F.       .T.      .F.          .F.        BN0015
       0   155      95       NA007                  NA008
        19    costello            152-43-2916   O00016   02/02/87    S      1       BN0015  B
E0019  BK0021    .F.        .F.       .F.       .T.      .F.          .F.        BN0015
       0   145      95
        20    hampton             010-53-6677   O00001   01/02/87    U      1       AH0018  C
H0024            .F.        .F.       .T.       .F.      .F.          .F.        CH0024
       0   140      90       HB026       HB004      HB002     HB004
```

FIG. 73

| | | | | | | | | |
|---|---|---|---|---|---|---|---|---|
| 21 | hampton | | 010-53-6677 | O00030 | 01/27/87 | S | 1 | AH0018 C |
| H0024 | .F. | .F. | .F. | .F. | .F. | | .F. | CH0024 |
| 0 150 | 90 | | | | | | | |
| 22 | hampton | | 324-53-0764 | O00004 | 01/10/87 | S | 1 | AP0004 |
| | .F. | .F. | .F. | .F. | .F. | | .F. | AP0004 |
| 0 | | | | | | | | |
| 23 | hampton | | 324-53-0764 | O00033 | 01/19/87 | U | 2 | AP0004 |
| | .F. | .T. | .F. | .F. | .F. | | .F. | AP0004 |
| 0 | | | IB029 | IB022 | IA024 | IB018 | | |
| 24 | hampton | | 324-53-0764 | O00036 | 03/19/87 | S | 1 | AP0004 |
| | .F. | .F. | .T. | .T. | .F. | | .F. | AP0004 |
| 0 | | | IB022 | | | | | |
| 25 | hampton | | 324-53-0764 | O00038 | 03/26/87 | S | 4 | AP0004 |
| | .F. | .F. | .F. | .F. | .F. | | .T. | AP0004 |
| 0 | | | LC021 | | IB025 | | | |
| 26 | hampton | | 324-53-0764 | O00041 | 04/01/87 | S | 5 | AP0004 |
| | .T. | .F. | .F. | .F. | .F. | | .F. | AP0004 |
| 160 | 90 | | IB029 | | IA024 | | | |
| 27 | hampton | | 324-53-0764 | O00044 | 04/08/87 | U | 1 | AP0004 |
| | .F. | .F. | .F. | .T. | .F. | | .F. | AP0004 |
| 0 160 | 90 | | IB022 | | | | | |
| 28 | hampton | | 454-12-3621 | O00006 | 01/23/87 | S | 1 | AC0005 B |
| H0012 BG0023 | .F. | .F. | .F. | .T. | .F. | | .F. | AC0005 |
| 0 150 | 89 | | | | | | | |
| 29 | hampton | | 454-12-3621 | O00029 | 02/04/87 | S | 2 | AC0005 B |
| H0012 BG0023 | .F. | .T. | .F. | .F. | .F. | | .F. | AC0005 |
| 0 150 | 89 | | KA012 | | KB026 | | | |
| 30 | hampton | | 324-53-0764 | O00046 | 04/14/87 | U | 1 | AP0004 |
| | .F. | .F. | .F. | .F. | .F. | | .F. | AP0004 |
| 0 | | | AB003 | BB006 | AB007 | | | |

FIG. 74

| Record# | CODETYPE | CODE | DESCRIPT |
|---|---|---|---|
| 1 | HA | 000 | crushing chest pain |
| 2 | HA | 001 | heavy chest pain,exercise |
| 3 | HA | 002 | pnd,orthopnea,sob at rest |
| 4 | HB | 003 | easy fatigue,sob,exercise |
| 5 | HB | 004 | weight gain,ankle swell |
| 6 | VA | 005 | acute claudication,rest |
| 7 | RB | 025 | mild jt pain,no swelling |
| 8 | IB | 023 | loss of appetite,malaise |
| 9 | IB | 022 | fatigue,weakness |
| 10 | IB | 030 | anxiety,headache |
| 11 | RB | 017 | intermitt.jt swelling |
| 12 | GA | 006 | acute abd.pain,vomit,weak |
| 13 | GB | 011 | bloody stools,intermitten |
| 14 | GA | 010 | ugi bleed,vomit,weakness |
| 15 | GC | 024 | chronic abd pain,no vomit |
| 16 | GC | 020 | diarrhea,mild |
| 17 | NA | 009 | severe headache,vomiting |
| 18 | KA | 008 | flank pain,vomiting,fever |
| 19 | KB | 013 | polyuria,polydipsia |
| 20 | KA | 012 | cid.urine,frequency,chill |
| 21 | RB | 014 | acute jt.swell,pain,fever |
| 22 | NA | 007 | slurry speech,hand weak |
| 23 | HB | 026 | chr.chest pain,exercise |
| 24 | LA | 016 | sputum,chst.pain,fever |
| 25 | VB | 015 | chr.numbness calf,exerc. |
| 26 | VB | 018 | int.numbness,feet |
| 27 | LA | 019 | sudden chest pain,dyspnea |
| 28 | LC | 021 | cough,mild sputum |
| 29 | KB | 028 | weak stream,frequency |
| 30 | IB | 029 | shaking chills,fever,weak |
| 31 | GA | 027 | ruq pain,colicky,vomiting |

FIG. 75

| Record# | CODETYPE | CODE | DESCRIPT |
|---|---|---|---|
| 1 | AH | 0000 | ACUTE ANGINA,UNSTABLE,CHF |
| 2 | AH | 0001 | ACUTE ANGINA,UNSTABLE |
| 3 | AR | 0002 | SYST.LUPUS + NEPHRITIS |
| 4 | AR | 0003 | PROG.SYST.SCLEROSIS,UREMI |
| 5 | AV | 0007 | MALIGNT.HYPERTENS.(SYMPT) |
| 6 | AL | 0010 | COPD,SEVERE HYPERCAPNIA |
| 7 | AV | 0006 | CLAUDICATION,REST,CALF |
| 8 | AN | 0009 | HYPERTENSIVE TIA |
| 9 | AP | 0004 | ACUTE BLASTOCYT.LEUKEMIA |
| 10 | AC | 0005 | METASTATIC CA + CHEMOTH. |
| 11 | AI | 0008 | AUTOIMN.DEFIENCY SYNDROME |
| 12 | BG | 0013 | ULCERATIVE COLITIS |
| 13 | BH | 0011 | CHRONIC ANGINA |
| 14 | BH | 0012 | CHF,CHR.VENT.HYPERTROPHY |
| 15 | BN | 0015 | CVA,RECENT |
| 16 | BK | 0016 | ACUTE GLOMERULONEPHRITIS |
| 17 | BE | 0019 | DIABETES MELLITUS |
| 18 | BL | 0018 | COPD,MILD HYPERCAPNIA |
| 19 | BV | 0017 | CHRONIC CLAUDICATION |
| 20 | BP | 0014 | MULTIPLE MYELOMA |
| 21 | BR | 0020 | ACUTE GOUTY ARTHRITIS |
| 22 | BR | 0022 | ACUTE RHUEMATOID ARTHR. |
| 23 | BG | 0023 | CHR.PANCREATITIS |
| 24 | CH | 0024 | CARDIOMEGALY,ASYMPT.RHD |
| 25 | BK | 0021 | CHRONIC PYELONEPHRITIS |
| 26 | CP | 0025 | PERNICOUS ANEMIA |
| 27 | CP | 0026 | IRON DEF.ANEMIA |
| 28 | CK | 0027 | CHRONIC RENAL STONES |
| 29 | CR | 0028 | OSTEROARTH.,SEVERE |
| 30 | CG | 0029 | CHRONIC PEPTIC ULCER |
| 31 | CL | 0030 | CHRONIC BRONCHITIS |

FIG. 76

| Record # | DOCTORE | EINVOICE | TINVOICE | LINVOICE | PT_ID | SINVOICE | KINVOICE | INVOICE CATEGORY | CODE CONDITION | COMPLAINT1 | DATE | HINVOICE FINDING1 | COMPLAINT2 | FINDING2 |
|---|---|---|---|---|---|---|---|---|---|---|---|---|---|---|
| 1 | | | | | 011-35-3777 | S00001 | | O00005 | AE1S AH0001 | K | f | 01/24/87 | | |
| 2 | | | | | 011-35-3777 | | | O00009 | AE2S AH0001 | Bu HA002 | f | 02/05/87 HA001 | 01 | HA002 |
| 3 | | | | | 013-32-5312 | | | O00000 | AE5U AI0008 | E IB029 | f | 01/12/87 LB013 | 23 | IB018 |
| 4 | | | | | 013-32-5312 | | | O00011 | AE2S AI0008 | Ar IB022 | f | 02/14/87 LC023 | | |
| 5 | | | | | 112-23-3145 | | | O00007 | AE1U AR0002 | A | f | 01/11/87 | | |
| 6 | | | | | 112-23-3145 | | | O00014 | AE5S AR0002 | Au RB014 | f | 02/01/87 RA022 | | IB025 |
| 7 | | | | | 114-24-3145 | | | O00002 | AE5U AL0010 | Br LA016 | f | 01/02/87 LA011 | | |
| 8 | | | | | 131-25-6721 | | | O00012 | AE1S BG0013 | E | f | 01/20/87 | | |
| 9 | | | | | 131-25-6721 | | | O00027 | AE2U BG0013 | Cr GC020 | f | 01/27/87 GB020 | | |
| 13 | | | | | 152-43-2916 | | | O00003 | AE5S BN0015 | A NA007 | f | 01/13/87 NA007 | | |
| 14 | | | | | 152-43-2916 | | | O00010 | AE3U BN0015 | Ar NA007 | f | 01/17/87 NA008 | | |
| 10 | | | | | 212-32-5487 | | | O00008 | AE1U AR0002 | B | f | 01/02/87 | | |
| 11 | | | | | 212-32-5487 | | | O00024 | AE2U AR0002 | C HA002 | f | 01/17/87 HA002 | | |
| 12 | | | | | 212-32-5487 | | | O00029 | AE3S AR0002 | Br RB014 | f | 02/05/87 RA022 | 22 | IA024 |
| 15 | | | | | 324-53-0764 | | | O00004 | AE1S AP0004 | A | f | 01/10/87 | | |
| 16 | | | | | 324-53-0764 | | | O00033 | AE2U AP0004 | Br IB029 | f | 01/19/87 IA024 | 22 | IB018 |
| 17 | | | | | 324-53-0764 | | | O00036 | AE1S AP0004 | E IB022 | f | 03/19/87 | | |
| 18 | | | | | 324-53-0764 | | | O00038 | AE4S AP0004 | A LC021 | f | 03/26/87 IB025 | | |
| 19 | | | | | 324-53-0764 | | | O00041 | AE5S AP0004 | Cr IB029 | f | 04/01/87 IA024 | | |
| 20 | | | | | 454-12-3621 | | | O00006 | AE1S AC0005 | A | f | 01/23/87 | | |
| 21 | | | | | 454-12-3621 | | | O00029 | AE2S AC0005 | Bu KA012 | f | 02/04/87 KB026 | | |

FIG. 77

CHRONIC PROBLEMS BY PATIENT(physical data)
PATIENT ID: 011-35-3777 LAST NAME cusson    BIRTH DATE 02/04/28    MALE
PRIMARY DIAGNOSIS ACUTE ANGINA,UNSTABLE    LAST HOSPITALIZATION 02/21/86

---

INVOICE NO.:O00005 DATE 01/24/87 CONDITION ACUTE ANGINA,UNSTABLE
SYSTOLIC PRESSURE 135 DIASTOLIC PRESSURE 95
THERE WERE NO SIGNIFICANT COMPLAINTS
THERE WERE NO SIGNIFICANT FINDINGS

---

INVOICE NO.:O00019 DATE 02/05/87 CONDITION ACUTE ANGINA,UNSTABLE
SYSTOLIC PRESSURE 175 DIASTOLIC PRESSURE 100
COMPLAINTS WERE pnd,orthopnea,sob at rest and heavy chest pain,exercise
FINDINGS WERE tachycardia,s3 and s3,third heart sound
problem unresolved

FIG. 78

CHRONIC PROBLEMS BY PATIENT(physical data)
PATIENT ID: 013-32-5312 LAST NAME kennedy        BIRTH DATE 01/23/11    FEMALE
PRIMARY DIAGNOSIS AUTOIMM.DEFIENCY SYNDROME     LAST HOSPITALIZATION 07/14/85
SECONDARY DIAGNOSIS: chf,mild,controlled

---

INVOICE NO.:O00000 DATE 01/12/87 CONDITION AUTOIMM.DEFIENCY SYNDROME
COMPLAINTS WERE shaking chills,fever,weak and loss of appetite,malaise
FINDINGS WERE lung consolidation and cachectic,anorectic
patient hospitalized

---

INVOICE NO.:O00011 DATE 02/14/87 CONDITION AUTOIMM.DEFIENCY SYNDROME
COMPLAINT(major)WAS fatigue,weakness
FINDING(major) was dry hacking cough
problem resolved

FIG. 79

CHRONIC PROBLEMS BY PATIENT(physical data)
PATIENT ID: 112-23-3145 LAST NAME paul      BIRTH DATE 11/13/19    MALE
PRIMARY DIAGNOSIS SYST.LUPUS + NEPHRITIS    LAST HOSPITALIZATION 11/21/86
SECONDARY DIAGNOSIS: chronic renal stones

---

INVOICE NO.:O00007 DATE 01/11/87 CONDITION SYST.LUPUS + NEPHRITIS
THERE WERE NO SIGNIFICANT COMPLAINTS
THERE WERE NO SIGNIFICANT FINDINGS

---

INVOICE NO.:O00014 DATE 02/01/87 CONDITION SYST.LUPUS + NEPHRITIS
COMPLAINT(major)WAS acute jt.swell,pain,fever
FINDINGS WERE joints tender + swollen and fever <=102
patient hospitalized
problem unresolved

FIG. 80

CHRONIC PROBLEMS BY PATIENT(physical data)
PATIENT ID: 114-24-3145 LAST NAME cutler     BIRTH DATE 01/30/32  FEMALE
PRIMARY DIAGNOSIS COPD,SEVERE HYPERCAPNIA    LAST HOSPITALIZATION 06/21/86
SECONDARY DIAGNOSIS: chf,mild,controlled

---

INVOICE NO.:O00002 DATE 01/02/87 CONDITION COPD,SEVERE HYPERCAPNIA
COMPLAINT(major)WAS sputum,chst.pain,fever
FINDING(major) was hypercapnia,pco2>55
patient hospitalized
problem resolved

FIG. 81

CHRONIC PROBLEMS BY PATIENT(physical data)
PATIENT ID: 131-25-6721 LAST NAME scruton      BIRTH DATE 07/21/30    FEMALE
PRIMARY DIAGNOSIS ULCERATIVE COLITIS           LAST HOSPITALIZATION 02/12/80
SECONDARY DIAGNOSIS: CHRONIC CLAUDICATION INVOICE NO.:O00012 DATE 01/20/87 CONDITION ULCERATIVE COLITIS
THERE WERE NO SIGNIFICANT COMPLAINTS
THERE WERE NO SIGNIFICANT FINDINGS INVOICE NO.:O00027 DATE 01/27/87 CONDITION ULCERATIVE COLITIS
COMPLAINT(major) WAS diarrhea,mild
FINDING(major) was mild abd tenderness
problem resolved

FIG. 82

CHRONIC PROBLEMS BY PATIENT(physical data)
PATIENT ID: 152-43-2916 LAST NAME grover     BIRTH DATE 09/12/51    FEMALE
PRIMARY DIAGNOSIS CVA,RECENT                 LAST HOSPITALIZATION 12/13/86
SECONDARY DIAGNOSIS: DIABETES MELLITUS

---

INVOICE NO.:O00003 DATE 01/13/87 CONDITION CVA,RECENT
SYSTOLIC PRESSURE 140 DIASTOLIC PRESSURE 90
COMPLAINT(major)WAS slurry speech,hand weak
FINDING(major) was aphasic,loss of function
patient hospitalized

---

INVOICE NO.:O00010 DATE 01/17/87 CONDITION CVA,RECENT
SYSTOLIC PRESSURE 155 DIASTOLIC PRESSURE 95
COMPLAINT(major)WAS slurry speech,hand weak
FINDING(major) was slurry speech,weakness
problem resolved

FIG. 83

CHRONIC PROBLEMS BY PATIENT(physical data)
PATIENT ID: 212-32-5487 LAST NAME purdy        BIRTH DATE 06/12/30    FEMALE
PRIMARY DIAGNOSIS SYST.LUPUS + NEPHRITIS      LAST HOSPITALIZATION 11/14/86

---

INVOICE NO.:O00008 DATE 01/02/87 CONDITION SYST.LUPUS + NEPHRITIS
THERE WERE NO SIGNIFICANT COMPLAINTS
THERE WERE NO SIGNIFICANT FINDINGS

---

INVOICE NO.:O00024 DATE 01/17/87 CONDITION SYST.LUPUS + NEPHRITIS
COMPLAINT(major) WAS pnd,orthopnea,sob at rest
FINDING(major) was s3,third heart sound

---

INVOICE NO.:O00029 DATE 02/05/87 CONDITION SYST.LUPUS + NEPHRITIS
COMPLAINTS WERE acute jt.swell,pain,fever and fatigue,weakness
FINDINGS WERE joints tender + swollen and fever >102
problem resolved

FIG. 84

CHRONIC PROBLEMS BY PATIENT(physical data)
PATIENT ID: 324-53-0764 LAST NAME canter    BIRTH DATE 09/13/53   FEMALE
PRIMARY DIAGNOSIS ACUTE BLASTOCYT.LEUKEMIA   LAST HOSPITALIZATION 06/24/86

---

INVOICE NO.:O00004 DATE 01/10/87 CONDITION ACUTE BLASTOCYT.LEUKEMIA
THERE WERE NO SIGNIFICANT COMPLAINTS
THERE WERE NO SIGNIFICANT FINDINGS

---

INVOICE NO.:O00033 DATE 01/19/87 CONDITION ACUTE BLASTOCYT.LEUKEMIA
COMPLAINTS WERE shaking chills,fever,weak and fatigue,weakness
FINDINGS WERE fever >102 and cachectic,anorectic
problem resolved

---

INVOICE NO.:O00036 DATE 03/19/87 CONDITION ACUTE BLASTOCYT.LEUKEMIA
COMPLAINT(major)WAS fatigue,weakness
THERE WERE NO SIGNIFICANT FINDINGS

---

INVOICE NO.:O00038 DATE 03/26/87 CONDITION ACUTE BLASTOCYT.LEUKEMIA
COMPLAINT(major)WAS cough,mild sputum
FINDING(major) was fever <=102

---

INVOICE NO.:O00041 DATE 04/01/87 CONDITION ACUTE BLASTOCYT.LEUKEMIA
COMPLAINT(major)WAS shaking chills,fever,weak
FINDING(major) was fever >=102
patient hospitalized
problem resolved

FIG. 85

CHRONIC PROBLEMS BY PATIENT(physical data)
PATIENT ID: 454-12-3621 LAST NAME henderson          BIRTH DATE 02/13/17    MALE
PRIMARY DIAGNOSIS METASTATIC CA + CHEMOTH.   LAST HOSPITALIZATION 03/24/83
SECONDARY DIAGNOSIS: chf,mild,controlled

---

INVOICE NO.:O00006 DATE 01/23/87 CONDITION METASTATIC CA + CHEMOTH.
THERE WERE NO SIGNIFICANT COMPLAINTS
THERE WERE NO SIGNIFICANT FINDINGS

---

INVOICE NO.:O00029 DATE 02/04/87 CONDITION METASTATIC CA + CHEMOTH.
COMPLAINT(major)WAS cld.urine,frequency,chill
FINDING(major) was cloudy urine
problem unresolved

FIG. 86

```
Record #  DOCTOR              PT_ID        DOB       LNAME          FNAME  SEX  DIAGNO
SIS1          CODE1    DATE1       MEDFLAG1  MEDINV1  DIAGNOSIS2                        C
ODE2    DATE2     MEDFLAG2  MEDINV2  DIAGNOSIS3                CODE3   DTE3     MEDFLA
G3 MEDINV3 MEDONE DESCRIPONE· AMTONE MEDTWO DESCRIPTWO  AMTTWO MEDTHREE DESCRI
PTHR    AMTTHREE MAJORSURG  PRIOR_HOSP  TREATMENT  LAST_HOSP  ALLERGIES
         NARRATIVE   WEIGHT  SYSTOLIC  DIASTOLIC  DATE
     1  abbott                011-26-3781  05/23/40  cuozzo                F    chroni
c angina,mild         BA 0012  09/10/88  .F.
  / /        .F.                                                        / /    .F.

.F.                5  .F.          10/05/87
        Memo            0                        / /
     2  abbott                011-35-3777  01/04/28  cusson                M    chf,mi
ld,controlled         BA0015   / /    .F.
  / /        .F.                                                        / /    .F.

.F.                8  .F.          02/21/87
        Memo            0                        / /
     3  abbott                114-24-3145  01/30/32  cutler                F    chroni
c angina,mild         BA0012   / /    .F.        chf,mild,controlled          B
A0015   / /    .F.
              .F.                4  .F.          06/21/87  penicillin
        Memo            0                        / /
     4  abbott                023-15-1643  10/12/20  kriesky               F    CHRONI
C PYELONEPHRITIS      CK0023   / /    .F.        uremia,mild,chronic           B
K0013   / /    .F.
              .F.                7  .F. 05/14/86
        Memo            0                        / /
     5  abbott                131-25-6721  07/21/30  SCRUTON       CARL  F    hypert
ensive tia            AB0006   / /    .F.                                     A
R0003   09/13/88   .T.    O00021                                        / /    .F.

.F.                5  .F.          02/12/80  penicillin
        Memo            0                        / /
     6  abbott                024-31-1357  10/24/21  kelly                 F    rheuma
toid arth.,acute      CR0028   / /    .F.        osteoarth.,severe             C
R0029   / /    .F.
              .T.                5  .T.          02/11/85
        Memo            0                        / /
     7  abbott                112-23-3145  11/13/19  paul                  M    copd,m
ild hypercapnia       CC0024   / /    .F.        chronic renal stones         C
K0026   / /    .F.
              .T.                                 11/21/86
        Memo            0                        / /
     8  abbott                013-32-5312  01/23/11  kennedy               F    chroni
c angina,mild         BA0012   / /    .F.        chf,mild,controlled          B
A0015   / /    .F.        osteoarth.,severe          CR0029                / /    .F.
              .T.               11  .T.          07/14/85  penicillin
        Memo            0                        / /
     9  abbott                212-32-5487  06/12/30  purdy                 F    METAST
ATIC CA + CHEMOTH.    AC0005   09/13/88  .T.     O00021
  / /        .F.                                                        / /    .F.

.F.                3  .F.          11/14/87   none
    10  costello              015-21-2341  11/21/24  jenkins               F    lupus
nephritis,recent      BK0011   / /    .F.        lupus arthr.,acute            C
R0022   / /    .F.
```

FIG. 87

```
                    .F.                3 .T. 11/21/86   none
         Memo       0
      11 costello              321-12-5432 02/22/16  kendall              F  uremia
,mild,chronc        BK0013  / /   .F.            chronic pyelonephritis      C
K0023  / /     .F.                                                 / /    .F.

.T.                3 .F. 11/21/84   penicillin
         Memo       0                            / /
      12 costello              152-43-2916 09/12/51  GROVER      MARY F  COPD,S
EVERE HYPERCAPNIA   AL0010 09/13/88 .T.  O00021  vent.arrytmias,controlled
A
A0010  / /     .F.                                                 / /    .F.

.F.                3 .T. 12/13/87
         Memo       0                            / /
      13 costello              030-12-3126 07/12/32  collins              F  copd,m
ild hypercapnia     CC0024  / /   .F.            chronic renal stones        C
K0026  / /     .F.                                                 / /    .F.

.T.                7 .T. 11/21/82
         Memo       0                            / /
      14 costello              414-42-4116 05/21/31  stevens              F  chroni
c claudication      BB0017  / /   .F.            cardiomegaly,asympt.rhd     C
A0027  / /     .F.                                                 / /    .F.

.T.                3 .F. 10/21/80
         Memo       0                            / /
      15 costello              041-23-1515 12/08/36  rothstein            F  multip
le myeloma,         BH0018  / /   .F.            chronic renal stones        C
K0026  / /     .F.                                                 / /    .F.

.F.                4 .F. 11/21/85
         Memo       0                            / /
      16 costello              915-32-6167 11/24/15  stennis              F  acute
chf,ashd            AA0005  / /   .F.            chronic renal stones        C
K0026  / /     .F.                                                 / /    .F.

.T.                8 .F. 10/21/54   penicillin
         Memo       0                            / /
      17 costello              712-21-3144 11/04/50  kirkland             F  hypert
ension,malignant    BB0016  / /   .F.                                        
  / /          .F.                                                 / /    .F.
                    .F.                3 .F. 09/23/87
         Memo       0                            / /
      18 costello              002-31-3621 11/19/41  kemp                 F  tia,re
cent                AB0007  / /   .F.            hypertension,malignant      B
B0016  / /     .F.       chronic claudication           BB0017     / /    .F.

.F.                9 .F. 12/01/87
         Memo       0                            / /
      19 hampton               071-12-5431 04/23/39  sakowski             F  cardio
megaly,mild,hbp     BA0021  / /   .F.            chronic pyelonephritis      C
K0023  / /     .F.                                                 / /    .F.

.T.                4 .F. 02/21/86
         Memo       0                            / /
      20 hampton               162-57-8925 09/17/25  kendrick             F  copd,s
evere hypercapnia   AC0009  / /   .F.            osteroarth.,severe          C
R0029  / /     .F.                                                 / /    .F.

.T.                7 .T. 07/13/82
         Memo       0                            / /
```

FIG. 88

```
          21  hampton                    454-12-3621  02/13/17  henderson              M  chroni
c angina,mild           BA0012   /  /   .F.                    chf,mild,controlled          B
A0015   /  /        .F.         CHR.PANCREATITIS                              BG0020   /  /   .F.
                        .T.             12  .F.  03/24/83
        Memo                    0                        /  /
          22  hampton                    324-53-0764  09/13/53  canter                 F  acute
chf,mild,ashd           AA0005   /  /   .F.                                        /  /   .F.
                        .T.              3  .T.  06/24/87
        Memo                    0                        /  /
          23  hampton                    152-67-9876  04/30/34  james                  F  acute
mi                      AA0002   /  /   .F.
        /  /        .F.                                                            /  /   .F.
                        .T.              8  .T.  11/09/84
        Memo                    0                        /  /
          24  hampton                    010-53-6677  12/16/20  WILLIAMS     WALT  M  multip
le myeloma              BH0018   /  /   .F.                    copd,mild hypercapnia        C
C0024   /  / .      .F.                                                            /  /   .F.
                        .F.              6  .T.  12/09/86
        Memo                    0                        /  /
          25                                                                              SYST.L
UPUS + NEPHRITIS        AR0002   /  /   .F.
        /  /        .F.                                                            /  /   .F.
                        .F.                    .F.       /  /
        Memo
          26                                              /  /  SMITH        BOB      ACUTE
ANGINA,UNSTABLE         AH0001   /  /   .F.                    METASTATIC CA + CHEMOTH.   A
C0005   /  /        .F.         CLAUDICATION,REST,CALF         AV0006                /  /   .F.
                        .F.                    .F.       /  /
        Memo                            09/24/88
```

FIG. 89

| Record # | DOCTOR | PT_ID | INVOICE | DATE | TYPE | STATUS | PRIM_DX | SEC_DX | TERT_DX | MED_CHANGE | NEW_MED | LAB_WORK | CONSULT | NEWPROBLEM | INJECTION | CONDITION | WEIGHT | SYSTOLIC | DIASTOLIC | COMPLAINT1 | COMPLAINT2 | FINDING1 | FINDING2 |
|---|---|---|---|---|---|---|---|---|---|---|---|---|---|---|---|---|---|---|---|---|---|---|---|
| 1 | abbott | 011-35-3777 | O00006 | 01/24/87 | S | 1 | AA0015 | | | .F. | .F. | .F. | .F. | .F. | .F. | AA0015 | 0 | 135 | 95 | | | | |
| 2 | abbott | 011-35-3777 | O00007 | 02/05/87 | S | 1 | AA0015 | | | .F. | .F. | .F. | .F. | .F. | .F. | mc0002 | 0 | 135 | 95 | | | | |
| 3 | abbott | 013-32-5312 | O00008 | 01/12/87 | U | 5 | AA0012 | BA0015 | CR0029 | .F. | .F. | .F. | .F. | .F. | .F. | BA0015 | 0 | | | | | | |
| 4 | abbott | 013-32-5312 | O00011 | 02/14/87 | S | 2 | AA0012 | BA0015 | CR0029 | .F. | .F. | .F. | .F. | .F. | .F. | mc0003 | 0 | | | | | | |
| 5 | abbott | 013-32-5312 | O00015 | 02/19/87 | S | 1 | AA0012 | BA0015 | CR0029 | .F. | .F. | .T. | .F. | .F. | .F. | CR0029 | 0 | | | | | | |
| 6 | abbott | 112-23-3145 | O00007 | 01/11/87 | U | 1 | AB0024 | CK0026 | | .F. | .F. | .F. | .F. | .F. | .F. | CK0026 | 0 | | | | | | |
| 7 | abbott | 112-23-3145 | O00014 | 02/01/87 | S | 1 | AB0024 | CK0026 | | .F. | .F. | .F. | .F. | .F. | .F. | CK0026 | 0 | | | | | | |
| 8 | abbott | 114-24-3145 | O00002 | 01/02/87 | U | 1 | BA0012 | BA0015 | BB0001 | .T. | .F. | .F. | .F. | .F. | .F. | BA0015 | 0 | | | | | | |
| 9 | abbott | 114-24-3145 | O00009 | 01/24/87 | S | 1 | BA0012 | BA0012 | BA0001 | .F. | .F. | .F. | .F. | .F. | .F. | BA0012 | 0 | | | | | | |
| 10 | abbott | 131-25-6721 | O00012 | 01/20/87 | S | 1 | AB0006 | | | .F. | .F. | .F. | .F. | .F. | .F. | AB0006 | 0 | 160 | 90 | | | | |
| 11 | abbott | 131-25-6721 | O00026 | 01/27/87 | U | 2 | AB0006 | | | .F. | .F. | .F. | .F. | .F. | .F. | AB0006 | 0 | 169 | 90 | | | | |
| 12 | abbott | 131-25-6721 | O00039 | 02/03/87 | S | 1 | AB0006 | | | .F. | .F. | .F. | .F. | .T. | .F. | AB0006 | 0 | 160 | 95 | | | | |
| 13 | abbott | 212-32-5487 | O00008 | 01/02/87 | U | 1 | AA0005 | | | .T. | .F. | .F. | .F. | .F. | .F. | AA0005 | 0 | | | | | | |
| 14 | abbott | 212-32-5487 | O00024 | 01/17/87 | U | 2 | AA0005 | | | .F. | .F. | .F. | .F. | .F. | .F. | AA0005 | 0 | | | | | | |
| 15 | abbott | 212-32-5487 | O00029 | 02/05/87 | S | 3 | AA0005 | | | .F. | .F. | .F. | .F. | .F. | .F. | AA0005 | 0 | | | | | | |
| 16 | abbott | 212-32-5487 | O00032 | 02/09/87 | S | 4 | AA0005 | | | .F. | .F. | .F. | .F. | .F. | .F. | AA0005 | | | | | | | |
| 17 | costello | 152-43-2916 | O00006 | 01/05/87 | S | 5 | AA0001 | AA0001 | H0010 | .F. | .F. | .F. | .F. | .F. | .F. | | 0 | 140 | 90 | | | | |
| 18 | costello | 152-43-2916 | O00013 | 01/17/87 | U | 3 | AA0001 | AH0010 | H0010 | .F. | .F. | .F. | .T. | .F. | .F. | | 0 | 140 | 90 | | | | |
| 19 | costello | 152-43-2916 | O00020 | 02/02/87 | S | 4 | AA0001 | AH0010 | H0010 | .F. | .F. | .F. | .F. | .F. | .F. | | 0 | 140 | 90 | | | | |
| 20 | hampton | 010-53-6677 | O00011 | 01/11/87 | U | 1 | AH0018 | CH0024 | C0024 | .F. | .F. | .F. | .F. | .F. | .F. | | 0 | 150 | 90 | HB0026 | HB004 | HB002 | |

FIG. 90

| | | | | | | | | |
|---|---|---|---|---|---|---|---|---|
| 21 | hampton | | 010-53-6677 | O00022 | 01/24/87 | S | 1 | AH0018 C |
| C0024 | .F. | .F. | .F. | .F. | .F. | | .F. | CH0024 |
| 0 150 | 90 | | | | | | | |
| 22 | costello | | 152-43-2916 | O00019 | 02/28/87 | S | 1 | cA0001 |
| | .F. | .F. | .T. | .F. | .F. | | .F. | AA0001 |
| | | HA002 | HB003 | | | | | |
| 23 | | | 131-25-6721 | O00020 | / / | | 1 | AB0006 |
| | .F. | .F. | .F. | .F. | .F. | | .F. | AV0006 |

FIG. 91

| Record # | DOCTOR | PT_ID | DATE | INVOICE | INVOICEFRM | BUN | CR | HG | HCT | SED_RATE | POTTASIUM | BLD_SUG | PH | P02 | PC02 | WBC | CALCIUM | EKG | CXR |
|---|---|---|---|---|---|---|---|---|---|---|---|---|---|---|---|---|---|---|---|
| 1 | abbott | 010-53-6677 | 01/07/87 | L00004 | O000005 | | | C2I26.3 | C2 | A1W45 | | | | | | | U56 | | |
| 2 | | 010-53-6677 | 01/18/87 | L00005 | O000007 | | | | S3 | | | | | | | | W40 | C2U30.5 | |
| 3 | | 010-53-6677 | 01/09/87 | L00006 | O000009 | T | C | | | A2I27.5 | | A1N432 | | | | | | T B | T B |
| 4 | | 010-53-6677 | 01/11/87 | L00007 | O000010 | | | T B | T | | | | | | | | C | A2W10.1 | A2N28.5 |
| 5 | | 010-53-6677 | 01/13/87 | L00008 | O000011 | | | | C2 | A2I28 | | A1U350 | | | | | I36.5 | | |
| 6 | | 010-53-6677 | 01/22/87 | L00017 | O000018 | | | | | | A1N6.2 | A2W206 | | | | | S4U10.6 | | |
| 7 | | 152-43-2916 | 01/01/87 | L00009 | O000004 | | | | S2I28.7 | | | | | | | A2I14.7 | A3N10.6 | A2U | A1W |
| 8 | | 152-43-2916 | 01/06/87 | L00010 | O000006 | | | | | A2I24 | A3W6.9 | | S2I55 | | | A2W14.7 | A4W7.3 | A2U | A2U |
| 9 | | 152-43-2916 | 01/14/87 | L00011 | O000008 | | | | | S3W27.4 | A4N2.9 | | | | | S1W27.9 | A2W14.8 | | |
| 10 | | 152-43-2916 | 01/18/87 | L00012 | O000013 | | | | A2 | | | | | | | S2I15.3 | N8.6 | A4W8.7 | S2I30.5 |
| 11 | | 152-43-2916 | 01/20/87 | L00014 | O000017 | | | | | A3W24.5 | A2U22.9 | C3W6.9 | A2N312 | | | | | | |
| 12 | | 152-43-2916 | 02/03/87 | L00018 | O000020 | | | | A2 | | A2I5.7 | | | | | | P10.4 | S3W6.6 | A3N14.5 |
| 13 | | 010-53-6677 | 01/25/87 | L00019 | O000022 | | | | A2 | | A2N4.9 | | | | | | N16.3 | A1W13.5 | |
| 14 | | 010-53-6677 | 01/26/87 | L00020 | O000023 | | | | A2 | A3U30.6 | | | | | | | W9.8 | | |
| 15 | | 010-53-6677 | 01/27/87 | L00021 | O000024 | | | T B | | T B | | | | | | | | A2N | |
| 16 | | 152-43-2916 | 02/25/87 | L00022 | O000024 | | | | A1W24.5 | S4W19.5 | | | | | | | | | |
| 17 | | 131-25-6721 | 01/28/87 | L00023 | O000026 | | | | | | | | | | | | | | |
| 18 | | 010-53-6677 | 01/29/87 | L00024 | O000030 | | | | C2I20.5 | | | | | | | | | | |
| 19 | | 010-53-6677 | 02/01/87 | L00025 | O000031 | | | | | | | | | | | | | | |
| 20 | | 152-43-2916 | 01/29/87 | L00026 | O000032 | | | | | | | | | | | | | | |

FIG. 92

|  |  |  |  |  |  |  |
|---|---|---|---|---|---|---|
| 21 |  |  | 010-53-6677 | 02/25/87 | L00027 | O00040 |
| 22 | T | B | 152-43-2916 | 01/26/87 | L00028 | O00041 |
| 23 |  |  | 152-43-2916 | 02/26/87 | L00029 | O00042 | S2
| 24 |  |  | 152-43-2916 | 02/27/87 | L00030 | O00042 |
| 25 |  |  | 152-43-2916 | 03/01/87 | L00031 | O00019 |

W13.5 (row 23)

S1W33.4 (row 25)

PATIENT RECORD REVIEW
patient:GROVER M                    PRIMARY DX:COPD.SEVERE HYPERCAPNIA LAB VALUES FOR INVOICE NO:O00020DATE:02/02/87
DATE DRAWN:02/03/87LAB INVOICE:L00018
ABNORMAL VALUE FOR CR:10.4ACUTE,MODERATELY HIGH prev. normal
ABNORMAL VALUE FOR HG:6.6 SUBACUTE,VERY LOW and WORSENED
ABNORMAL VALUE FOR CALCIUM:14.5ACUTE,VERY LOW and 1st TIME

FIG. 94A

B largest abnormal value is 33.400 on date:03/01/87
smallest anormal value is 14.700 on date:01/06/87

FIG. 94B

```
Record #  DOCTOR         PT_ID       DOB      LNAME       FNAME     SEX  DIA
GNOSIS1          CODE1       DATE1     MEDFLAG1  MEDINV1  DIAGNOSIS2
     CODE2   DURATION2  MEDFLAG2  MEDINV2  DIAGNOSIS3            CODE3    DURATION3
MEDFLAG3  MEDINV3  DESCRIPONE  AMTONE  MEDONE  MEDTWO  DESCRIPTWO    AMTTWO   MEDTHREE
   DESCRIPTHR   AMTTHREE  MAJORSURG  PRIOR_HOSP  TREATMENT  LAST_HOSP  ALLERGIES
             WEIGHT   SYSTOLIC   DIASTOLIC  DATE
     1   abbott                   011-26-3781  05/23/40  cuozzo    samuel         F   chr
onic angina,mild         BH0011         5  .F.
         0   .F.
.F.
                     .F.                5  .F.  10/05/87
           0                            / /
     2   abbott                   011-35-3777  02/04/28  cusson    E              M   ACU
TE ANGINA,UNSTABLE   AH0001        10  .F.
         0   .F.       / /           .F.                                               0
.F.
                     .F.                8  .F.  02/21/87
           0                            / /
     3   abbott                   114-24-3145  01/30/32  cutler                   F   COP
D,SEVERE HYPERCAPNIA  AL0010       4  .T.        chf,mild,controlled
      BH0012       2  .F.                                   BK0016                     0
.F.
                     .F.                4  .F.  06/21/87  penicillin
           0                            / /
     4   abbott                   023-15-1643  10/12/20  kriesky   A              F   CHR
ONIC PYELONEPHRITIS   BK0021      16  .F.                      uremia,mild,chronic
      CP0026      10  .F.
.F.
                     .F.                7  .F.  05/14/86
           0                            / /
     5   abbott                   131-25-6721  07/21/30  scruton   C              F   UCL
ERATIVE COLITIS          BG0013   10  .F.    CHRONIC CLAUDICATION
      BV0017       0  .F.        ACUTE GOUTY ARTHRITIS  BR0020                         0
.F.
                     .F.                5  .F.  02/12/80   penicillin
           0                            / /
     6   abbott                   024-31-1357  10/24/21  kelly     R              F   rhe
umatoid arth.,acute      BR0022   10  .F.                      osteoarth.,severe
      CR0028       6  .F.                                                              0
.F.
                     .T.                5  .T.  02/11/85
           0                            / /
     7   abbott                   112-23-3145  11/13/19  paul      I              M   SYS
T.LUPUS + NEPHRITIS      AR0002   10  .F.                      chronic renal stones
      CK0027       4  .F.                                                              0
.F.
                     .T.                4  .T.  11/21/86
           0                            / /
     8   abbott                   013-32-5312  01/23/11  kennedy   L              F   AUT
OIMM.DEFIENCY SYNDROME  AI0008     5  .F.          chf,mild.controlled
      BH0012      20  .F.     osteoarth.,severe              CR0028                   20
.F.
                     .T.               11  .T.           07/14/85   penicillin
           0                            / /
     9   abbott                   212-32-5487  06/12/30  purdy     M              F   SYS
T.LUPUS + NEPHRITIS      AR0002   10  .F.
         0   .F.
.F.
                     .F.                3  .F.  11/14/87   none
           0                            / /
```

FIG. 95

| | | | |
|---|---|---|---|
| 10 costello us nephritis,recent BK0011 CR0022 1 .F. .F. .F. 0 | 015-21-2341 11/21/24 jenkins B 2 .F. lupus arthr.,acute 3 .T. 11/21/86 none / / | F lup 0 | |
| 11 costello mia,mild,chronc BK0013 CK0023 12 .F. .F. .T. 0 | 321-12-5432 02/22/16 kendall D 5 .F. chronic pyelonephritis m0025 aldomet 750 3 .F. 11/21/84 penicllin / / | F ure 0 | |
| 12 costello ,RECENT BN0015 BE0019 1 .F. .F. Aldomet 1000 .F. 0 | 152-43-2916 09/12/51 Grover F 2 .F. DIABETES MELLITUS CHRONIC PYELONEPHRITIS BK0021 m0025 3 .T. 12/13/87 / / | F CVA 0 | |
| 13 costello d,mild hypercapnia CC0024 CK0026 9 .F. .F. .T. 0 | 030-12-3126 07/12/32 collins E 4 .F. chronic renal stones 7 .T. 11/21/82 / / | F cop 0 | |
| 14 costello tiple myeloma, BH0018 CK0026 3 .F. .F. .F. 0 | 041-23-1515 12/08/36 rothstein M 3 .F. chronic renal stones 4 .F. 11/21/85 / / | F mul 0 | |
| 15 costello ertension,malignant BB0016 0 .F. .F. .F. 0 | 712-21-3144 11/04/50 kirkland R 3 .F. 3 .F. 09/23/87 / / | F hyp 0 | |
| 16 costello ,recent AB0007 BB0016 14 .F. 4 .F. .F. 0 | 002-31-3621 11/19/41 kemp K 25 .F. hypertension,malignant chronic claudication BB0017 9 .F. 12/01/87 / / | F tia | |
| 17 hampton diomegaly,mild,hbp BA0021 CK0023 14 .F. .F. .T. 0 | 071-12-5431 04/23/39 sakowski P 9 .F. chronic pyelonephritis 4 .F. 02/21/86 / / | F car 0 | |
| 18 hampton d,severe hypercapnia AC0009 CR0029 10 .F. .F. .T. 0 | 162-57-8925 09/17/25 kendrick M 8 .F. osteroarth.,severe 7 .T. 07/13/82 / / | F cop | |
| 19 hampton ASTATIC CA + CHEMOTH.AC0005 BH0012 15 .F. .F. .T. 0 .F. | 454-12-3621 02/13/17 henderson E 7 .F. chf,mild,controlled CHR.PANCREATITIS BG0023 12 .F. 03/24/83 / / | M MET 5 | |
| 20 hampton TE BLASTOCYT.LEUKEMIA AP0004 | 324-53-0764 09/13/53 canter S 2 .F. | F ACU | |

| Record # | DOCTOR | PT_ID | DATE | INVOICE | INVOICEFRM | BUN | CR |
| --- | --- | --- | --- | --- | --- | --- | --- |
| HG | HCT | SED_RATE | POTTASIUM | BLD_SUG | PH | P02 | PC02 | WBC |
| CALCIUM | EKG | CXR | | | | | |
| 1 | abbott | 011-35-3777 | 01/15/87 | L00007 | O00005 | C2U29.6 | C2 |
| U4.3 | A2I11.4 | C3U29.4 | A2W5.0 | | | | A4P3.5 |
| A1U12.6 | A2P | | | | | | |
| 2 | abbott | 011-35-3777 | 01/21/87 | L00010 | O00010 | A1N21.0 | A2 |
| W5.2 | S3U10.2 | C4U32.5 | A1N19.0 | | | | |
| | A1P | | | | | | |
| 3 | abbott | 011-35-3777 | 01/15/87 | L00017 | O00011 | | C2 |
| U56 | | C1I29.1 | A1W45 | | | | |
| 4 | abbott | 011-35-3777 | 02/20/87 | L00019 | O00015 | | S3 |
| W40 | | C2U30.5 | S2W17.4 | | | | |
| | A21 | | | | | | |
| 5 | abbott | 131-25-6721 | 01/02/87 | L00000 | O00007 | | |
| T B | T B | A2W27.8 | T C | A1N432 | | | |
| T C | | | | | | | |
| 6 | abbott | 131-25-6721 | 01/14/87 | L00005 | O00009 | T B | T |
| C | A1I9.9 | A2N28.5 | S2I30.7 | A1P5.3 | | | A4U2.9 |
| T | | | | | | | |
| 7 | abbott | 131-25-6721 | 01/20/87 | L00009 | O00012 | | C2 |
| 136.5 | T B | | A2I28 | A3W3.2 | | | |
| | A2W | | | | | | |
| 8 | abbott | 212-32-5487 | 01/10/87 | L00002 | O00004 | S2I28.7 | A1 |
| U5.3 | S3U9.8 | | A2U24.7 | | | | A2I22.2 |
| S2U | S1W | | | | | | |
| 9 | abbott | 212-32-5487 | 01/13/87 | L00004 | O00008 | S2I15.6 | A1 |
| W4.3 | C4W7.9 | | A2I24 | | A3N6.9 | S2N55 | |
| 10 | abbott | 212-32-5487 | 02/17/87 | L00018 | O00024 | A2W12.4 | |
| | S1U10.5 | S3N27.4 | S2I20.5 | A4N2.9 | | | A2W12.8 |
| A2N14.8 | | | | | | | |
| 11 | hampton | 010-53-6677 | 01/02/87 | L00001 | O00000 | A2N24.1 | |
| | A2N12.0 | S2N29.9 | A2N22.9 | C3N6.9 | | | C2N14.7 |
| | S1N | | | | | | |
| 12 | hampton | 010-53-6677 | 02/03/87 | L00014 | O00019 | | |
| | A2I10.3 | C4U30.2 | S2I22.9 | | | | S2I14.0 |
| S2I30.5 | A1W | | | | | | |
| 13 | hampton | 010-53-6677 | 02/09/87 | L00016 | O00025 | S2U21.0 | |
| | A1U10.6 | S1I231.7 | S1W30.5 | | | | C4W4.3 |
| | A2U | | | | | | |
| 14 | hampton | 454-12-3621 | 01/27/87 | L00012 | O00009 | | |
| | A2U10.5 | S1W31.5 | | S2U4.7 | A2W349 | | |
| 15 | hampton | 454-12-3621 | 01/08/87 | L00003 | O00002 | | |
| | S2P9.2 | | S1U17.4 | A1N5.2 | | | A2N13.6 |
| 16 | hampton | 454-12-3621 | 01/25/87 | L00011 | O00006 | | |
| | S2P9.2 | | S1U17.4 | A1N5.2 | | | A2N13.6 |
| 17 | hampton | 454-12-3621 | 02/01/87 | L00013 | O00014 | | |
| | S2U9.8 | A2U32.6 | | S1U4.3 | | | |
| | T C | | | | | | |
| 18 | hampton | 454-12-3621 | 02/05/87 | L00015 | O00028 | | |
| | S2U9.8 | T B | A2W21.4 | C2U5.0 | | | S2U14.8 |
| | T B | | | | | | |
| 19 | abbott | 131-25-6721 | 03/04/87 | L00020 | O00031 | A2U17.0 | |
| | S4U10.6 | | A2I28 | A1W6.2 | | | |
| 20 | abbott | 212-32-5487 | 03/09/87 | L00021 | O00032 | A2W21.0 | A2 |
| N8.6 | | S2I30.5 | S1W18.4 | S2I4.7 | | | C2W15.3 |

FIG. 98

| | | S1U | | | | | | | |
|---|---|---|---|---|---|---|---|---|---|
| U12.8 | 21 A3N11.6 | hampton | A2U29.0 | | 324-53-0764 | 01/14/87 | L00006 | E00000 | A2I20.6 S1 S1U12.6 |
| | 22 A3W9.9 | hampton | S2U29.0 | | 324-53-0764 A1N5.3 | 01/19/87 | L00008 | O00033 | A2U20.3 S2U14.7 |
| | 23 | hampton S2U31.7 | | | 324-53-0764 C2U3.4 | 03/27/87 A2U324 | L00029 | O00038 | A1P14.7 |
| C | 24 | hampton S2U32.0 | S1I26.9 | | 324-53-0764 | 04/01/87 | L00032 | O00041 | T |

```
canter         patient i.d.:324-53-0764 amount:75
james          patient i.d.:152-67-9876 amount:100
schneiderman   patient i.d.:014-34-5284 amount:125
stennis        patient i.d.:010-53-6677 amount:150
```

WBC 01/02/87 14.700
WBC 02/03/87 14.000
WBC 02/09/87 4.300 want to view another patient(or medication)? Y/N

B

PATIENT I.D. 212-32-5487  DATE:03/17/87
COMPLAINT:pnd,orthopnea,sob at rest
FINDINGS:s3,third heart sound
CHANGE:prednisone   80mg
CHANGE:aminophyllin2QID

C

PATIENT I.D. 212-32-5487  DATE:03/13/87
COMPLAINT:heavy chest pain,exercise
COMPLAINT:pnd,orthopnea,sob at rest
ADDITION:prednisone    4
ADDITION:aminophyllin1QID

D

PATIENT I.D. 011-35-3777  DATE:03/15/87
COMPLAINT:pnd,orthopnea,sob at rest
COMPLAINT:heavy chest pain,exercise
FINDINGS:tachycardia,s3
CHANGE:lasix     100m
CHANGE:low salt   850
INTRAVENOUS:lasix    50

FIG. 100

| Record# | PT_ID | INVOICE | MED1 | AMOUNT1 | ACTION1 | LENGTH1 | MED2 | AMOUNT2 | ACTION2 | LENGTH2 | MED3 | AMOUNT3 | ACTION3 | LENGTH3 |
|---|---|---|---|---|---|---|---|---|---|---|---|---|---|---|
| 1 | 454-12-3621 | O00001 | m0000 | 25 | A | | m0001 | 40 | A | | m009 | 1000 | A | |
| 2 | 011-35-3777 | O00002 | m0001 | 40 | A | | m0009 | 500 | A | | | | | |
| 3 | 013-32-5312 | O00003 | m0001 | 40 | C | | | | | | | | | |
| 4 | 011-35-3777 | O00004 | m0001 | 80 | C | | m0009 | 1000 | C | 0. | | | | |
| 5 | 212-32-5487 | O00008 | m0005 | 4 | A | | m0018 | 1QID | A | 0. | | | | |
| 6 | 114-24-3145 | O00005 | m0018 | 500 | A | | m0020 | 1QID | C | | | | | |
| 7 | 112-23-3145 | O00006 | m0019 | 1600 | C | | m0005 | 40 | C | | | | | |
| 8 | 131-25-6721 | O00007 | m0005 | 20 | A | | m0013 | 1TID | A | | | | | |
| 9 | 112-23-3145 | O00009 | m0005 | 60 | C | | m0019 | 800 | C | | | | | |
| 10 | 324-53-0764 | O00010 | m0005 | 60 | C | | m0011 | 2000 | C | | | | | |
| 11 | 454-12-3621 | O00011 | m0009 | 750 | C | | | | | | | | | |
| 12 | 013-32-5312 | O00012 | m0001 | 60 | A | | m0008 | 1000 | A | | | | | |
| 13 | 013-32-5312 | O00013 | m0001 | 80 | C | | m0008 | 2000 | C | | | | | |
| 14 | 114-24-3145 | O00014 | m0018 | 1000 | C | | m0020 | 2QID | C | | | | | |
| 15 | 131-25-6721 | O00015 | m0005 | 30 | C | | m0013 | 2TID | C | | | | | |
| 16 | 324-53-0764 | O00016 | m0006 | 4QID | C | | m0005 | 40 | A | | m0011 | 1000 | A | |
| 17 | 324-53-0764 | O00017 | m0006 | 4qD | A | | | | | | | | | |
| 18 | 454-12-3621 | O00018 | m0022 | 120m | A | | m0001 | 60 | C | | m0008 | 500 | A | |
| 19 | 212-32-5487 | O00024 | m0005 | 80mg | C | | m0018 | 2QID | C | | | | | |
| 20 | 010-53-6677 | O00020 | m0001 | 120 | C | | | | | | | | | |
| 21 | 212-32-5487 | O00021 | m0005 | 60mg | C | | m0018 | 3QID | C | | | | | |
| 22 | 131-25-6721 | O00022 | m0005 | 40 | C | | m0013 | 2QID | C | | | | | |
| 23 | 131-25-6721 | O00023 | m0005 | 50 | C | | m0013 | 3TID | C | | | | | |
| 24 | 324-53-0764 | O00025 | m0006 | 3QID | C | | m0005 | 45mg | C | | m0011 | 1500 | C | |
| 25 | 324-53-0764 | O00026 | m0006 | 1TID | C | | m0011 | | D | | m0005 | | D | |
| 26 | 454-12-3621 | O00027 | m0001 | 120m | C | | m0008 | 1000 | C | | | | | |
| 27 | 112-23-3145 | O00028 | m0019 | 1200 | A | | m0005 | 20 | A | | | | | |
| 28 | 152-43-2916 | O00029 | m0002 | 40 | A | | m0022 | 1TID | A | | | | | |
| 29 | 152-43-2916 | O00030 | m0022 | 2QID | C | | m0002 | 80 | C | | | | | |
| 30 | 152-43-2916 | O00031 | m0022 | 3QID | C | | m0002 | 120 | C | | | | | |
| 31 | 011-35-3777 | O00019 | m0001 | 100m | C | | m0009 | 850 | C | | m0001 | 50 | I | |

FIG. 101

| Record # | DOCTOR | PT_ID | DATE | INVOICE | INVOICEFRM | BUN | CR | HG | HCT | SED_RATE | POTTASIUM | BLD_SUG | PH | PO2 | PCO2 | WBC | CALCIUM | EKG | CXR |
|---|---|---|---|---|---|---|---|---|---|---|---|---|---|---|---|---|---|---|---|
| 11 | hampton | 010-53-6677 | 01/02/87 | L00001 | O00000 | A2N24.1 | | A2N12.0 | S2N29.9 | A2N22.9 | | C3N6.9 | | | | C2N14.7 | | S1N | |
| 12 | hampton | 010-53-6677 | 02/03/87 | L00014 | O00019 | | | A2I10.3 | C4U30.2 | S2I22.9 | | | | | | S2I14.0 | | A1W | |
| 13 | hampton | 010-53-6677 | 02/17/87 | L00022 | O00025 | S2U21.0 | | A1U10.6 | S1231.7 | S1W30.5 | | | | | | C4W4.3 | | A2U | |
| 1 | abbott | 011-35-3777 | 01/15/87 | L00007 | O00005 | C2U29.6 | C2 | U4.3 | A2I11.4 | C3U29.4 | | A2W5.0 | | | | A4P3.5 | A1U12.6 | T A | T B |
| 2 | abbott | 011-35-3777 | 01/21/87 | L00010 | O00010 | A1N21.0 | A2 | W5.2 | S3U10.2 | C4U32.5 | A1N19.0 | | | | | | | A1P | |
| 3 | abbott | 011-35-3777 | 02/15/87 | L00017 | O00011 | C2 | | U56 | | C1I29.1 | A2W45 | | | | | | | | |
| 4 | abbott | 011-35-3777 | 02/20/87 | L00019 | O00015 | S3 | | W40 | | C2U30.5 | S2W17.4 | | | | | | | A2I | |
| 17 | abbott | 011-35-3777 | 01/15/87 | L00007 | O00005 | C2U29.6 | C2 | U4.3 | A2I11.4 | C3U29.4 | A1N19.0 | | | | | | | A1P | A3U |
| 18 | abbott | 011-35-3777 | 01/21/87 | L00010 | O00010 | A1N21.0 | A2 | W5.2 | S3U10.2 | C4U32.5 | A1N19.0 | | | | | | | | |
| 19 | abbott | 011-35-3777 | 02/15/87 | L00017 | O00011 | C2 | | U5.6 | | C1I29.1 | A1W45 | | | | | | | | |
| 20 | abbott | 011-35-3777 | 02/20/87 | L00019 | O00015 | S3W40 | | | C2U30.5 | S2W17.4 | | | | | | | | | |
| 5 | abbott | 131-25-6721 | 01/02/87 | L00000 | O00007 | | | | T B | T B | A2W27.8 | T C | A1N432 | | | | | T C | |
| 6 | abbott | 131-25-6721 | 01/14/87 | L00005 | O00009 | T B | T | C | A1I9.9 | A2N28.5 | S2I30.7 | A1P5.3 | | | | A4U2.9 | | T C | |
| 7 | abbott | 131-25-6721 | 01/20/87 | L00009 | O00012 | C2 | | I36.5 | T B | | A2I28 | A3W3.2 | | | | | | A2W | |
| 8 | abbott | 212-32-5487 | 01/10/87 | L00002 | O00004 | S2I28.7 | A1 | U5.3 | S3U9.8 | | A2U24.7 | | | | | A2I22.2 | | S2U | S1W |
| 9 | abbott | 212-32-5487 | 01/13/87 | L00004 | O00008 | S2I15.6 | A1 | W4.3 | C4W7.9 | | A2I24 | | A3N6.9 | | | S2N55 | | | |
| 10 | abbott | 212-32-5487 | 02/17/87 | L00018 | O00024 | A2W12.4 | | | S1U10.5 | S3N27.4 | S2I20.5 | A4N2.9 | | | | A2W12.8 | A2N14.8 | | |
| 21 | hampton | 324-53-0764 | 01/14/87 | L00006 | E00000 | A2I20.6 | S1 | U12.8 | A3N11.6 | | A2U29.0 | | | | | S1U12.6 | | | |
| 22 | hampton | 324-53-0764 | 01/19/87 | L00008 | L00033 | A2U20.3 | | | A3W9.9 | | S2U29.0 | A1N5.3 | | | | | | | |
| 23 | hampton | 324-53-0764 | 03/27/87 | L00029 | O00038 | A1P14.7 | | | | S2U31.7 | | C2U3.4 | A2U324 | | | S3U15.7 | | | |

FIG. 102

| | | | | | | | |
|---|---|---|---|---|---|---|---|
| C | 24 | hampton S2U32.0 S1I26.9 | | 324-53-0764 | 04/01/87 | L00032 O00041 | T |
| | 14 S2P9.2 | hampton | S1U17.4 | 454-12-3621 A1N5.2 | 01/08/87 | L00003 O00002 | A2N13.6 |
| | 15 S2U10.4 | hampton | A1W20.4 | 454-12-3621 A2U5.9 | 01/25/87 | L00011 O00006 | A1W16.8 |
| | 16 S2U9.8 | hampton A2U32.6 T C | | 454-12-3621 S1U4.3 | 02/01/87 | L00013 O00014 | |

FIG. 103

| Record # | DOCTOR | PT_ID | INVOICE | DATE | TYPE | STATUS | PRIM_DX | SEC_DX | TERT_DX | MED_CHANGE | NEW_MED | LAB_WORK | CONSULT | NEWPROBLEM | INJECTION | CONDITION | WEIGHT | SYSTOLIC | DIASTOLIC | COMPLAINT1 | COMPLAINT2 | FINDING1 | FINDING2 |
|---|---|---|---|---|---|---|---|---|---|---|---|---|---|---|---|---|---|---|---|---|---|---|---|
| 31 | | 011-35-3777 | O00039 | 02/19/87 | | | | | .F. | .F. | .F. | .F. | .F. | | .F. | | | | | | | | |
| 1 | abbott | 011-35-3777 | O00005 | 01/14/87 | S | 2 | AH0001 | | .F. | .F. | .T. | .F. | .F. | | .F. | AH0001 | 0 | 135 | 95 | | | | |
| 2 | abbott | 011-35-3777 | O00019 | 03/15/87 | S | 3 | AH0001 | | .F. | .T. | .F. | .F. | .F. | | .F. | AH0001 | 0 | 175 | 100 | HA002 HA001 | | HA001 | HA002 |
| 3 | abbott | 011-35-3777 | O00010 | 01/21/87 | S | 1 | AH0001 | | .F. | .F. | .T. | .F. | .F. | | .F. | AH0001 | 0 | | | IB029 IB023 | | LB013 | IB018 |
| 4 | abbott | 011-35-3777 | O00011 | 02/14/87 | S | 1 | AH0001 | | .F. | .F. | .T. | .F. | .F. | | .F. | AH0001 | 0 | | | IB022 | | LC023 | |
| 5 | abbott | 011-35-3777 | O00015 | 02/17/87 | S | 1 | AH0001 | | .F. | .F. | .T. | .F. | .F. | | .F. | AA0001 | 0 | | | HA000 | | HA000 | |
| 6 | abbott | 212-32-5487 | O00004 | 01/09/87 | S | 2 | AR0002 | C | K0027 | .F. | .T. | .T. | .F. | .F. | .F. | AR0002 | 0 | | | HA000 | | HA000 | |
| 8 | abbott | 131-25-6721 | O00007 | 01/02/87 | U | 5 | BG0013 | B | V0017 BR0020 | .F. | .T. | .F. | .F. | .F. | .F. | BG0013 | 0 | | | LA016 | | LA011 | |
| 9 | abbott | 131-25-6721 | O00009 | 01/14/87 | S | 1 | BG0013 | B | V0017 BR0020 | .F. | .F. | .F. | .F. | .F. | .F. | BG0013 | 0 | | | LC021 | | | |
| 10 | abbott | 131-25-6721 | O00012 | 01/20/87 | S | 1 | BG0013 | B | V0017 BR0020 | .F. | .F. | .T. | .F. | .F. | .F. | BG0013 | 0 | 160 | 90 | | | | |
| 11 | abbott | 131-25-6721 | O00027 | 01/27/87 | U | 2 | BG0013 | B | V0017 BR0020 | .F. | .F. | .F. | .F. | .F. | .F. | BG0013 | 0 | 169 | 90 | GC020 | | GB020 | |
| 12 | abbott | 131-25-6721 | O00031 | 03/08/87 | S | 1 | BG0013 | B | V0017 BR0020 | .F. | .F. | .T. | .F. | .F. | .F. | BG0013 | 0 | 160 | 95 | | | | |
| 13 | abbott | 212-32-5487 | O00008 | 03/13/87 | S | 3 | AH0002 | | | .F. | .T. | .T. | .F. | .T. | .F. | AH0002 | 0 | | | HA001 HA002 | | | |
| 14 | abbott | 212-32-5487 | O00024 | 03/17/87 | S | 3 | AH0002 | | | .F. | .T. | .T. | .F. | .F. | .F. | AH0002 | 0 | | | HA002 | | HB002 | |
| 15 | abbott | 212-32-5487 | O00029 | 02/25/87 | S | 3 | AR0002 | | | .F. | .F. | .F. | .F. | .F. | .F. | AR0002 | 0 | | | RB014 IB022 | | RA022 | IA024 |
| 16 | abbott | 212-32-5487 | O00032 | 03/09/87 | S | 1 | AR0002 | | | .F. | .F. | .T. | .F. | .F. | .F. | AR0002 | 0 | | | | | | |
| 7 | hampton | 454-12-3621 | O00014 | 02/01/87 | S | 1 | AC0005 | B | H0012 BG0023 | .F. | .F. | .T. | .F. | .F. | .F. | BG0023 | 0 | | | RB014 | | RA022 | IB025 |
| 17 | hampton | 010-53-6677 | O00000 | 01/01/87 | S | 1 | AC0005 | B | E0019 CK0026 | .F. | .F. | .T. | .F. | .F. | .F. | AC0005 | 0 | 140 | 90 | NA007 | | NA007 | |
| 18 | hampton | 010-53-6677 | O00016 | 01/17/87 | U | 3 | AC0005 | B | E0019 CK0026 | .F. | .F. | .F. | .F. | .T. | .F. | BE0019 | 0 | 155 | 95 | NA007 | | NA008 | |
| 19 | hampton | 010-53-6677 | O00019 | 02/02/87 | S | 1 | AC0005 | B | E0019 CK0026 | .F. | .F. | .F. | .F. | .F. | .F. | BE0019 | 0 | 145 | 95 | | | | |

FIG. 104

| | | | | | | | | | |
|---|---|---|---|---|---|---|---|---|---|
| 20 | hampton | | | 010-53-6677 | O000025 | 02/09/87 | S | 1 | AC0005 B |
| E0019 | CK0026 | .F. | .F. | .T. | .F. | .F. | | .F. | CK0026 |
| 0 | 140 | | 90 | HB026 HB004 | | HB002 | | HB004 | |
| 21 | hampton | | | 010-53-6677 | O000030 | 02/27/87 | S | 1 | AC0005 B |
| E0019 | CK0026 | .F. | .F. | .F. | .F. | .F. | | .F. | BE0019 |
| 0 | 150 | | 90 | | | | | | |
| 22 | hampton | | | 324-53-0764 | O000001 | 01/10/87 | S | 1 | AP0004 |
| | | .F. | .F. | .F. | .F. | .F. | | .F. | AP0004 |
| 0 | | | | | | | | | |
| 23 | hampton | | | 324-53-0764 | O000033 | 01/19/87 | S | 1 | AP0004 |
| | | .F. | .F. | .T. | .F. | .F. | | .F. | AP0004 |
| 0 | | | | IB029 IB022 | | IA024 | | IB018 | |
| 24 | hampton | | | 324-53-0764 | O000036 | 03/19/87 | S | 1 | AP0004 |
| | | .F. | .F. | .F. | .F. | .F. | | .F. | AP0004 |
| 0 | | | | | | | | | |
| 25 | hampton | | | 324-53-0764 | O000038 | 03/26/87 | S | 4 | AP0004 |
| | | .F. | .F. | .F. | .F. | .F. | | .F. | AP0004 |
| 0 | | | | LC021 | | IB025 | | | |
| 26 | hampton | | | 324-53-0764 | O000041 | 04/01/87 | S | 1 | AP0004 |
| | | .F. | .F. | .T. | .F. | .F. | | .F. | AP0004 |
| 0 | 160 | | 90 | IB029 | | IA024 | | | |
| 27 | hampton | | | 454-12-3621 | O000002 | 01/08/87 | U | 1 | AC0005 B |
| H0012 | BG0023 | .F. | .F. | .F. | .F. | .F. | | .F. | BH0012 |
| 0 | 160 | | 90 | IB022 | | | | | |
| 28 | hampton | | | 454-12-3621 | O000006 | 01/23/87 | S | 1 | AC0005 B |
| H0012 | BG0023 | .F. | .F. | .T. | .F. | .F. | | .F. | AC0005 |
| 0 | 150 | | 89 | | | | | | |
| 29 | hampton | | | 454-12-3621 | O000028 | 02/04/87 | S | 1 | AC0005 B |
| H0012 | BG0023 | .F. | .F. | .T. | .F. | .F. | | .F. | AC0005 |
| 0 | 150 | | 89 | KA012 | | KB026 | | | |
| 30 | hampton | | | 454-12-3621 | O000046 | 04/14/87 | U | 1 | AC0005 B |
| H0012 | BG0023 | .F. | .F. | .F. | .F. | .F. | | .F. | BG0023 |
| 0 | | | | AB003 BB006 | | AB007 | | | |

FIG. 105

DOCTOR hampton STATUS 1 LAB WORK
PATIENT:henderson ID:454-12-3621DOB:02/13/17
PRIMARY DIAGNOSIS:METASTATIC CA + CHEMOTH. LAST HOSP:03/24/83
SECONDARY DIAGNOSIS:chf,mild,controlled
TERTIARY DIAGNOSIS:CHR.PANCREATITIS LAB VALUES FOR OFFICE VISIT:O00006DATE:01/23/87
CONDITION:METASTATIC CA + CHEMOTH.DATE DRAWN:01/25/87
HG ABNORMAL:9.2 AND ABNORMAL on 01/08/87 9.2
CONDITION WAS CHF,CHR.VENT.HYPERTROPHY STATUS was 1
SED_RATE ABNORMAL:17.4 AND ABNORMAL on 01/08/87 17.4
CONDITION WAS CHF,CHR.VENT.HYPERTROPHY STATUS was 1
POTTASIUM ABNORMAL:5.2 NO PRIOR TEST
WBC ABNORMAL:13.6 NO PRIOR TEST LAB VALUES FOR OFFICE VISIT:O00014DATE:02/01/87
CONDITION:CHR.PANCREATITISDATE DRAWN:02/01/87
HG Abnormal:9.8 and prior from ER
HCT Abnormal:32.6and prior from ER
POTTASIUM Abnormal:4.3 and prior from ER
EKG NORMAL and NO PRIOR TEST LAB VALUES FOR OFFICE VISIT:O00028DATE:02/04/87
CONDITION:METASTATIC CA + CHEMOTH.DATE DRAWN:02/05/87
HG ABNORMAL:9.8 AND ABNORMAL on 02/01/87 9.8
CONDITION WAS CHR.PANCREATITIS STATUS was 1
HCT NORMAL and ABNORMAL ON 02/01/87 32.6
CONDITION was CHR.PANCREATITISSTATUS 1
SED_RATE ABNORMAL:21.4 AND ABNORMAL on 01/25/87 17.4
CONDITION WAS METASTATIC CA + CHEMOTH. STATUS was 1
POTTASIUM ABNORMAL:5.0 AND ABNORMAL on 02/01/87 4.3
CONDITION WAS CHR.PANCREATITIS STATUS was 1
WBC ABNORMAL:14.8 AND ABNORMAL on 01/25/87 13.6
CONDITION WAS METASTATIC CA + CHEMOTH. STATUS was 1
EKG NORMAL and NORMAL ON 02/01/87
CONDITION was CHR.PANCREATITIS STATUS 1

FIG. 106

DOCTOR hampton STATUS 1 LAB WORK
PATIENT:canter ID:324-53-0764DOB:09/13/53
PRIMARY DIAGNOSIS:ACUTE BLASTOCYT.LEUKEMIA LAST HOSP:06/24/87

LAB VALUES FOR OFFICE VISIT:O00033DATE:01/19/87
CONDITION:ACUTE BLASTOCYT.LEUKEMIADATE DRAWN:01/19/87
BUN Abnormal:20.3and prior from ER
HG Abnormal:9.9 and prior from ER
SED_RATE Abnormal:29.0and prior from ER
POTTASIUM ABNORMAL:5.3  NO PRIOR TEST
WBC Abnormal:14.7and prior from ER LAB VALUES FOR OFFICE VISIT:O00041DATE:04/01/87
CONDITION:ACUTE BLASTOCYT.LEUKEMIADATE DRAWN:04/01/87
CR NORMAL and NO PRIOR TEST
HCT ABNORMAL:32.0 AND  ABNORMAL on 03/27/87 31.7
CONDITION WAS ACUTE BLASTOCYT.LEUKEMIA STATUS was 4
SED_RATE ABNORMAL:26.9 AND  ABNORMAL on 01/19/87 29.0
CONDITION WAS ACUTE BLASTOCYT.LEUKEMIA STATUS was 1

FIG. 107

DOCTOR abbott STATUS 1 LAB WORK
PATIENT:purdy ID:212-32-5487DOB:06/12/30
PRIMARY DIAGNOSIS:SYST.LUPUS + NEPHRITIS LAST HOSP:11/14/87

---

LAB VALUES FOR OFFICE VISIT:O00008DATE:01/13/87
CONDITION:SYST.LUPUS + NEPHRITISDATE DRAWN:01/13/87
BUN ABNORMAL:15.6 AND   ABNORMAL on 01/10/87 28.7
CONDITION WAS SYST.LUPUS + NEPHRITIS STATUS was 2
CR ABNORMAL:4.3   AND   ABNORMAL on 01/10/87 5.3
CONDITION WAS SYST.LUPUS + NEPHRITIS STATUS was 2
HG ABNORMAL:7.9  AND   ABNORMAL on 01/10/87 9.8
CONDITION WAS SYST.LUPUS + NEPHRITIS STATUS was 2
SED_RATE ABNORMAL:24    AND      ABNORMAL on 01/10/87   24.7
CONDITION WAS SYST.LUPUS + NEPHRITIS STATUS was 2
PH ABNORMAL:6.9   NO PRIOR TEST
PCO2  ABNORMAL:55    NO PRIOR TEST

---

LAB VALUES FOR OFFICE VISIT:O00024DATE:02/17/87
CONDITION:SYST.LUPUS + NEPHRITISDATE DRAWN:02/17/87
BUN ABNORMAL:12.4 AND   ABNORMAL on 01/13/87 15.6
CONDITION WAS SYST.LUPUS + NEPHRITIS STATUS was 1
HG ABNORMAL:10.5   AND    ABNORMAL on 01/13/87 7.9
CONDITION WAS SYST.LUPUS + NEPHRITIS STATUS was 1
HCT ABNORMAL:27.4 NO PRIOR TEST
SED_RATE ABNORMAL:20.5  AND    ABNORMAL on 01/13/87  24
CONDITION WAS SYST.LUPUS + NEPHRITIS STATUS was 1
POTTASIUM ABNORMAL:2.9   NO PRIOR TEST
WBC ABNORMAL:12.8  AND    ABNORMAL on 01/10/87 22.2
CONDITION WAS SYST.LUPUS + NEPHRITIS STATUS was 2
CALCIUM ABNORMAL:14.8 NO PRIOR TEST

---

LAB VALUES FOR OFFICE VISIT:O00032DATE:03/09/87
CONDITION:SYST.LUPUS + NEPHRITISDATE DRAWN:03/09/87
BUN ABNORMAL:21.0  AND   ABNORMAL on 02/17/87  12.4
CONDITION WAS SYST.LUPUS + NEPHRITIS STATUS was 1
CR ABNORMAL:8.6   NO PRIOR TEST
HCT ABNORMAL:30.5 AND   ABNORMAL on 02/17/87  27.4
CONDITION WAS SYST.LUPUS + NEPHRITIS STATUS was 1
SED_RATE ABNORMAL:18.4  AND   ABNORMAL on 02/17/87   20.5
CONDITION WAS SYST.LUPUS + NEPHRITIS STATUS was 1
POTTASIUM ABNORMAL:4.7  AND    ABNORMAL on 02/17/87   2.9
CONDITION WAS SYST.LUPUS + NEPHRITIS STATUS was 1
WBC ABNORMAL:15.3  AND    ABNORMAL on 02/17/87  12.8
CONDITION WAS SYST.LUPUS + NEPHRITIS STATUS was 1
CXR ABNORMAL:       AND   ABNORMAL on 01/10/87
CONDITION WAS SYST.LUPUS + NEPHRITIS STATUS was 2

FIG. 108

DOCTOR abbott STATUS 1 LAB WORK
PATIENT:scruton ID:131-25-6721DOB:07/21/30
PRIMARY DIAGNOSIS:ULCERATIVE COLITIS LAST HOSP:02/12/80
SECONDARY DIAGNOSIS:CHRONIC CLAUDICATION
TERTIARY DIAGNOSIS:ACUTE GOUTY ARTHRITIS LAB VALUES FOR OFFICE VISIT:O00012DATE:01/20/87
CONDITION:ULCERATIVE COLITISDATE DRAWN:01/20/87
CR ABNORMAL:36.5 Normal on 01/14/87
CONDITION WAS ULCERATIVE COLITIS STATUS 1
HG NORMAL and ABNORMAL ON   01/14/87  9.9
CONDITION was ULCERATIVE COLITISSTATUS 1
SED_RATE ABNORMAL:28   AND    ABNORMAL on 01/14/87  30.7
CONDITION WAS ULCERATIVE COLITIS STATUS was 1
POTTASIUM ABNORMAL:3.2   AND    ABNORMAL on 01/14/87  5.3
CONDITION WAS ULCERATIVE COLITIS STATUS was 1
CXR ABNORMAL:      Normal on 01/14/87
CONDITION WAS ULCERATIVE COLITIS STATUS 1

LAB VALUES FOR OFFICE VISIT:O00031DATE:03/08/87
CONDITION:ULCERATIVE COLITISDATE DRAWN:03/04/87
BUN ABNORMAL:17.0 Normal on 01/14/87
CONDITION WAS ULCERATIVE COLITIS STATUS 1
HG ABNORMAL:10.6 Normal on 01/20/87
CONDITION WAS ULCERATIVE COLITIS STATUS 1
SED_RATE ABNORMAL:28   AND    ABNORMAL on 01/20/87  28
CONDITION WAS ULCERATIVE COLITIS STATUS was 1
POTTASIUM ABNORMAL:6.2   AND    ABNORMAL on 01/20/87  3.2
CONDITION WAS ULCERATIVE COLITIS STATUS was 1

FIG. 109

DOCTOR abbott STATUS 1 LAB WORK
PATIENT:cusson ID:011-35-3777DOB:02/04/28
PRIMARY DIAGNOSIS:ACUTE ANGINA,UNSTABLE LAST HOSP:02/21/87

LAB VALUES FOR OFFICE VISIT:O00010DATE:01/21/87
CONDITION:ACUTE ANGINA,UNSTABLEDATE DRAWN:01/21/87
BUN ABNORMAL:21.0 NO PRIOR TEST
CR ABNORMAL:5.2   AND   ABNORMAL ON 01/15/87   4.3
CONDITION WAS ACUTE ANGINA,UNSTABLE STATUS was 2
HG ABNORMAL:10.2 AND   ABNORMAL ON 01/15/87   11.4
CONDITION WAS ACUTE ANGINA,UNSTABLE STATUS was 2
HCT ABNORMAL:32.5 AND   ABNORMAL on 01/15/87   29.4
CONDITION WAS ACUTE ANGINA,UNSTABLE STATUS was 2
SED_RATE ABNORMAL:19.0 NO PRIOR TEST
EKG ABNORMAL:   AND   ABNORMAL on 01/15/87
CONDITION WAS ACUTE ANGINA,UNSTABLE STATUS was 2

LAB VALUES FOR OFFICE VISIT:O00011DATE:02/14/87
CONDITION:ACUTE ANGINA,UNSTABLEDATE DRAWN:02/15/87
CR ABNORMAL:56   AND   ABNORMAL on 01/21/87   5.2
CONDITION WAS ACUTE ANGINA,UNSTABLE STATUS was 1
HCT ABNORMAL:29.1 AND   ABNORMAL on 01/21/87   32.5
CONDITION WAS ACUTE ANGINA,UNSTABLE STATUS was 1
SED_RATE ABNORMAL:45    AND   ABNORMAL on 01/21/87   19.0
CONDITION WAS ACUTE ANGINA,UNSTABLE STATUS was 1

LAB VALUES FOR OFFICE VISIT:O00015DATE:02/19/87
CONDITION:ACUTE ANGINA,UNSTABLEDATE DRAWN:02/20/87
CR ABNORMAL:40   AND   ABNORMAL on 02/15/87   56
CONDITION WAS ACUTE ANGINA,UNSTABLE STATUS was 1
HCT ABNORMAL:30.5 AND    ABNORMAL on 02/15/87   29.1
CONDITION WAS ACUTE ANGINA,UNSTABLE STATUS was 1
SED_RATE ABNORMAL:17.4 AND   ABNORMAL on 02/15/87   45
CONDITION WAS ACUTE ANGINA,UNSTABLE STATUS was 1
EKG ABNORMAL:   AND   ABNORMAL on 01/21/87
CONDITION WAS ACUTE ANGINA,UNSTABLE STATUS was 1

FIG. 110

DOCTOR hampton STATUS 1 LAB WORK
PATIENT:stennis ID:010-53-6677DOB:04/23/40
PRIMARY DIAGNOSIS:metastatic ca LAST HOSP:02/24/83
SECONDARY DIAGNOSIS:diabetes mellitus
TERTIARY DIAGNOSIS:CHRONIC RENAL STONES

---

LAB VALUES FOR OFFICE VISIT:O00000DATE:01/01/87
CONDITION:METASTATIC CA + CHEMOTH.DATE DRAWN:01/02/87
BUN ABNORMAL:24.1 NO PRIOR TEST
HG ABNORMAL:12.0 NO PRIOR TEST
HCT ABNORMAL:29.9 NO PRIOR TEST
SED_RATE ABNORMAL:22.9 NO PRIOR TEST
POTTASIUM ABNORMAL:6.9 NO PRIOR TEST
WBC ABNORMAL:14.7 NO PRIOR TEST
CXR ABNORMAL:      NO PRIOR TEST

---

LAB VALUES FOR OFFICE VISIT:O00025DATE:02/09/87
CONDITION:DATE DRAWN:02/09/87
BUN ABNORMAL:21.0 AND  ABNORMAL on 01/02/87  24.1
CONDITION WAS METASTATIC CA + CHEMOTH. STATUS was 1
HG ABNORMAL:10.6 AND  ABNORMAL on 02/03/87  10.3
CONDITION WAS DIABETES MELLITUS STATUS was 1
HCT ABNORMAL:31.7 AND  ABNORMAL on 02/03/87  30.2
CONDITION WAS DIABETES MELLITUS STATUS was 1
SED_RATE ABNORMAL:30.5 AND  ABNORMAL on 02/03/87  22.9
CONDITION WAS DIABETES MELLITUS STATUS was 1
WBC ABNORMAL:4.3 AND  ABNORMAL on 02/03/87  14.0
CONDITION WAS DIABETES MELLITUS STATUS was 1
CXR ABNORMAL:     AND  ABNORMAL on 02/03/87
CONDITION WAS DIABETES MELLITUS STATUS was 1

```
want to continue?(Y/y) or leave(N/n)
Record #  DOCTOR           PT_ID       DOB      LNAME      FNAME    SEX  DIA
GNOSIS1        CODE1    DURATION1      MEDFLAG1  MEDINV1  DIAGNOSIS2
    CODE2   DURATION2  MEDFLAG2  MEDINV2  DIAGNOSIS3        CODE3    DURATION3
MEDFLAG3 MEDINV3 DESCRIPONE  AMTONE  MEDONE  MEDTWO  DESCRIPTWO  AMTTWO  MEDTHREE
DESCRIPTHR  AMTTHREE  MAJORSURG  PRIOR_HOSP  TREATMENT  LAST_HOSP  ALLERGIES
            WEIGHT  SYSTOLIC  DIASTOLIC  DATE
       1   abbott             011-26-3781  05/23/40  cuozzo     samuel    F    chr
onic angina,mild         BG0023          5  .F.
    CR0028      0  .F.                                                         0
.F.
                      .F.             5  .F.             10/05/87
              0                      / /
       2   abbott             011-35-3777  02/04/28  cusson     E         M    ACU
TU ANGINA,UNSTABLE       AH0001        10  .F.
    BG0023      0  .F.                                   CR0028                0
.F.
                      .F.             8  .F.             02/21/87
              0                      / /
       3   abbott             114-24-3145  01/30/32  cutler     F         F    COP
D,SEVERE HYPERCAPNIA     AV0006         4  .T.           chf,mild,controlled
    AI0008      2  .F.                                   BG0023                0
.F.
                      .F.             4  .F.             06/21/87   penicillin
              0                      / /
       4   abbott             023-15-1643  10/12/20  kriesky    A         F    CHR
ONIC PYELONEPHRITIS      BG0023        16  .F.           uremia,mild,chronic
    CR0028     10  .F.                                                         0
.F.
                      .F.             7  .F.             05/14/86
              0                      / /
       5   abbott             131-25-6721  07/21/30  scruton    C         F    ULC
ERATIVE COLITIS          BG0013        10  .F.           CHRONIC CLAUDICATION
    BV0017      0  .F.        ACUTE GOUTY ARTHRITIS      BG0023                0
.F.
                      .F.             5  .F.             02/12/80   penicillin
              0                      / /
       6   abbott             024-31-1357  10/24/21  kelly      R         F    rhe
umatoid arth.,acute      CH0024        10  .F.           osteoarth.,severe
    CR0028      6  .F.                                                         0
.F.
                      .T.             5  .T.             02/11/85
              0                      / /
       7   abbott             112-23-3145  11/13/19  paul       I         M    SYS
T.LUPUS + NEPHRITIS      CH0024        10  .F.           chronic renal stones
    CP0025      4  .F.                                   CR0028                0
.F.
                      .T.             4  .T.             11/21/86
              0                      / /
       8   abbott             013-32-5312  01/23/11  kennedy    L         F    AUT
OIMM.DEFIENCY SYNDROME AI0008  5  .F.                    chf,mild,controlled
    BH0012     20  .F.        osteoarth.,severe          CR0028               20
.F.
                      .T.            11  .T.             07/14/85   penicillin
              0                      / /
       9   abbott                                                 / /
                         BL0018       .F.
    BE0019         .F.                                   CP0026
.F.
                      .F.            .F.                         / /
                                     / /

FIG. 112
```

| | | | | | |
|---|---|---|---|---|---|
| | 10 abbott | | | | |
| | | | AH0001 | .F. | |
| BG0013 | | .F. | | | |
| .F. | | | | | |
| | | | .F. | .F. | / / |
| | | | | | / / |
| | 11 costello | | | | |
| | | | BN0015 | .F. | |
| CR0028 | | .F. | | | |
| .F. | | | | | |
| | | | .F. | .F. | / / |
| | | | | | / / |
| | 12 costello | | | | |
| | | | AI0008 | .F. | |
| CP0026 | | .F. | | | CR0028 |
| .F. | | | | | |
| | | | .F. | .F. | / / |
| | | | | | /. / |
| | 13 costello | | | | |
| | | | BN0015 | .F. | |
| CP0026 | | .F. | | | |
| .F. | | | | | |
| | | | .F. | .F. | / / |
| | | | | | / / |
| | 14 costello | | | | |
| | | | AV0006 | .F. | |
| BK0021 | | .F. | | | CR0028 |
| .F. | | | | | |
| | | | .F. | .F. | / / |
| | | | | | / / |
| | 15 costello | | | | |
| | | | BG0013 | .F. | |
| BV0017 | | .F. | | | |
| .F. | | | | | |
| | | | .F. | .F. | / / |
| | | | | | / / |
| | 16 costello | | | | |
| | | | BH0011 | .F. | |
| BN0015 | | .F. | | | CP0026 |
| .F. | | | | | |
| | | | .F. | .F. | / / |
| | | | | | / / |
| | 17 costello | | | | |
| | | | AI0008 | .F. | |
| CR0028 | | .F. | | | |
| .F. | | | | | |
| | | | .F. | .F. | / / |
| | | | | | / / |
| | 18 costello | | | | |
| | | | AN0009 | .F. | |
| AL0010 | | .F. | | | CP0026 |
| .F. | | | | | |
| | | | .F. | .F. | / / |
| | | | | | / / |
| | 19 costello | | | | |
| | | | CP0025 | .F. | |
| CK0027 | | .F. | | | CR0028 |
| .F. | | | | | |
| | | | .F. | .F. | / / |
| | | | | | / / |
| | 20 costello | | | | |
| | | | BG0013 | .F. | |
| CP0026 | | .F. | | | CR0028 |

FIG. 113

| | | | | |
|---|---|---|---|---|
| .F. | | | | |
| | | .F. | .F. | / / |
| | 21 hampton | | / / | |
| | | CH0024 | / / | |
| CP0026 | | .F. | .F. | |
| .F. | | | | |
| | | .F. | .F. | / / |
| | 22 hampton | | / / | |
| | | AN0009 | / / | |
| BG0013 | | .F. | .F. | CP0026 |
| .F. | | | | |
| | | .F. | .F. | / / |
| | 23 hampton | | / / | |
| | | AV0006 | / / | |
| BV0017 | | .F. | .F. | |
| .F. | | | | |
| | | .F. | .F. | / / |
| | 24 hampton | | / / | |
| | | BH0011 | / / | |
| CR0028 | | .F. | .F. | CG0029 |
| .F. | | | | |
| | | .F. | .F. | / / |
| | 25 hampton | | / / | |
| | | CP0025 | / / | |
| CP0026 | | .F. | .F. | |
| .F. | | | | |
| | | .F. | .F. | / / |
| | 26 hampton | | / / | |
| | | AI0008 | / / | |
| AN0009 | | .F. | .F. | BG0013 |
| .F. | | | | |
| | | .F. | .F. | / / |
| | 27 hampton | | / / | |
| | | AR0003 | / / | |
| AV0006 | | .F. | .F. | BG0013 |
| .F. | | | | |
| | | .F. | .F. | / / |
| | 28 hampton | | / / | |
| | | AN0009 | / / | |
| BV0017 | | .F. | .F. | CR0028 |
| .F. | | | | |
| | | .F. | .F. | / / |
| | 29 hampton | | / / | |
| | | BH0011 | / / | |
| BH0012 | | .F. | .F. | BG0013 |
| .F. | | | | |
| | | .F. | .F. | / / |
| | 30 hampton | | / / | |
| | | AP0004 | / / | |
| AV0006 | | .F. | .F. | CL0030 |
| .F. | | | | |
| | | .F. | .F. | / / |
| | | | / / | |

FIG. 114 the diagnosis iron def.anemia is from category C
the total number with that is  9
dr.abbott has  1 for  11%
the number in category A is  3
dr.abbott has none
the number in category B is  4
dr.abbott has  1
the number in category C is  2
dr.abbott has none

FIG. 115

'New Clinical Problems'

| Record # | DOCTOR | PT_ID | DATE | INVOICE | INVOICEFRM | BUN | CR |
|---|---|---|---|---|---|---|---|
| HG | HCT | SED_RATE | POTTASIUM | BLD_SUG | PH | P02 | PC02 | WBC |
| CALCIUM | EKG | CXR | | | | | |
| 1 | hampton | 010-53-6677 | 01/04/87 | L00000 | O00015 | | C2U29.6 |
| 2 | abbott | | 112-23-3145 | 01/18/87 | L00001 | O00007 | |
| S3U10.2 | C4U32.5 | | | | | | |
| 3 | abbott | | 011-35-3777 | 02/02/87 | L00002 | O00006 | C2 |
| U56 | | A1W45 | | | | | |
| 4 | | | 112-23-3145 | 01/14/87 | L00003 | O00013 | S3 |
| W40 | | C2U30.5 | | | | | |
| 5 | | | 112-23-3145 | 01/17/87 | L00004 | O00015 | |
| T | B | T | B | T | C | A1N432 | |
| 6 | | | 010-53-6677 | 01/08/87 | L00005 | O00021 | T B T |
| C | | A2N28.5 | | | | | |
| 7 | | | 011-35-3777 | 01/11/87 | L00006 | O00012 | C2 |
| 136.5 | | A2I28 | | | | | |
| 8 | | | 131-25-6721 | 01/04/87 | L00008 | O00008 | |
| S4U10.6 | | | A1N6.2 | A2W206 | | | |
| 9 | | | 131-25-6721 | 01/13/87 | L00009 | O00014 | S2I28.7 |
| S2U | S1W | | | | | | |
| 10 | | | 454-12-3621 | 01/06/87 | L00010 | O00010 | |
| | | A2I24 | | A3W6.9 | | S2I55 | |
| 11 | | | 454-12-3621 | 01/14/87 | L00011 | O00016 | |
| | | S3W27.4 | A4N2.9 | | | | |
| A2W14.8 | | | | | | | |
| 12 | | | 152-43-2916 | 01/03/87 | L00012 | O00011 | A2 |
| N8.6 | | S2I30.5 | | | | | C2W15x3 |
| 13 | | | 152-43-2916 | 01/07/87 | L00013 | O00017 | |
| | | A2U22.9 | C3W6.9 | | | | |
| 14 | | | 212-32-5487 | 02/04/87 | L00013 | O00025 | |
| | | C4U30.2 | | | | | |

FIG. 117

| Record # | DOCTOR | PT_ID | INVOICE | CATEGORY | CODE | DATE | HINVOICE | EINVOICE | TINVOICE | LINVOICE | SINVOICE | CONDITION | COMPLAINT1 | FINDING1 | HCOMPLAINT2 | FINDING2 |
|---|---|---|---|---|---|---|---|---|---|---|---|---|---|---|---|---|
| 10 | hampton | 010-53-6677 | O00015 | BP2S | G | 01/02/87 | | | | | | I20021 | IB022 | IB025 | IB023 | |
| 11 | hampton | 010-53-6677 | O00021 | BPS | N | 01/06/87 | | | | | | I20021 | LA016 | NA021 | | IA024 |
| 2 | abbott | 011-35-3777 | O00006 | BP1S | P | 01/09/87 | | | | | | R30030 | VB018 | BA015 | | |
| 3 | abbott | 011-35-3777 | O00012 | BP2UMH | | 01/15/87 | | | | | | R30030 | VB018 | VA009 | IB023 | |
| 17 | | 011-35-3777 | O00019 | A2 | M | 01/18/87 | | | | | | BB0007 | BA010 | BA015 | | |
| 4 | abbott | 112-23-3145 | O00007 | CP3UIE | | 01/02/87 | | | | | | L30023 | LC021 | LB013 | | |
| 5 | abbott | 112-23-3145 | O00013 | CP4SIP | | 01/12/87 | | | | | | L30023 | LC021 | LC023 | IB022 | IB018 |
| 6 | abbott | 112-23-3145 | O00015 | CP4S | G | 01/15/87 | | | | | | L30023 | LC021 | LB014 | IB022 | |
| 7 | abbott | 131-25-6721 | O00008 | AP2U | F | 01/02/87 | | | | | | L20017 | IB029 | LB013 | LA016 | IA024 |
| 8 | abbott | 131-25-6721 | O00014 | AP2S | N | 01/11/87 | | | | | | L20017 | LC021 | LC023 | | IA024 |
| 9 | abbott | 131-25-6721 | O00031 | AP4S | | 01/14/87 | | | | | | L20017 | LC021 | LB013 | | |
| 14 | costello | 152-43-2916 | O00011 | AP2S | F | 01/02/87 | | | | | | R20024 | RB017 | RA022 | | IB025 |
| 16 | costello | 152-43-2916 | O00016 | AP2S | I | 01/13/87 | | | | | | R20024 | RB025 | | | |
| 15 | costello | 152-43-2916 | O00017 | AP3S | H | 01/05/87 | | | | | | R20024 | RB017 | RA022 | IB029 | |
| 1 | abbott | 212-32-5487 | O00024 | A33S | C | 01/17/87 | | | | | | V10005 | VB018 | VA028 | | |
| 12 | hampton | 454-12-3621 | O00010 | AP2 | H | 01/04/87 | | | | | | V30019 | IB030 | IC017 | | |
| 13 | hampton | 454-12-3621 | O00016 | AP2 | F | 01/11/87 | | | | | | V30019 | NA009 | HB005 | LA019 | HC006 |

FIG. 118

NEWPROBLEM SUMMARY BY PATIENT(LAB VALUES)
PATIENT I.D.:454-12-3621

LAB VALUES FOR INVOICE NO:O00010DATE:01/04/87 CONDITION:

DATE DRAWN:01/06/87LAB INVOICE:L00010
ABNORMAL VALUE FOR SED_RATE:24   ACUTE,MODERATELY HIGH and IMPROVED
ABNORMAL VALUE FOR PH:6.9  ACUTE,VERY LOW and WORSENED
ABNORMAL VALUE FOR PCO2:55  SUBACUTE,MODERATELY HIGH and IMPROVED

LAB VALUES FOR INVOICE NO:O00016DATE:01/11/87 CONDITION:

DATE DRAWN:01/14/87LAB INVOICE:L00011
ABNORMAL VALUE FOR HCT:27,4SUBACUTE,VERY LOW and WORSENED
ABNORMAL VALUE FOR POTTASIUM:2.9 ACUTE,MODERATELY LOW and Ist TIME
ABNORMAL VALUE FOR CALCIUM:14.8ACUTE,MODERTELY HIGH and WORSENED

FIG. 119

NEWPROBLEM SUMMARY BY PATIENT(LAB VALUES)
PATIENT I.D.:212-32-5487

NO LAB TESTS WERE DRAWN FOR INVOICE NO:O00024 DATE:01/17/87

FIG. 120

NEWPROBLEM SUMMARY BY PATIENT(LAB VALUES)
PATIENT I.D.:152-43-2916

LAB VALUES FOR INVOICE NO:O00011DATE:01/02/87 CONDITION:

DATE DRAWN:01/03/87LAB INVOICE:L00012
ABNORMAL VALUE FOR CR:8.6 ACUTE,MODERATELY HIGH and 1st TIME
ABNORMAL VALUE FOR HCT:30.5SUBACUTE,MODERATELY HIGH and IMPROVED
ABNORMAL VALUE FOR WBC:15x3CHRONIC,MODERATELY HIGH and WORSENED

NO LAB TESTS WERE DRAWN FOR INVOICE NO:O00016 DATE 01/13/87

LAB VALUES FOR INVOICE NO:O00017DATE:01/05/87 CONDITION:

DATE DRAWN:01/07/87LAB INVOICE:L00013
ABNORMAL VALUE FOR SED_RATE:22.9ACUTE,MODERATELY HIGH and UNCHANGED
ABNORMAL VALUE FOR POTTASIUM:6.9 CHRONIC VERY LOW and WORSENED

FIG 121

NEWPROBLEM SUMMARY BY PATIENT(LAB VALUES)
PATIENT I.D.:131-25-6721

LAB VALUES FOR INVOICE NO:O00008DATE:01/02/87 CONDITION:

DATE DRAWN:01/04/87LAB INVOICE:L00008
ABNORMAL VALUE FOR HG:10.6SUBACUTE,MODERATELY LOW and UNCHANGED
ABNORMAL VALUE FOR POTTASIUM:6.2 ACUTE,VERY HIGH and 1ST TIME
ABNORMAL VALUE FOR BLD_SUG:206 ACUTE,MODERAELY HIGH and WORSENED

LAB VALUES FOR INVOICE NO:O00014DATE:01/11/87 CONDITION:

DATE DRAWN:01/13/87LAB INVOICE:L00009
ABNORMAL VALUE FOR BUN:28.7SUBACUTE,MODERATELY HIGH and IMPROVED
ABNORMAL VALUE FOR EKG:    SUBACUTE,MILDLY ABNORMAL and UNCHANGED
ABNORMAL VALUE FOR CXR:    SUBACUTE,VERY ABNORMAL and WORSENED

NO LAB TETS WERE DRAWN FOR INVOICE NO:O00031 DATE:01/14/87

FIG 122

NEWPROBLEM SUMMARY BY PATIENT(LAB VALUES)
PATIENT I.D.:112-23-3145

LAB VALUES FOR INVOICE NO:O00007DATE:01/02/87 CONDITION:

DATE DRAWN:01/18/87LAB INVOICE:L00001
ABNORMAL VALUE FOR HG:10.2SUBACUTE,VERY LOW and UNCHANGED
ABNORMAL VALUE FOR HCT:32.5CHRONIC,MODERATELY LOW and UNCHANGED

LAB VALUES FOR INVOICE NO:O00013DATE:01/12/87 CONDITION:

DATE DRAWN:01/14/87LAB INVOICE:L00003
ABNORMAL VALUE FOR CR:40   SUBACUTE,VERY LOW and WORSENED
ABNORMAL VALUE FOR HCT:30.5CHRONIC,MODERATELY HIGH and UNCHANGED

LAB VALUES FOR INVOICE NO:O00015DATE:01/15/87 CONDITION:

DATE DRAWN:01/17/87LAB INVOICE:L00004
NORMAL TEST FOR HG AND ABNORMAL ON:01/18/87
NORMAL TEST FOR HCT AND ABNORMAL ON:01/14/87
NORMAL TEST FOR POTTASIUM NO  PRIOR TESTS ON RECORD
ABNORMAL VALUE FOR BLD_SUG:432 ACUTE,VERY HIGH and 1st TIME

FIG 123

NEWPROBLEM SUMMARY BY PATIENT(LAB VALUES)
PATIENT I.D.:011-35-3777

LAB VALUES FOR INVOICE NO:O00006DATE:01/09/87 CONDITION:

DATE DRAWN:02/02/87LAB INVOICE:L00002
ABNORMAL VALUE FOR CR:56   CHRONIC,MODERATELY HIGH and UNCHANGED
ABNORMAL VALUE FOR SED_RATE:45   ACUTE,VERY HIGH and WORSENED

LAB VALUES FOR INVOICE NO:O00012DATE:01/15/87 CONDITION:

DATE DRAWN:01/11/87LAB INVOICE:L00006
ABNORMAL VALUE FOR CR:36.5CHRONIC,MODERATELY HIGH and IMPROVED
ABNORMAL VALUE FOR SED_RATE:28   ACUTE,MODERATELY HIGH and IMPROVED

RECORD NOT FOUND ?DATA ENTRY ERROR FOR INVOICE NO:O00019 DATE:01/18/87

FIG 124

NEWPROBLEM SUMMARY BY PATIENT(LAB VALUES)
PATIENT I.D.:010-53-6677

LAB VALUES FOR INVOICE NO:O00015DATE:01/02/87 CONDITION:

DATE DRAWN:01/04/87LAB INVOICE:L00000
ABNORMAL VALUE FOR BUN:29.6CHRONIC,MODERATELY HIGH and UNCHANGED

LAB VALUES FOR INVOICE NO:O00021DATE:01/06/87 CONDITION:

DATE DRAWN:01/08/87LAB INVOICE:L00005
NORMAL TEST FOR BUN AND ABNORMAL ON:01/04/87
NORMAL TEST FOR CR NO PRIOR TESTS ON RECORD
ABNORMAL VALUE FOR HCT:28.5ACUTE,MODERATELY HIGH and 1st TIME

FIG 125

| Record# | CODENAME | DESCRIPTN |
|---|---|---|
| 1 | m0000 | digoxin |
| 2 | m0001 | lasix |
| 3 | m0002 | inderal |
| 4 | m0003 | nitroglyceri |
| 5 | m0004 | isordil |
| 6 | m0005 | prenisone |
| 7 | m0006 | chemotherapy |
| 8 | m0007 | nalfon |
| 9 | m0008 | keflin |
| 10 | m0009 | low salt |
| 11 | m0010 | low protein |
| 12 | m0011 | penicillin |
| 13 | m0012 | hydrodiuril |
| 14 | m0013 | maalox |
| 15 | m0014 | inderide |
| 16 | m0015 | kcl |
| 17 | m0016 | librium |
| 18 | m0017 | insulin |
| 19 | m0018 | aminophyllin |
| 20 | m0019 | aspirin |
| 21 | m0020 | ippb,epi |
| 22 | m0021 | dilantin |
| 23 | m0022 | vasodilan |
| 24 | m0023 | calcium |

FIG. 126

| Record# | PT_ID | INVOICE | MED1 | AMOUNT1 | ACTION1 | LENGTH1 | MED2 | AMOUNT2 | ACTION2 | LENGTH2 | MED3 | AMOUNT3 | ACTION3 | LENGTH3 |
|---|---|---|---|---|---|---|---|---|---|---|---|---|---|---|
| 1 | 454-12-3621 | O00004 | m0000 | 25 | A | | m0001 | 40 | A | | m009 | 1000 | A | |
| 2 | 011-35-3777 | O00000 | m0001 | 40 | A | | m0009 | 500 | A | | | | | |
| 3 | 010-53-6677 | O00009 | m0001 | 80 | C | | | | | | | | | |
| 4 | 011-35-3777 | O00006 | m0001 | 80 | C | | m0009 | 1000 | C | 0. | | | | |
| 5 | 212-32-5487 | O00024 | m0010 | 4 | A | | m0001 | 30 | A | 0. | | | | |
| 6 | 024-31-1357 | O00023 | m0019 | 1 | | | m0007 | | | 0. | | | | |
| 7 | 112-23-3145 | O00007 | m0018 | 1600 | C | | | | | | | | | |
| 8 | 131-25-6721 | O00002 | m0001 | 80 | A | | m0014 | 60 | A | | | | | |
| 9 | 112-23-3145 | O00013 | m0005 | 60 | C | | m0018 | 800 | C | | | | | |
| 10 | 010-53-6677 | O00003 | m0001 | 60 | A | | m0010 | 40 | A | | | | | |
| 11 | 454-12-3621 | O00016 | m0009 | 750 | C | | | | | | | | | |
| 12 | 015-21-2341 | O00034 | m0005 | 60g | | | | | | | | | | |
| 13 | 030-12-3126 | O00035 | m0018 | 1.0g | | | m0020 | 4q.d | | | | | | |
| 14 | 041-23-1515 | O00036 | m0006 | 2.0g | | | m0001 | 40qd | | | | | | |
| 15 | 131-25-6721 | O00008 | m0001 | 40 | C | | m0014 | 100 | C | | | | | |
| 16 | 321-12-5432 | O00037 | m0001 | 4 | | | m0010 | 40q | | | | | | |
| 17 | 414-42-4116 | O00038 | m0023 | 4qd | | | | | | | | | | |
| 18 | 454-12-3621 | O00039 | m0022 | 120m | A | | | | | | | | | |
| 19 | 212-32-5487 | O00029 | m0001 | 80mg | C | | m0010 | 1. | C | | | | | |
| 20 | 010-53-6677 | O00015 | m0001 | 120 | C | | | | | | | | | |
| 21 | 212-32-5487 | O00032 | m0001 | 40mg | C | | m0010 | 6 | C | | | | | |
| 22 | 131-25-6721 | O00014 | m0001 | 80 | C | | m0014 | 120 | C | | | | | |
| 23 | 131-25-6721 | O00020 | m0015 | 40 | A | | | | | | | | | |
| 24 | 324-53-0764 | O00004 | m0000 | 25mg | | | m0001 | 40mg | | | | | | |
| 25 | 010-53-6677 | O00021 | m0010 | 60 | C | | | | | | | | | |
| 26 | 454-12-3621 | O00010 | m0001 | 120m | C | | m0009 | 500 | C | | | | | |
| 27 | 112-23-3145 | O00001 | m0018 | 1200 | A | | m0005 | 20 | A | | | | | |
| 28 | 152-43-2916 | O00011 | m0023 | 40 | C | | m0021 | 400 | C | | | | | |
| 29 | 152-43-2916 | O00017 | m0023 | 120 | C | | | | | | | | | |
| 30 | 152-43-2916 | O00005 | m0021 | 200 | A | | m0023 | 80 | A | | | | | |
| 31 | 011-35-3777 | O00012 | m0001 | 100m | C | | m0009 | 850 | C | | | | | |

FIG. 127

NEWPROBLEM SUMMARY BY PATIENT(MED. CHANGE DATA)
PATIENT ID: 454-12-3621 LAST NAME henderson    BIRTH DATE 02/13/17    MALE
PRIMARY DIAGNOSIS: chronic angina,mild    LAST HOSPITALIZATION 03/24/83
SECONDARY DIAGNOSIS: chf,mild,controlled
TERTIARY DIAGNOSIS: CHR.PANCREATITIS MED CHANGES FOR INVOICE NO:O00010 DATE01/04/87CONDITION:hypertension,mild lasix FROM;40mgm/day  TO:120mmgm/day
low salt FROM:1000mgm/day   TO:500mgm/day MED CHANGES FOR INVOICE NO:O00016   DATE01/11/87CONDITION:hypertension,mild low salt FROM:500mgm/day   TO:750mgm/day

FIG 128

NEWPROBLEM SUMMARY BY PATIENT(MED. CHANGE DATA)
PATIENT ID: 212-32-5487LAST NAME purdy    BIRTH DATE 06/12/30    FEMALE
PRIMARY DIAGNOSIS: acute chf,ashd          LAST HOSPITALIZATION 11/14/87

NO MED CHANGES FOR INVOICE NO:O00024   01/17/87CONDITION:acute thrombosis,legs

MED CHANGES FOR INVOICE NO:O00029   DATE02/05/87CONDITION:acute thrombosis,legs lasix FROM:   30mgm/day   TO:80mgmgm/day
low protein FROM:   4mgm/day   TO:   1.mgm/day MED CHANGES FOR INVOICE NO:O00032   DATE02/09/87CONDITION:acute thrombosis,legs lasix FROM:80mgmgm/day   TO:40mgmgm/day
low protein FROM:   1.mgm/day   TO:6mgm/day

FIG 129

NEWPROBLEM SUMMARY BY PATIENT(MED. CHANGE DATA)
PATIENT ID: 152-43-2916 LAST NAME grover    BIRTH DATE 09/12/51    FEMALE
PRIMARY DIAGNOSIS: acute mi,v. tach.    LAST HOSPITALIZATION 12/13/87
SECONDARY DIAGNOSIS: vent.arrytmias,controlled

---

MED CHANGES FOR INVOICE NO:O00011    DATE01/02/87CONDITION:acute polyarthritis calcium FROM:80mgm/day    TO:40mgm/day
dilantin FROM:200mgm/day    TO:400mgm/day NO MED CHANGES FOR INVOICE NO:O00016    01/13/87CONDITION:acute polyarthritis MED CHANGES FOR INVOICE NO:O00017    DATE01/05/87CONDITION:acute polyarthritis calcium FROM:40mgm/day    TO:120mgm/day

NEWPROBLEM SUMMARY BY PATIENT(MED. CHANGE DATA)
PATIENT ID: 131-25-6721 LAST NAME scruton    BIRTH DATE 07/21/30    FEMALE
PRIMARY DIAGNOSIS: HYPERTENSIVE TIA    LAST HOSPITALIZATION 02/12/80

MED CHANGES FOR INVOICE NO:000008   DAE01/02/87CONDITION:pneumonia lasix FROM:80mgm/day   TO:40mgm/day
inderide FROM:60mgm/day   TO:100mgm/day MED CHANGES FOR INVOICE NO:000014   DATE01/11/87CONDITION:pneumonia lasix FROM:40mgm/day   TO:80mgm/day
inderide FROM:100mgm/day   TO:120mgm/day NO MED CHANGES FOR INVOICE NO: 000013  01/14/87CONDITION:pneumonia

FIG 131

NEWPROBLEM SUMMARY BY PATIENT(MED. CHANGE DATA)
PATIENT ID: 112-23-3145LAST NAME paul          BIRTH DATE 11/13/19     MALE
PRIMARY DIAGNOSIS: copd,mild hypercapnia       LAST HOSPITALIZATION 11/21/86
SECONDARY DIAGNOSIS: chronic renal stones NO MED CHANGES FOR INVOICE NO:000007   01/02/87CONDITION:chronic bronchitis MED CHANGES FOR INVOICE NO:000013   DATE01/12/87CONDITION:chronic bronchitis prednisone FROM:20mgm/day   TO:60mgm/day
aminophyllin FROM:1600mgm/day   TO:800mgm/day NO MED CHANGES FOR INVOICE NO: 000015   01/15/87CONDITION:chronic bronchitis

FIG 132

NEWPROBLEM SUMMARY BY PATIENT(MED. CHANGE DATA)
PATIENT ID: 011-35-3777LAST NAME cusson    BIRTH DATE 02/04/28    MALE
PRIMARY DIAGNOSIS: chf,mild,controlled    LAST HOSPITALIZATION 02/21/87

MED CHANGES FOR INVOICE NO:O00006   DATE01/09/87CONDITION:acute low back pain lasix FROM:40mgm/day   TO:80mgm/day
low salt FROM:500mgm/day   TO:1000mgm/day MED CHANGES FOR INVOICE NO:O00012   DATE01/15/87CONDITION:acute low back pain lasix FROM:80mgm/day   TO:100mmgm/day
low salt FROM:1000mgm/day   TO: 850mgm/day NO MED CHANGES FOR INVOICE NO: O00019   01/18/87CONDITION:ERROR,BAD CONDITION CODE

FIG 133

NEWPROBLEM SUMMARY BY PATIENT(MED. CHANGE DATA)
PATIENT ID: 010-53-6677 LAST NAME williams    BIRTH DATE 12/16/20    MALE
PRIMARY DIAGNOSIS: multiple myeloma    LAST HOSPITALIZATION 12/09/86
SECONDARY DIAGNOSIS: copd,mild hypercapnia NO MED CHANGES FOR INVOICE NO:000015    01/02/87 CONDITION:fever,malaise,anorexia MED CHANGES FOR INVOICE NO:000021    DATE01/06/87 CONDITION:fever,malaise,anorexia low protein FROM:40mgm/day    TO:60mgm/day

FIG 134

```
Record#   DOCTOR            PT_ID      DOB       LNAME               SEX  DIAGNOSIS1
          CODE1  DURATION1  DIAGNOSIS2                  CODE2  DURATION2  DIAGNO
SIS3           CODE3  DURATION3  MEDONE  DESCRIPONE    AMTONE  MEDTWO  DESCRIPTW
O   AMTWO  MEDTHREE  DESCRIPTHR  AMTTHREE  MAJORSURG  PRIOR_HOSP  TREATMENT  LAST_HO
SP   ALLERGIES          NARRATIVE  WEIGHT  SYSTOLIC  DIASTOLIC  DATE
          1     abbott              011-26-3781  05/23/40  cuozzo         F    chronic angi
na,mild         BH0012              5
                                             0
                                                  .F.                    5  .F.    10/05/8
7
          2     abbott              011-35-3777  02/04/28  cusson         M    chf,mild,con
trolled         BH0015              10
                                             0
                                                  .F.                    8  .F.    02/21/8
7
          3     abbott              114-24-3145  01/30/32  cutler         F    chronic angi
na,mild         BH0012              4  chf,mild,controlled   BH0015           2
                                             0
                                                  .F.                    4  .F.    06/21/8
7   penicillin                              Memo        0
          4     abbott              023-15-1643  10/12/20  kriesky        F    CHRONIC PYEL
ONEPHRITIS       CK0023             16 uremia,mild,chronic   BK0013           10
                                             0
                                                  .F.                    7  .F.    05/14/8
6
          5     abbott              131-25-6721  07/21/30  scruton        F    hypertensive
   tia          AV0006              10
                                             0
                                                  .F.                    5  .F.    02/12/8
0   penicillin                              Memo        0
          6     abbott              024-31-1357  10/24/21  kelly          F    rheumatoid a
rth.,acute      CR0028              10 osteoarth.,severe     CR0029           6
                                             0
                                                  .T.                    5  .T.    02/11/8
5
          7     abbott              112-23-3145  11/13/19  paul           M    copd,mild hy
percapnia       CL0024              10 chronic renal stones  CK0026           4
                                             0
                                                  .T.                    4  .T.    11/21/8
6
          8     abbott              013-32-5312  01/23/11  kennedy        F    chronic angi
na,mild         BH0012              5  chf,mild,controlled   BH0015           20 osteoa
rth.,severe              CR0029     20
                                                  .T.                    11 .T.    07/14/8
5   penicillin                              Memo        0
          9     abbott              212-32-5487  06/12/30  purdy          F    acute chf,as
hd              AH0005              10
                                             0
                                                  .F.                    3  .F.    11/14/8
7   none                                    Memo        0
          10    costello            015-21-2341  11/21/24  jenkins        F    lupus nephri
tis, recent     BK0011              2  lupus arthr.,acute    CR0022           1
                                             0
                                                  .F.                    3  .T.    11/21/8
6   none                                    Memo        0
          11    costello            321-12-5432  02/22/16  kendall        F    uremia,mild,
chronc          BK0013              5  chronic pyelonephritis CK0023          12
                                             0
                                                  .T.                    3  .F.    11/21/8
4   penicillin                              Memo        0
          12    costello            152-43-2916  09/12/51  grover         F    acute mi,v.
tach.           AH0001              2  vent.arrytmias,controlled AH0010      1
                                             0
```

FIG. 135

| | | | | | | | | | | |
|---|---|---|---|---|---|---|---|---|---|---|
| 7 pecapnia | 13 | costello CL0024 | | .F. Memo 030-12-3126 4 chronic renal stones 0 | 0 07/12/32 | collins CK0026 | 3 | .T. F | 12/13/8 / / copd,mild hy 9 | |
| 2 dication | 14 | costello BV0017 | | .T. Memo 414-42-4116 4 cardiomegaly,asympt.rhd 0 | 0 05/21/31 | stevens CH0027 | 7 | .T. F | 11/21/8 / / chronic clau 4 | |
| 0 loma, | 15 | costello BB0018 | | .T. Memo 041-23-1515 3 chronic renal stones 0 | 0 12/08/36 | rothstein CK0026 | 3 | .F. F | 10/21/8 / / multiple mye 3 | |
| 5 hd | 16 | costello AH0005 | | .F. Memo 915-32-6167 13 chronic renal stones 0 | 0 11/24/15 | stennis CK0026 | 4 | .F. F | 11/21/8 / / acute chf,as 4 | |
| 4 penicillin ,malignant | 17 | costello BV0016 | | .T. Memo 712-21-3144 3 0 | 0 11/04/50 | kirkland | 8 | .F. F | 10/21/5 / / hypertension 0 | |
| 7 c claudication | 18 | costello AN0007 BV0017 | | .F. Memo 002-31-3621 25 hypertension,malignant 4 | 0 11/19/41 | kemp BV0016 | 3 | .F. F | 09/23/8 / / tia,recent 14 chroni | |
| 7 ,mild,hbp | 19 | hampton BH0021 | | .F. Memo 071-12-5431 9 chronic pyelonephritis 0 | 0 04/23/39 | sakowski CK0023 | 9 | .F. F | 12/01/8 / / cardiomegaly 14 | |
| 6 hypercapnia | 20 | hampton AL0009 | | .T. Memo 162-57-8925 8 osteoarth.,severe 0 | 0 09/17/25 | kendrick CR0029 | 4 | .F. F | 02/21/8 / / copd,severe 10 | |
| 2 na,mild NCREATITIS | 21 | hampton BH0012 BH0020 | | .T. Memo 454-12-3621 7 chf,mild,controlled 5 | 0 02/13/17 | henderson BH0015 | 7 | .T. M | 07/13/8 / / chronic angi 15 CHR.PA | |
| 3 Id,ashd | 22 | hampton AH0005 | | .T. Memo 324-53-0764 2 0 | 0 09/13/53 | canter | 12 | .F. F | 03/24/8 / / acute chf,mi 0 | |
| 7 | 23 | hampton AH0002 | | .T. Memo 152-67-9876 4 0 | 0 04/30/34 | james | 3 | .T. F | 06/24/8 / / acute mi 0 | |
| 4 loma | 24 | hampton BB0018 | | .T. Memo 010-53-6677 5 copd,mild hypercapnia 0 | 0 12/16/20 | williams CL0024 | 8 | .T. M | 11/09/8 / / multiple mye 14 | |
| 6 | | | | .F. Memo | 0 | | 6 | .T. | 12/09/8 / / | |

FIG. 136

| | 25 | hampton | | 334-43-9973 | 03/24/19 | sanderson | | F | chr.pancreat |
| itis | | | BG0020 | 10 chronic renal stones | | | CK0026 | | 16 |
| | | | | 0 | | | | | |
| | | | | | .T. | | | 13 .F. | 10/23/8 |
| 1 | | penicillin | | Memo | 0 | | | | / / |
| | 26 | lisbon | | 222-78-2121 | 12/09/21 | koltrain | | F | acute angina |
| ,severe | | | AH0003 | 2 rheumatoid arth.,acute | | | CR0028 | | 5 |
| | | | | 0 | | | | | |
| | | | | | .T. | | | 4 .T. | 11/21/8 |
| 6 | | | | Memo | 0 | | | | / / |
| | 27 | lisbon | | 616-55-7777 | 04/13/40 | sokoloff | | F | hypertensive |
| tia | | | AN0006 | 5 | | | | | 0 |
| | | | | 0 | | | | | |
| | | | | | .F. | | | 3 .F. | 10/22/8 |
| 4 | | | | Memo | 0 | | | | / / |
| | 28 | lisbon | | 727-43-4333 | 04/21/50 | kennard | | F | metastatic c |
| a | | | AM0008 | 2 | | | | | 0 |
| | | | | 0 | | | | | |
| | | | | | .T. | | | 1 .F. | 12/18/8 |
| 5 | | | | Memo | 0 | | | | / / |
| | 29 | lisbon | | 014-34-5284 | 03/26/43 | schneiderman | | F | acute mi |
| | | | AH0002 | 7 | | | | | 0 |
| | | | | 0 | | | | | |
| | | | | | .F. | | | 1 .F. | 08/01/8 |
| 1 | | | | Memo | 0 | | | | / / |
| | 30 | lisbon | | 256-56-5656 | 06/23/14 | macadam | | F | chronic angi |
| na,mild | | | BH0012 | 7 | | | | | 0 |
| | | | | 0 | | | | | |
| | | | | | .T. | | | 4 .T. | 12/03/8 |
| 6 | | | | Memo | 0 | | | | / / |

FIG. 137

| Record# | CODETYPE | CODE | DESCRIPT |
|---|---|---|---|
| 1 | HA | 000 | crushing chest pain |
| 2 | HA | 001 | heavy chest pain,exercise |
| 3 | HA | 002 | pnd,orthopnea,sob at rest |
| 4 | HB | 003 | easy fatigue,sob,exercise |
| 5 | HB | 004 | weight gain,ankle swell |
| 6 | VA | 005 | acute claudication,rest |
| 7 | RB | 025 | mild jt pain,no swelling |
| 8 | IB | 023 | loss of appetite,malaise |
| 9 | IB | 022 | fatigue,weakness |
| 10 | IB | 030 | anxiety,headache |
| 11 | RB | 017 | intermitt.jt swelling |
| 12 | GA | 006 | acute abd.pain,vomit,weak |
| 13 | GB | 011 | bloody stools,intermitten |
| 14 | GA | 010 | ugi bleed,vomit,weakness |
| 15 | GC | 024 | chronic abd pain,no vomit |
| 16 | GC | 020 | diarrhea,mild |
| 17 | NA | 009 | severe headache,vomiting |
| 18 | KA | 008 | flank pain,vomiting,fever |
| 19 | KB | 013 | polyuria,polydipsia |
| 20 | KA | 012 | cld.urine,frequency,chill |
| 21 | RB | 014 | acute jt.swell,pain,fever |
| 22 | NA | 007 | slurry speech,hand weak |
| 23 | HB | 026 | chr.chest pain,exercise |
| 24 | LA | 016 | sputum,chst.pain,fever |
| 25 | VB | 015 | chr.numbness calf,exerc. |
| 26 | VB | 018 | int.numbness,feet |
| 27 | LA | 019 | sudden chest pain,dyspnea |
| 28 | LC | 021 | cough,mild sputum |
| 29 | KB | 028 | weak stream,frequency |
| 30 | IB | 029 | shaking chills,fever,weak |
| 31 | GA | 027 | ruq pain,colicky,vomiting |

FIG. 138

| Record# | CODETYPE | CODE | DESCRIPT |
| --- | --- | --- | --- |
| 1 | HA | 000 | rales,s3.low b/p,pvc s |
| 2 | HA | 001 | tachycardia,s3 |
| 3 | HB | 002 | s3,third heart sound |
| 4 | HC | 003 | sinus tachycardia |
| 5 | HB | 004 | elevated cvp,low b/p |
| 6 | HB | 005 | cardiomegaly,bilateral |
| 7 | HC | 006 | left vent.hypertrophy |
| 8 | NA | 007 | aphasic,loss of function |
| 9 | NA | 008 | slurry speech,weakness |
| 10 | VA | 009 | loss of pulse,popliteal |
| 11 | VA | 010 | loss of pulse,foot |
| 12 | LA | 011 | hypercapnia,pco2>55 |
| 13 | LB | 012 | hypercapnia,pco2<55 |
| 14 | LB | 013 | lung consolidation |
| 15 | LB | 014 | increased breathsounds |
| 16 | VA | 015 | absent pulse,calf |
| 17 | VB | 016 | weak pulse calf,bilateral |
| 18 | IC | 017 | acute anxiety,diaphoretic |
| 19 | IB | 018 | cachectic,anorectic |
| 20 | GA | 019 | ruq tenderness,mass |
| 21 | GB | 020 | mild abd tenderness |
| 22 | NA | 021 | obtunded,somnolent |
| 23 | RA | 022 | joints tender + swollen |
| 24 | LC | 023 | dry hacking cough |
| 25 | IA | 024 | fever >102 |
| 26 | IB | 025 | fever <=102 |
| 27 | KB | 026 | cloudy urine |
| 28 | KA | 027 | severe flank tenderness |
| 29 | VA | 028 | hypovolemia,low b/p |
| 30 | IA | 029 | septicemia |
| 31 | IB | 030 | bacteremia |

FIG. 139

| Record# | CODETYPE | CODE | DESCRIPT |
|---|---|---|---|
| 1 | H1 | 0000 | acute mi |
| 2 | H1 | 0002 | chf,acute, |
| 3 | H1 | 0003 | angina,no ischemia |
| 4 | H1 | 0004 | early chf |
| 5 | V1 | 0005 | acute thrombosis,legs |
| 6 | R3 | 0030 | acute low back pain |
| 7 | G1 | 0006 | acute abdomen |
| 8 | N1 | 0010 | acute cva |
| 9 | N2 | 0011 | tia,intermittent |
| 10 | V2 | 0013 | malignant hypertension |
| 11 | V3 | 0019 | hypertension,mild |
| 12 | L1 | 0007 | r/o acute pulm embolus |
| 13 | L1 | 0008 | acute pulm insufficiency |
| 14 | L3 | 0023 | chronic bronchitis |
| 15 | L2 | 0016 | acute asthma |
| 16 | E2 | 0012 | ketosis + hyperglycemia |
| 17 | E3 | 0015 | hyperglycemia,glyceruria |
| 18 | L2 | 0017 | pneumonia |
| 19 | I1 | 0014 | septicemia,hypotension |
| 20 | I2 | 0018 | bacteremia |
| 21 | G1 | 0001 | peritonitis |
| 22 | G2 | 0020 | ugi bleed,hypotension |
| 23 | L3 | 0028 | uri,no sputum |
| 24 | G2 | 0022 | lgi bleed |
| 25 | G3 | 0026 | gastritis,mild |
| 26 | K1 | 0009 | acute urinary obstruction |
| 27 | K2 | 0027 | bacteuria,heavy |
| 28 | K3 | 0025 | weak urinary stream |
| 29 | I2 | 0021 | fever,malaise,anorexia |
| 30 | R2 | 0024 | acute polyarthritis |
| 31 | I3 | 0029 | functional dissorder |

FIG. 140

| Record # | DOCTOR EINVOICE | PT_ID TINVOICE | LINVOICE | SINVOICE KINVOICE | INVOICE CONDITION | CATEGORY COMPLAINT1 | CODE FINDING1 | DATE | HINVOIC COMPLAINT2 | FINDING2 |
|---|---|---|---|---|---|---|---|---|---|---|
| 12 | hampton | 010-53-6677 | O00015 | BP2S G I20021 | t | IB022 | IB025 | 01/02/87 | IB0 | 23 |
| 13 | hampton | 010-53-6677 | O00021 | BPS N I20021 | t | LA016 | NA021 | 01/06/87 | IA024 | |
| 4 | abbott | 011-35-3777 | O00006 | BP1S P R30030 | t | VB018 | VA015 | 01/09/87 | | |
| 5 | abbott | 011-35-3777 | O00012 | BP2UMH R30030 | t | VB018 | VA009 | 01/15/87 | IB0 | 23 |
| 19 | | 011-35-3777 | O00019 | A2 M BB0007 | t | VA015 | VA015 | 01/18/87 | | |
| 6 | abbott | 112-23-3145 | O00007 | CP3UIE L30023 | t | LC021 | LB013 | 01/02/87 | | |
| 7 | abbott | 112-23-3145 | O00013 | CP4SIP L30023 | t | LC021 | LC023 | 01/12/87 | IB0 | 22 IB018 |
| 8 | abbott | 112-23-3145 | O00015 | CP4S G L30023 | t | LC021 | LB014 | 01/15/87 | IB0 | 22 |
| 9 | abbott | 131-25-6721 | O00008 | AP2U F L20017 | t | IB029 | LB013 | 01/02/87 | LA0 | 16 IA024 |
| 10 | abbott | 131-25-6721 | O00014 | AP2S N L20017 | t | LC021 | LC023 | 01/11/87 | | IA024 |
| 11 | abbott | 131-25-6721 | O00031 | AP4S L20017 | t | LC021 | LB013 | 01/14/87 | | |
| 16 | costello | 152-43-2916 | O00011 | AP2S F R20024 | t | RB017 | RA022 | 01/02/87 | | IB025 |
| 18 | costello | 152-43-2916 | O00016 | AP2S I R20024 | t | RB025 | | 01/13/87 | | |
| 17 | costello | 152-43-2916 | O00017 | AP3S H R20024 | t | RB017 | RA022 | 01/05/87 | IB0 | 29 |
| 1 | abbott | 212-32-5487 | O00024 | A33S C V10005 | t | VB018 | VA028 | 01/17/87 | | |
| 2 | abbott | 212-32-5487 | O00029 | A32S B V10005 | t | VB018 | VA010 | 02/05/87 | | VA015 |
| 3 | abbott | 212-32-5487 | O00032 | A32U B V10005 | t | VB015 | VB016 | 02/09/87 | | IB025 |
| 14 | hampton | 454-12-3621 | O00010 | AP2 H V30019 | t | IB030 | IC017 | 01/04/87 | | |
| 15 | hampton | 454-12-3621 | O00016 | AP2 F V30019 | t | NA009 | HB005 | 01/11/87 | LA0 | 19 HC006 |

FIG. 141

| Record # | DOCTOR | PT_ID | INVOICE | CATEGORY | CODE | DATE | HINVOICE | EINVOICE | TINVOICE | LINVOICE | SINVOICE | CONDITION | COMPLAINT1 | FINDING1 | COMPLAINT2 | FINDING2 | KINVOICE |
|---|---|---|---|---|---|---|---|---|---|---|---|---|---|---|---|---|---|
| 1 | abbott | 131-25-6721 | O00031 | A33S | G | f | 02/03/87 | | | | | | | | | | |
| 2 | abbott | 131-25-6721 | O00027 | A32U | E | f | 01/27/87 | | | | | | | | | | |
| 3 | | 131-25-6721 | O00012 | A32S | D | f | 01/20/87 | | | | | | | | | | |
| 4 | abbott | 212-32-5487 | O00024 | A33S | C | t | 01/17/87 | | | | | V10005 | VB018 | VA028 | | | |
| 5 | abbott | 212-32-5487 | O00029 | A32S | B | t | 02/05/87 | | | | | V10005 | VB018 | VA010 | | V | A015 |
| 6 | abbott | 212-32-5487 | O00032 | A32U | B | t | 02/09/87 | | | | | V10005 | VB015 | VB016 | | I | B025 |
| 7 | hampton | 324-53-0764 | O00036 | A33S | H | f | 03/19/87 | | | | | | | | | | |
| 8 | hampton | 324-53-0764 | O00033 | A31S | | f | 03/12/87 | | | | | | | | | | |
| 9 | hampton | 324-53-0764 | O00038 | A33S | G | f | 03/26/87 | | | | | | | | | | |
| 10 | hampton | 324-53-0764 | O00041 | A32S | G | f | 04/01/87 | | | | | | | | | | |
| 11 | hampton | 324-53-0764 | O00044 | A33U | A | f | 04/08/87 | | | | | | | | | | |
| 12 | abbott | 011-35-3777 | O00006 | BP1S | P | t | 01/09/87 | | | | | R30030 | VB018 | VA015 | | | |
| 13 | abbott | 011-35-3777 | O00012 | BP2UMH | | t | 01/15/87 | | | | | R30030 | VB018 | VA009 | IB023 | | |
| 14 | abbott | 112-23-3145 | O00007 | CP3UIE | | t | 01/02/87 | | | | | L30023 | LC021 | LB013 | | | |
| 15 | abbott | 112-23-3145 | O00013 | CP4SIP | | t | 01/12/87 | | | | | L30023 | LC021 | LC023 | IB022 | I | B018 |
| 16 | abbott | 112-23-3145 | O00015 | CP4S | G | t | 01/15/87 | | | | | L30023 | LC021 | LB014 | IB022 | | |
| 17 | abbott | 131-25-6721 | O00008 | AP2U | F | t | 01/02/87 | | | | | L20017 | IB029 | LB013 | LA016 | I | A024 |
| 18 | abbott | 131-25-6721 | O00014 | AP2S | N | t | 01/11/87 | | | | | L20017 | LC021 | LC023 | | I | A024 |
| 19 | abbott | 131-25-6721 | O00031 | AP4S | | t | 01/14/87 | | | | | L20017 | LC021 | LB013 | | | |
| 20 | hampton | 010-53-6677 | O00015 | BP2S | G | t | 01/02/87 | | | | | I20021 | IB022 | IB025 | IB023 | | |

FIG. 142

|   |    |         |              |        |      |   |   |          |       |   |
|---|----|---------|--------------|--------|------|---|---|----------|-------|---|
|      | 21 | hampton  | 010-53-6677 | O00021 | BPS  | N | t | 01/06/87 |       |   |
| A024 |    |          | I20021       |        | LA016 |   |   |          |       | I |
|      | 22 | hampton  | 454-12-3621 | O00010 | AP2  | H | t | 01/04/87 |       |   |
|      |    |          | V30019       |        | IB030 |   |   |          | IC017 |   |
|      | 23 | hampton  | 454-12-3621 | O00016 | AP2  | F | t | 01/11/87 |       |   |
| C006 |    |          | V30019       |        | NA009 |   |   | HB005    | LA019 | H |
|      | 24 | costello | 152-43-2916 | O00011 | AP2S | F | t | 01/02/87 |       |   |
| B025 |    |          | R20024       |        | RB017 |   |   | RA022    |       | I |
|      | 25 | costello | 152-43-2916 | O00017 | AP3S | H | t | 01/05/87 |       |   |
|      |    |          | R20024       |        | RB017 |   |   | RA022    | IB029 |   |
|      | 26 | costello | 152-43-2916 | O00016 | AP2S | I | t | 01/13/87 |       |   |
|      |    |          | R20024       |        | RB025 |   |   |          |       |   |
|      | 27 |          | 011-35-3777 | O00019 | A2   | M | t | 01/18/87 |       |   |
|      |    |          | BB0007       |        | VB015 |   |   | VA015    |       |   |

FIG. 143

NEWPROBLEM SUMMARY BY PATIENT(physical data)
PATIENT ID: 454-12-3621LAST NAME henderson    BIRTH DATE 02/13/17    MALE
PRIMARY DIAGNOSIS: chronic angina,mild    LAST HOSPITALIZATION 03/24/83
SECONDARY DIAGNOSIS: chf,mild,controlled INVOICE NO.:O00010DATE 01/04/87   CONDITION hypertension,mild
SYSTOLIC PRESSURE 150DIASTOLIC PRESSURE 89
COMPLAINT(major) was anxiety,headache
FINDING major was acute anxiety,diaphoretic INVOICE NO.:O00016DATE 01/11/87   CONDITION hypertension, mild
SYSTOLIC PRESSURE 155DIASTOLIC PRESSURE 85
COMPLAINTS WERE severe headache,vomiting and sudden chest pain,dyspnea
FINDINGS WERE cardiomegaly,bilateral and left vent.hypertrophy

FIG 144

NEWPROBLEM SUMMARY BY PATIENT(physical data)
PATIENT ID: 212-32-5487LAST NAME purdy       BIRTH DATE 06/12/30      FEMALE
PRIMARY DIAGNOSIS: acute chf,ashd            LAST HOSPITALIZATION 11/14/87

INVOICE NO.:O00024DATE 01/17/87   CONDITION acute thrombosis,legs
SYSTOLIC PRESSURE 160DIASTOLIC PRESSURE 100
COMPLAINT(major) was int.numbness,feet
FINDING major was hypovolemia,low b/p INVOICE NO.:O00029DATE 02/05/87   CONDITION acute thrombosis,legs
SYSTOLIC PRESSURE 155DIASTOLIC PRESSURE 95
COMPLAINT(major) was int.numbness,feet
FINDINGS WERE loss of pulse,foot and absent pulse,calf INVOICE NO.:O00032DATE 02/09/87   CONDITION acute thrombosis,legs
COMPLAINT(major) was chr.numbness calf,exerc.
FINDINGS WERE weak pulse calf,bilateral and fever <=102

FIG 145

NEWPROBLEM SUMMARY BY PATIENT(physical data)
PATIENT ID: 152-43-2916 LAST NAME grover    BIRTH DATE 09/12/51    FEMALE
PRIMARY DIAGNOSIS: acute mi,v. tach.    LAST HOSPITALIZATION 12/13/87
SECONDARY DIAGNOSIS: vent.arrytmias,controlled

---

INVOICE NO.:O00011 DATE 01/02/87   CONDITION acute polyarthritis
SYSTOLIC PRESSURE 160 DIASTOLIC PRESSURE 95
COMPLAINT(major) was intermitt.jt swelling
FINDINGS WERE joints tender + swollen and fever <=102

---

INVOICE NO.:O00016 DATE 01/13/87   CONDITION acute polyarthritis
SYSTOLIC PRESSURE 140 DIASTOLIC PRESSURE 90
COMPLAINT(major) was mild jt pain,no swelling
there were no significant findings

---

INVOICE NO.:O00017 DATE 01/05/87   CONDITION acute polyarthritis
SYSTOLIC PRESSURE 145 DIASTOLIC PRESSURE 100
COMPLAINTS WERE intermitt.jt swelling and shaking chills,fever,weak
FINDING major was joints tender + swollen

FIG 146

NEWPROBLEM SUMMARY BY PATIENT(physical data)
PATIENT ID: 131-25-6721 LAST NAME scruton     BIRTH DATE 07/21/30     FEMALE
PRIMARY DIAGNOSIS: hypertensive tia           LAST HOSPITALIZATION 02/12/80

INVOICE NO.:O00008 DATE 01/02/87   CONDITION pneumonia
SYSTOLIC PRESSURE 160 DIASTOLIC PRESSURE 90
COMPLAINTS WERE shaking chills,fever,weak and sputum,chst.pain,fever
FINDINGS WERE lung consolidation and fever >102

INVOICE NO.:O00014 DATE 01/11/87   CONDITION pneumonia
SYSTOLIC PRESSURE 169 DIASTOLIC PRESSURE 90
COMPLAINT(major) was cough,mild sputum
FINDINGS WERE dry hacking cough and fever >102

INVOICE NO.:O00031 DATE 01/14/87   CONDITION pneumonia
SYSTOLIC PRESSURE 160 DIASTOLIC PRESSURE 95
COMPLAINT(major) was cough,mild sputum
FINDING major was lung consolidation

FIG 147

NEWPROBLEM SUMMARY BY PATIENT(physical data)
PATIENT ID: 112-23-3145LAST NAME paul    BIRTH DATE 11/13/19    MALE
PRIMARY DIAGNOSIS: chronic renal stones    LAST HOSPITALIZATION 11/21/86
SECONDARY DIAGNOSIS: copd,mild hypercapnia INVOICE NO.:O00007DATE 01/02/87   CONDITION chronic bronchitis
COMPLAINT(major) was cough,mild sputum
FINDING major was lung consolidation INVOICE NO.:O00013DATE 01/12/87   CONDITION chronic bronchitis
COMPLAINTS WERE cough,mild sputum and fatigue,weakness
FINDINGS WERE dry hacking cough and cachectic,anorectic INVOICE NO.:O00015DATE 01/15/87   CONDITION chronic bronchitis
COMPLAINTS WERE cough,mild sputum and fatigue,weakness
FINDING major was increased breathsounds

FIG 148

NEWPROBLEM SUMMARY BY PATIENT(physical data)
PATIENT ID: 011-35-3777 LAST NAME cusson     BIRTH DATE 02/04/28     MALE
PRIMARY DIAGNOSIS: chf,mild,controlled     LAST HOSPITALIZATION 02/21/87

---

INVOICE NO.:O00006 DATE 01/09/87   CONDITION acute low back pain
COMPLAINT(major) was int.numbness,feet
FINDING major was absent pulse,calf

---

INVOICE NO.:O00012 DATE 01/15/87   CONDITION acute low back pain
COMPLAINTS WERE int.numbness,feet and loss of appetite,malaise
FINDING major was loss of pulse,popliteal

---

INVOICE NO.:O00019 DATE 01/18/87   CONDITION
COMPLAINT(major) was chr.numbness calf,exerc.
FINDING major was absent pulse,calf

FIG 149

NEWPROBLEM SUMMARY BY PATIENT(physical data)
PATIENT ID: 010-53-6677  LAST NAME williams         BIRTH DATE 12/16/20     MALE
PRIMARY DIAGNOSIS: multiple myeloma           LAST HOSPITALIZATION 12/09/86
SECONDARY DIAGNOSIS: copd,mild hypercapnia INVOICE NO.:O00015  DATE 01/02/87   CONDITION fever,malaise,anorexia
COMPLAINTS WERE fatigue,weakness and loss of appetite,malaise
FINDING major was fever <=102

INVOICE NO.:O00021  DATE 01/06/87   CONDITION fever,malaise,anorexia
COMPLAINT(major) was sputum,chst.pain,fever
FINDINGS WERE obtunded,somnolent and fever >102

FIG. 150

CLINICAL DATABASE OF CLASSIFIED OUT-PATIENTS FOR TRACKING PRIMARY CARE OUTCOME

This application is a continuation of Ser. No. 07/276,414 filed Jan. 23, 1989 abandoned.

BACKGROUND TO THE INVENTION

American medical care has been placing this country under a tremendous financial strain and will continue to absorb an increasingly higher share of its resources into the indefinite future. Over the past 20 years its average cost increases, primarily of the institutional kind (hospitals, lab tests etc.), has risen annually at over twice the rate of inflation compared to the rest of the economy and will remain for the forseeable future as the most expensive sector of our consumer-driven society.

The reasons are chronic and multiple and in most cases simply reflect and stem from cultural features unique to 20th century American society. For example, an increasingly ageing population that will continue to consume a disproportionate share of our clinical resources, increased leisure time by all age groups that allows for such discretionary indulgences as more 'health care' consumption that only creates more demand on a medical care system that is already oversubscribed, the virtual doubling of american medical school graduates since the early 70's along with almost no effort to limit the entry of foreign medical graduates which in itself greatly expands the size of an already very elastic medical marketplace (i.e. the number of cars or refrigerators we buy is pretty fixed but not the number of times we might see a doctor). There is also the ever-present fear by doctors and hospitals of costly malpractice litigation that increases both front-end costs by higher insurance premiums and higher day-to-day costs by the defensive use of expensive tests and high-tech procedures done simply to lessen the risk of and protect against any future lawsuits.

In the wake of this dilemma in an open and free society several measures have been initiated separately and independently over time to curb costs and even improve quality of care. Unfortunately none have succeeded and the costs continue to skyrocket. That's primarily because none have addressed how we actually examine in a precise and large scale way how the daily practice of medicine is delivered and what the results actually are, especially on a comparative basis.

Up until now the 'solutions' have only been regulatory and administrative in nature that in fact only interfere in the natural practice of every day medicine without a mechanism for actually assessing what has happened on a large-scale and precise analytical basis. And in many cases has only led to divisiveness and polarization amongst health care providers.

For example, the corporatization of American medicine by HMO's that use high-powered ad techniques and the 'magic' of fixed pre-payments for subscribers as a way to control costs while never publicly acknowledging how their member doctors are gently co-erced to hold the line in the trenches by rationing through the limiting of tests and even office visits. But several HMO's, in Massachusetts for example, have already begun to experience financial problems and have been forced to merge due to an oversubcription by the elderly and the resultant encounter of greater than projected costs through vast and unanticipated increases in the use of resources. Also, despite the promise of cost reduction through so-called health care competition, the appearance of 'alternate health care providers' like nurse practitioners and physicians assistants has been a failure in controlling costs primarily because it too only increases the size of the medical marketplace while also causing confusion over who does what, turf battles and duplication of effort. It has also caused a massive over-concentration of health care providers since these paraprofessionals always seem to locate in areas that are already heavily populated by doctors. As another example of the failure to control the cost of something as unpredictable and complicated as medicine, and therefore its consumption, is the lack of measurable success with DRG's or Diagnostic Related Groups. Basically, they are a method for assigning costs and fees to certain disease categories that's used by hospitals and insurance companies for pre-determining how much they should spend during a hospitalization. As such, they only address one aspect of medical care; hospitalization, are unable to examine on a large and precise basis the individual practices of doctors on a comparative basis and they create artificial boundaries that are overly and too neatly drawn between medical conditions that are often related and overlap clinically, and are naturally unable to take into account the many hidden uncertainties that frequently appear in clinical medicine and as such deal poorly if at all with unforseen complications. They have been operative for some time but they have failed to control costs while adding nothing to the quality of medical care.

None of the above measures have succeeded because they are superficial, politically expedient and often costly in themselves due to their promotion of additional regulations and new agencies that increase the administrative and bureacratic cost of medical care. Unfortunately none of them are designed to look directly at and examine what actually happens on a day-to-day basis at the level of the patient-physician encounter at that point in the medical care system that has traditionally been the most responsible for eventually determining how much we will spend; the primary care, general practice, out-patient setting. Until now, no one has bothered to look at what happens and why at the level of the primary care out-patient physician practice where all the medical-consumer habits, trends and diseases originate.

Primary care, out-patient medicine is the most frequent point of contact in the medical care system and until a method for its precise and large-scale analysis is found, a rational basis for cost control in medicine will never be obtained.

What is therefore needed is an automated method for looking at what doctors do, their observations, tests, treatments, and diagnoses, etc., on a daily basis to a large, organized and well defined population of out-patients in a primary care setting under clearly spelled out and uniform conditions and circumstances. A kind of primary care 'audit trail system' that uses the power and flexibility of the computer to collect, store and process data under pre-defined conditions that enable applying uniform standards of analyzing care by doctors to patients in regard to both outcome and resource utilization.

My computer-based system, with its database and programs, is a model for demonstrating the feasibility of doing just that. It is an information-management-system for the analysis of clinical data processed by the computer in such a way as to reflect what has happened during the natural and traditional way out-patient medicine is conducted. It records the identical set of data under an identical method for all patients and then processes that data for specific groups of out-patients according to uniform criteria that create specific aspects of primary care medicine through the 'customized' design of computer-program software.

Both out-patients and their doctors are members of the database. Each out-patient is placed into one of three diagnostic categories for the purpose of selective data processing that depends upon the single or combined value of up to three chronic diagnosis any one patient may have. Other elements of the system are a family of related files that store separate, related aspects and items of clinical medicine, many of which are linked to each out-patient as individual clinical attributes that contribute to the total medical profile of each out-patient. And as with other types of more common database systems, this one has two general types of files; transactional and inventory. The former are event-based, its records accumulating over time through data entry programs and how many of them any one patient has depends upon the condition or disease activity of that out-patient. On the other hand the inventory type files contain a fixed number of records and consist of data items that are used to affix those clinical attributes appropriate to any out-patient, i.e. symptoms, diagnosis, medicines, etc. that can clinically define them at any point in time.

Such a database, with its integrated set of related files of both types, then serves as the informational base for the processing operations conducted by a separate set of computer programs (other than the data entry ones) that are designed to simulate or mimic aspects or conditions of out-patient medicine. With such distinct and 'logical views' that create special facets of out-patient clinical medicine drawn by such programs that now process that centralized pool of integrated clinical data stored in separate files, it becomes possible to apply precise and large-scale analysis uniformly from an outcome based perspective while also being able to look at what doctor did what and for what reason. Under uniform and standardized conditions you can now analyze clinical results about any number of out-patients from both the same diagnostic group or make comparative results between different diagnostic groups. And you can establish a level of priority in the analysis of results and resource usage that includes a measure of expectation by the selective processing of different diagnostic groups or out-patients within any group that differ by chronic diagnosis.

In short, my model database system collects and loads the same set of clinical data in the same way for out-patients classified according to diagnostic groupings. The data reflects the natural activity that normally occurs every day in a primary care setting. The data is then processed by an associated set of programs that select for certain clinical conditions and criteria that by design create special aspects of out-patient medicine. For example, viewing lab test results ordered during a special type of office visit in conjunction with other salient clinical data observed during that same visit that then enable determining if said lab tests ordered were justified in view of what that doctor observed about that out-patient. As another example, a computer program in this model system enables one to look at both symptoms and medications ordered during a special type of office visit for a group of patients with the same chronic diagnosis who are being cared for by the same doctor. In this way analysis is possible under conditions uniformly applied to groups of patients and doctors from highly focused aspects of out-patient, primary care medicine that make such analysis easy because it creates identical reference points for comparisons.

Such a model system, as outlined in this specification, can at least be used for one important purpose; to supplement the traditional 'non-system' of medical record keeping. It can remedy the current system which, as everyone knows, is non-integrated and non-standardized, which is manually based and highly individualized from physician to physician depending upon that physician's personal bias or style. And as such is totally incapable of being viewed from specially created clinical circumstances through program design for special emphasis or on a large scale basis that can offer comparative analysis.

My model, computer-based system doesn't have to replace anything and it doesn't have to interfere with the way things have been done. But it offers, by way of proven technology, a new, different way of looking and analyzing the outcome and resource usage at the most frequent and critical point of our health care system from the long-term point of view: the primary care, out-patient setting.

SUMMARY OF THE INVENTION

A computerized clinically oriented out-patient medical database for the retrospective and outcome-based tracking and monitoring of both quality of care and the proper utilization of clinical resources from a variety of medical aspects and conditions that characterize a primary care setting.

This model 'audit trail' system, its data pool, file relationships and programs that process the data to load, manipulate, print and query the clinical data along with its method of triaged data processing by out-patient diagnostic categories, now enables the unlimited versatility of storing, accessing and reporting computer-based clinical data for classified out-patients, both individually and by groups, and from a variety of medical aspects or clinical perspectives that allow for special emphasis or particular focus. For example, detecting the overuse of office visits by out-patients pre-selected by diagnostic category, monitoring the actions by physicians during protracted episodes of out-patient illnesses, and the separate reporting of physical, medication and lab test results from the same office visits selected by the primary reason, acute or chronic diagnosis, for the office visit.

Such a system can readily supplement the only other current, highly individualized and vagaried record-keeping 'non-system' doctors have traditionally used. An anachronism in today's computer age since the way in which patient data is viewed and expressed often reflects personal physician biases. For instance it is always looked at on a patient by patient basis, isolated and in a non-comparative way, manually and without the capacity for special or particular clinical emphasis and in the absence of fixed and uniform standards that enable legitimate comparisons amongst and between the same and differently classified patient groups.

The out-patients of this database would ideally be fixed adult subscribers to a Managed Health Care Plan such as an HMO with each patient assigned to one of several database doctors. Upon a first record creation a new patient automatically classified into one of three diagnostic categories depending upon the nature and the amount of up the three chronic, long-term diagnosis any out-patient may have. The classification is based upon the relative positions of that patient's diagnosis in reference to the other chronic diagnoses' present in a table of chronic diagnosis that contain the entire pool of diagnosis that any database patient may have and which is arranged according to a sorting of the chronic diagnosis by prognosis or clinical urgency. If an out-patient is placed into the uppermost diagnostic category of the chronic diagnosis table, it is because that patient has at least one diagnosis from that highest table category and is then ranked for the purpose of selective data processing within the highest priority group. Since the classification enables the ranking and therefore the selection of out-patients by diagnostic categorys into priority groups, the classification itself serves as an initial clinical focus for many programs in this system's data processing because it enables anyone to view the resultant data from the kind of clear reference point that clinical urgency or prognosis is. And therefore enabling users of the system to be alerted sooner and easier to the need for more immediate attention to such priority based clinical data.

After the initial out-patient record selection, each program then contains deeper level code for specifying further criteria and conditions that further limit the data generated to a particular and narrow aspect of out-patient medicine. For example, a program might first select only office visit records of those out-patients from the highest ranked diagnostic category and then further limit the clinical aspect to only cardiac patients within that highest priority group, excluding for instance patients with fulminant lupus or bad liver disease, etc.. Then through additional program code it may further limit the clinical aspect or condition to only those office visit (records) in which those cardiac patients were documented to be very symptomatic (ill). And then, as a final criteria or facet, to complete the particular clinical 'configuration', the program may only select the physical data (signs and symptoms) observed and any medication changes enacted by the physician during those office visits, and excluding other data from being processed in this program that is also present in each office visit record. And it is then possible to limit the information generated to only a few database doctors or even just one in particular.

This kind of 'configurating' in which narrow and specific aspects of out-patient primary care medicine can be drawn by individual facts being combined together through sequential program criteria is, thanks to database software, a process that is potentially unlimited in its versatility.

It should also be noted that this computerized medical database system, with its adaptation of business database software, is analogous to a standard and more familiar computerized accounts receivable section of a mail ordering business, a traditional application for database software. In the first place, the office visit record parallels the pivotal nature of the orders/invoice record since they both represent each system's most frequent, initial contact point as principal data entry processes and the primary source from which other related data records are generated. Secondly, and as a derivative of the first example, both the medicine-activity and lab test records are similar to a payments/financial record since they reflect actions subsequent to the initial, respectively, office visit and the orders/incoice encounters.

Thirdly, the system medication and physical data files are both analogous in in purpose and function to an inventory or parts file. They both contain a fixed number of 'stock' or attributes that reflect the distinct nature of the two systems; clinical features of patients in the former and the consumer choice of customers in the latter. Lastly, the analogy between the master medical record and the customer record since they contain both current and biographical data for use as reference information with other data for each individual patient or customer.

A full elaboration of the features and functions of this invention are found in the description section of the specification. There is a complete narration of the preferred embodiments as represented by the program flow diagrams of FIGS. 17–55 and another set of descriptions that refer to the drawings of FIGS. 1–16 and 56–150 which include both the system's data files and sample input/output data used with and generated by the system's computer programs illustrated by FIGS. 1 and 2.

BRIEF DESCRIPTION OF THE DRAWINGS
(BDD)

Referring to FIG. 3, the classification table of chronic long-term diagnosis, chrmedli.dbf, arranged by increasing clinical urgency or worsening prognosis in ascending order. Each out-patient is classified into one of three diagnostic categories depending upon the relative positions in the table of up to three chronic diagnosis any out-patient may have. The first character designates to which of three diagnostic categories that table entry belongs while the second indicates its clinico-pathological group. The assignment of an A category diagnosis to any patient automatically places that patient in the A diagnostic category while the presence of three chronic diagnosis assigned to any patient that are all from either B or C category automatically places that patient into the next higher (A or B) category.

Referring to FIG. 4, the system's primary care office visit record, encounte.dbf, and the principal unit of information for most of the system's data processing. The TYPE field is either 'S' for scheduled or 'U' for unscheduled and the STATUS field will contain 1 of 5 possibilities numbered 1–5; 1 for normal or base-line, 2 for mild severity of symptoms, 3 for serious, severe symptoms, 4 for clinical improvement from most previous visit and 5 for hospitalization ordered from that visit. Each record may have up to three chronic diagnosis and in cases were an out-patient has only one, that chronic diagnosis alone, by virtue of its relative position in the table, determines which diagnostic category that patient is to be placed in. Otherwise it is usually the diagnosis from the highest category in reference to the table that determines the diagnostic category of that patient.

Figure 1:
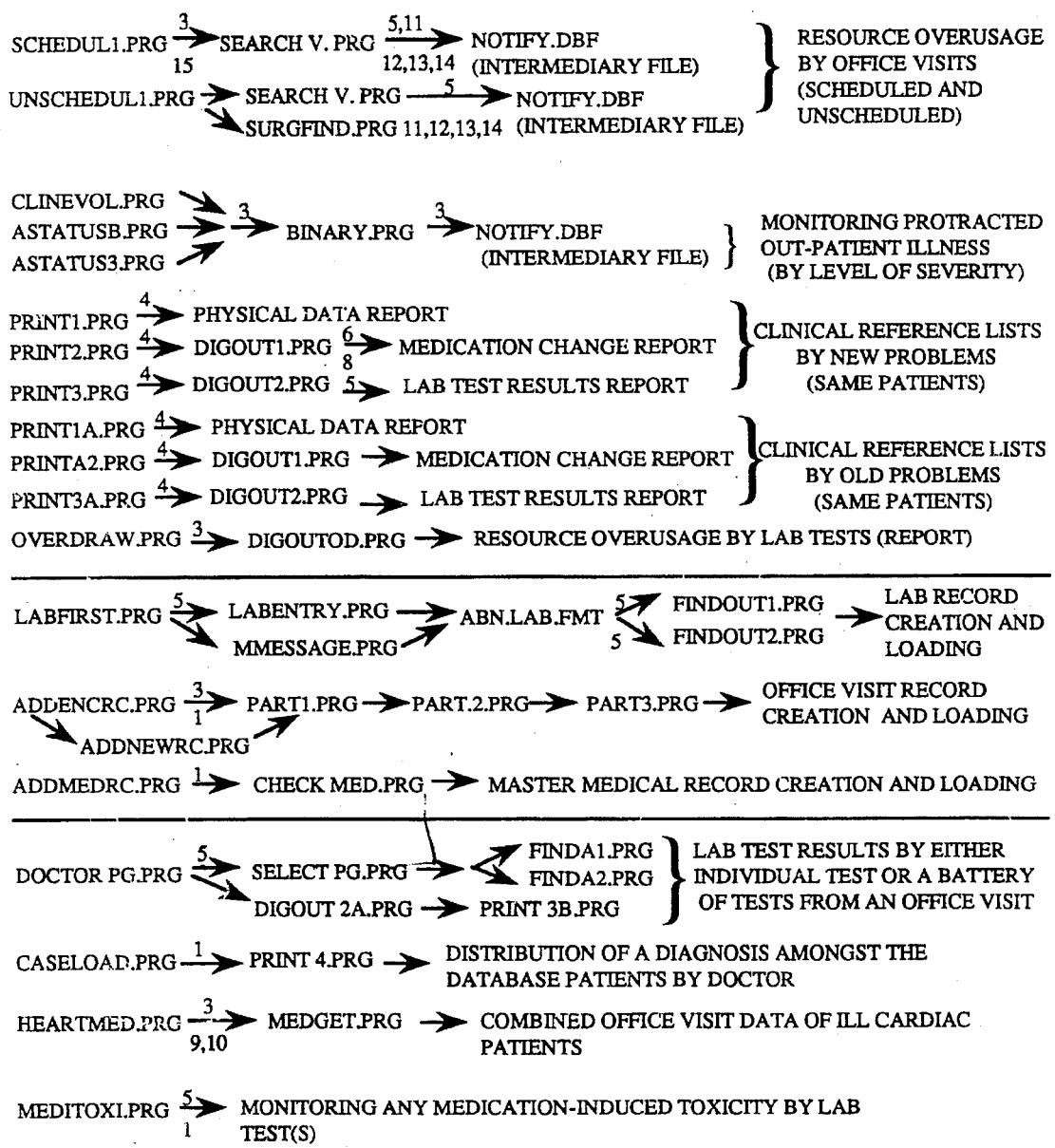
Referring to FIG. 1, a complete list of the system's computer programs (data processing routines) grouped into three categories. The main calling programs are on the left with each of it's subroutines to the right. One subroutine may be associated with more than one main calling program and any one main calling program may have more than one subroutine. The top group are intermediary routines that compile data into new, intermediary records, the middle group are data entry routines and the bottom group are pre-written queries. The numbers indicate the main files, illustrated in FIG. 2, that are used in each of the programs listed.
Figure 2:
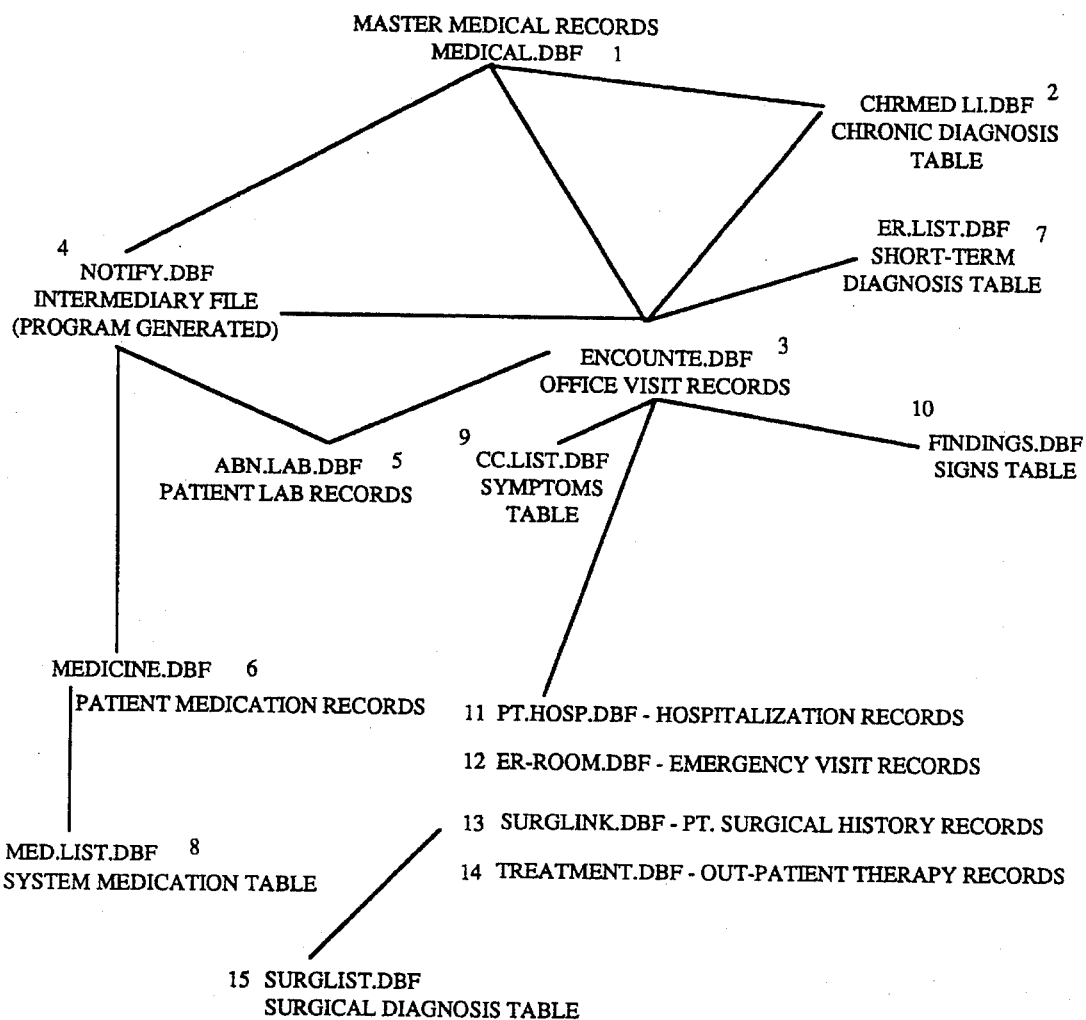
Referring to FIG. 2, an overview of the system's database files and their general inter-relationships during data processing. Files numbered 2,7,8,9,10 and 15 are inventory in type from which a variety of out-patient clinical attributes are obtained and used to profile each patient. The rest are transactional in nature and reflect the extent and nature of out-patient clinical activity over time.

The CONDITION field of the office visit record will contain either a chronic long term diagnosis or an acute short-term diagnosis as the main or primary reason for that office visit. If it is a chronic one then it will be any of up to three chronic diagnosis that patient already has while a short-term diagnosis indicates either a new as yet uncharacterized problem or possibley a complication or 'flare up' of an existing chronic diagnosis. Note the presence of four physical data fields, each as 5 digit codes for indicating up to 2 signs (findings) and 2 symptoms (complaints) with both types of physical data items derived from their respective signs and symptoms tables. Each office visit record is most uniquely identified by it's six digit INVOICE field since it is entirely possible that any out-patient may be seen for an office visit twice in the same day.

Referring to FIG. 5, the system's intermediary file, notify.dbf. As a derivative file each record is created during program execution, and the data compiled from and representing one office visit record. The records are then used as basic unit of information for other system programs. Which fields contain data and the nature of that data depends upon which program type was responsible for creating the notify.dbf records. The type of data the notify.dbf records contain consist of data compiled and written from the original office visit records of the encounte.dbf file and 'conditional' data depending upon the nature of the program's input data. Note the CATEGORY and the CODE fields. The category field generally identifies the name of the program responsible for creating that notify.dbf record, the diagnostic category of the out-patient whose office visit record was being processed and that notify.dbf record represents, clinical status of that out-patient at the time of the office visit, whether the visit was scheduled or not, a single letter code for indicating the nature of what the physician did during that visit, whether there was any injection during the visit and by what route. If the program responsible for the creation of notify.dbf records is intended to find unscheduled office visits that occur consecutively by any out-patient then the above field will contain, alternatively, an integer for indicating the consecutive number for that unscheduled visit. If the programs that identify protracted out patient illnesses are being run then a problem resolution indicator will be encoded in that field during processing. The data in the CODE field also depends upon what program type is being run and therefore responsible for creating the office visit derived records of notify.dbf It can be used to indicate that absolute justification for an early scheduled office visit has been found or the occurrence of one or more consecutive unscheduled office visits for any out-patient.

Referring to FIG. 6, the system's master medical record file, medical.dbf.. There is one for each out-patient in the database and it stores both current diagnostic and medication data and background, biographical information. The data field named DIAGNOSIS1 store that patient's highest category diagnosis, if there are two or more diagnosis from the same category then the one from the highest position in the chronic diagnosis reference table occupies that field position. Similarly, any chronic diagnosis present in the DIAGNOSIS2 field will be from a higher position in the chronic diagnosis reference table than any one in the DIAGNOSIS3 field. The MEDFLAGN and MEDINV(N) fields are used to indicate the last time that chronic diagnosis was assigned to that patient. It is a tracking device since it 'points' to that office visit (record) during which that diagnostic change, addition, etc. occurred and therefore when that patient's master medical record was updated t reflect that activity. Note the full documentation of all 3 possible current medications. The last 3 fields are for both the first recorded office visit blood pressure (top) and bottom readings) and the date of that master medical record creation.

Referring to FIG. 7, the system's laboratory test file, abn_lab.dbf. The date field refers to when the tests were done since the date ordered is the same date as the office visit or emergency room visit from which the tests were ordered. Each lab record has two invoices, one denoting it as a lab test invoice and the other for representing either the office visit or emergency room visit parent (or source) record that serves as a cross-link. There are 14 fields for storing the results of 14 possible types of lab tests. Each field is divided into two segments, one for storing the numeric amount with abnormal results and the other for the historical or parameter data for profiling the track record of that lab test's results over time. The parameter data consists of 3 letters that encode a compilation of prior results for any abnormal test result and is determined by obtaining such aspects of prior results as date and value of first abnormality, date and value of last abnormality, consistency of the results and the most recent result of that test for comparison. The three single letters that constitute the parameter data that accompanys the abnormal result data in each lab test field are, from left to right, duration of the abnormality (chronic, acute, intermediate), intensity of abnormality and comparison to most recent result (improved, worsened, etc.). Normal results contain only a single letter in the first position of the parameter field and another in the first position of the numeric field for comparison with any most recent result for that test.

Referring to FIG. 8, the system's short-term, acute or new problem diagnosis table, er_list.dbf. It is identical in basic structure to the 6 digit chronic diagnosis code except that the clinico-pathological group indicator is in the first position instead of the second. These entries are for alternate use in the CONDITION CODE field of the office visit record in instances of a new clinical problem or an as yet uncharacterized complication of an established, chronic diagnosis, and under those conditions replaces a chronic diagnosis as the primary reason for that office visit. As in traditional record-keeping, it is meant to serve as a temporary clinical device for describing in a non-etiological manner the nature of the new problem before and while its exact nature and basis for it is being determined. At which point another or an existent chronic diagnosis for that out-patient will assigned. The entries from the short-term, acute diagnosis table, er_list.dbf, may also be used for the only diagnosis field of the emergency room record in a similar instance when the exact and causitive nature of the clinical problem is not as yet fully understood or it appears to be a complication of an established chronic diagnosis of that out-patient.

Referring to FIG. 9, the medicine-activity record file named medicine.dbf. It is for storing up to three medications acted upon during an office visit. The med(n) fields store the generic name of the medication and are derived from the medication inventory table, med_list.dbf. The ACTION(n) field is to record the nature of the activity; a change, addition, deletion, etc. of a medication. The amount(n) fields can accomodate total dosage per day, tablets per day or amount and route of any parental (injection) dosage.

Referring to FIG. 10, the system's physical findings (or signs) file of records, findings.dbf. It is the data from both the CODETYPE and CODE fields of any record from findings.dbf file that is loaded onto an office visit record in cases where that particular physical data item was documented during an office visit. The first character of the codetype field is the same indicator used with both chronic and acute diagnosis for indicating what clinico-pathological group that particular clinical attribute belongs. Also, but not used, in the same manner as both acute and chronic diagnosis, the second character can place the physical data item into one of three categorys depending upon its relative clinical urgency or priority.

Referring to FIG. 11, the system's physical symptom's (complaints) file,cc_list.dbf. Except for it storing the other type of physical data, it is identical in structure and purpose as the physical signs table previously described with its data elements being handled and accessed in the same way.

Referring to FIG. 12, the system's medication inventory table, med_list.dbf. It stores the complete list of medications available to the system in the form of their generic names.

Referring to FIG. 13 a table containing a list of surgical procedures involving various clinico-pathological groups as indicated by the coded letters of the second position. It is another type of inventory table that provides the appropriate clinical attribute for a patient with a surgical history.

Referring to FIG. 14, two transactional type system files, surglink.dbf and treatmen.dbf. The former stores each surgical procedure any database patient has had with the date the surgery was done. The SURGCODE field will contain any of the entries from the surgfind.dbf table. The latter file stores records of various out-patient treatments for common ailments performed by physical therapists. The REASON field of a treatmen.dbf record will contain the chronic diagnosis of that out-patient for which that treatment is being performed while the RX field is a literal definition or text of the treatment being performed, i.e. 'inhalation therapy'. The STATUS field is for indicating the therapist's assessment of that patient's condition at the end of each therapy session. It will be either one of four possibilities, improved, same as before, worse or hospitalization recommended.

Referring to FIG. 15, the system's out-patient emergency room record, ER_ROOM.dbf. It is similar in general structure and kind of data stored as the office visit record (see encounte.dbf, FIG. 4) but much abbreviated in comparison and with a few important exceptions. There is only one diagnosis field which is for storing the primary reason for the patient coming to the emergency room. It may be from either the acute, short-term or the chronic long-term diagnosis table depending upon the evaluation of the emergency room physician. The status field is for encoding one of three types of dispositions the e.r. physician will make; follow-up office visit necessary or not and if hospitalization was advised. The condition field is for indicating the presence of and degree of clinical instability of the patient at the time of the e.r. visit. As another type of transaction file, the 6 digit INVOICE field is the emergency room record's most unique data item of identification. Referring to FIG. 16, the system's in-hospital record for any hospitalized out-patient, pt_hosp.dbf. Like the surgical history file (see surglink.dbf, FIG. 14), it serves mainly to document its occurrence and stores only that data that can be o use in out-patient management. There are two diagnosis fields, one upon admission and the other at the time of discharge. They may be the same and both may be from either the short-term, acute or the chronic, long-term diagnosis field. The narrative field allows for a brief synopsis of hospital course that is optional.

Figure 17:
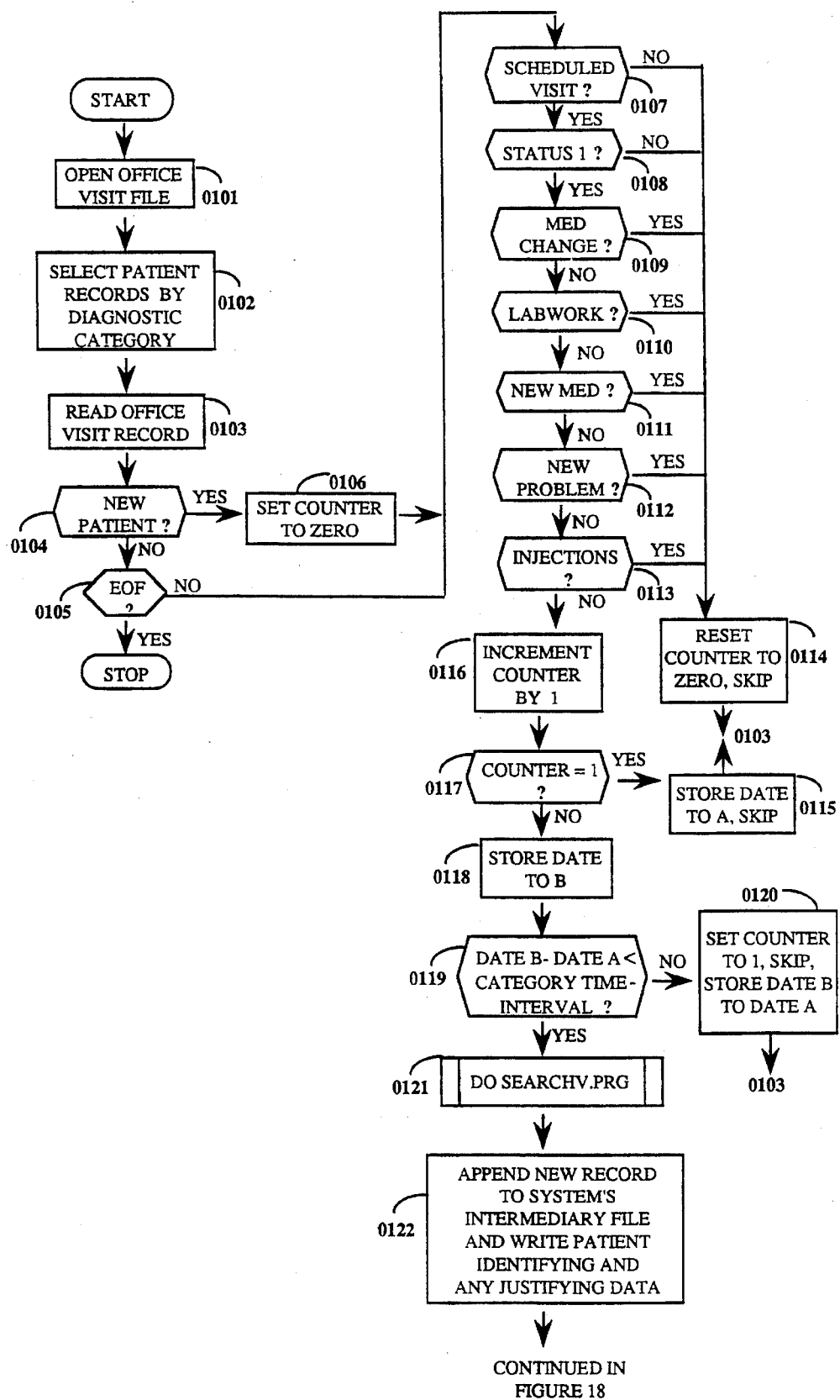

Referring to FIG. 17, a main computer program entitled schedul1.prg that detects actual or possible overuse of office visit resources by identifying two successive office visits of any out-patient that were both scheduled, completely unremarkable and uneventful, and which occured within a time interval as prescribed by that patient's diagnostic category. Upon identification, a sub-routine is called that searches through a set of clinical 'transaction' files on that patient in order to find any data that indicate activity of some type occuring between those two visits that could justify that early, second scheduled visit.

Figure 18:
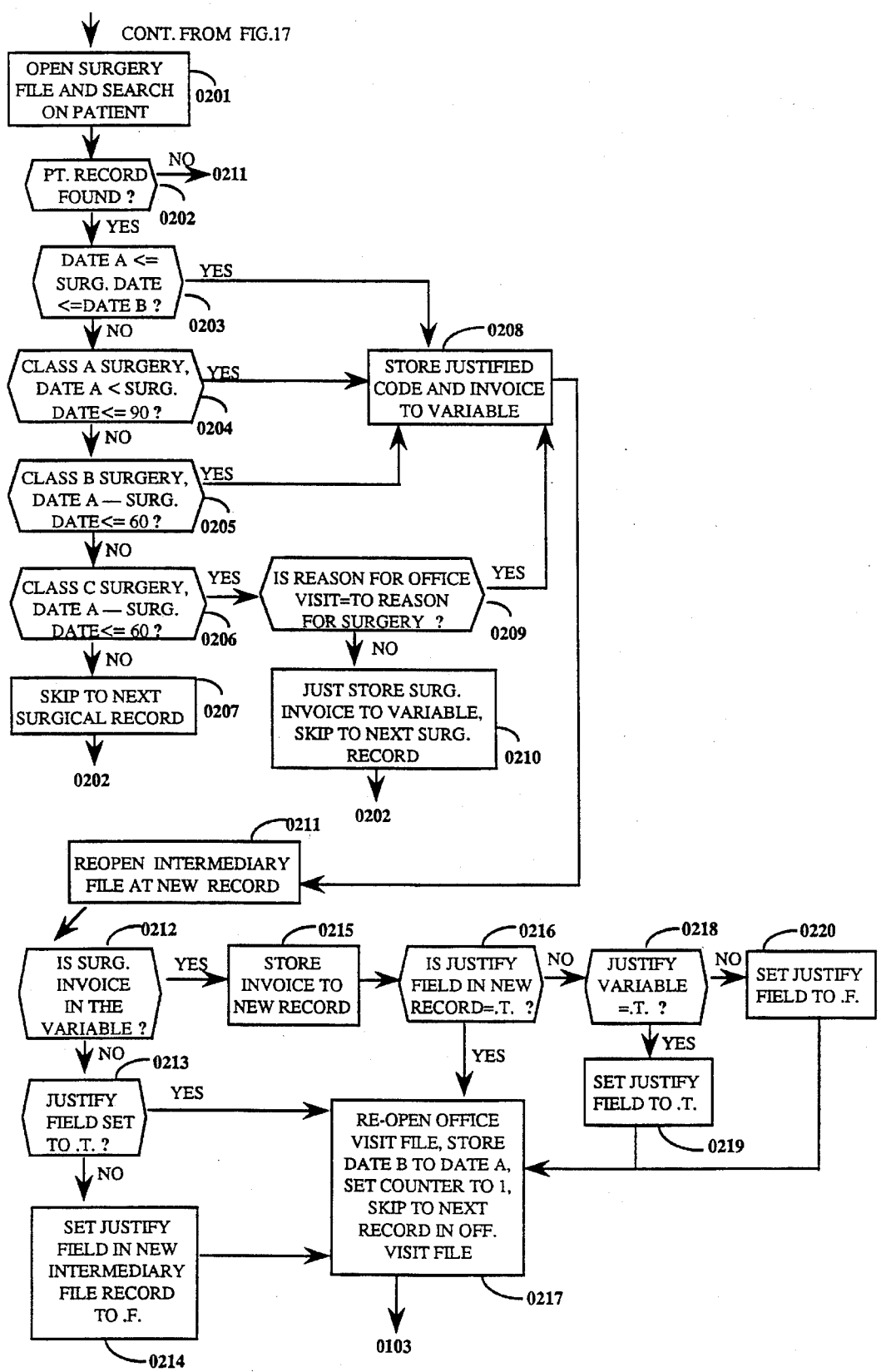

Referring to FIG. 18, a continuation of FIG. 17 that illustrates the process whereby a search is also conducted on the system's surgical history file in order to find any data, based upon certain criteria, of a past surgical event for that patient that could justify, in itself, that early, second visit.

Figure 19:
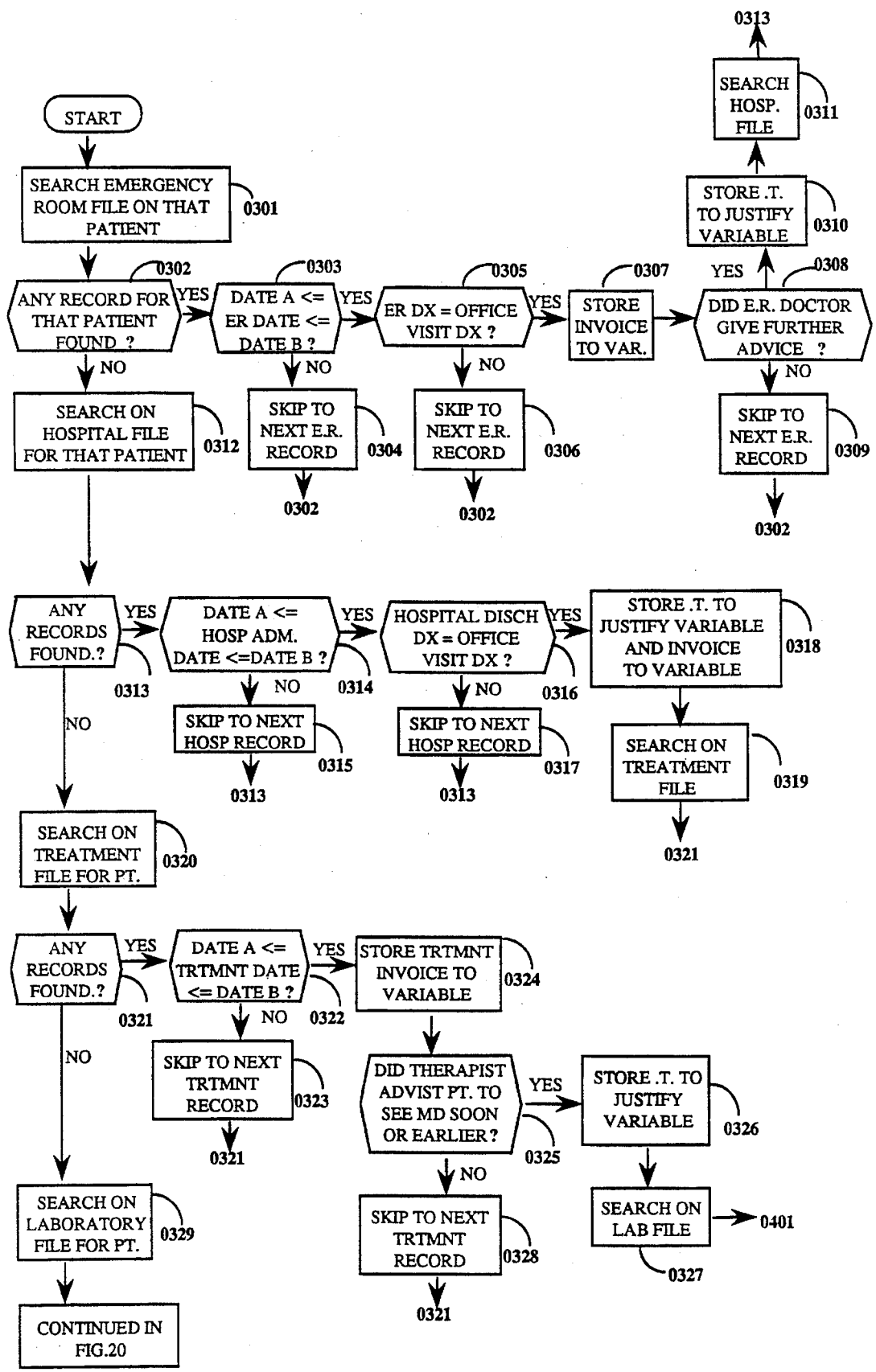

Referring to FIG. 19, a subroutine entitled Searchv.prg called by Schedul1.prg that will search on 4 clinical file types (emergency room, treatment, hospitalization, lab test results) in order to find, by a set of criteria dependent upon the type of file, clinical activity occuring between the two office visits in question that are of such a nature as to justify the early, second visit. If and when that occurs the data is then passed back to the main program and written to a newly created, intermediary record.

Figure 20:
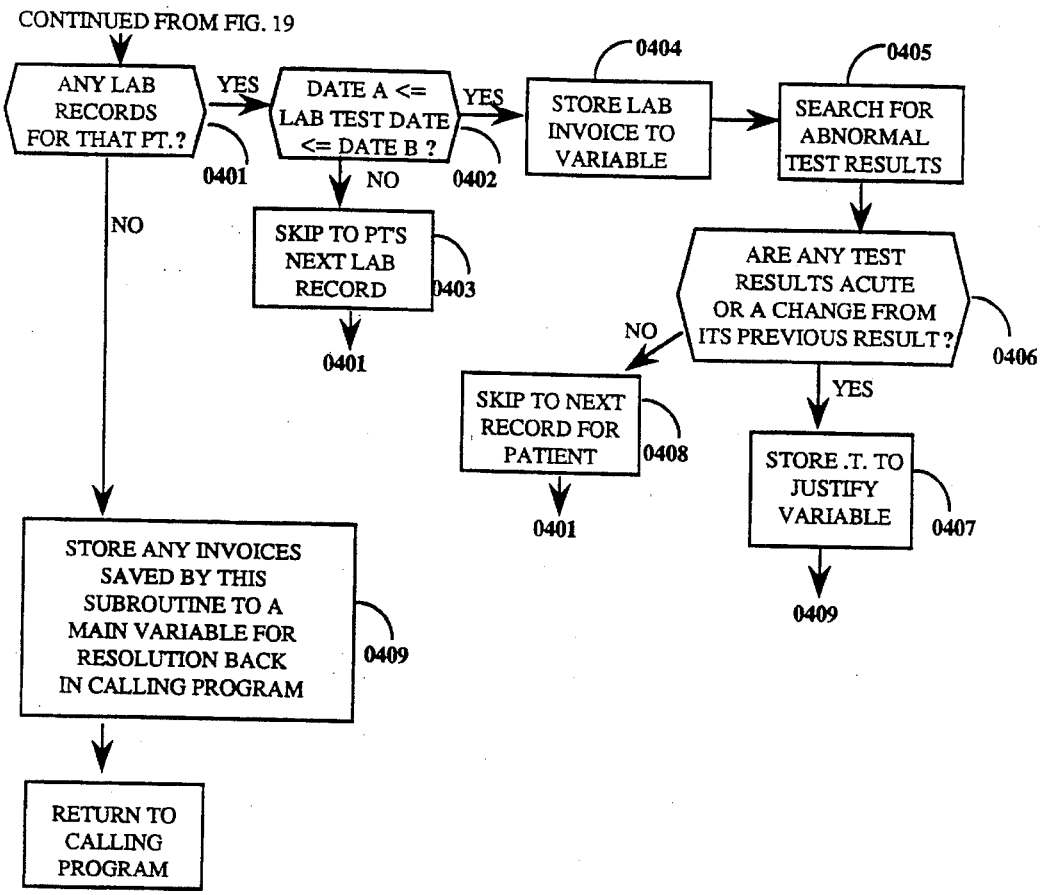

Referring to FIG. 20, a continuation of the processing of FIG. 19 showing the criteria used and the decision making involved in establishing whether or not any data found in, this case, the lab test file indicating activity from between those two types of office visits that could justify the early, second scheduled visit.

Figure 21:
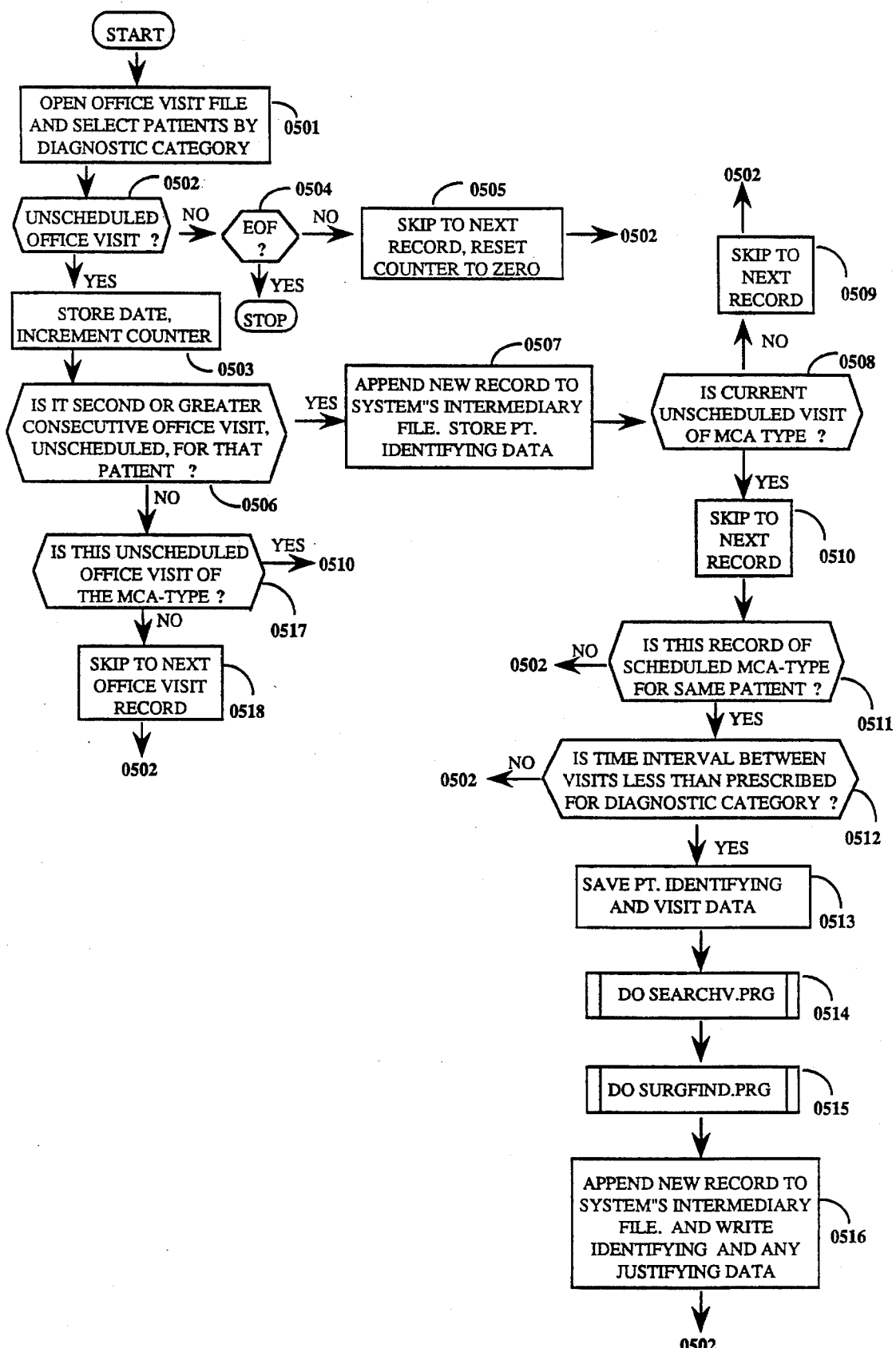

Referring to FIG. 21, a main computer program entitled unschedul.prg that is similar in part to schedul1.prg since it also looks for office visit overuse but with a primary emphasis upon unscheduled visits. Therefore, it identifies two types of problems; unscheduled visits occuring in succession for any out-patient and a scheduled one of a completely unremarkable nature that has occured right after an unscheduled one for that out-patient that is also completely unremarkable and within a time interval (i.e., too early) as prescribed for that patient's diagnostic category. Upon identifying the latter, the subroutine searchv.prg is also called from this main program.

Figure 22:
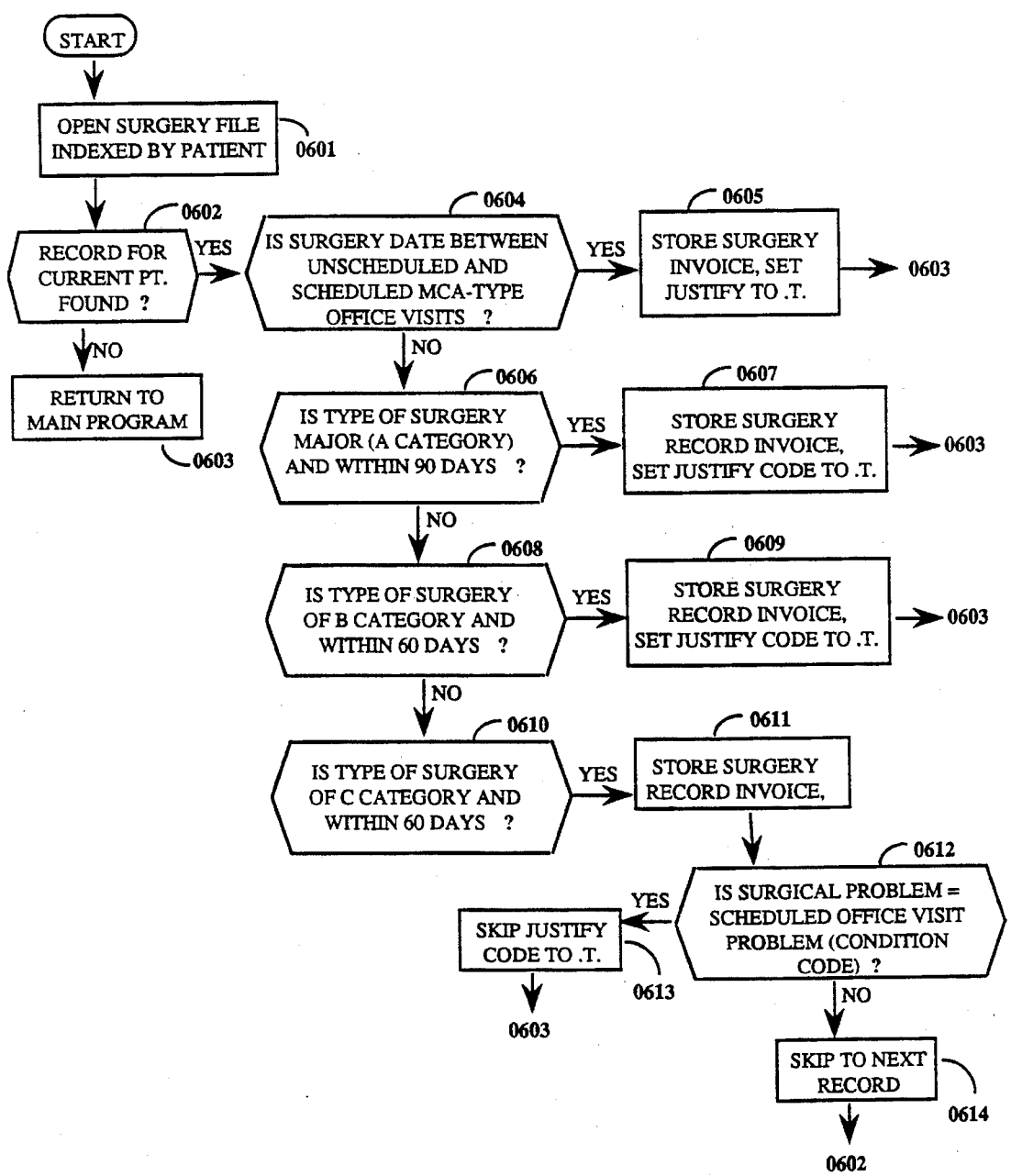

Referring to FIG. 22, a subroutine entitled surgfind.prg called by the program unschedul.prg to search for any prior surgical event of that out-patient that by its nature could justify that early second visit of a completely unremarkable nature. Its steps are identical to a bloc of source code present in schedul1.prg, but due to the size of unschedul.prg a separate subroutine had to be written to accomodate it.

Figure 23:
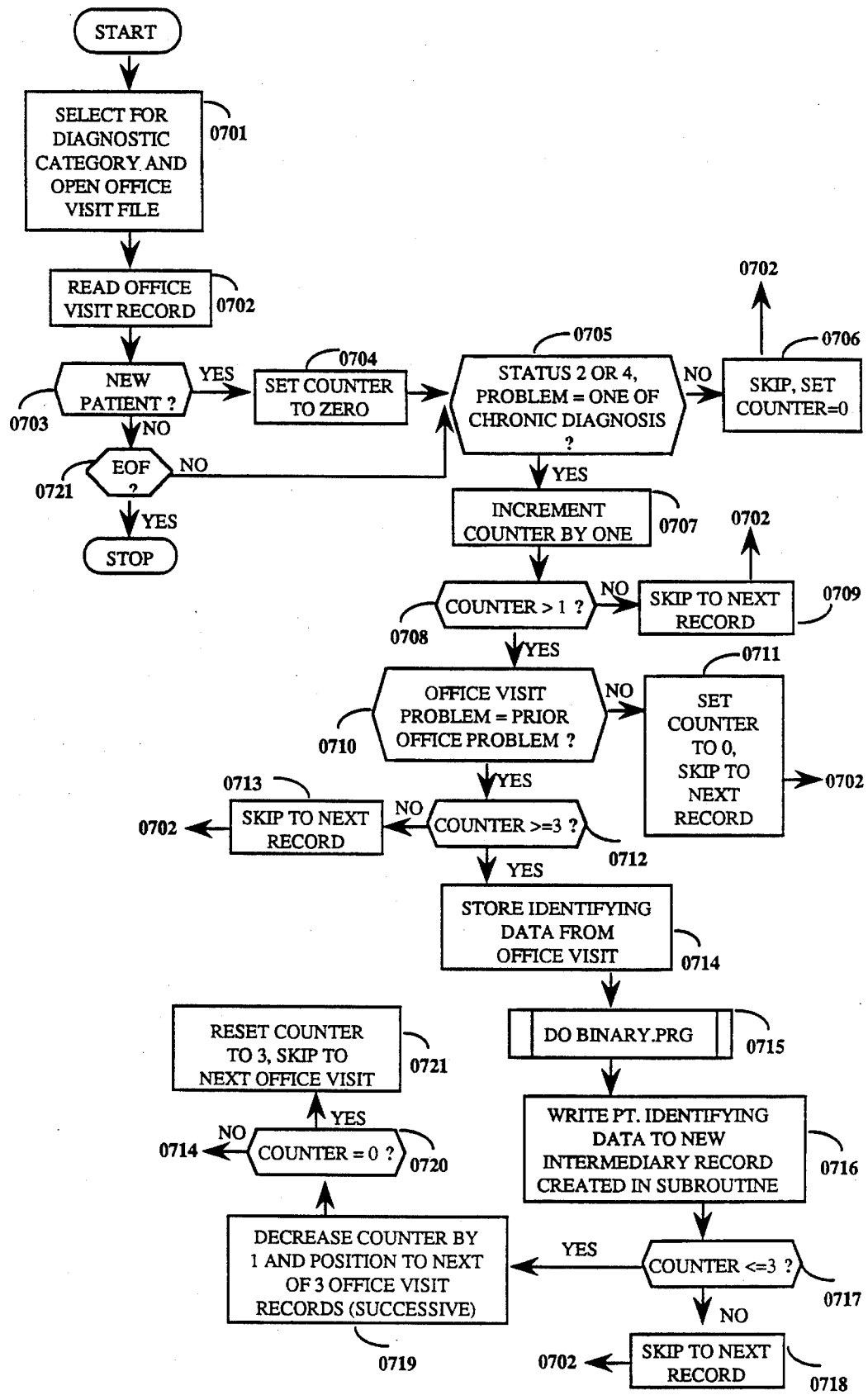

Referring to FIG. 23, a main program entitled AstatusB.prg that is one of three in this system that identifies and processes contiguous, successive office visit records that represent a protracted out-patient illness. In this program the minimum number necessary in order to trigger processing is three since the illness, by its selection of only certain types of records, is only of a moderate degree. It calls a subroutine, binary.prg., for accessing encoded physical data present in each record involved and for determining the extent and nature of the actions taken by the physician during each visit in response to the illness.

Figure 24:
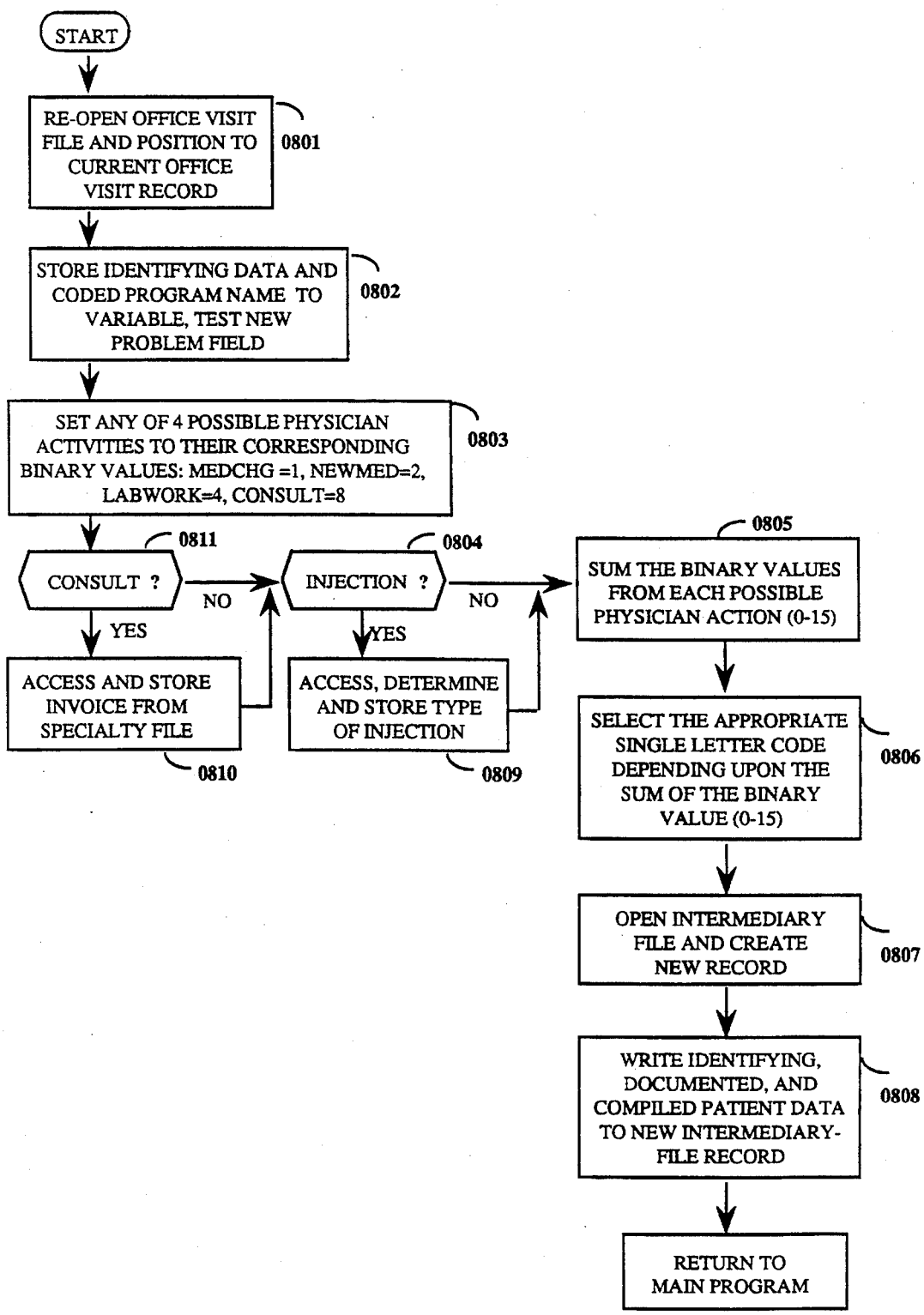

Referring to FIG. 24, a subroutine entitled Binary.prg called by AstatusB.prg that accesses encoded physical observations during each visit of the illness and what, if any, kinds of actions were undertaken in the treatment and management of the patient during each visit. By a scheme based upon binary numbering the subroutine compiles into a single letter code any combination of several possible actions taken by the physician during each visit and it also provides for pointing to other records storing other clinical data emanating from that visit during that illness. And for the purpose of later accessing specific records created as a result of this type of processing, this subroutine also determines and encodes for the name of the particular main program that has called it, since in this system there may be three that do.

Figure 25:
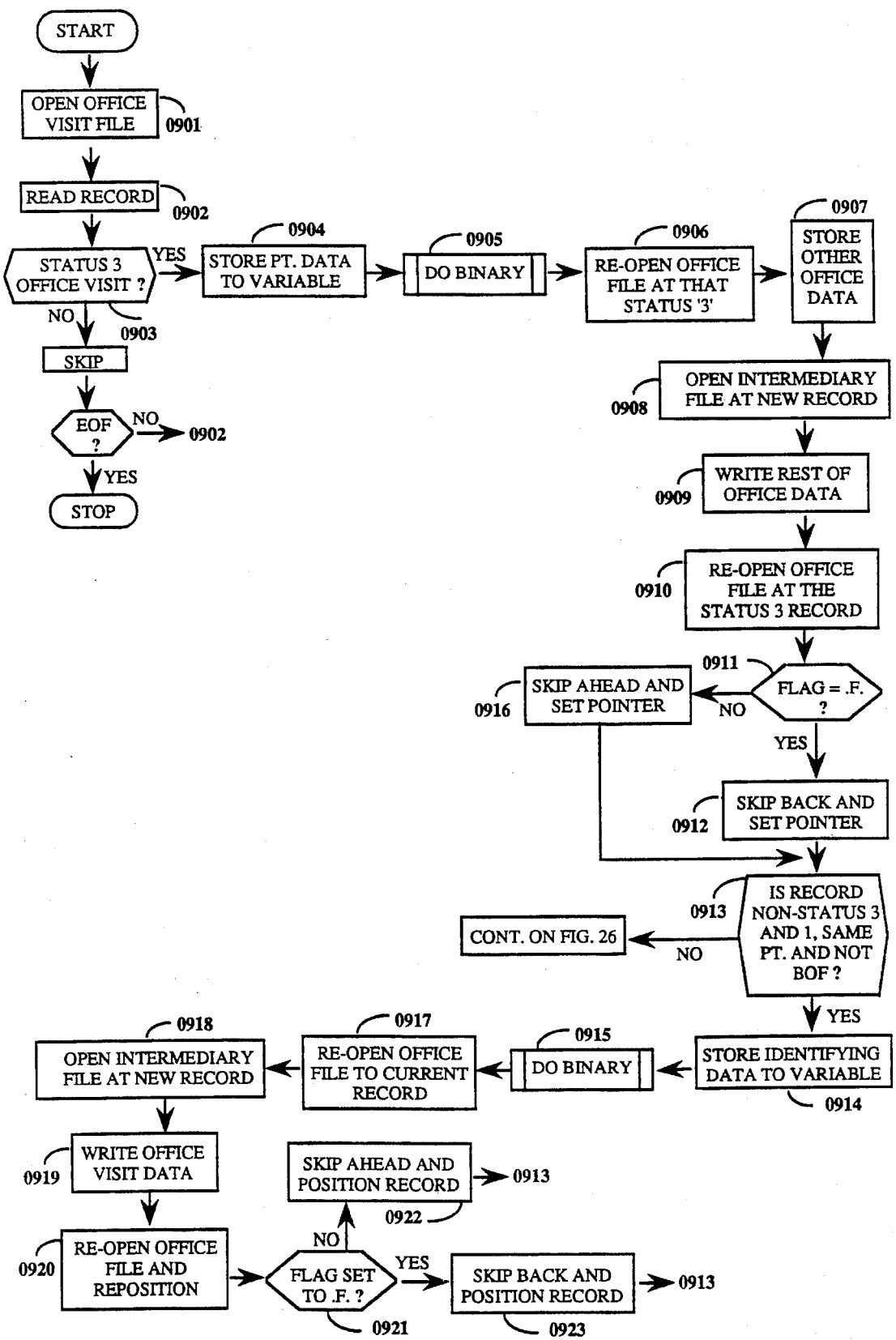

Referring to FIG. 25, a main program entitled Astatus3 that is similar to AstatusB since it also identifies and processes what might turn out to represent a protracted out-patient illness but its threshold for activation is different.

It first has to identify an office visit record with a clinical status of 3 indicating severe symptomatology and possibley need for hospitalization before processing begins and then it will process all contiguous antecedent and subsequent office visit records of that out-patient that also indicate disease activity (i.e., non-1 clinical status). And, like AstatusB.prg the number of records involved depends upon the length of that out-patient's uninterrupted illness. And it to calls the subroutine binary.prg for each record involved.

Figure 26:
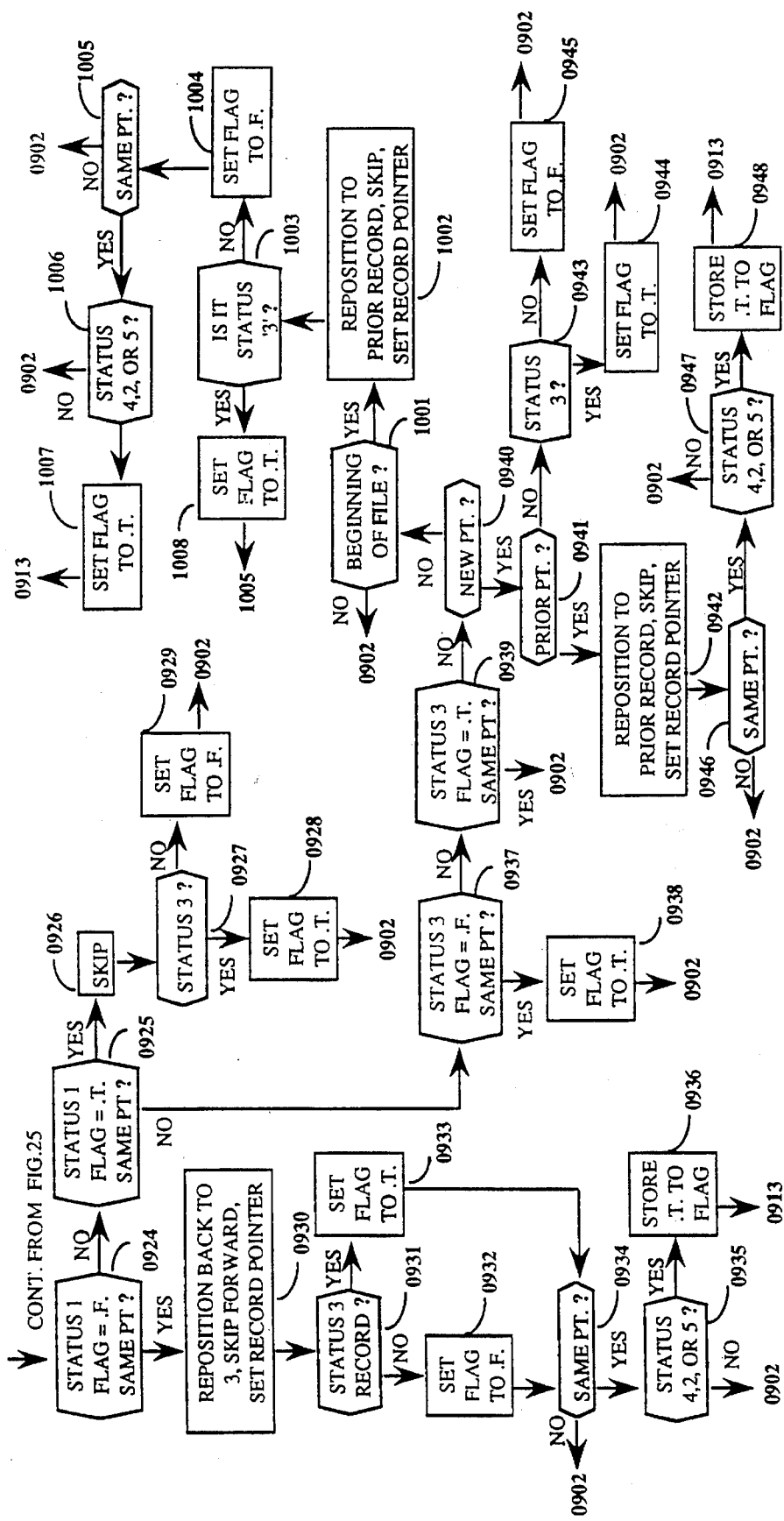

Referring to FIG. 26, a continuation of FIG. 25 showing stepwise program logic and note how there is movement of the record pointer in both directions and how the program is informed each time.

Figure 27:
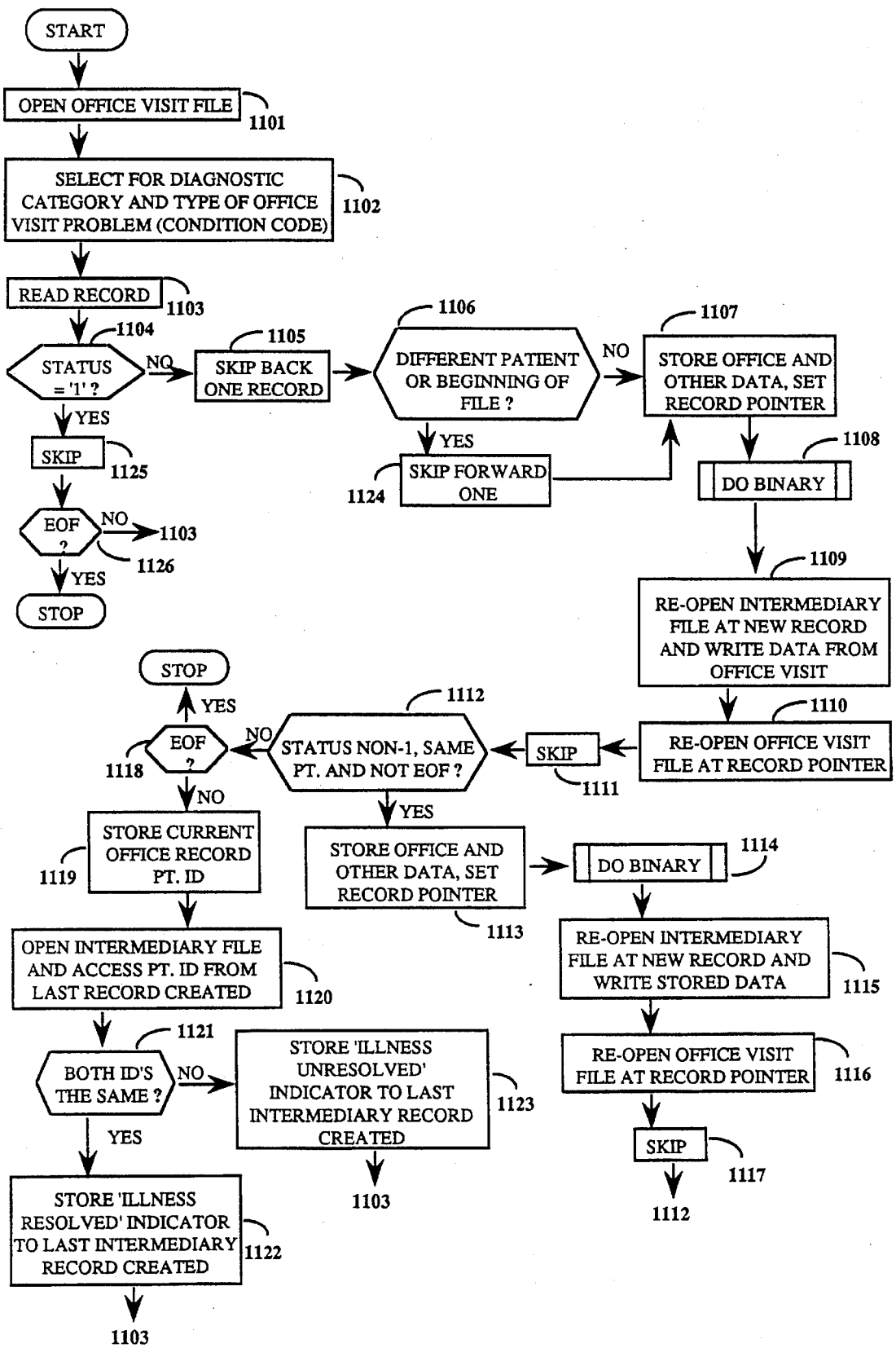

Referring to FIG. 27, a main program entitled clinevol.prg that, like AstatusB.prg and Astatus3.prg, identifies and processes a string of successive office visit records that represent a protracted out-patient illness. The basic difference here is that processing is triggered whenever a non-1 clinical status record is encountered, there is no minimum number of records necessary and no particular level of disease intensity required. But it will also process, if present, the most previous office record of that out-patient (a status 1) in order to obtain the 'baseline' condition of that patient just prior to the onset of that illness. The number of records involved here also depends upon the length of the continuous illness and after each record involved is detected the subroutine binary.prg is also called.

Figure 28:
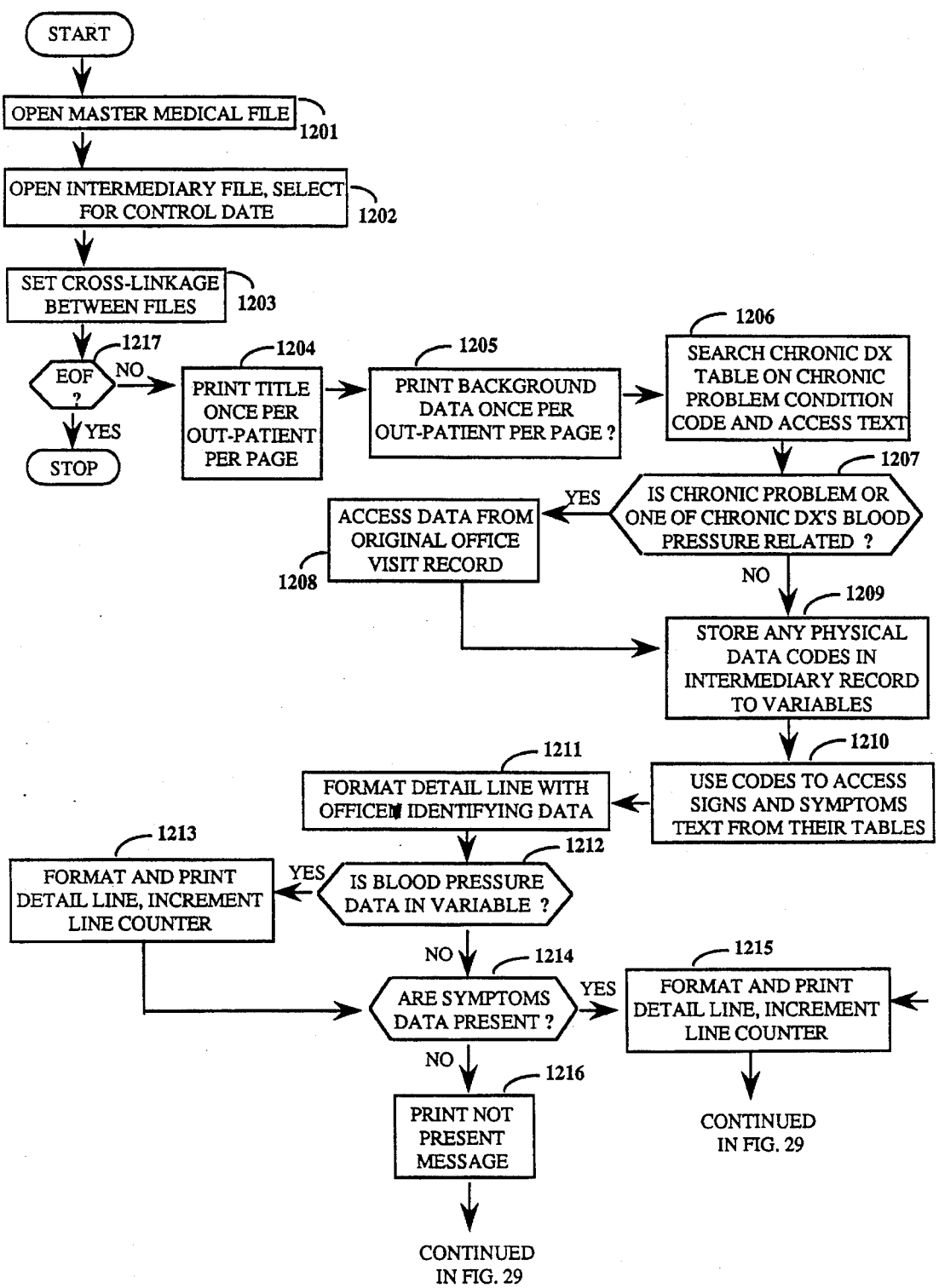

Referring to FIG. 28, a print program entitled print1a.prg that reports out physical data (signs and symptoms) in combination with other salient data of both an identifying and clinical nature from office visit-derived records created during one of the three main programs mentioned previously, in this case clinevol.prg. As such it represents continuity of data flow through program sequencing.

Figure 29:
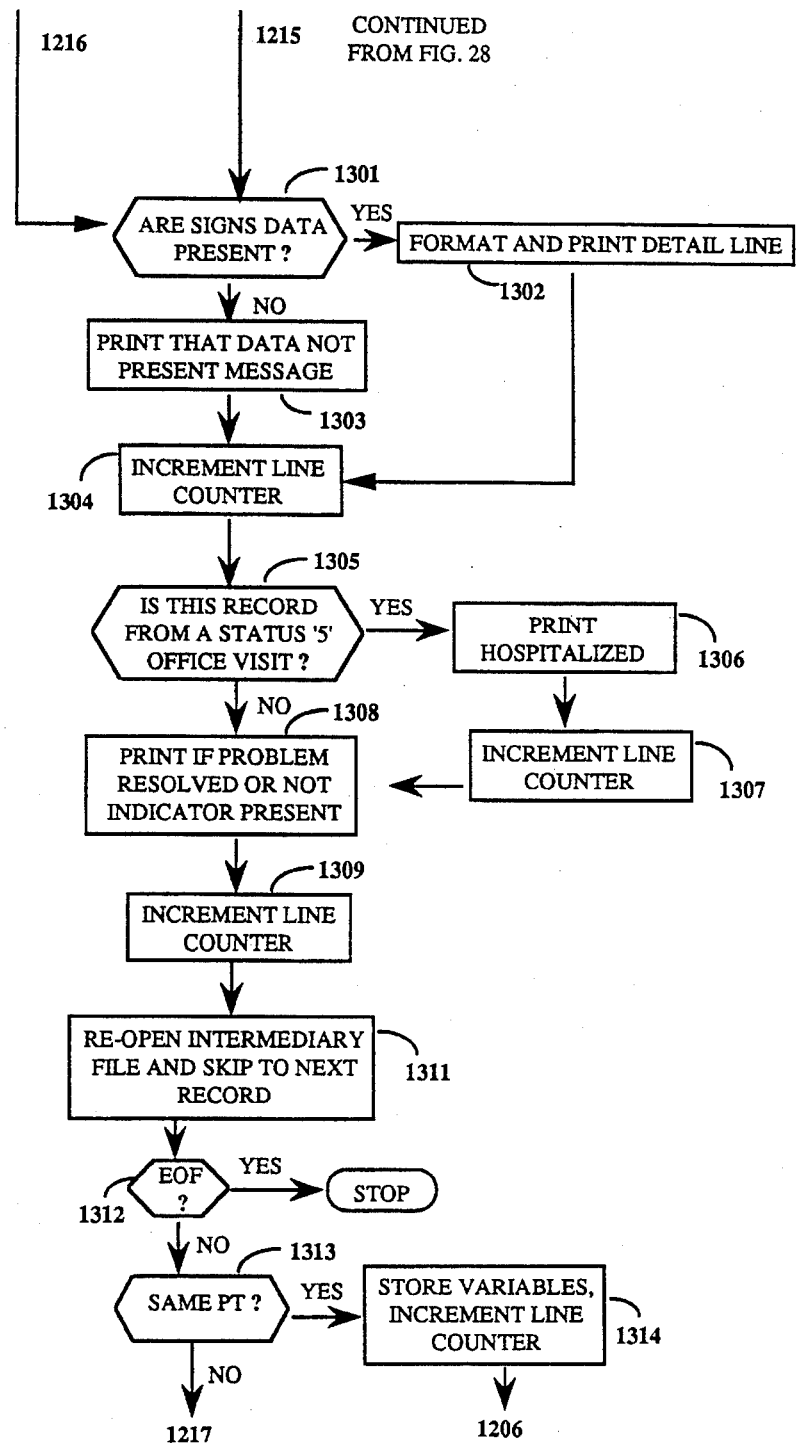

Referring to FIG. 29, a continuation of the print program print1a.prg. Note how additional clinical data, if indicated, is also printed from the same office visit in combination with the signs and symptoms.

Figure 30:
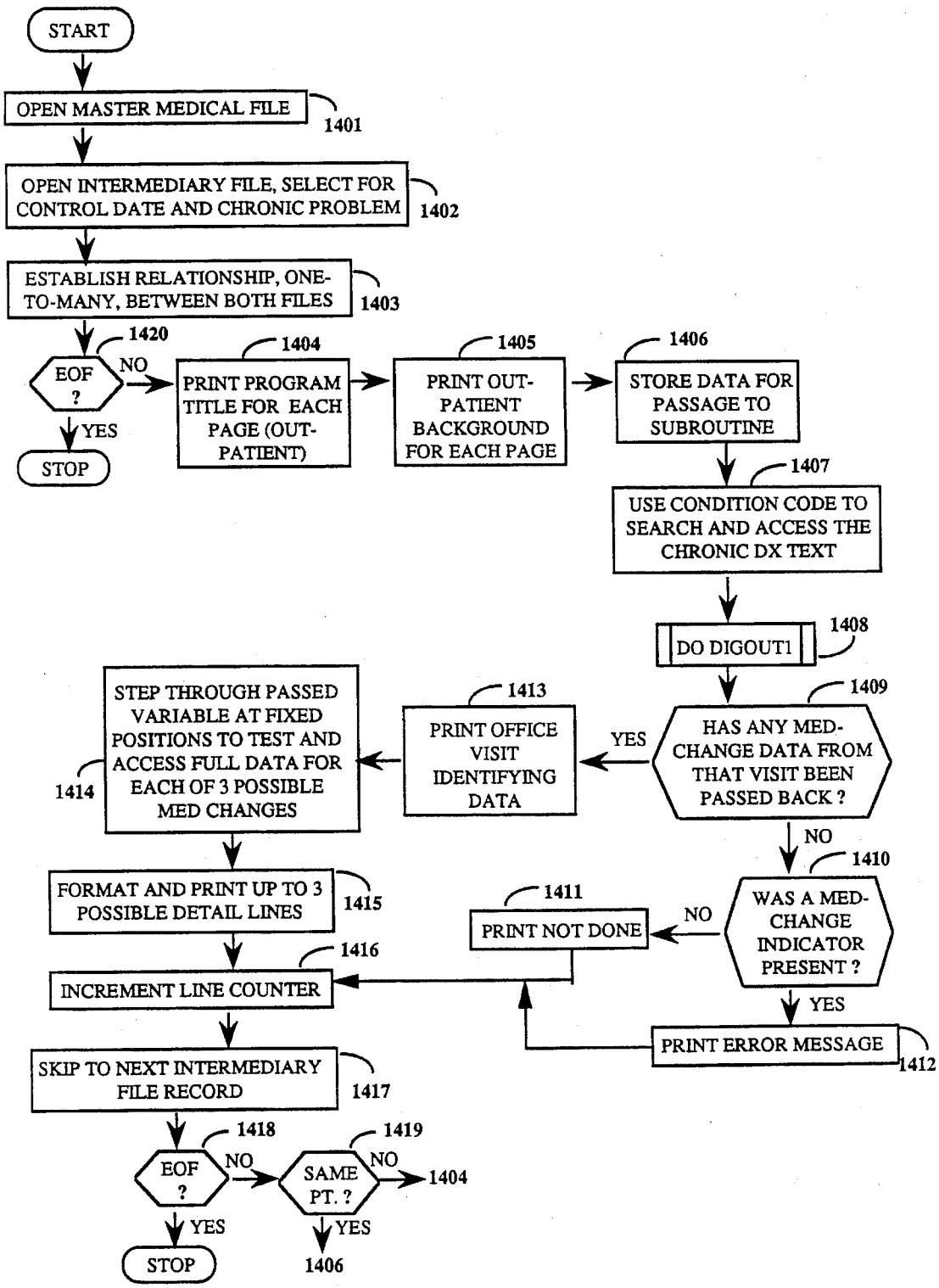

Referring to FIG. 30, another print program entitled print2a.prg that complements print1a.prg by printing out medication activity data from the same office visits. In order to access the medicines involved in that visit it calls a subroutine digout1.prg.

Figure 31:
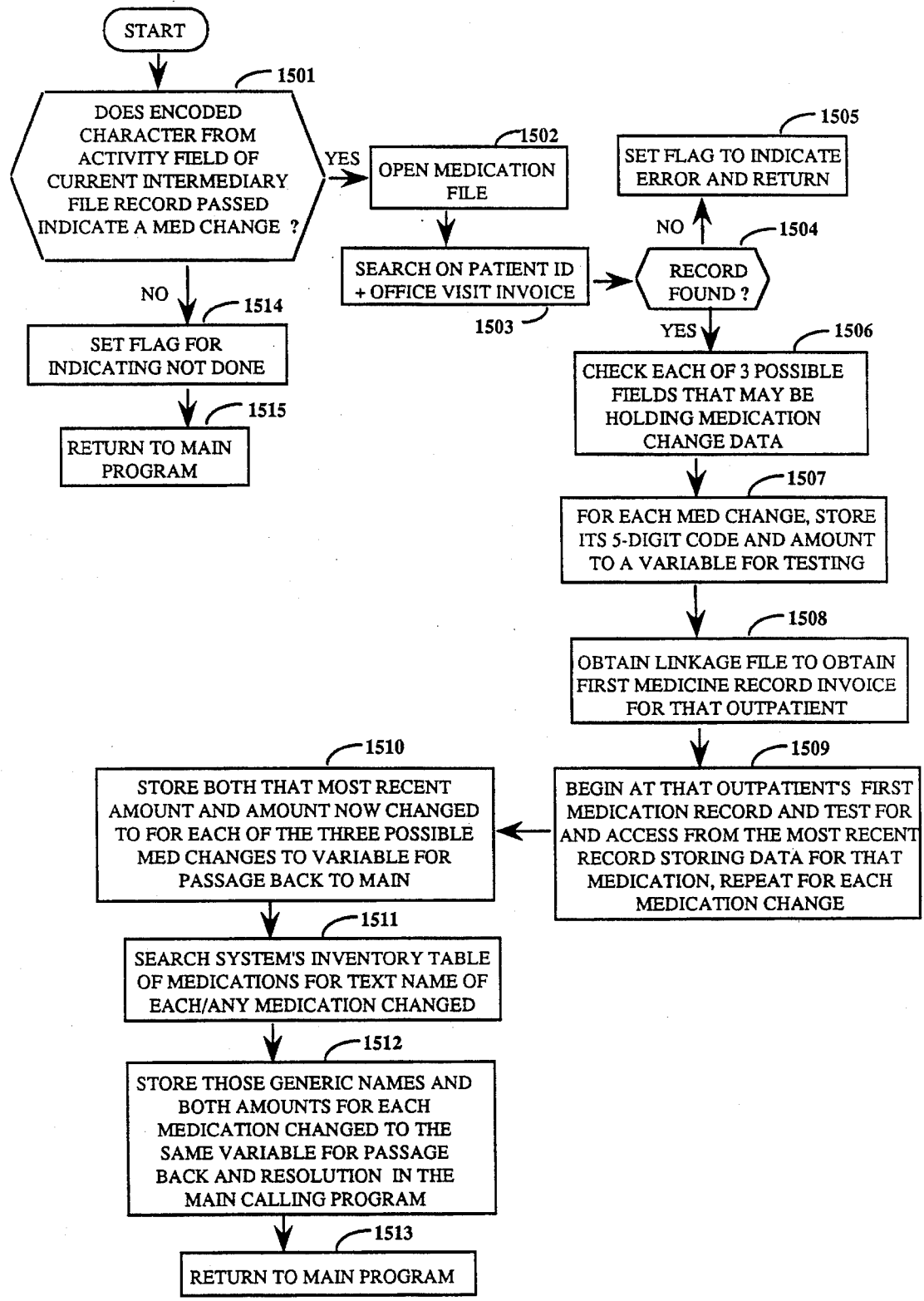

Referring to FIG. 31, a subroutine entitled digout1.prg called by print2a.prg in order to locate the medicine activity record linked to the office visit currently being processed for the purpose of organizing the data and encoding it for printing it back in print2a.prg.

Figure 32:
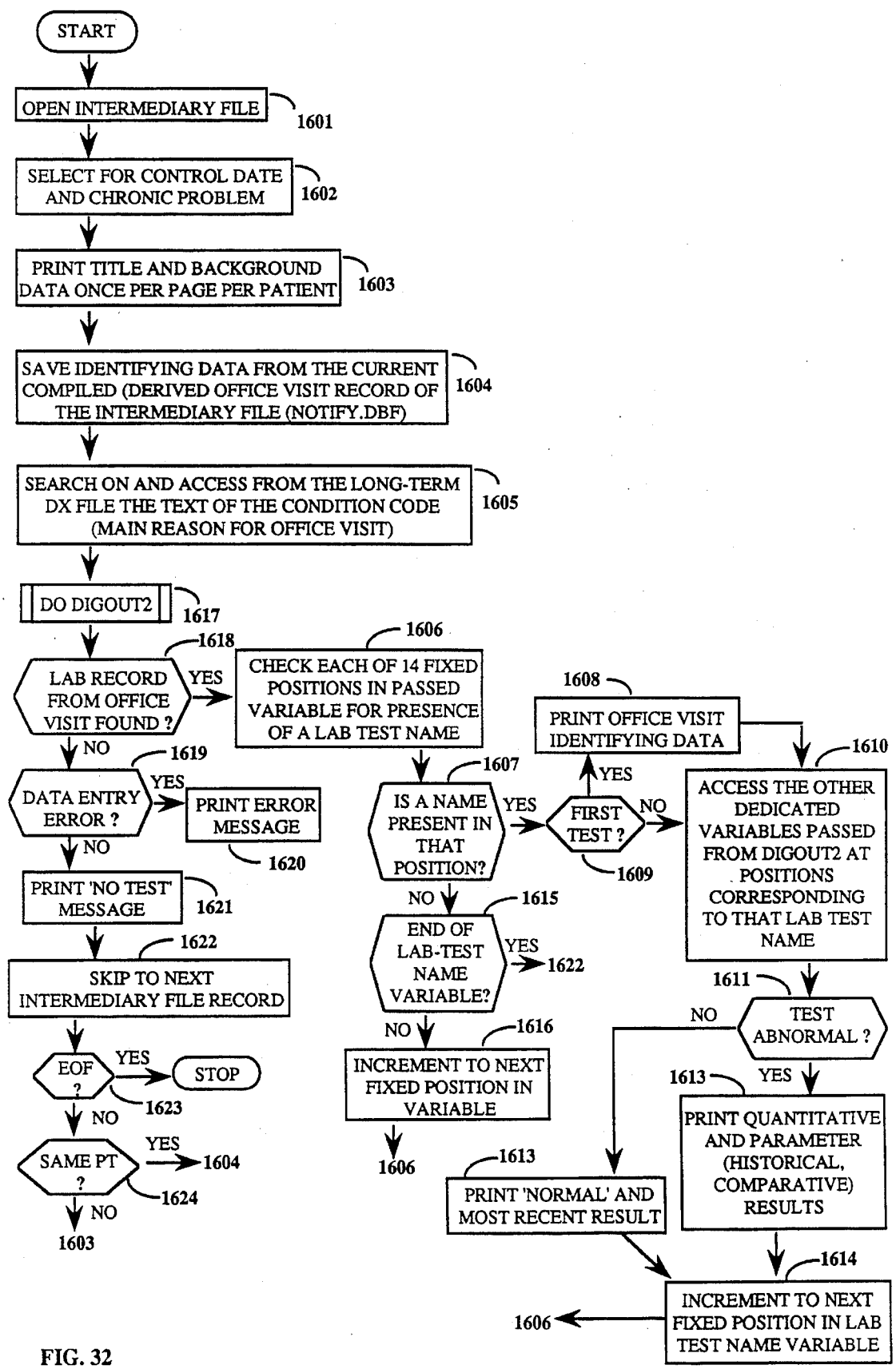

Referring to FIG. 32, a print program entitled print3.prg that complements both print1a.prg and print2a.prg by reporting out another clinical aspect of each of those office visits originally processed by clinevol.prg, this time it is lab test results. It also calls a subroutine.

Figure 33:
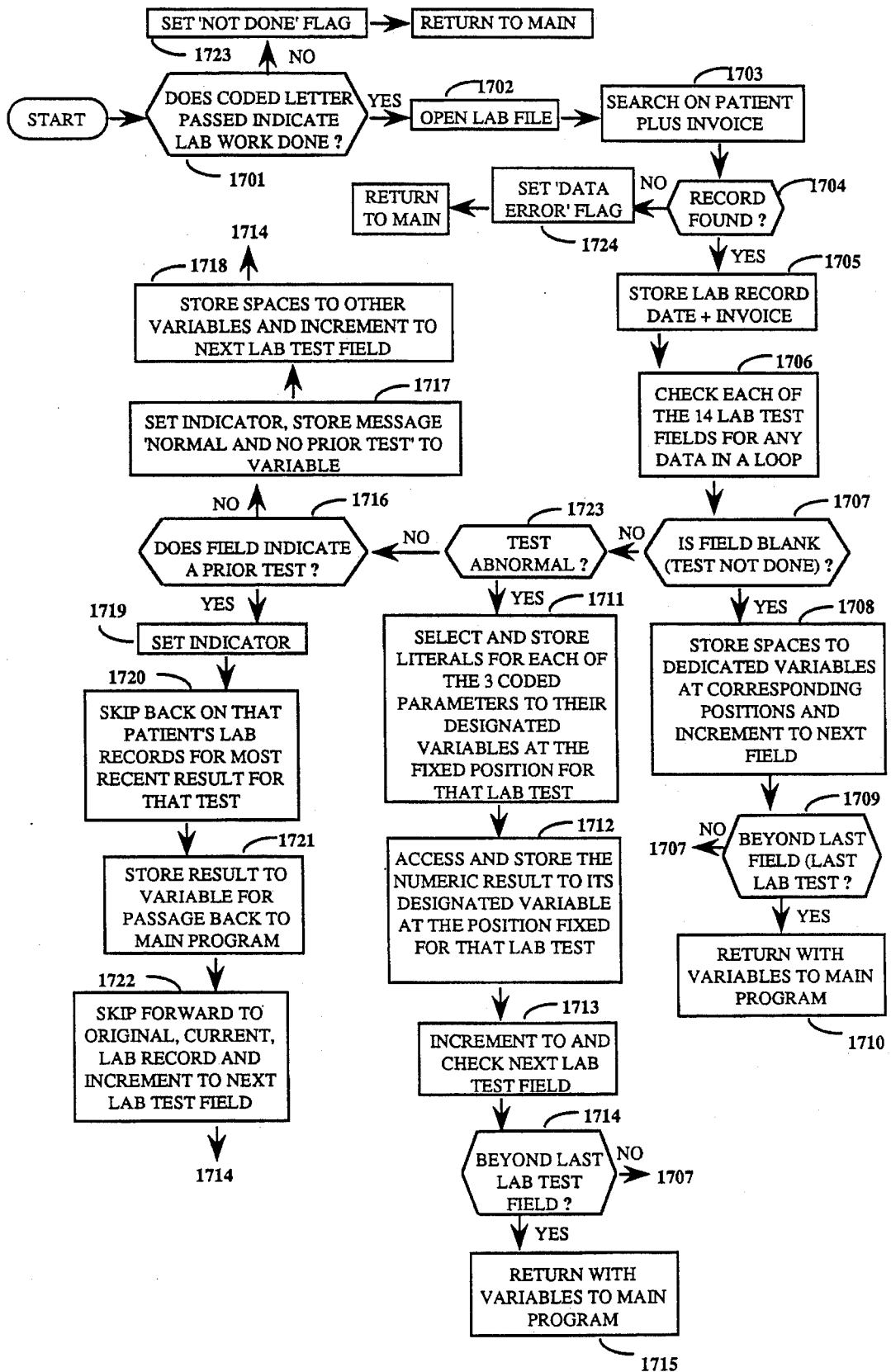

Referring to FIG. 33, a subroutine entitled digout2.prg called by print3a.prg in order to access the lab test results from lab records linked to that office visit record currently being processed.

Figure 34:
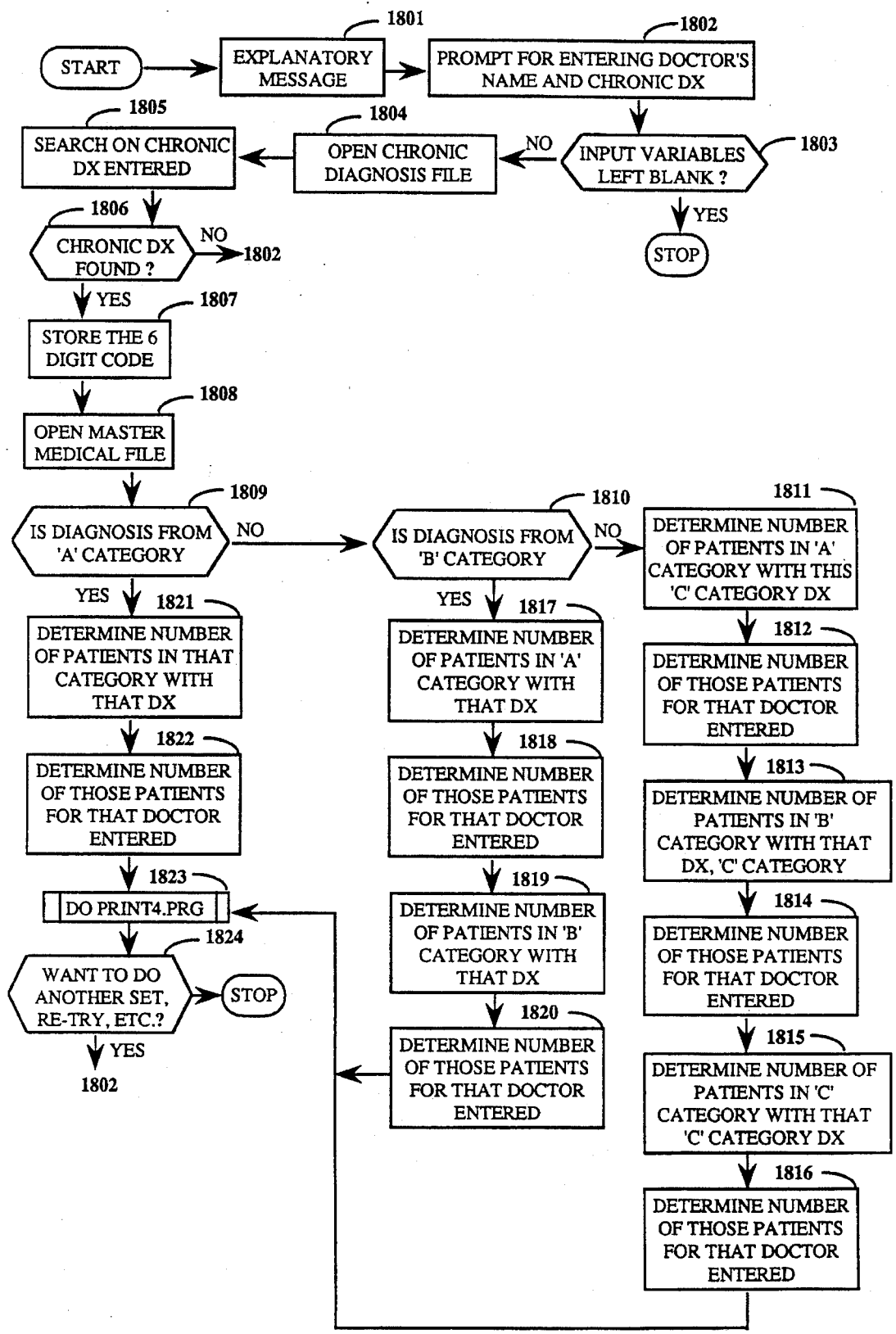

Referring to FIG. 34, an interactive query routine entitled Caseload.prg that has a monitoring function. By counting on the system's master medical file it determines if there is a proper balance or distribution of out-patients on the database with a particular diagnosis amongst the database doctors. Is there any doctor who carries an inordinate amount of patients with a particular condition, since the database consists of non-specialist, primary care doctors?

Figure 35:
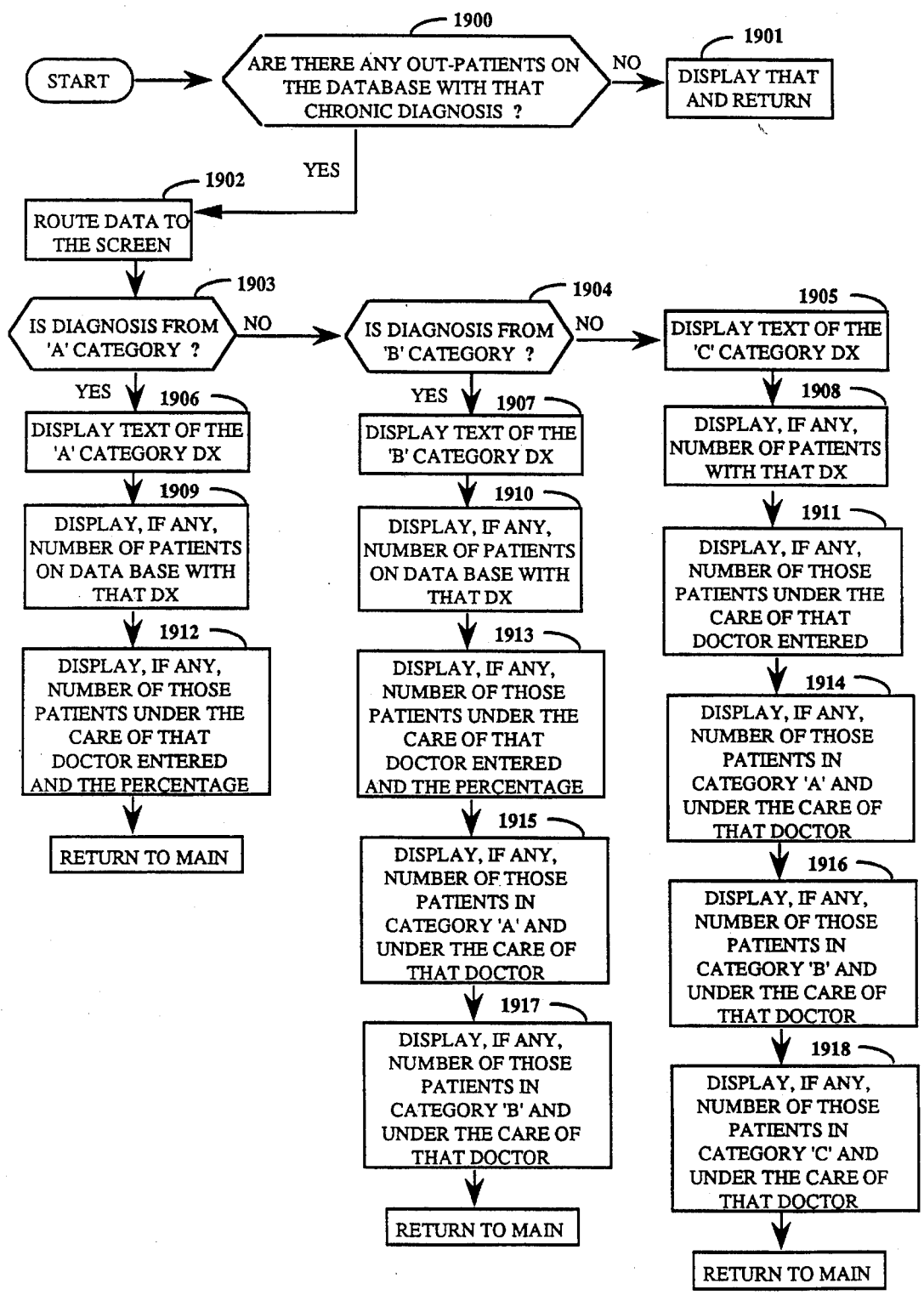

Referring to FIG. 35, a subroutine entitled print4.prg called by Caseload.prg for the purpose of computing and formatting the data into percentage terms and displaying it to the screen.

Figure 36:
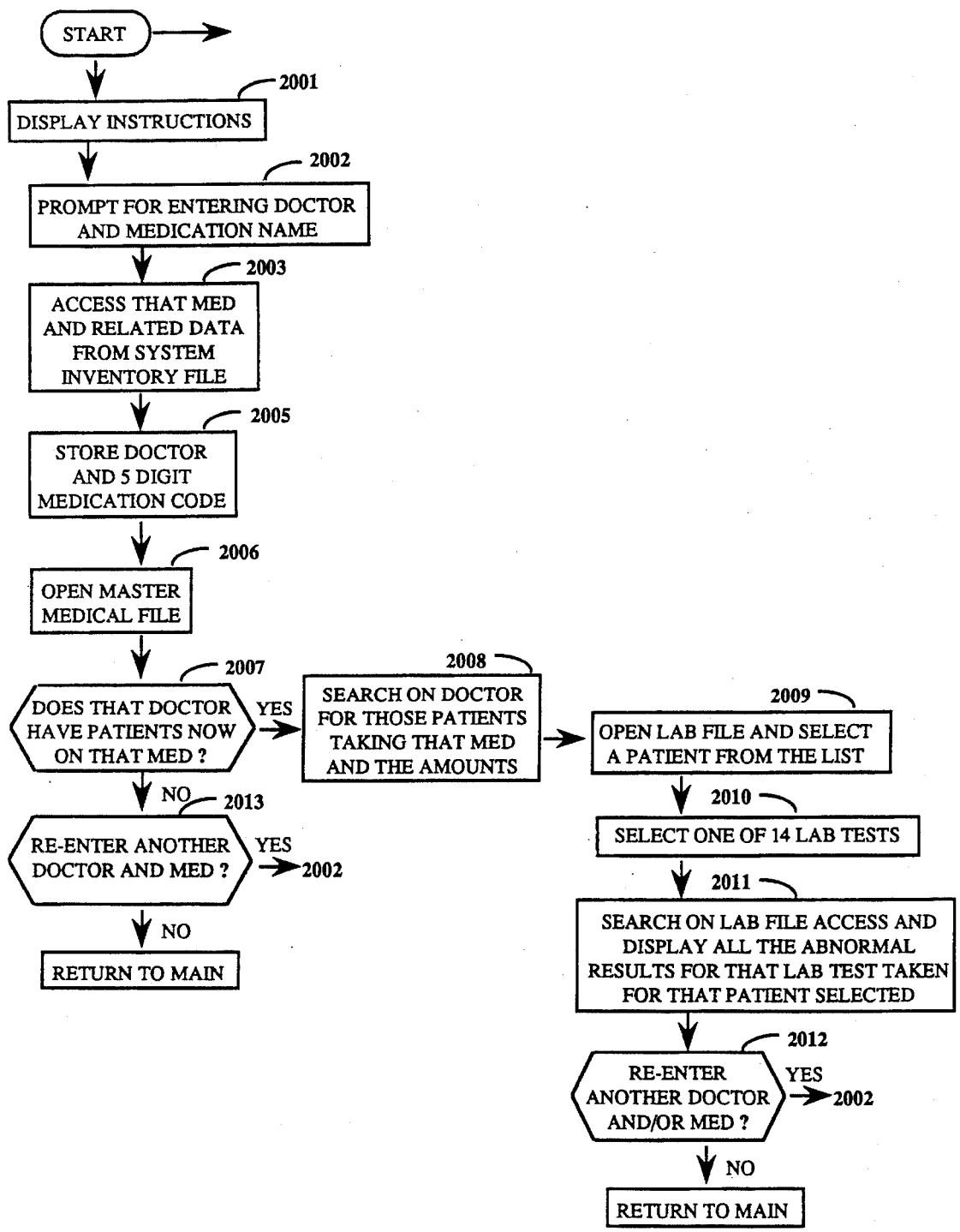

Referring to FIG. 36, another interactive query routine entitled meditoxi.prg that serves another type of monitoring function. For any given medication and database doctor, who are the patients under the care of that doctor and on that medication, if any, who are in an actual or impending situation of medication induced toxicity. As such it displays lab test results in chronological order that are known to be sensitive to the adverse effects of the medication inquired into along with the amounts that patient is taking.

Figure 37:
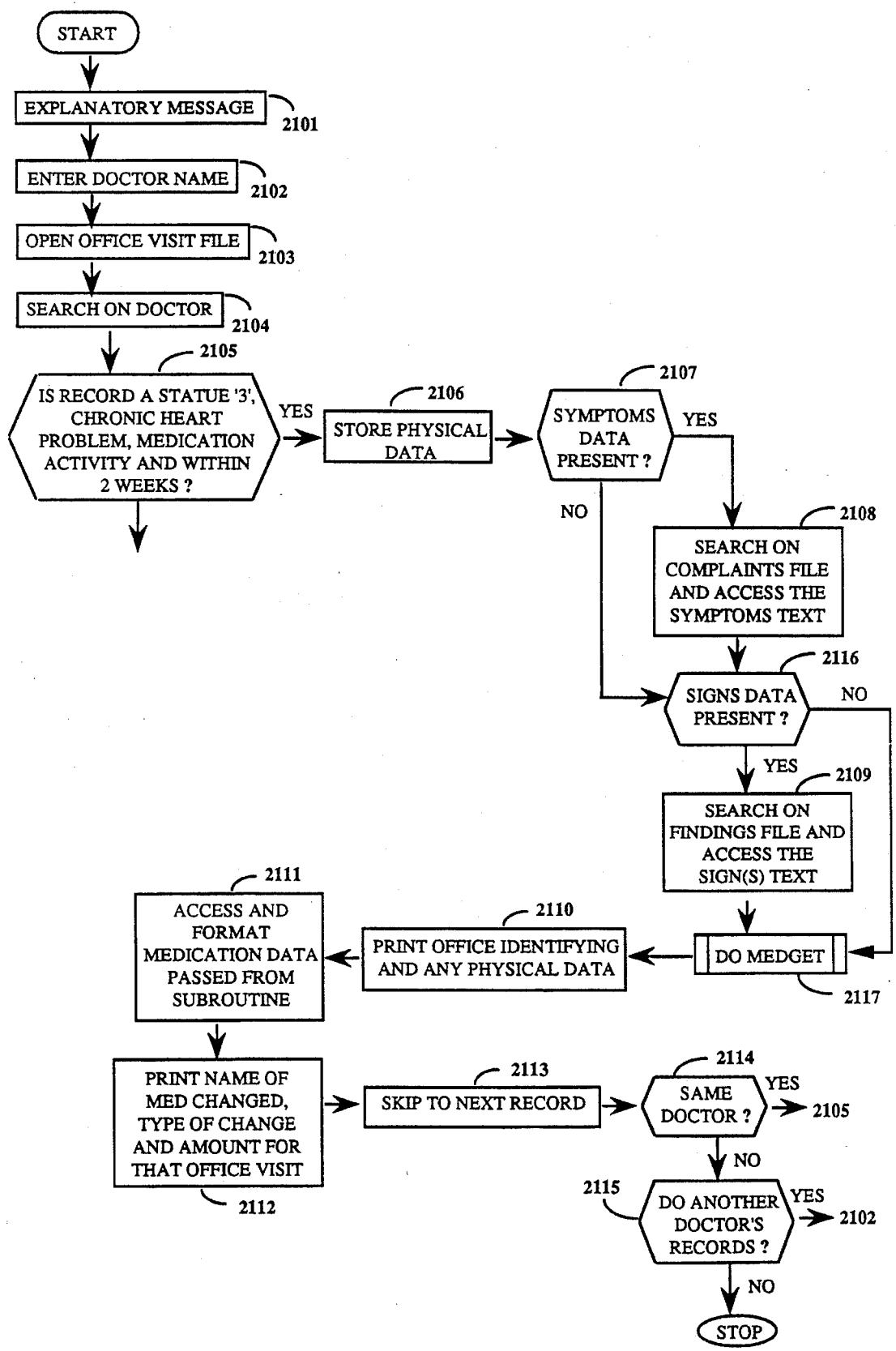

Referring to FIG. 37, another interactive query routine entitled Heartmed.prg that also produces summary type and narrowly focused clinical data. It identifies office visit records of out-patients who have at least one diagnosis indicating chronic Heart disease of some nature and who have been documented at that visit of being in a clinical status of 3 (severe symptoms). Upon that, the program combines the physical data and any medication data and displays it on the screen with other identifying data. In order to access the medication data, it calls a subroutine.

Figure 38:
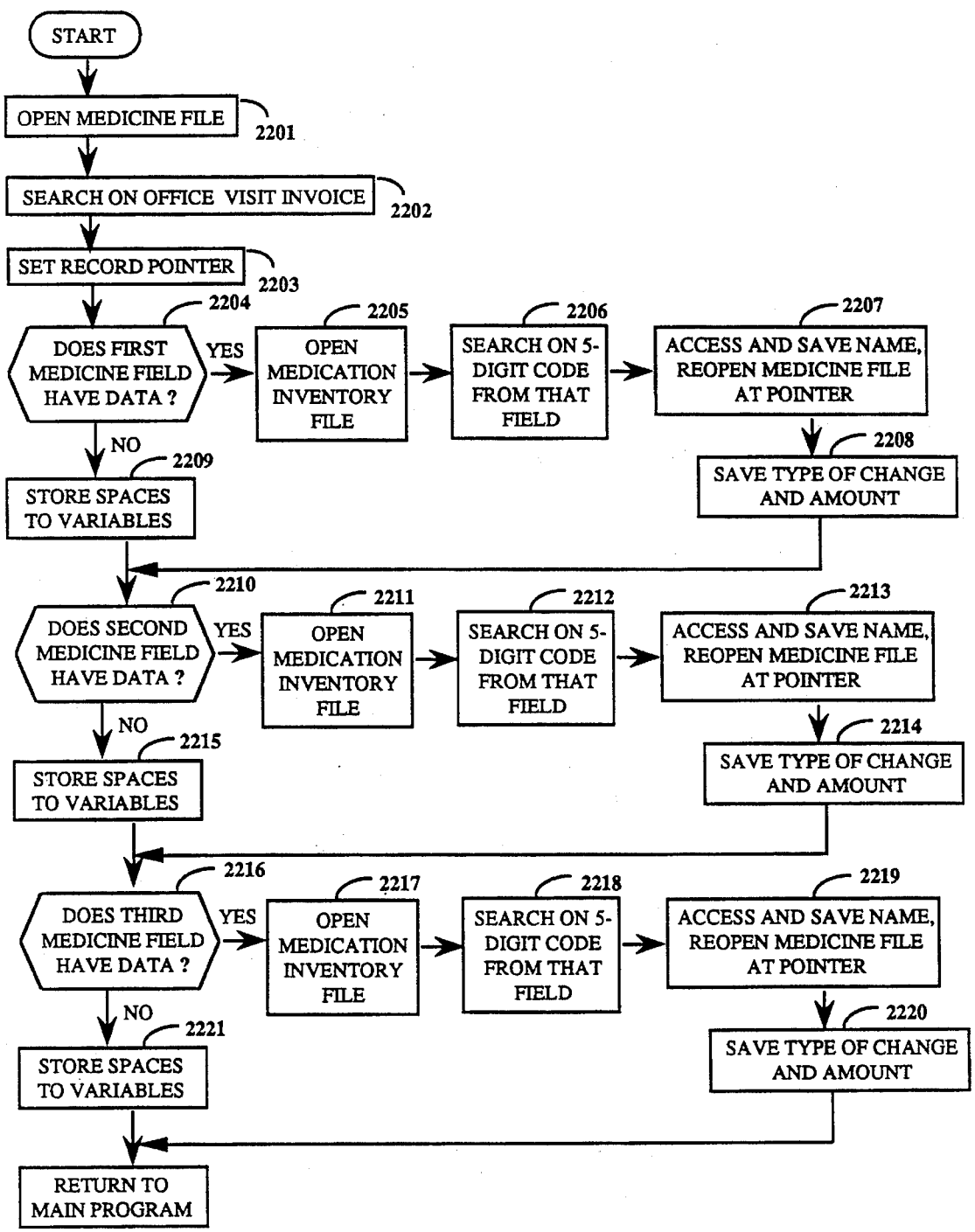

Referring to FIG. 38, a subroutine entitled Medget.prg that is called by Heartmed in order to search for and test the medication activity record linked to the office visit under processing for evidence of change data. It then organizes that data for passage back to Heartmed for display to the screen along with the physical data.

Figure 39:
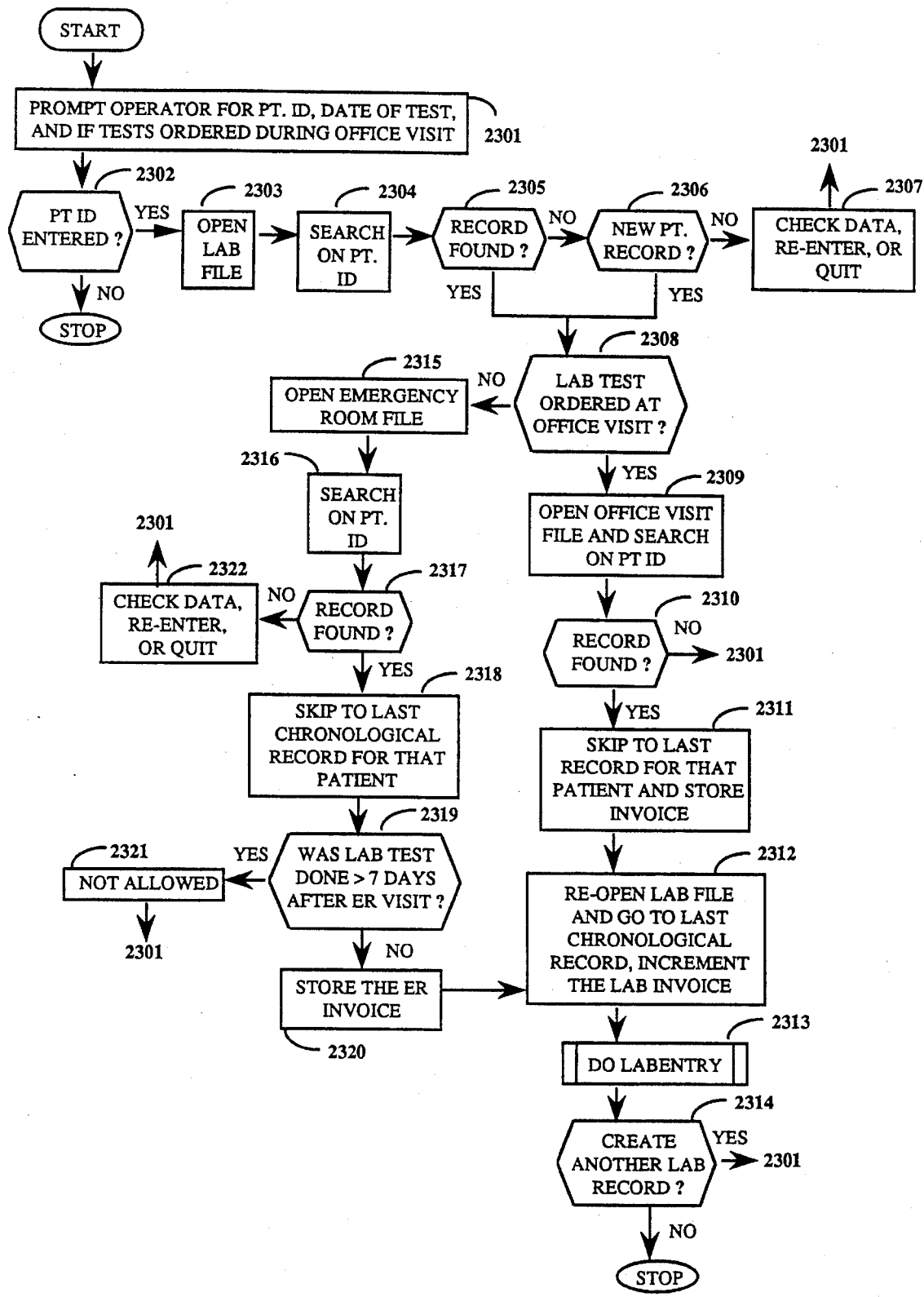

Referring to FIG. 39, the top, main calling program entitled labfirst.prg in the overall process that creates and loads records with lab test results. Note it is primarily involved with the entry of initial identifying data and then determining the invoice (or most unique aspect of any record type) to be assigned to the record that will be created. It then passes control to lower level programs that perform other specific functions in the process.

Figure 40:
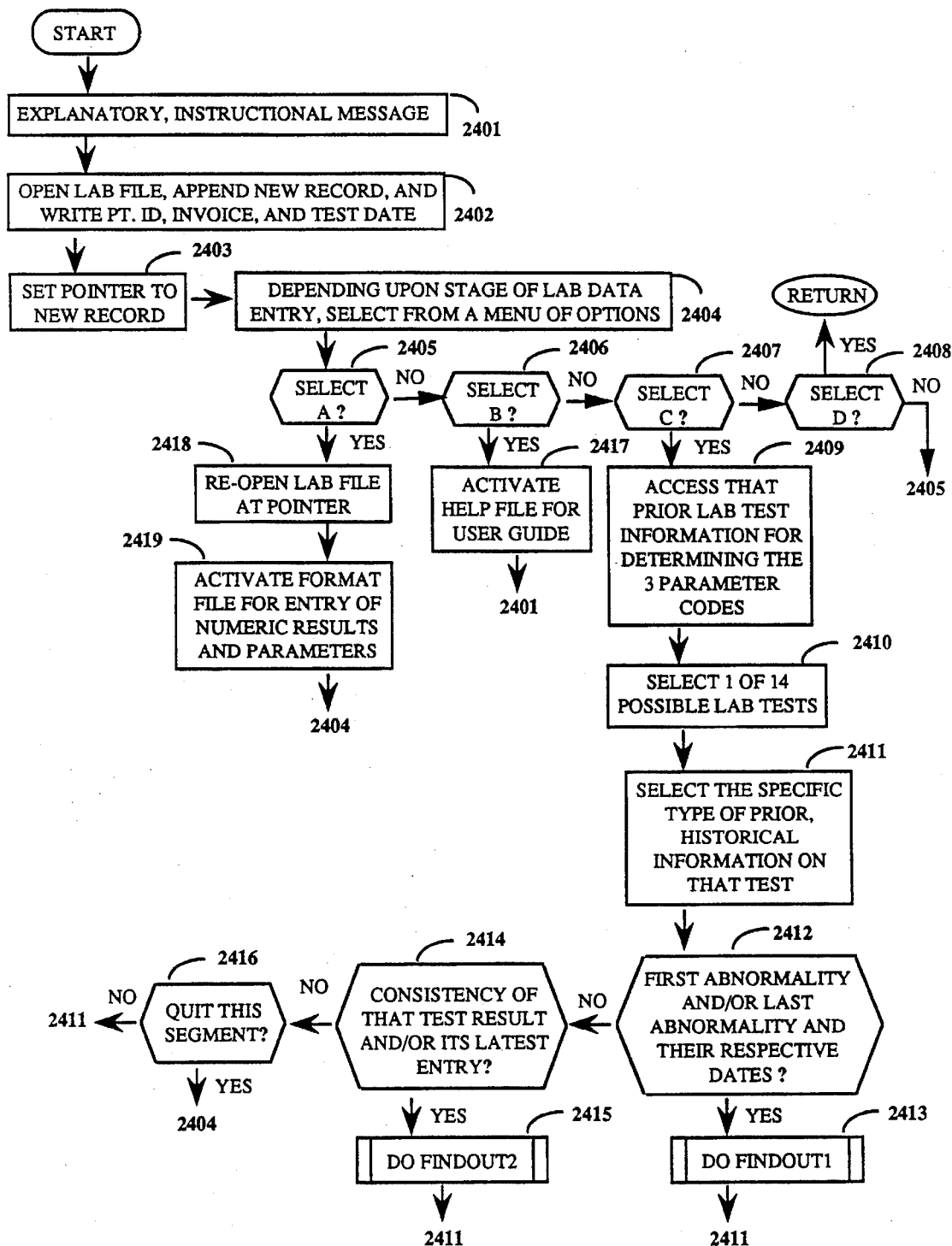

Referring to FIG. 40, the main subroutine entitled labentry.prg controlling several functions including the actual creation and loading of the test results along with their parameter data. It generates a menu that enables the selection from which other lower level routines are called in order to access prior results from several different aspects for each current lab test result present for entry. From there control is returned to labfirst.prg when finished.

Figure 41:
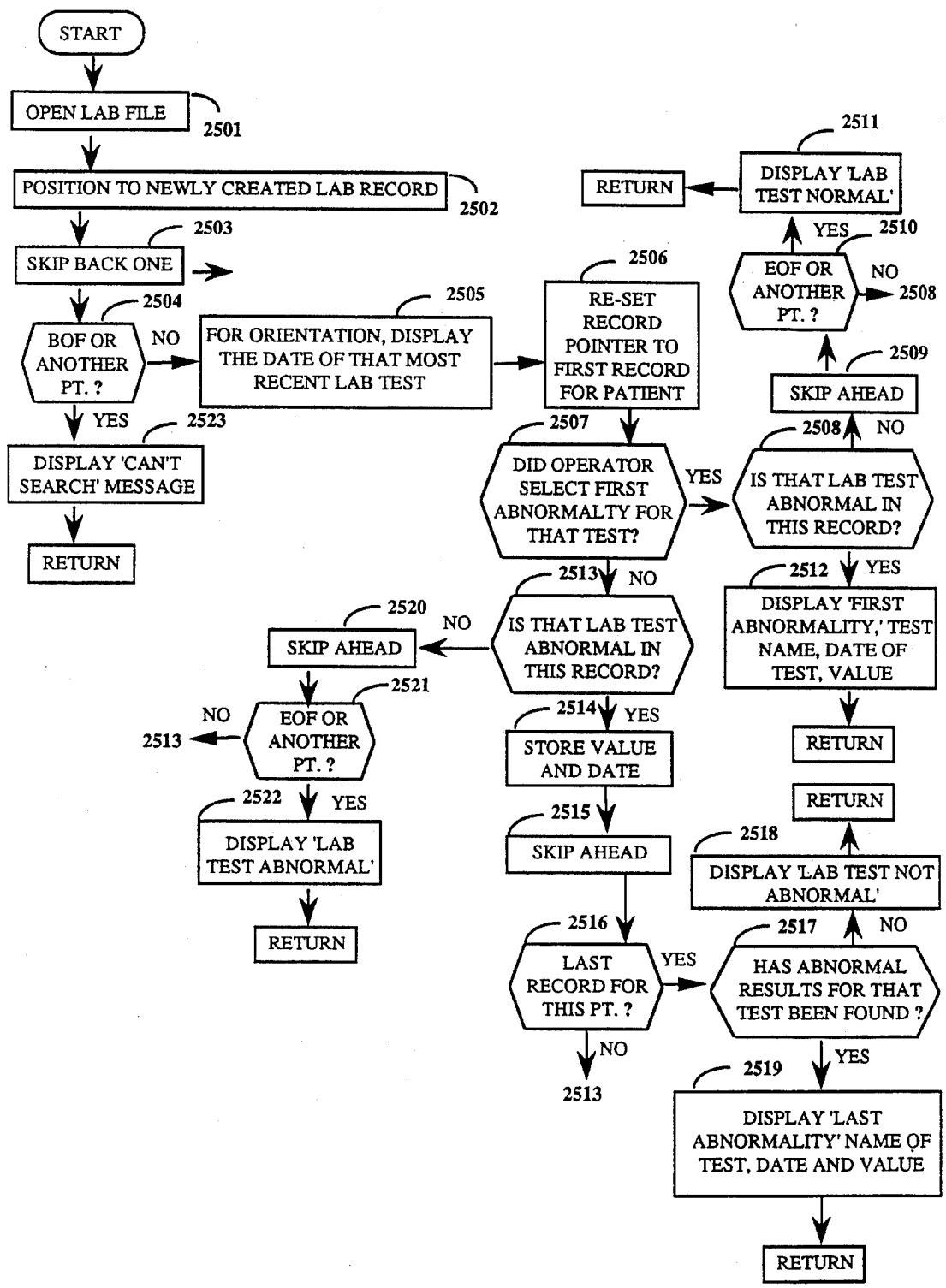

Referring to FIG. 41, a subroutine entitled Findout1.prg that is entered if the user had selected from a menu of options in the higher subroutine labentry.prg to obtain either the first date abnormality for any lab test and the results or the last date of abnormality for that test and the results. Control is then passed back to labentry.prg.

Figure 42:
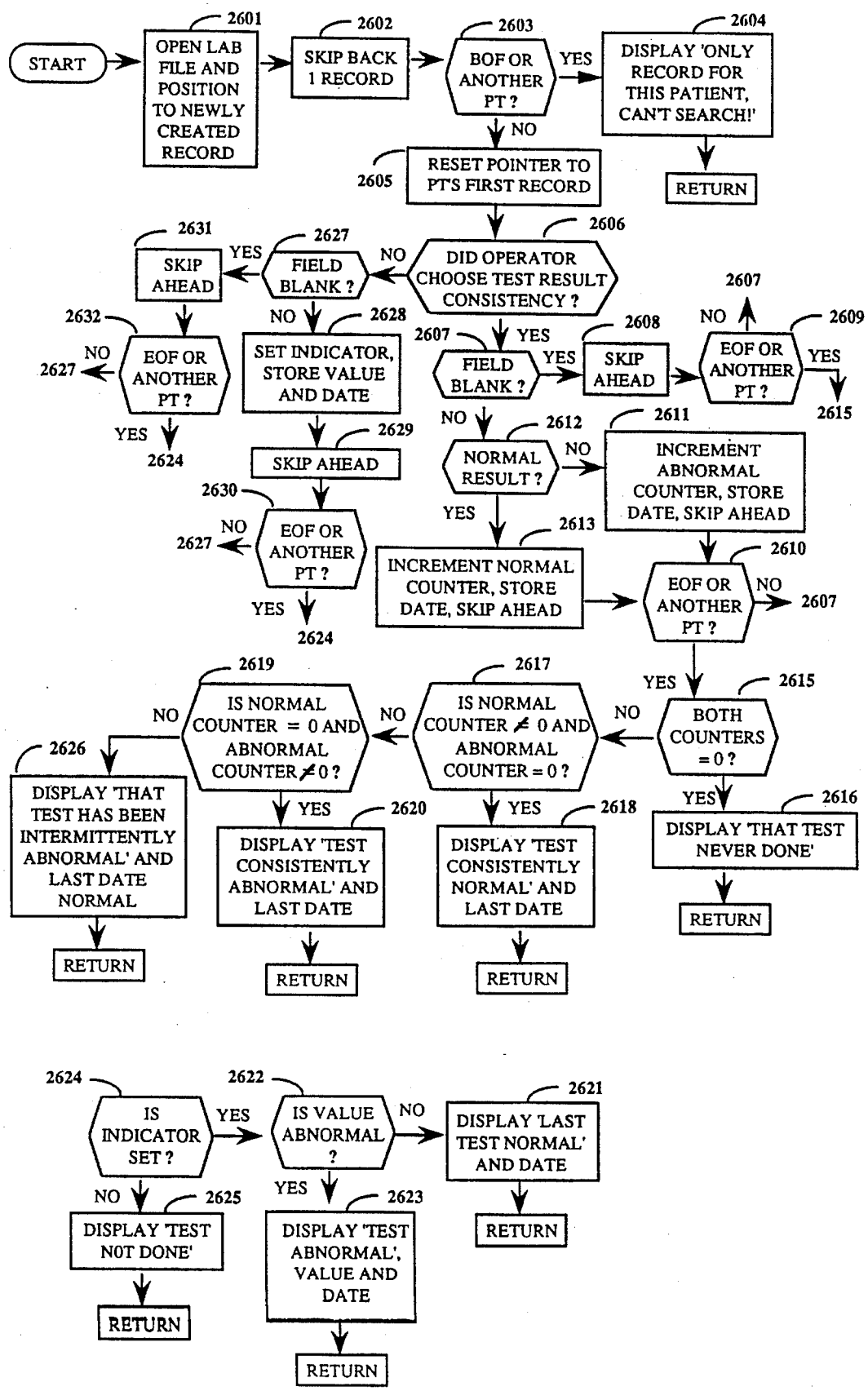

Referring to FIG. 42, a subroutine entitled findout2.prg that is entered if the user had selected from a menu of options in the higher subroutine labentry.prg to obtain either how consistent the results have been for that lab test or the most recent result for that test. Control is returned back to labentry.prg.

Figure 43:
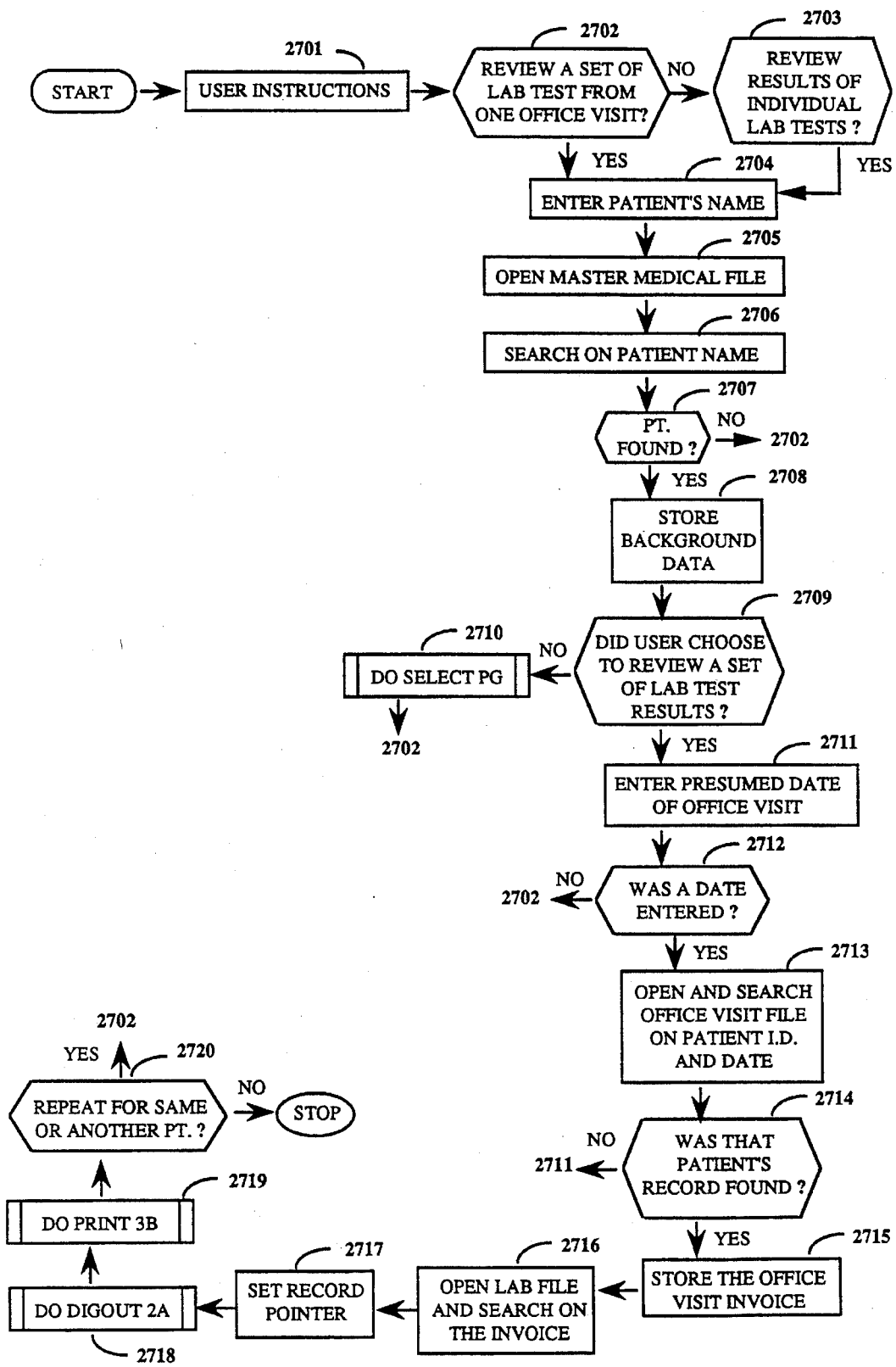

Referring to FIG. 43, the top, main calling program entitled Doctorpg.prg of another interactive query routine that generates narrowly focuse clinical data. In this case either a set of lab test results from a particular office visit or individual results of any lab test from several different, prior aspects. In this routine that choice is made and the name of the name of the patient whose data is to be looked is entered. It then calls a lower level subroutine.

Figure 44:
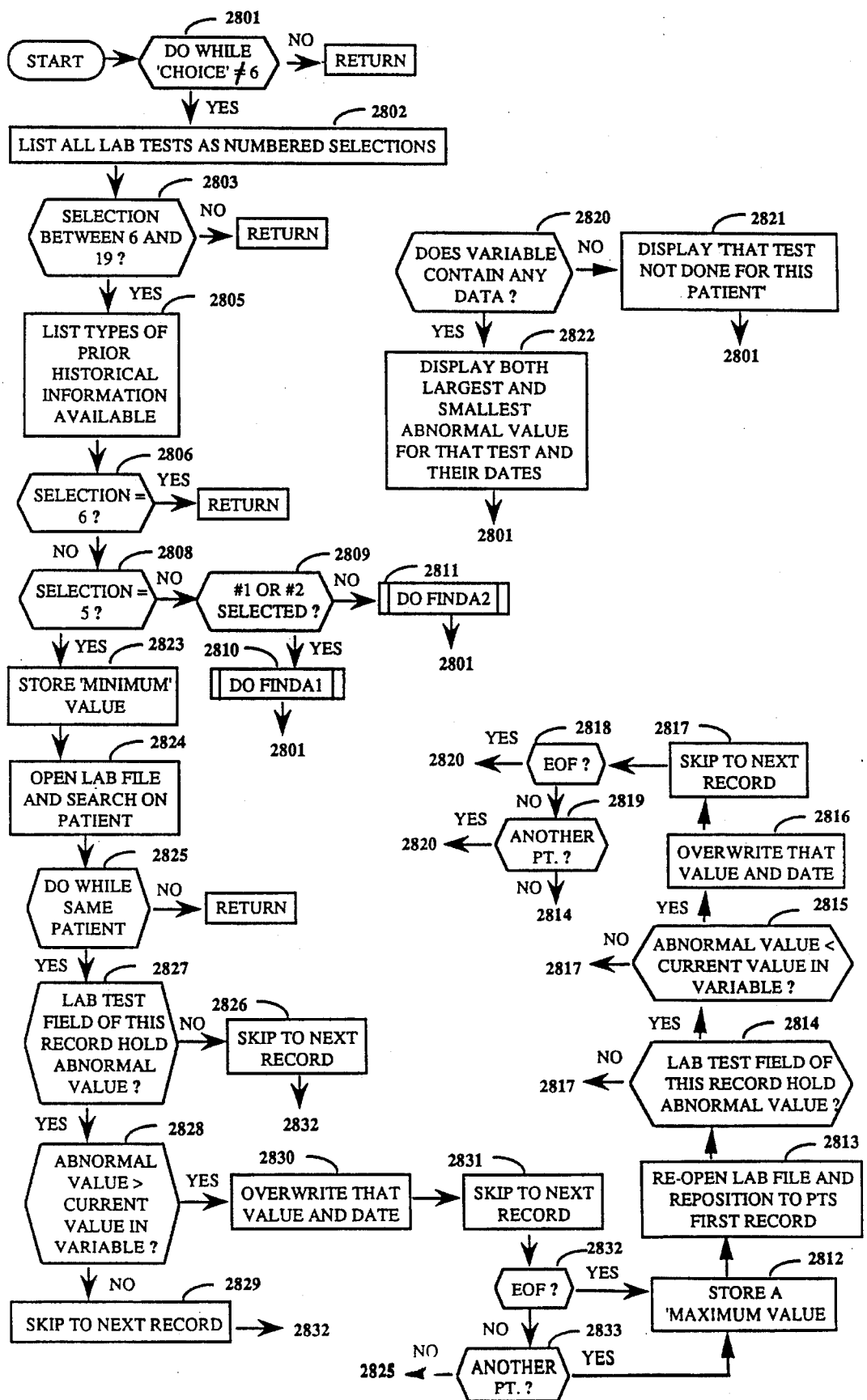

Referring to FIG. 44, a main subroutine of the interactive query routine whose main program is illustrated in FIG. 43. It is this subroutine that is entered if the results of individual lab tests was selected in Doctorpg.prg, and form here the selection is made on what prior aspects of that lab test should the results be expressed. The two lower routines called by selectpg.prg are not shown since they are identical to the two lowest subroutines of the labfirst.prg that creates and loads lab records.

Figure 45:
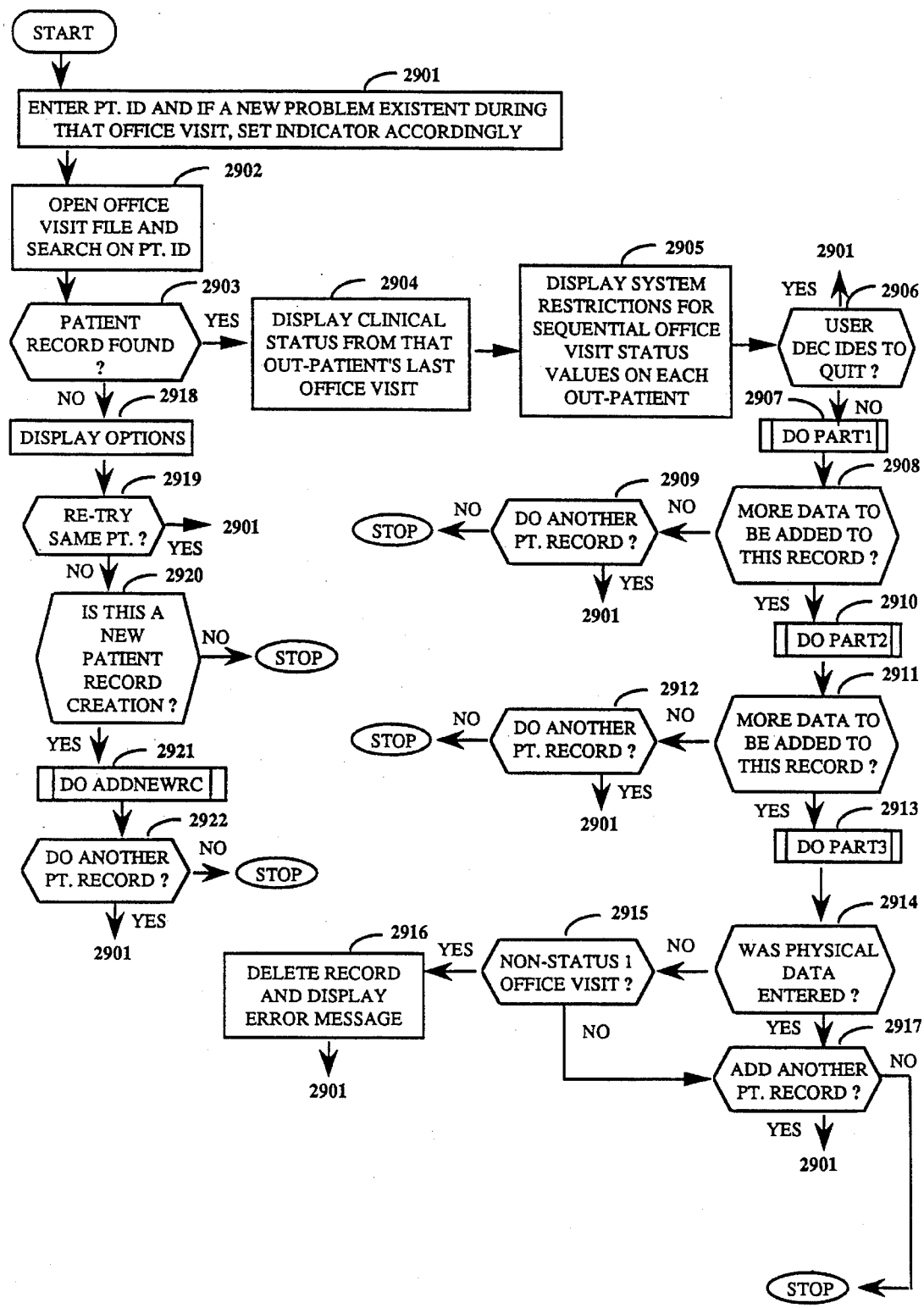

Referring to FIG. 45, the main, top calling program entitled addencrc.prg that controls the process that creates and loads a new office visit record. The only data entered here is the patient ID number and whether or not the main reason for that visit was a new problem. Otherwise all the other data is accessed and entered from lower subroutines under its control.

Figure 46:
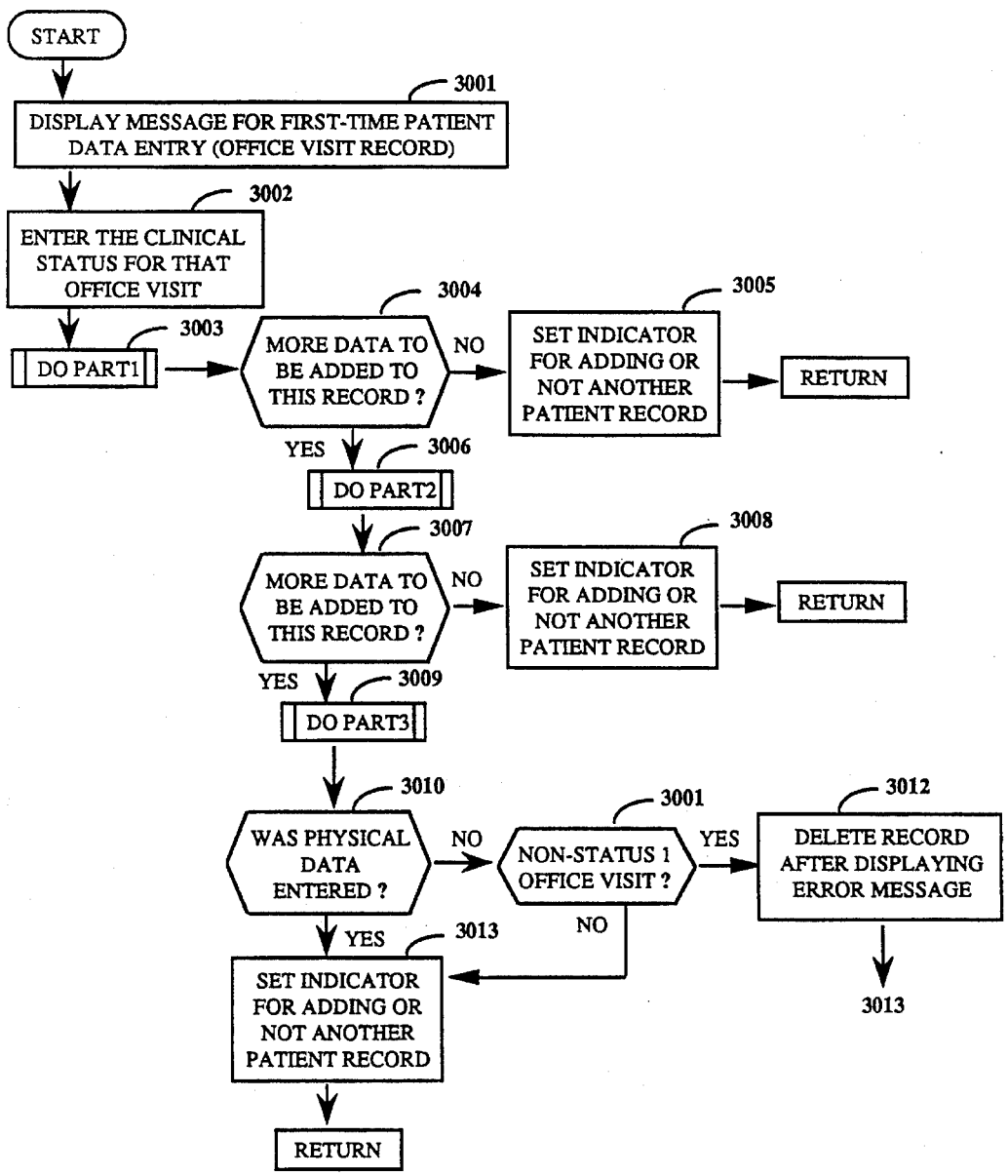

Referring to FIG. 46, the subroutine addnewrc.prg called by addencrc.prg for a first time office visit record creation and data entry. Once entered it acts like addencrc.prg in controlling the processing of the lower subroutines.

Figure 47:
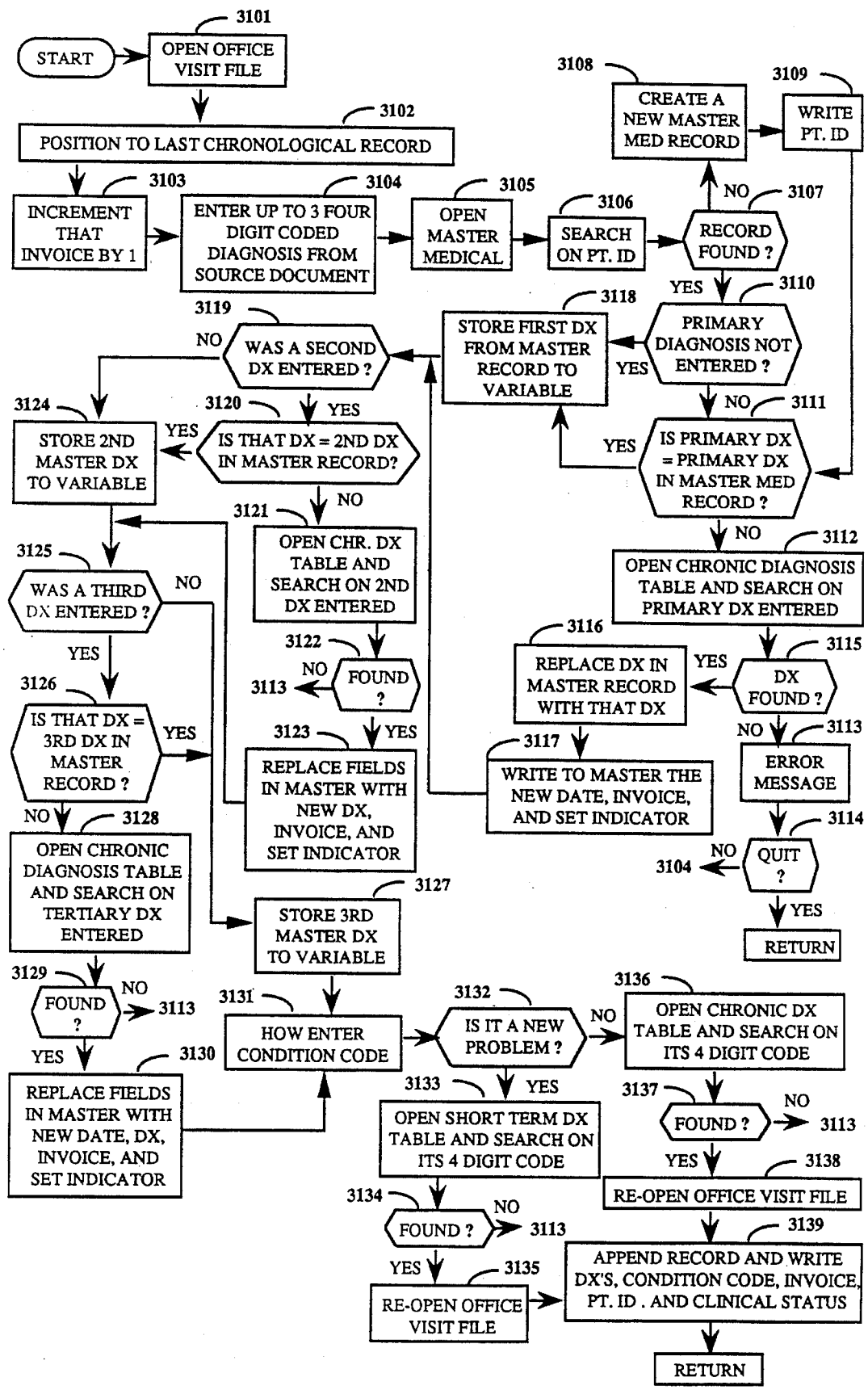

Referring to FIG. 47, the main subroutine entitled part1.prg of the office visit data entry. It is here that the record is created and the main data is written to it. It includes the multiple steps involved in accessing the full 6 digit codes of the chronic diagnoses, and the 6 digit code for the condition code field which represents the main reason for that office visit. It also controls entry into the two lower subroutines that load the physical data.

Figure 48:
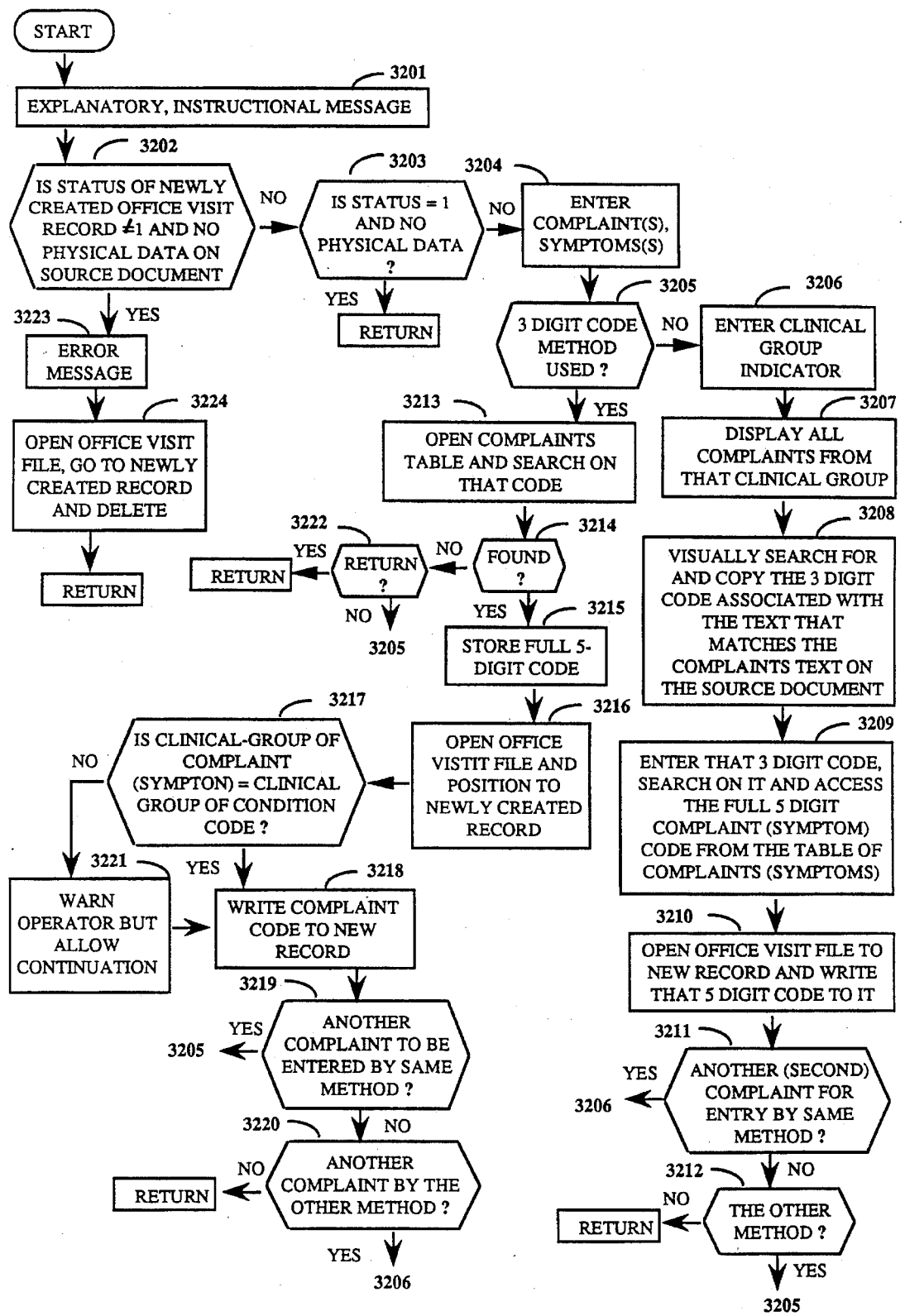

Referring to FIG. 48, a lower level subroutine entitled part2.prg called by part1 in order to load up to two physical symptoms that may be present on the data entry form to the new office visit record.

Figure 49:
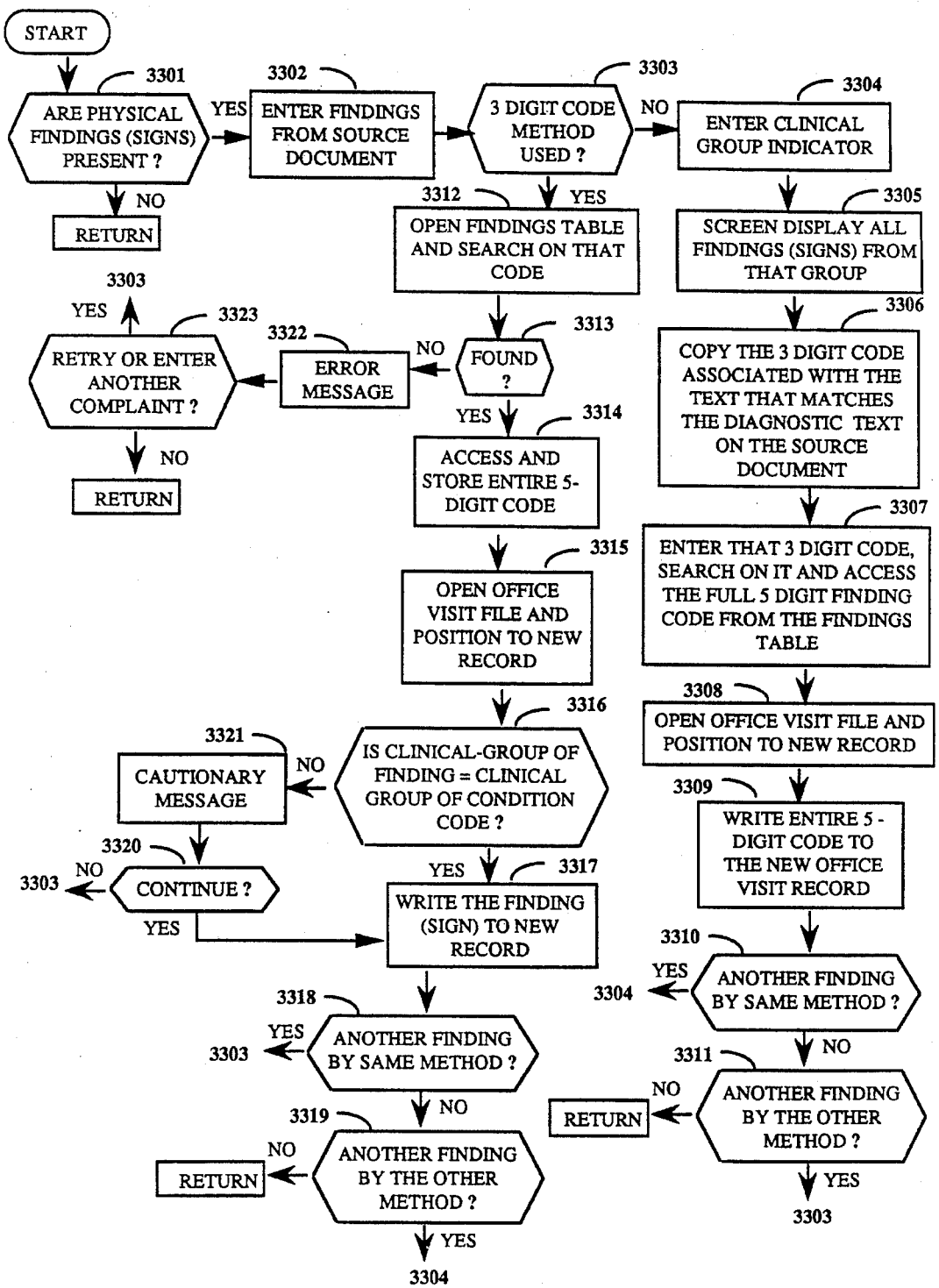

Referring to FIG. 49, a lower level subroutine entitled part3.prg called by part1 in order to load up to two physical signs that may be present on the data entry form to the new office visit record.

Referring to FIG. 50, an illustration of the model data entry source document used for loading the office visit record created in addencrc.prg. Note how it provides for two alternate methods for entering the physical data (signs and symptoms)

Figure 51:
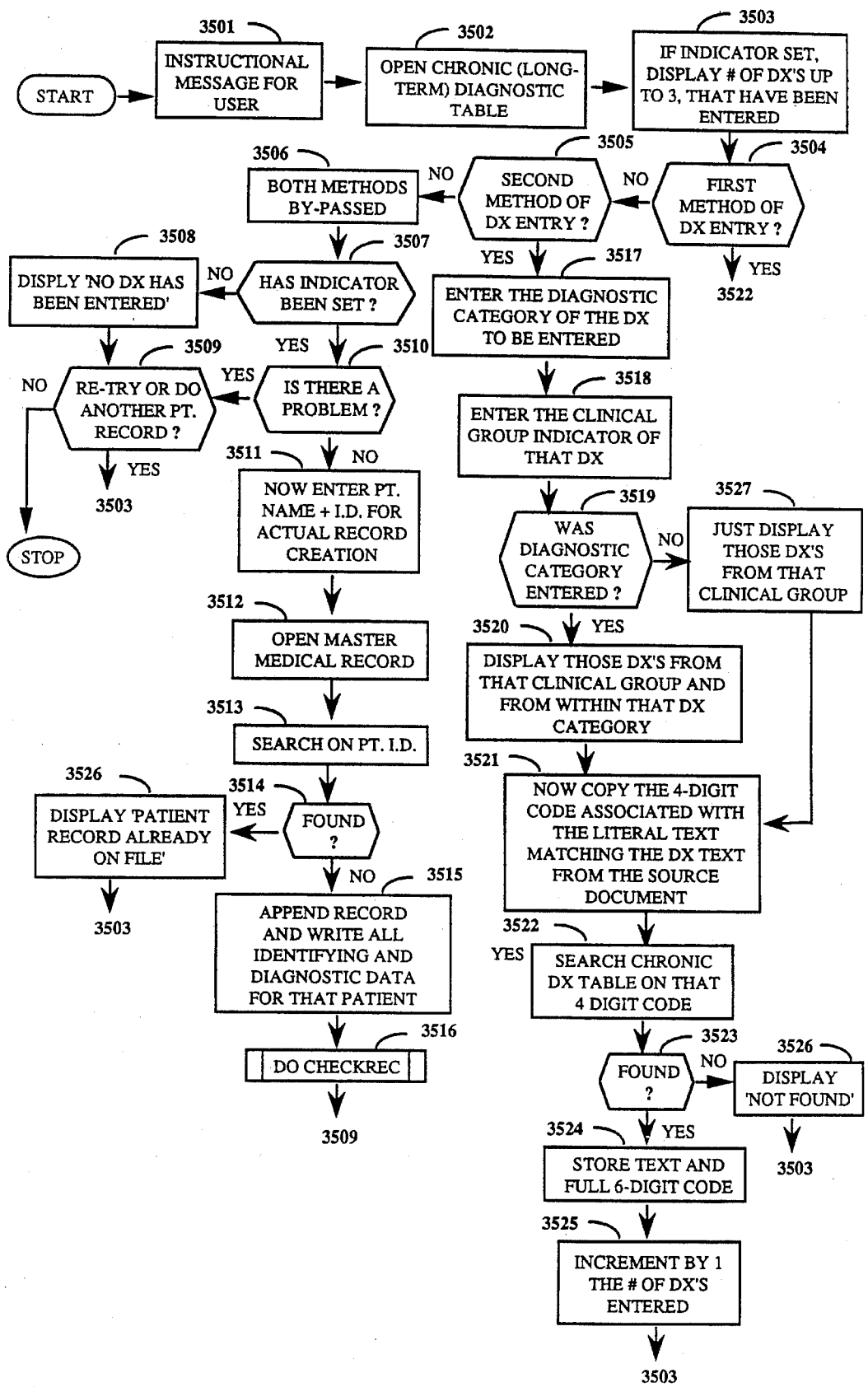

Referring to FIG. 51, a main program entitled Addmedrc.prg that creates and loads a master medical record once for each out-patient on the database. The program uses two alternate methods for the entry of up to three diagnosis for any out-patient. There is only one master medical record for each out-patient on the database.

Referring to 52, a subroutine entitled checkrec.prg called by addmedrc.prg that tests if the chronic diagnosis that were entered to the master medical record created is properly sequenced in relation to each other depending upon their relative positions in the chronic diagnosis table.

Figure 53:
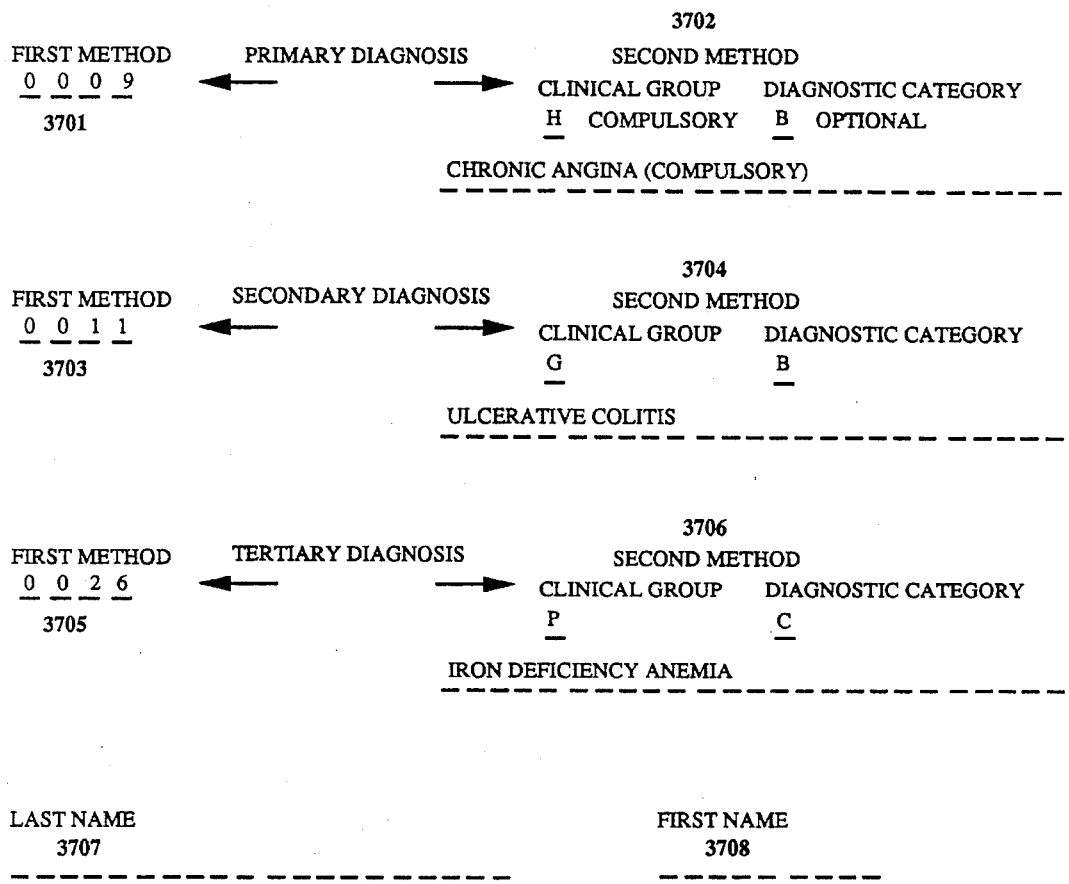

Referring to FIG. 53, a model source document for use in the data entry program that creates and loads one master medical record for each out-patient on the database. Note the presence of two alternate methods for entering the chronic diagnoses.

Figure 54:
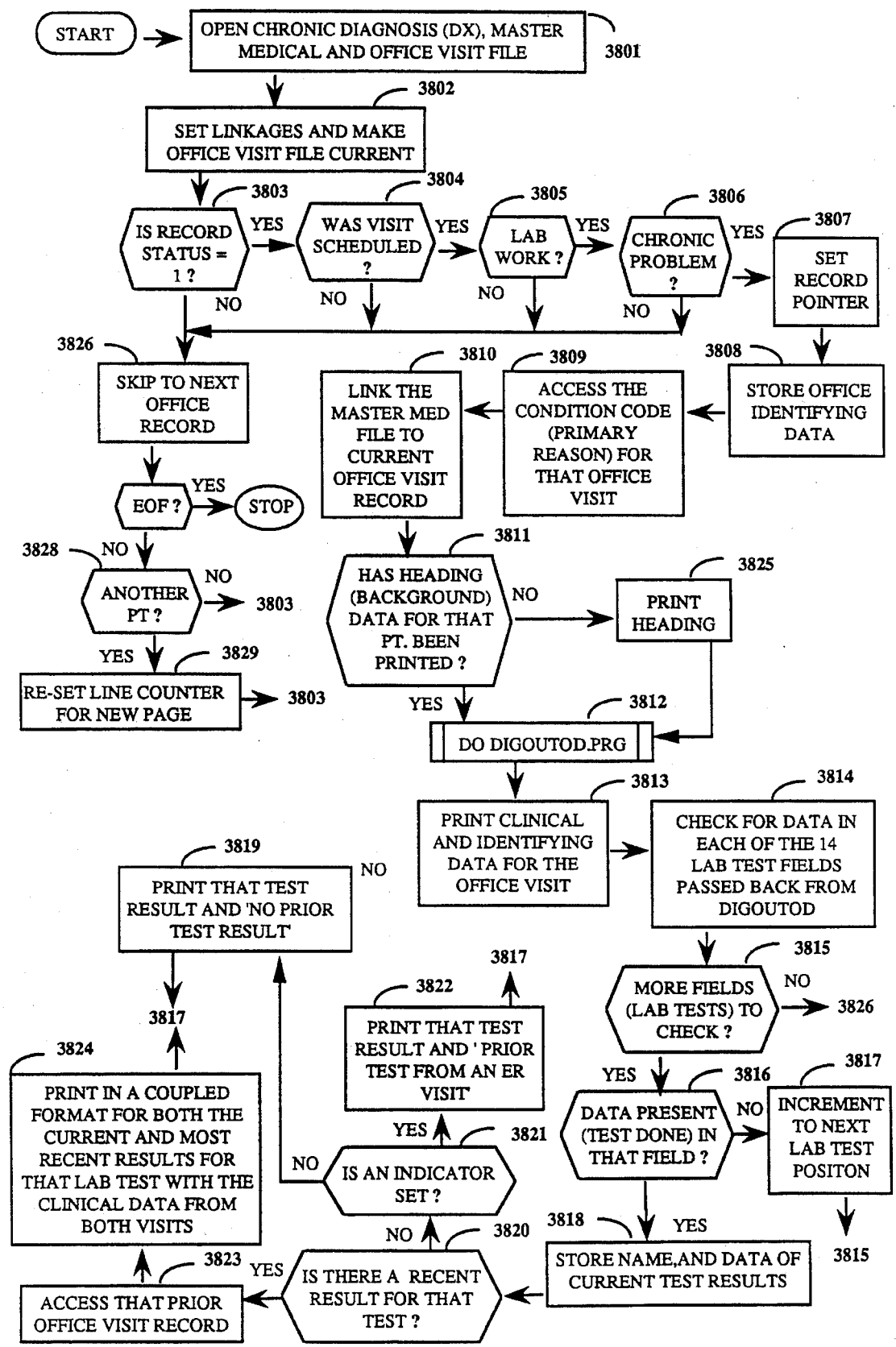

Referring to FIG. 54, a main program entitled Overdrawn.prg that monitors for the overuse of office visit based lab tests. It searches for results from lab tests drawn during office visits that were entirely unremarkable and uneventful, and then combines those results with their most recent results along with other salient data from both their respective visits in order to determine why the later tests were drawn. In order to access the lab data it calls a subroutine.

Figure 55:
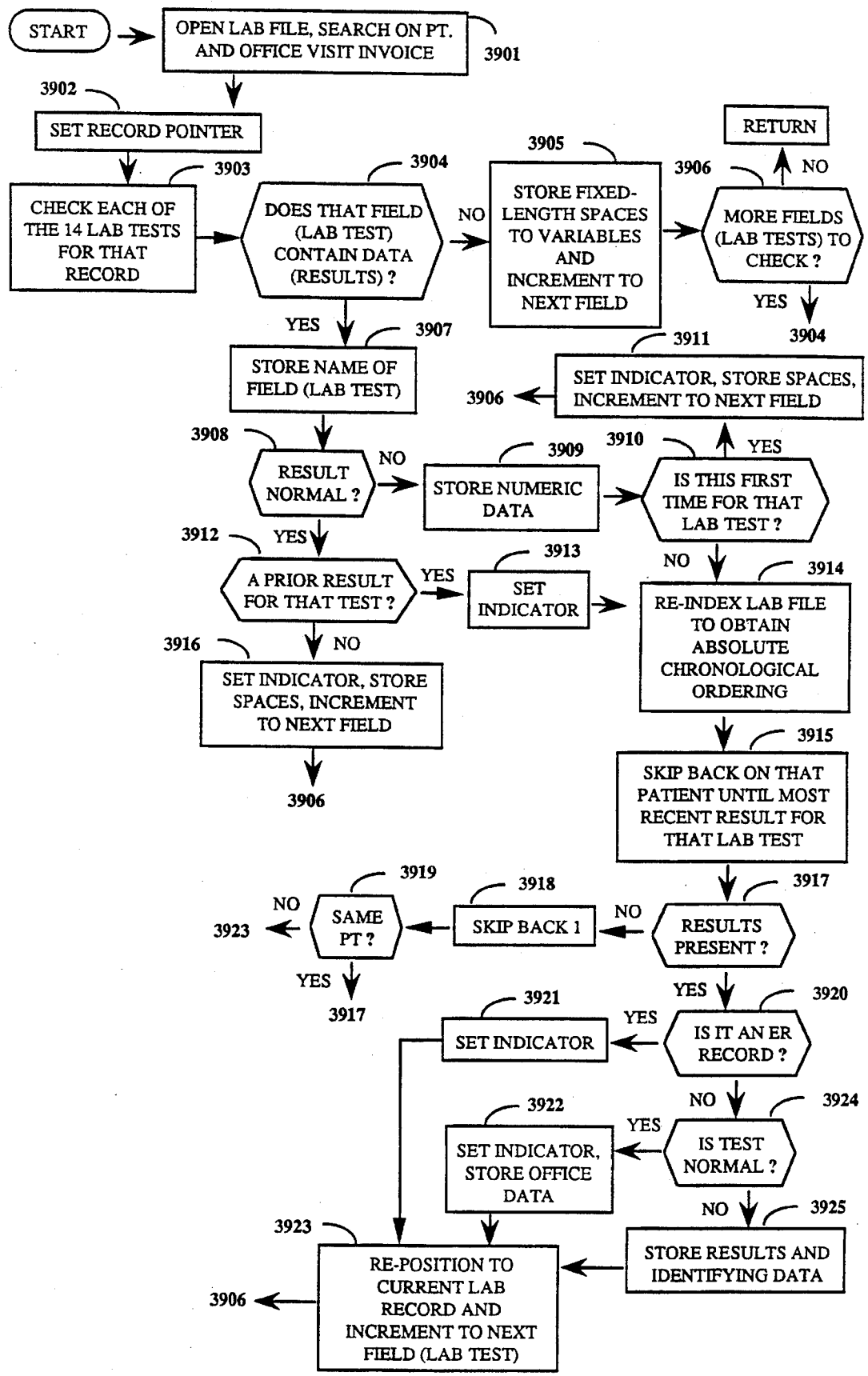

Referring to FIG. 55, a subroutine entitled digoutod.prg called by overdrawn.prg for accessing both lab results from the currently identified office visit, and for each test present it accesses it's most recent result from any of that outpatient's prior lab records.

Referring to FIG. 56, the system's office visit file, encounte.dbf, loaded with sample data for processing by schedule1.prg in order to detect and justify any early and consecutively uneventful office visit by an out-patient.

Referring to FIG. 57, the remaining office visit records of the file depicted in FIG. 56.

Referring to FIG. 58, the system intermediary file, notify.dbf, as the output from a run by schedul1.prg while using the sample data of FIGS. 56 and 57 as the basic unit of information. Note the anomalous type of condition code in record #1 and how it has no effect on processing since only the setting in the new problem field is tested and not the actual nature of the 6 digit condition code itself.

Referring to FIG. 59, the system laboratory test file, abn_lab.dbf, sample loaded and as one of several related out-patient files for use in schedul1.prg in the search for data justifying the early consecutively uneventful office visit of an out-patient.

Referring to FIG. 60, the remaining four system files that contain related out-patient data for use in searching for clinical data in schedul1.prg that can justify an early consecutively uneventful office visit by an out-patient. They are er_room.dbf(A), surgfind.dbf(B), pt_hosp.dbf (C) and treatmen.dbf(D). All are loaded with sample data.

Referring to FIG. 61, a version of the office visit file for serving as basic input to the program unsched1.prg.

Referring to FIG. 62, the remaining office records of the file named encountu.dbf depicted in FIG. 61 and which is identical, except for name, as the office visit file encounte.dbf. (its last letter changed to identify it as sample loaded for special use by a particular program)

Referring to FIG. 63, the system intermediary file, notify.dbf, now represented as output from an unsched1.prg run. Note the presence of the 'C' indicator written to the CODE field of a notify.dbf record in instances of consecutive unscheduled office visits for the same patient that the program unschedul.prg is designed to identify while the same field is used for indicating an absolute justification in instances of early scheduled and consecutive office visits by the same outpatient, something which unschedl.prg is also capable of identifying and documenting.

Referring to FIG. 64, a version of the office visit file named encountb.dbf that serves as basic input to astatusb.prg.

Referring to FIG. 65, the remaining office visit records of the file depicted in FIG. 64.

Referring to FIG. 66, the system intermediary file now as output from the program astatusb.prg. Note the second character in the CATEGORY field that indicates the name of the program.

Referring to FIG. 66A, a translation table for illustrating how, in the binary.prg subroutine, the assignment is made of a single letter code to each of 16 possible types or combinations of physicianaction or intervention occurred during an office visit, including the code for none at all.

Referring to FIG. 67, schematic of computer program execution sequences that demonstrate continuity of data flow. Output to an intermediary file, notify.dbf, is then used as input to a print program in both the upper and lower diagram.

Referring to FIG. 68, the system medicine-activity record file, medicine.dbf, sample loaded for use with the program atatus3.prg.

Referring to FIG. 69, another sample loaded version of the office visit record file as the basic input to astatus3.prg. Note how the last letter of name has been changed in order to properly identify and access this particular version of the office visit file for use with astatus3.prg.

Referring to FIG. 70, remaining office visit records of the encount3.dbf file.

Referring to FIG. 71, the system intermediary file, notify.dbf, now as output from astatus3.prg. Note the relationship between record #1 and #5 of notify.dbf and that of #8 and #30 in medicine.dbf of FIG. 68.

Referring to FIG. 72, the system's physical signs table, findings.dbf. For use in the physical data report of print1a.prg.

Referring to FIG. 73, another sample loaded version of the office visit file, encounte.dbf for use as basic input for clinevol.prg.

Referring to FIG. 74, remaining office visit records of the encounte.dbf file.

Referring to FIG. 75, the system's physical symptoms table, cc_list.dbf, for use in the physical data report of print1a.prg.

Referring to FIG. 76, the system's chronic diagnosis table, chrmed1i.dbf, for use in print1a.prg.

Referring to FIG. 77, another example of the system intermediary file, notify.dbf, generated as output from clinevol.prg and now serves as basic input to print1a.prg, which is based upon a chronic diagnosis as the primary reason for an office visit.

Referring to FIG. 78, an out-patient office based physical data report. Note the indication of whether or not resolution of the out-patient illness has or hasn't occured. Note that two physical data items of the same type (signs or symptoms) present in the same office visit record are separated by the "and" when both are printed out during that out-patient's processing.

Referring to FIG. 79, an out-patient office based physical data report which, like in FIG. 78, shows two visits by the same patient. Note hospitalization indicator while the clinical resolution indicator is set to positive because the next record in the office visit file is that out-patient's and its clinical status is a 1 indicating a return of the patient's clinical condition to normal or baseline and therefore termination of the out-patient illness.

Referring to FIG. 80, another out-patient physical data report.

Referring to FIG. 81, another out-patient physical data report, this time only one visit for an out-patient is involved. Note that it resulted in a hospitalization but at the next office visit, that out-patient was found to be without continuing illness due to the presence of a clinical status of 1 resulting in the 'problem resolved' indicator as shown.

Referring to FIG. 82, another out-patient physical data report involving two visits by the same patient.

Referring to FIG. 83, another out-patient physical data report.

Referring to FIG. 84, another out=patient physical data report, this time involving 3 office visits.

Referring to FIG. 85, another out-patient physical data report, this time involving 5 office visits by the same patient. Note that after the second record there has a temporary termination of the illness as indicated by the 'problem resolved' message but that was apparently only a brief remission followed by a re-occurrence of another period of illness.

Referring to FIG. 86, another out-patient physical data report.

Referring to FIG. 87, another sample loaded version of the system master medical record file, medical.dbf, for use in the querying of lab data by the program doctorpg.prg.

Referring to FIG. 88, continuation of the master medical file, medical.dbf. Note record #12 for use as the sample data that generates the display illustrated in a higher number figure.

Referring to FIG. 89, the continuation of medical.dbf records displayed in FIGS. 87 and 88.

Referring to FIG. 90, another sample loaded version of the system office visit file for use in the querying of out-patient lab data. Note the sample data of record #19 for use in generating the display to be found in a higher numbered figure.

Referring to FIG. 91, continuation of the office file records of FIG. 90.

Referring to FIG. 92, a sample loaded version of the system laboratory test file, abn_lab.dbf, for use in the querying of out-patient lab data. Note records numbered 8 and 25 for use in generating the display to be found in a higher-numbered figure.

Referring to FIG. 93, continuation of the system laboratory test file of FIG. 92.

Referring to FIG. 94, alternate displays of the lab data querying routine depending upon the user's choice. Subfigure A displays all the test results ordered from the same office visit while subfigure B represents the results of an individual lab test from one of several historical perspectives.

Referring to FIG. 95, another sample loaded version of the system master medical file, medical.dbf, for use in the querying routine named meditoxi.prg.

Referring to FIG. 96, continuation of the system master medical file of FIG. 95.

Figure 97:
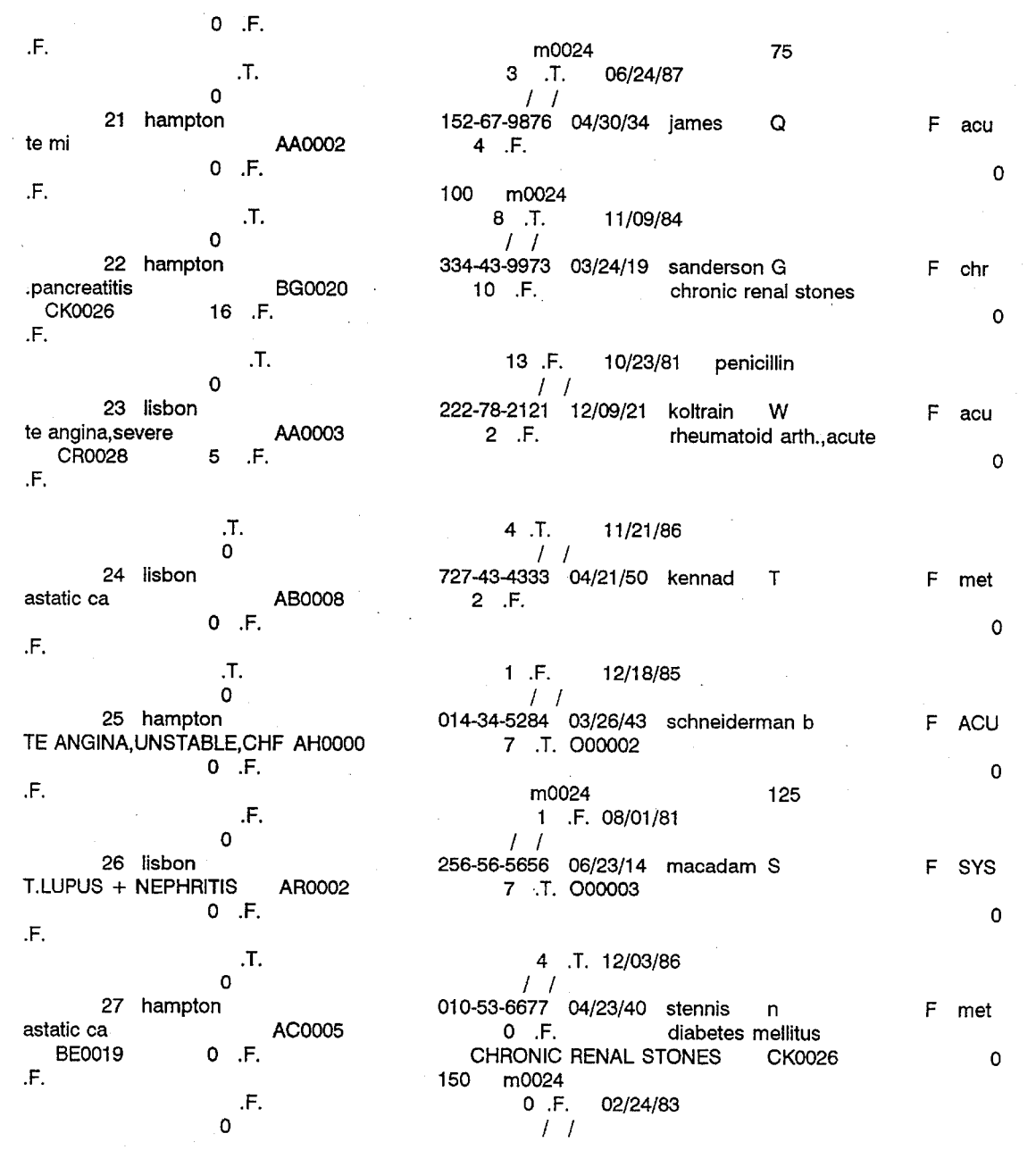

Referring to FIG. 97, continuation of the system master medical file displayed in FIGS. 95 and 96.

Referring to FIG. 98, another sample loaded version of the system laboratory test file, abn_lab.dbf, for use in the querying routine meditoxi.prg. Note records 11, 12, 13 and the 'wbc' field for use in the meditoxi.prg screen display of a higher numbered figure.

Referring to FIG. 99, continuation of the system laboratory file, abn_lab.dbf, from FIG. 98.

Referring to FIG. 100, subfigure A displays two separate sequential steps of meditoxi.prg. First is a listing of all out-patients who are currently taking the medication entered at the top of the routine and who are under the care of the doctor whose name was also entered at the top of the routine. Then after one of the names of the patients listed is entered, all the results of that test on file for that patient are listed in chronological order. Subfigures B, C and D are displays from the querying routine named Heartmed.prg. They list the physical data documented and any medication activity enacted by a database doctor for those out-patients selected on the basis of chronic cardiac disease and who were very symptomatic(ill) during an office visit.

Referring to FIG. 101, a sample loaded version of the system medicine-activity file medicine.dbf, used in the heartmed.prg query routine.

Referring to FIG. 102, a sample loaded version of the laboratory test file, abn_lab.dbf, for use in the report program, overdraw.prg, the output of which is illustrated in a higher numbered drawing.

Referring to FIG. 103, continuation of the laboratory test file of FIG. 102.

Referring to FIG. 104, another sample loaded version of the system office visit file, encounte.dbf, for use in the overdraw.prg report program.

Referring to FIG. 105, continuation of the office visit file of FIG. 104.

Referring to FIG. 106, an out-patient report generated by the program overdraw.prg. It involves three office visits. Note how the most recent result for any two tests ordered at the same office visit (and therefore drawn at the same time) may have been ordered from different prior office visits and therefore found in different lab records of that patient.

Referring to FIG. 107, another out-patient report from the overdraw.prg program. This involves two office visits.

Referring to FIG. 108, another out-patient report from overdraw.prg. Note how the Sed Rate test result from the office visit of 01/13/87 then appears on the right hand side as a most recent result of that test ordered during the subsequent office visit of 02/17/87. Note that three visits for that patient are involved.

Referring to FIG. 109, another out-patient report from the overdraw.prg program.

Referring to FIG. 110, another out-patient report from the overdraw.prg program. Note how, for the ekg results from the third office visit, the most recent ekg results are drawn from a different prior lab record than the other results for that patient.

Referring to FIG. 111, another out-patient report from the overdraw.prg program.

Referring to FIG. 112, another sample loaded version of the system master medical file, medical.dbf, for use in the caseload.prg program.

Referring to FIG. 113, continuation of the system master medical file of FIG. 112. Note the sample use of the 6 digit chronic diagnosis code CP0026, iron deficeincy anemia, for use in the caseload program display present in a higher numbered figure(drawing).

Referring to FIG. 114, continuation of the master medical file of FIG. 112 and 113.

Referring to FIG. 115, output from the program caseload.prg. Note the out-patient breakdown into diagnostic categories for the doctor whose name was entered.

Figure 116:
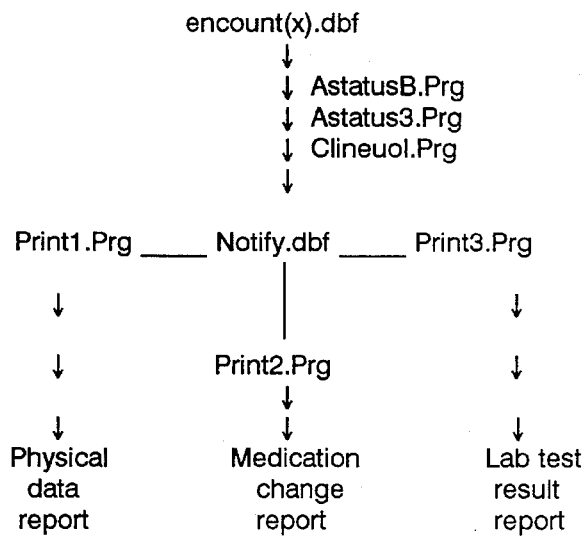

Referring to FIG. 116, diagrammatic outline of sequential computer programs and progression of data flow. Office visit records are first processed by any of 3 routines that identify office visits that represent protracted out-patient illnesses and determine what the physician observed and did. The data compiled into those records created and written to as a result of the aforementioned processing are then used for any of 3 print programs that report out clinical data from those original visits. The phrase 'new clinical problems' indicates that the office visit(records) selected were on the basis of a new clinical problem(or an as yet uncharacterized complication of an established diagnosis) as the primary reason for that patient's office visit.

Referring to FIG. 117, a version of the laboratory test file loaded with sample data for use in the lab test data report program, print3.prg.

Referring to FIG. 118, a sample loaded version of the system intermediary file, notify.dbf, for use with the lab test report program print3.prg. It is identical to that present in FIG. 141 but has less total records since the print3.prg cutoff date is different from that of print1.prg and print2.prg.

Referring to FIG. 119, an out-patient lab test report by print3.prg.

Referring to FIG. 120, an out-patient lab test report by print3.prg.

Referring to FIG. 121, an out-patient lab test report by print3.prg.

Referring to FIG. 122, an out-patient lab test report by print3.prg.

Referring to FIG. 123, an out-patient lab test report by print3.prg.

Referring to FIG. 124, an out-patient lab test report by print3.prg.

Referring to FIG. 125, an out-patient lab test report by print3.prg.

Referring to FIG. 126, the system's inventory type medication table listing the generic names of the medicines available to the database patients, med_list.dbf.

Referring to FIG. 127, a sample loaded version of the transactional type medicine-activity record file, medicine.dbf, for use in the execution of print2.prg.

Referring to FIG. 128, an out-patient medication change report by print2.prg.

Referring to FIG. 129, an out-patient medication change report by print2.prg.

Referring to FIG. 130, an out-patient medication change report by print2.prg.

Referring to FIG. 131, an out-patient medication change report by print2.prg.

Referring to FIG. 132, an out-patient medication change report by print2.prg.

Referring to FIG. 133, an out-patient medication change report by print2.prg.

Referring to FIG. 134, an out-patient medication change report by print2.prg.

Referring to FIG. 135, a sample loaded version of the system master medical file, medical.dbf.

Referring to FIG. 136, a continuation of the master medical file of FIG. 135.

Referring to FIG. 137, a continuation of the master medical file of FIG. 136 and 135

Referring to FIG. 138, the physical complaints or symptoms table, cc_list.dbf, for use in physical data report print1.prg.

Referring to FIG. 139, the physical findings or signs table, findings.dbf, for use in the physical data report print1.prg.

Referring to FIG. 140, the short term diagnosis table, er_list.dbf, for use in the newproblem report of print1.prg.

Referring to FIG. 141, by initial processing, an abbreviated segment of the intermediary file, notify.dbf, for use in print1.prg.

Referring to FIG. 142, the system intermediary file, notify.dbf, for use in and just prior to initial processing by print1.prg Referring to FIG. 143, continuation of the intermediary file, notify.dbf, from FIG. 142 and as it exists just prior to initial processing by print1.prg.

Referring to FIG. 144, an out-patient physical data report by print1.prg.

Referring to FIG. 145, an out-patient physical data report by print1.prg.

Referring to FIG. 146, an out-patient physical data report by print1.prg

Referring to FIG. 147, an out-patient physical data report by print1.prg.

Referring to FIG. 148, an out-patient physical data report by print1.prg.

Referring to FIG. 149, an out-patient physical data report by print1.prg.

Referring to FIG. 150, an out-patient physical data report by print1.prg.

DPE DESCRIPTION OF PREFERRED EMBODIMENTS

Referring to FIG. 17, a main computer program entitled Schedul1.prg that identifies, compiles data and creates records for the storage of information about potentially over-scheduled and unnecessary office visits. If a number of specific criteria, to be enumerated, are found in two successive office visits by the same out-patient, and that occured too quickly, the program and its subroutine will search on a set of related out-patient files, each storing different aspects of medical data, for any clinical data that either might or will justify the early second office visit. It will access information for determining if there was any valid reason for the second scheduled office visit if it turns out to be as unremarkable as the first and has occured too early, therefore representing a waste of clinical time and resources in that out-patient's care.

Initially, as indicated by step 0102, office visit records (see FIG. 4, encounte.dbf) are selected by diagnostic category and those set of records then serve as the basic unit of information processing for this routine. Next, as in steps 0103 thru 0120, the program skips through each office visit record until one of the MINIMUM CLINICAL ACTIVITY type is identified. That is defined as being 1) a scheduled visit as opposed to an unscheduled one, 2) the clinical status of the out-patient is a 1 indicating normal or baseline, with no new or unusually active problems, 3) no medication ordered during that office visit, 4) no lab tests ordered, 5) no specialty referrals made, and 6) the main or primary reason for the office visit being one of the out-patient's chronic, long term diagnosis as opposed to an acute short-term one. In short, an uneventful and unremarkable office visit. But if another just like that for that out-patient occurs next and it's too early for that diagnostic category then someone (?doctor) may be scheduling that out-patient too soon, often and without any valid reason.

It is the purpose of this program to identify and resolve that.

Upon identifying a first record of the MCA type, and as illustrated, counters and indicators are set and a group of values from that out-patient's record are temporarily stored. If the next record is from that same out-patient, it is then subjected to the same tests to see if it is also of the same scheduled MCA type. If it is not the same patient or of the same type, counters and indicators are re-set, previous stored values are cleared and the program skips to the next record. If it is a scheduled visit for the same out-patient and it is determined to be of the MCA type, the program then computes the interval of time between the two successive visits and if the interval is equal to or greater than that prescribed for that out-patient's diagnostic category the same thing as above happens and that second MCA record then becomes the first for that out-patient. However, if the time interval is less then a possible condition of resource over-usage exists and at step 0121, therefore, a subroutine named searchv.prg is called (see FIG. 19 and 20) to determine if that second, early MCA type visit for that out-patient is in any way justified on clinical grounds.

As FIG. 19 illustrates a set of related out-patient files, each storing different aspects of clinical data, is searched for any intervening event or activity between the two MCA visits that might or could justify the early second one. As step 0301 illustrates, the search begins on the system's emergency room file (see er_room.dbf, FIG. 15) to find a record with a date within that time interval. If found then that invoice is saved as a low level or soft justification but an absolute justification isn't made until two further criteria are met; a clinical status that indicates a need for a follow-up soon with an office visit or even the suggestion of hospitalization during the ER visit and the ER record condition code field is identical to that of the second, early MCA office visit of that out-patient (i.e. the same reason and type of diagnosis for both visits). If absolute justification isn't found the subroutine continues searching for another ER record for that out-patient with an intervening date. If found that invoice overwrites the first one and the two additional criteria are tested for, if absolute justification is ever found an indicator is set and the search on that file ends. If a record with even an intervening date is never found then an invoice is not saved and if more than one record with an intervening date is found, the invoice from that out-patient's latest record is saved. Regardless of the outcome, the subroutine searches next on the system's hospital record file for any data that might or could justify that out-patient's second, early MCA visit.

As step 0312 in FIG. 19 illustrates, processing on the hospital file is very similar to that on the ER file. If a record with an intervening date is found indicating a hospitalization the invoice is saved but absolute justification is not established unless there is exact identity between the 6 digit discharge diagnosis code and the 6 digit conition code field of the second, early MCA type office visit record indicating continuity and consistency of out-patient care. Once again, as with the ER file processing, one of three possibilities will exist in regard to clinical justification; no intervening date at all and therefore no invoice saved or even soft low level justification, an intervening date but no absolute justification by testing and absolute justification with an indicator set for informing the main program of that when control is returned there. And as before, if absolute justification is found searching on that file is terminated.

At that point, the system's treatment file is searched for any intervening record dates for that out-patient to see whether or not there is any clinical data present during any of those sessions to indicate a reason for the early, second MCA type office visit.

As step 0320 of FIG. 19 illustrates, and as before, if a treatment file (see FIG. 14, treatmen.dbf) record with an intervening date is found between the two MCA office visits the invoice of that record is saved for indicating at least low level justification. For absolute justification a field in that record is tested for either a value indicating a complication has occured or just a suggestion by the therapist that the out-patient return to see the primary care doctor earlier than already scheduled due to some problem the therapist thinks existent. As step 0325 illustrates, if that was the case then absoute justification is established, the indicator is set (it is set no matter how many times absolute justification is found) and the treatment file search on that out-patient ends. And as before, if just low level or soft justification is found but exists in more than one record (i.e. intervening date) it is the invoice from that out-patient's last record in that file that is saved.

As is seen by step 0329 in FIG. 19, the search is then continued on the laboratory file in order to find any data there that could serve as a basis for that early, second MCA out-patient visit. As the next step 0401 in FIG. 20 shows, a record is looked for with a date between the two MCA type visits (i.e. when the tests were taken) and if found an invoice from that lab record is saved. Then each of the 14 lab test fields that store different lab test results are searched for any abnormal results (normal results are disregarded since they can't provide a basis for absolute justification). If an abnormal result is found it is then tested for an indicator that documents that abnormal value as either acute in onset or a significant change from a most recent result of that test for that out-patient. If either of those indicators are found associated with an abnormal result for a lab test from a record for that out-patient with a date between those two MCA type visits, then absolute justification for that second, early MCA visit is established since that is a pretty good reason why a physician would want to see a patient earlier than scheduled. (see abn_lab.dbf, FIG. 7) And as before, the search on that file ends.

And as again, it is the invoice from the first record that provides absolute justification, if such is found, that is saved and passed to the main program and if just soft or low level justification is found, it is the invoice from the last record with an intervening date that is saved.

As can be seen by step 0409, FIG. 20, program control is then returned back to step 0122 of FIG. 17 upon terminating the laboratory file search.

Upon return to the main program (see FIG. 17) at step 0122, a new record in the system's intermediary file (see FIG. 5, notify.dbf) is created and written to with salient out-patient identifying data and if present both or any type of justifying data found during the searches in the subroutine searchv.prg. Now, any additional justifying data is sought in the main program by searching on the surgical history file (see surgfind.dbf, FIG. 13). Unlike a simple hospitalization occuring between the two dates of two MCA's not being an automatic hard or absolute justification for the second, early MCA, any surgery occuring within the two dates is of course automatically presumed to be with both invoice saved and the indicator set. However, even if there wasn't any intervening surgery between the two MCA dates, if that out-patient has had surgery in the recent past, depending upon its nature and data in the office visit itself as well as when the surgery occured, that past surgery even though occuring as much as months before may provide at least partial or soft justification for the early second MCA visit (see steps 0204 0205 0206). As is illustrated, the more extensive or critical the surgery, i.e. the higher the category it occupies in the surgical inventory table (see FIG. 13, surglist.dbf), then a greater amount of time is allowed between that event and the first MCA type visit for that out-patient for it to justify the second, early MCA type visit. In addition and as illustrated in step 0209 of FIG. 18, for a category C surgery an additional criteria must be met; in instances such as hernia surgery there must be an identity between the clinical group indicator for that kind of surgery (i.e. GI track) and that present in the 6 digit condition code reflecting the main or primary reason for the second, early MCA visit.

Upon terminating the search on the system's surgical history file, the effort to find justifying data to support that out-patient's second-in-a-row unremarkable and uneventful office visit in which nothing new or important was found or done and that also occured too early, no more searches are conducted on that out-patient in regard to those two MCA's.

The newly created intermediary file record will now contain out-patient and the second MCA type visit identifying data that includes; patient I.D. No., Date, diagnostic category, name of the data processing routine by code, doctor, condition code and of course any and all invoices from potentially justifying records as well as a code for indicating if absolute justification was found. In effect, a compiled story on what was found, when and for whom and by whom.

As seen by step 0217 of FIG. 18, after the above processing the program then resets the second MCA type office visit as the first, resets the counter and then skips to the next office visit to test for the same patient, same MCA type or new out-patient, whatever the case may be and until end of office visit file.

Referring to FIG. 21 and 22, a main computer program that, like schedul1.prg, also identifies potential instances of clinical resource overusage by office visits and compiles said data into new records. But this program detects overuse by the patient too and not just presumabely the physician as in schedul1.prg since the kind of office visit that triggers processing is the unscheduled one even though it may include the MCA type one as well. As such it detects two types of problems, all consecutive unscheduled visits after a first one for that out-patient (?patient's fault) and an early scheduled MCA type following an unscheduled MCA type visit (physician's fault?)

As is illustrated in step 0501, initially office visit records are selected by diagnostic category for group specific analysis (as in schedul1.prg). As seen by step 0502, further program specific processing isn't triggered until and if an office visit record indicating an unscheduled type is identified. When that happens that record is then tested to see if it is the first of that type for that out-patient. If it isn't but instead a second or more consecutive unscheduled visit for that out-patient, a new record in the system's intermediary file is then created for each of those consecutive unscheduled visits beyond the first one and pertinent identifying data is naturally written to them. Such data includes patient i.d. no., clinical status during office visit, what consecutive number, the program name, type of visit, date, diagnostic category of patient, invoice of office visit, etc. Then as is illustrated in step 0517, even in cases where it is the first unscheduled office visit and data for that record won't be collected, tests are done to it to see if it is of the MCA type in order to prepare for the possibility that the next office visit record may also be of the MCA type for that out-patient but of the scheduled type (which would make it the physician's fault if it is also too early). And if that is the case then, as in step 0512, the time interval between the unscheduled and the scheduled MCA for that out-patient is computed and compared against that time interval as prescribed for that out-patient's diagnostic category. If found to be less than the prescribed interval of time then, as in the previous routine schedul1.prg, the subroutine searchv.prg is called for the same reason; (see step 0514) to search on related system files each linked to that out-patient by common fields and which store different aspects of medical data for the purpose of finding any intervening event or activity that could justify the second, early scheduled MCA type visit of that out-patient and thereby provide a reason for what otherwise appears to be a waste of clinical resources. Then, and as in schedul1.prg. a new record is created and pertinent out-patient and office visit identifying data are written to it as well as the source of any potentially justifying data as well, whether or not absolute justification was found. However, and independent of whether or not searchv.prg is called and since that just-processed record for that out-patient was of the scheduled type, the 'chain' is broken in this program since it is centered around the unscheduled office visit and therefore counters are reset to zero, stored values are cleared and then the program will skip to the next office visit record until another unscheduled type of that or another out-patient is again encountered or end of file is reached.

In this program and unlike schedul1.prg at the end of office visit file there are, or might be, two type of new records created (i.e. holding different data) in the system's intermediary file (see FIG. 5, notify.dbf). One type that identifies all consecutive unscheduled office visits for out-patients and tallys the number of consecutive ones in each new corresponding intermediary file record (notify.dbf) created as a result. The other type is, except for name of program, identical in data types and content as the one created in schedul1.prg for each early, second MCA type scheduled successive visit for any out-patient that is found.

Referring to FIG. 22, a subroutine entitled surgfind.prg that is called by this main program, unschedul.prg, for searching on the out-patient surgical history file for any jusitfying clinical data. In source code and function it is identical to that block of code for doing the same thing in schedul1.prg but in this program it was made a separate subprogram or subroutine due to lack of 'byte' space in the program unschedul.prg.

Referring to FIG. 23, a main computer program entitled AstatusB.prg that detects and isolates a group of office visit records that represent a protracted out-patient illness of moderate severity (not worse than clinical status 2) and then compiles data to new records, each indicating what was found and done during each of the visits during said protracted illness. In order to trigger program processing a minimum number of 'abnormal' records in succession must be found for any one out-patient. And the records are only of two types of clinical statuses; one is a status 2 indicating moderate symptoms and the only other may be a 4 indicating an improvement in symptoms, and lessening of severity.

Initially, as is seen by step 0701, office visit records are selected by diagnostic category for group specific analysis. As is illustrated in steps 0705-0712, at least 3 consecutive office visit records for any out-patient must be found before any further program specific processing occurs. Also, all of the contiguous out-patient records must have the same chronic diagnosis in the condition code field as the primary reason for the office visit. Once that minimum number of records in succession occurs, another subroutine called binary.prg is called that will now process as a group each of those 'abnormal' out-patient records that occured in succession. As will be discussed, that subroutine will determine and resolve exactly what was done by the physician during each of those visits involved in that protracted episode of moderate illness. After that minimun of 3 records are processed together, control goes back to the main program AstatusB.prg and if any further successive or consecutive records for that out-patient are found of the same status type, 2 or 4, each record at that point is sent individually into the binary.prg subroutine for separate processing. Once a non-2 or non-4 status is encountered or another out-patient record is found, the program counter is reset to zero and another minimum of three records consisting only of those 2 status types must be found before program processing can begin again. At the time the end of office visit file is reached and for each of any office visit record involved in program specific processing of any protracted out-patient illness, a corresponding new record in the system's intermediary file, notify.dbf, is created storing patient and office visit identifying data and an encoded compilation of what was done, including medication, lab tests, referrals, etc.

Referring to FIG. 24, the subroutine binary.prg firsts positions to the office visit record to be processed in the main program. It then tests a passed indicator to test for which of three possible main programs has called it, AstatusB being only one, and sets aside an appropriate code for designating that. As is illustrated in step 0802, it then saves patient and office visit identifying data, and as an independent check it also sets another indicator depending upon the nature of the office visit condition code (i.e. primary reason for the office visit): whether it is a new acute problem or a chronic, established one. At this point and as illustrated in step 0803, it determines which or how many of the 4 possible actions or types of physician intervention took place during each of said office visits involved in said protracted illness for any out-patient, which may include new medication, change in existing medication, laboratory tests and speciality referrals. The determination is made possible since each of the 4 actions occupy fixed positions within a four digit binary number and therefore each has a designated place value corresponding to an assigned field in the office visit record. Therefore, any combination of those 4 physician intervention activities will result in a distinct sum ranging from 0 thru 15 (16 possibilities) depending upon which, if any, of the 4 possibilities were done during any office visit. Each of the 16 possible numbers representing what, if anything, was done are then assigned a single letter as code ranging from A(0)–0(15), During the subroutine processing, binary.prg determines which ones, if any, of the logical fields corresponding to the 4 actions are turned on or set to true (i.e..T.), it then computes the sum and then selects the corresponding single letter code for indicating accumulatively what, if anything, was done during that office visit. In addition to that subroutine processing of a given office visit record involved in the above said type of protracted illness processing, in instances where a referral was made, step 0811, or an injection was given, step 0804, further processing occurs to access for the purpose of tracking, the invoice from that specialty record and in the case of medicine injections during an office visit, the appropriate record in the system's medicine file for indicating the precise route of injection given to that out-patient, i.e. IM or IV. Then a new record in the system's intermediary file is created corresponding to that particular office visit record just processed and all of the above mentioned data identifying the patient, office visit, primary reason for office visit, actions by the physician, dates, etc. are written as compiled data to fixed positions in that new record (notify.dbf). Control is then passed back to any of three possible main calling programs, which in the one under discussion is AstatusB.prg. (the other two discussed later)

Referring to FIGS. 25 and 26, a main computer program entitled Astatus3.prg that, similar to astatusB.prg, processes a continous uninterrupted sequence of office visit records of various length that constitute a protracted out-patient illness. However, unlike astatusb.prg the protracted episodes here are of more severity and may involve hospitalization. Also, and unlike Astatusb.prg, Astatus3prg does not require a minimum number of office visit record status types for a given out-patient to be present contiguously. Instead, its processing is triggered whenever a status 3 office visit record is encountered which indicates a level of severity greater than any involved in astatusb.prg processing and in terms of nature or degree of illness is considered pre-hospitalization, which if occurs during any office visit would then make that visit a status 5. After the initiating status 3 office visit record, the program then processes all of any antecedent and then subsequent or succeeding contiguous non-status 1 records for that out-patient. Following the identification of said record types as defined by their clinical status indicating severity of illness (1 being normal or baseline), the subroutine binary.prg is called to make the same determinations and access the same data and write the same kind of compiled data to a newly created record in the system's intermediary file as occured during Astatusb.prg, the only difference being, since binary.prg is being called by a different main calling program, a different letter code is placed in the newly created record for indicating that.

The most critical aspect of processing in this program is the constant determination of the proper direction for record skipping and continual repositioning to the appropriate record during processing, and how that control is maintained. That is necessary because as is seen in step 0903, processing only begins when a status 3 record is encountered. Therefore, the program must be continuously 'informed' as to which side of the initiating status 3 record the record pointer is on in order to 'know' whether or not to move back or to skip forward to examine any next record for that out-patient. As can be seen in the figure, any subsequent direction of the record pointer is always determined by constant reference to a program flag which is always set based upon the last direction in which it skipped and the value of the status field of the current office visit record under processing.

As is illustrated in step 0903, processing is first triggered when a status 3 record is identified. At that point the subroutine binary prg is called and except for writing a program specific indicator into a newly created record of the system's intermediary file, processing identical to that described during AstatusB.prg processing also occurs in binary.prg during this main program processing. As seen in step 0911 and assuming first time thru for this out-patient, the program flag controlling movement of the record pointer (i.e. record skipping) is set to 'false'. Therefore, after processing through the subroutine, the record pointer moves back to test for and if necessary subroutine process any non-status 1 record for that out-patient which is prior and contiguous to the status 3 identified and processed just before. For any found, the subroutine binary.prg is again called for each one with the record pointer continuing to move back until either a status 1 record for that out-patient is identified or another out-patient's office visit record is encountered or of course beginning of file (see steps 0912 thru 0923). Beginning in step 0924, the program provides for that by then resetting a flag for forward skipping and repositioning the record pointer to one office visit record beyond the initiating or triggering status 3 for that out-patient. In this way all subsequent (later) and contiguous non-status 1 office visit records for that out-patient will also be processed in the identical way to all prior (earlier) contiguous office visit records for that out patient. Beginning at step 0924 the subsequent processing simply ensures that all subsequent status 3 records for that out-patient are processed through the subroutine binary.prg from a different point or block of source code in the main program from that for the status 2,4 and 5's, while maintaining the proper setting for the flag controlling direction of record skipping depending upon current setting and the value of the office visit record status.

As an example and to assist in following the logic, assume a hypothetical out-patient has two current office visit records on file, a status 1 preceding a status 3. The program will skip over the first but begins processing when it encounters that out-patient's status 3 record. After returning from the binary.prg subroutine and with the flag having been set initially to false, the record pointer is skipped back one record by the program. However, since it is a status 1 record, even though the same out-patient, that record won't be included in the processing. At that point and in order to check for later records for that out-patient (after the initiating status 3 record) the flag is set to .T. and the record pointer is moved by the program (i.e. records are skipped) to one record beyond the initiating status 3. But since that record is from another out-patient, current out-patient processing is terminated and the program flag is reset back to .F. or false in preparation for eventually encountering a status 3 record in another out-patient. It is important to note that once a status 3 record is processed, any antecedent non-status 1 record(s) for that out-patient are always processed before any non-status 1 records for that out-patient that are after (later) the initiating status 3 record of that out-patient. Conversely, and central to this program, if there isn't any status 3 records on file for any out-patient at the time the program is run, none of that patient's non-status 1 records will be processed either; that out-patient will not be included in the processing.

At the end of the program (after the last record in the office visit file) the system intermediary file (notify.dbf) will contain new notify.dbf records containing compiled data that identifies that out-patient and office visit, as with the AstatusB.prg program, for the purpose of tracking and both what the physician found and what was done during each office visit involved in processing. And, as with AstatusB.prg, for each office visit record included in processing, one corresponding notify.dbf record is created. And the only difference as far as data is concerned is the single letter code written to indicate the name of the main calling program, in this case Astatus3.prg.

Referring to FIG. 27, a main computer program entitled Clinevol.prg that, like AstatusB and Astatus3.prg, identifies, isolates, determines and compiles data from a cluster or groups of out-patient records that represent a protracted out-patient illness of varying severity and duration. However, and like each of the prior two main programs, the degree of severity or threshold necessary for triggering processing is different, as well as the office visit statuses necessary to initiate the processing and for being included in it.

Processing in this program is initiated by any first non-status 1 record, regardless of type. Once that identity is made, the program will skip back to include any prior status 1 for that out-patient. That is for the purpose of establishing a baseline, for reference, because it is apparent that the status 1 or 'normal medical condition' office visit was the last time that out-patient was seen before the onset of the current illness. The program will then continue forward to process through binary.prg all further, later non-status 1 records for that out-patient that occur consecutively until a status 1 record is found or a record of another out-patient is encountered or end of file.

Although its criteria for triggering processing is less 'selective' than either AstatusB and Astatus3.prg, it provide a more natural and complete view of the evolution and management of an out-patient illness in an uninterrupted way.

As seen in step 1102 and as in the two prior programs, out-patient records are pre-selected by diagnostic category to enable group specific analysis. As was mentioned above and as illustrated in steps 1104 thru 1109, any first non-status 1 record will initiate processing. Once that type of record is encountered and before binary.prg is called, the program moves back one record to check if it is a status 1 for the same out-patient. If that is so then that record is sent into the subroutine binary.prg first for determining, collecting and compiling what may be important baseline pre-illness data for reference since it just precedes the record indicating onset of that out-patient's illness. Until step 1120, the general processing flow is the same as in AstatusB and Astatus3 programs; for each office visit record included in the processing, a new intermediary file record is created, what was found and determined during that visit by the binary.prg subroutine is saved and encoded and then after returning to the main calling program is written into the newly created record including patient and office visit identifying data, However, there is an additional step performed by this program, clinevol.prg,. As is seen in the steps 1120–1123, testing is done to determine if a final resolution of that illness has occured at least by the time the program is run. And as is illustrated, that is done by determining the reason why that out-patient's record processing was terminated, i.e. was it due to the presence of a status 1 record for that out-patient indicating return to normal or baseline and therefore end of illness or due to encountering the record of another out-patient, or end of file.

As in Astatus3 and AstatusB, for each office visit record included in processing, a corresponding new intermediary file record is created through the binary.prg subroutine. However the difference in clinical.prg, and aside from the coded letter indicating the program name as part of the new compiled data written to each new record, this main program, clinevol.prg, also writes to the last new record a letter, or leaves a space, for indicating whether or not clinical resolution of that out-patient's illness has occured.

Referring to FIGS. 28 and 29, a computer program (and without an associated sub routine) entitled print1a.prg for printing out physical data (signs and symptoms) from office visits grouped by out-patient diagnostic category. Its primary data source or basic unit of information is the system intermediary file, notify.dbf. As such, records for use in this program were created and written to in previously discussed main programs, in this case clinevol.prg. And the criteria used for selecting said intermediary file records are the same here as they were in the previous main program for the selection of office visit records. Therefore, print1a.prg is a sequential program or follow-on routine that demonstrates the system's potential for unlimited kinds of continuity in data flow and flexibility of data usage.

As is illustrated in steps 1201–1204, the program also selects by a control date and then an inter-file relationship is established that will link by out-patient the system's master medical file (medical.dbf) in a most likely one to many relationship with the system intermediary file, used in this main program as once again the basic unit of information processing. In this way and prior to the detail line printing of clinica data, pertinent back-ground and identifying data for each out-patient involved in processing is printed once per page as heading. Then, and since all the office visit derived records of the system's intermediary file, notify.dbf, that are pre-selected for processing in this main program contain only a Chronic, established diagnosis as the 6 digit condition code or the primary reason for the office visit, it is the system's Chronic Diagnosis Table, Chrmedli.dbf, that is searched on and accessed for obtaining the literal, medical, text of that diagnosis corresponding to that 6 digit code. Then it is saved for later printing with other office visit data. Then a check is made, step 1207, to see if the condition code, a chronic diagnosis in this program, or any of the two other possible chronic diagnoses for that out-patient, is of a blood pressure related and sensitive clinico-pathological group (heart, neurology, etc.). If it is, the original office visit record corresponding to the current notify.dbf record being processed is searched for and the blood pressure recorded at that time is accessed and temporarily saved. In step 1210, any physical data present in the notify.dbf records are then used to access from their respective tables the corresponding literal, medical, text for later printing of both symptoms and signs documented at the original office visit and was later written during program processing to the notify.dbf records from the office visit records.

The first detail line for printing clinical data from that office visit derived record in notify.dbf is then printed with pertinent identifying data only.

After step 1211, the program then determines which of the above potential data (i.e. signs and symptoms in encoded form) were actually present in said office visit derived notify.dbf records, and therefore what further detail lines for that office visit are to be printed.

If blood pressure data is present, that is printed first. If physical symptoms data was documented during the original office visit that is printed on the next line, and if both fields were devoid of data due to the absence of any documentation during that original office visit then a 'no symptoms are present' message is printed instead. The same process applies to the physical signs data for the next line. The next step, 1305, is for testing and then indicating if a hospitalization occured during that original office visit, as indicated by the status field data that was written to the office visit derived notify.dbf record. The next step determines if, in the case of a last record processed for that out-patient by the original clinevol.prg and pre-selected in this main program for reporting out on, that protracted illness has ended or in fact resolved by the time this program runs. If it is a last notify.dbf record for that out-patient then one of three possibilities exist; the next record on file for that patient is a status 1 indicating a 'cure' of that protracted illness, the next record on file is that belonging to another out-patient and therefore the illness of the prior out-patient remains unresolved or it is end of file and unresolved. Whatever the cause, a brief message is printed on the last line of data from the last intermediary file (notify.dbf) record for that out-patient.

Then the out-patient ID No. in the next record is tested and if it is still the same, a single dotted line is printed to separate the clinical data from two office visits by the same out-patient. If it is a different out-patient then the program skips to the next page, prints this out-patient's pertinent identifying data and repeats the process of searching, accessing, resolving and printing of any signs, symptoms and other clinical data for that out-patient.

Note that this program's 'acute problem' counterpart or companion, print1.prg, (see FIG. 1) is virtually identical in source code except that the condition code from the office visit derived records of notify.dbf reflects an acute, short-term diagnosis as the primary reason for the visit in that group of records and which in fact were pre-selected on that basis also (as opposed to a chronic, long term established diagnosis in this main program, print1a.prg) and therefore it is the short term diagnosis table, er_list.dbf, that is searched on by the 6 digit code from the condition code field in order to eventually be able to print out, as in this program, the primary reason for those office visits in conjunction with other clinical data. For Print1.prg, see source code listings in the attached appendix.

Referring to FIG. 30, a main computer program entitled Print2a.prg that processes and reports out any medication change activity during chronic problem office visits by use of the same office visit derived records from the system intermediary file (notify.dbf) that was used in Print1a.prg, those created and compiled from a run by clinevol.prg (see FIG. 27). As another sequential, follow-on type program since it also uses records built from a previous program. It complements print1a by reporting on a related but separate clinical aspect, in this case medication, of those same out-patient primary care office visits.

As in print1a.prg each printed page represents data from a single out-patient and may contain data from separate office visits with each separated by a single broken line. And again as in print1a, at step 1403, a one-to-many relationship is established between the out-patient master medical file (medical.dbf) and the system intermediary file (notify.dbf) for accessing and then printing out out-patient background data as heading once per page. Data for passage to and resolution of in this program's subroutine (digout1.prg) is saved and then the condition code from the notify.dbf record is used to search upon and access from the chronic diagnosis table its corresponding medical text for use in printing.

At this point the subroutine is called (see FIG. 31, digout1.prg) for determining what medicines and how much were changed, and then accessing for printing back in the main program with other data from that primary care office visit.

Upon return from the subroutine a test is made to determine if in fact any medication changes occured during that office visit. If none did, a message identifying the office visit and indicating that is printed. In addition, if a medication record from that office visit can't be found despite that activity being indicated during the above test, or it is found but no changes are indicated in that medicine record then a data error message is printed. If a medication change code in that notify.dbf record is present, i.e. one of several possible single letters that indicate that at least a medication change occured during that office visit, and medication-change data is found in the related, linked medicine record of that out-patient, the data is accessed, placed in variables and then processed from those variables for detail line printing (see step 1414). Since there is the possibility of up to 3 medication changes during any office visit, the group of variables passed back to the main program are then tested for and accessed three times at three fixed positions corresponding to each of the 3 possible medication names that may be present and if so then their accompanying amounts changed from and to expressed either in milligrams/day or tablets/day. Just prior to printing up to three possible detail lines corresponding to each medication change, and as in print1a, identifying data for that office visit is printed.

As in print1a.prg the program here checks the next record after printing to see if it's the same out-patient.

If it is then a broken line separating that office visit and its data from the next for that out-patient is printed and the above process is repeated. If it's a different out-patient then the program skips to the next page, prints program title, background data for that new out-patient and then repeats the above process until the end of the intermediary file, notify.dbf.

Note that this program's 'acute problem' counterpart, print2.prg (see FIG. 1) is virtually identical except that the main or primary reason for each office visit is an acute, short-term diagnosis and therefore the 6 digit condition code representing that is used to search on the acute, short-term diagnosis table (er_list.dbf).

Referring to FIG. 31, a subroutine entitled Digout1.prg., mentioned in the previous main program discussion since it is called by print2a.prg. Its purpose is to test for the presence of one of several single letter indicators that mean at least that a medication change had been ordered by the physician during any office visit. It then locates the appropriate medicine record for the out-patient storing those changes, accesses them and temporarily saves that data for resolution in the main program prior to printing.

The routine begins by testing the single letter code in the category field of the office visit derived notify.dbf record of that out-patient. That single, coded, letter indicates which, if any, of four possible actions the physician took during an office visit (see page 8 for explanation). The single letter code from the category is tested for identity against 8 single letters indicating at least the existence of a medication change. If a match is not made then that single letter from that out-patient's record is not one of the eight and control is passed back to the main program, print2a.prg, and a 'not done' message is printed for that office visit beneath its identifying data. If one of the 8 is present but the corresponding medicine record (see FIG. 9, medicine.dbf) isn't found a data error message is printed.

If that office visit derived record has one of those 8 letters indicating a medication change and the corresponding medicine record is found, each of the 3 medication fields are in turn tested for the indication of change activity, as opposed to an addition, deletion, etc., As in step 1506, for each field in which a change indicator is found the 5 digit medication code and the amount that out-patient is now on (amount changed to) is copied and saved.

The subroutine now will find the most recent medicine record for that out-patient that stores each of up to three medicines that may have been changed. If there were 3 medication changes, the most recent amounts for each of the three may be in three separate records for that out-patient.

The way that is done is by first positioning to that out-patient's first medicine record on file. That is done by first searching on a linkage file (see firstmed.dbf) that stores the invoice for each out-patient's first medicine record, accessing that invoice and then turning to the medicine file and using that invoice to position to the first record for that out-patient. Then, for each of 3 possible medications that might have been changed, the corresponding 5 digit code previously saved is tested against each of the three fields in each of that out-patient's subsequent medicine records on file up to but not including the current or last record on file. For any of the three possible changes present, each time a match is found in one of the fields in any of the earlier medicine records for that out-patient and the associated indicator means either an add or a change, the corresponding amount is written to a variable. And each time another match against that same 5 digit code is found then that amount will over-write the previous amount for that medication, in that way ensuring that the most recent amount for that out-patient will be obtained. That amount is then stored with the current amount, which is present in the last, latest medicine record for that out-patient. Lastly, the 5 digit code is then used to access the full generic name of that medication by searching on the system's medicine inventory table, (see med_list.dbf). That is then also stored to the same variable holding both medication amounts; changed to and from.

The above process is repeated for each medication change found in the most recent medicine record in the medicine.dbf file for that out-patient. Back in the main program, print2a, the variables passed from the subroutine are stepped through and the medication name and both amounts are individually accessed and then formatted for printing in the detail lines following the office visit identifying data.

Referring to FIG. 32, a main computer program entitled print3a.prg that complements the previous two main programs, print1a and print2a, by reporting on another separate but related clinical aspect of the same out-patient office visits; laboratory test results.

At step 1602 and as in the previous programs, records are pre-selected from the system intermediary file notify.dbf by control date (cut-off date) and the presence of a chronic diagnosis in the condition code field of the office visit derived records indicating that as the primary reason for the visit. However, unlike the previous two and due to the size of this program there isn't any pertinent background data printed once per page for each out-patient and therefore the linkage between the system master medical file and the office visit derived record file (notify.dbf) is not established in this program.

As is seen in step 1604, office visit identifying data written to the current intermediary file office visit derived record (notify.dbf) is accessed and saved while the chronic diagnosis table is searched on the condition code to access the literal text corresponding to the 6 digit code in the condition code field. The subroutine digout2.prg is called (to be discussed later) to determine if any lab work was done during that office visit and if so, search the system lab file on the office visit invoice (lab records have dual invoices) for that related out-patient lab record storing test results ordered during that visit. That accessed data is then store to variables at discrete positions specific for both the numeric results and the historical, parameter data associated with each test for that out-patient that was done. After a search is made upon all the 14 lab test fields for the presence of data (fields are blank for tests not done) and all that are present are accessed and saved, passage back to the main program, print3a, occurs.

The rest of the main program basically involves determining which if any of the 14 tests were done by stepping through to fixed points in each of the variables passed back from the subroutine and that hold separate aspects of that test result. Each test result occupies a fixed position in each of the passed variables that correspond to its relative field position in the lab record. After access, the test results are formatted and printed, each test result constituting a detail line.

As is seen in step 1618, upon return to print3a a test is done to determine if in fact any test result data was present and therefore passed back. If not, and as will be seen, it is either due to the absence of any ordering of the tests by the physician during that office visit or although tests were ordered and an indicator set during data entry as a result, no record is found during program processing, i.e. a data error. Depending upon what happens, flags are set in digout2.prg and based upon that indication the appropriate message is printed in print3a.prg, see steps 1619–1622.

When lab test data is passed back from digout2.prg to print3a.prg, the variable dedicated to storing the names of the lab tests (i.e.hct,wbc,bld sugar, etc) are tested first. Each of the 14 are alloted equal space within that 'dedicated' variable and the main program steps through it at fixed positions 14 times testing for the presence of data. Whenever a name is found, that indicates that the other aspects of that test result are present in the other variables dedicated to those other aspects of that lab test result such as the quantitative abnormal result, parameter data like consistency of results, chronicity of abnormality comparison to most recent result and in cases of normal result the date of results. These are accessed in the same way as the test name; by stepping through to fixed positions in each of the dedicated variables depending upon the relative field number of that particular test.

Immediately upon determining the first instance of a test name present in that variable, print3a will print that office visit's identifying data and lab record identifying data (i.e. lab invoice and test date). Then as each test result is found the separate data items as other aspects of the test result are also accessed, formatted and printed. After all 14 positions in the 'name' variable passed from the digout2.prg subroutine are tested for within that iterative loop process and each lab test result present is printed as a separate detail line, the next intermediary file record is skipped to and, as in previous programs, if it is the same out-patient, a single broken line is printed while if the next record is another out patient then a double broken line is printed and the program skips to the next page. In either case and as before, the process continues until the end of the intermediary file is reached.

Note that this main program's counterpart, print3, is virtually identical in design (structure and source code) except that, and as with the previous two main programs, office visit derived records that contain a short term, acute diagnosis in their 6 digit condition code field as the primary reason for the office visit are pre-selected for processing instead of, as in print3a, a chronic, long term one.

Referring to FIG. 33, the subroutine entitled digout2.prg called by print3a.prg for the purpose of accessing from the system's laboratory record file any outpatient test results that were ordered during the visit represented by the current office visit derived record being processed.

As in step 1701, the subroutine first tests for the presence of one of eight possible single letters, present in the 6th position of the category field of the office visit derived record passed from print3a, that indicates that at least lab tests were ordered during that office visit (see page 8 for explanation). If not then a flag is set, control is returned back to print3a.prg, and by printing, that office visit is identified as in which lab tests were not ordered during that office visit. That information is placed as a detail line in the same way had there been actual test results present for printing. If one of the eight is present but the corresponding out-patient lab record is not found, another type of flag is set, control returned to the main program, print3a.prg, and a data error is printed along with that office visit invoice.

In either of the above two cases and once the reason why there is no lab data associated with that visit is printed, the main program skips to the next record and if not end of file repeats the above process.

If one of the 8 is present and that out-patient lab record is found that is associated with the office visit represented by the office visit derived record currently being processed, the lab record identifying data is saved. Then, as is seen by step 1706, the subroutine within an iterative loop processing tests each of the 14 lab test field of that lab record for the presence of any data since a lab test not done will have its respective field blank. For every field found to be blank (test not done) a fixed number of blank spaces are stored to each of the dedicated variables that hold the separate aspects of each test result that were spoken about before. And as mentioned before both the result data, and in cases where the test wasn't ordered just blank spaces, are in the same position relative to other test results (or blank spaces) in those variables as they are in the lab test record. (see step 1708). And as mentioned before the 'dedicated variables' store lab test name, abnormal results numerically expressed, encoded duration of abnormality, comparison to any previous result for that out-patient's test, and for normal results the date and result for that most recent test if on file.

As in step 1711, if data in that field is found, the above aspects are stored; test name, its lab record field number, literal text corresponding to each of the three parameter codes (duration, intensity, comparison to previous result) and the actual abnormal result expressed as a decimal number. If the data in that field indicates a normal result then a test is made on that field to further determine if a prior result of that test is on file for that out-patient. If there isn't a prior result for that normal test result then a flag is set for use back in the main program, print3a.

If the test indicates a prior result then the subroutine skips back on that out-patient's lab records to access the most recent result for that test. In this way for every normal test result an effort is made to find and access most recent test data for that lab test. Also the date of that most previous result is accessed for printing in print3a.prg..

After each of the 14 fields of that lab record associated with the current office visit record being processed has been tested, each of the dedicated variables will contain an amount of actual data that depends upon how many tests were ordered but at all times and regardless of the actual number of tests ordered and done, each of the dedicated variables will be filled to the maximum at the end of the digout2.prg because if they aren't filled with actual results, they will be filled with blanks. In any event and after any lab record is processed control is passed back to print3a.prg and resolution of what was done is made, results are formatted for printing and each detail line correspons to one lab test result.

Referring to FIG. 34, an interactive pre-written query entitled caseload.prg for determining both the incidence of any chronic diagnosis amongst the database population of out-patients and what percentage of those patients with that diagnosis are under the care of any given database doctor.

The routine is a form of bias check by monitoring whether or not there is a balanced distribution of any one disease entity amongst the non-specialist, primary care doctors of this database.

As is seen in step 1801, the program first displays an explanatory message that orients the user. Then, under the influence of a prompt, both a chronic diagnosis (exactly spelled) and the name of the database doctor are entered. On the basis of the diagnostic text entered, the system's chronic diagnosis table, chrmed1i.dbf, is searched and its corresponding full 6 digit code is accessed. The system's master medical file (medicl.dbf) is then opened and by use of that 6 digit code a count is made on the total number of out-patients on the database with that diagnosis as one of three possible ones for every out-patient.

As in step 1809, a further effort is made to determine the percentage distribution of that diagnosis amongst the three diagnostic categories. If the diagnosis entered is from a category A then all patients with that chronic diagnosis are Category A out-patients. If a category B chronic diagnosis is entered then the out-patients with that diagnosis and who have two others from category B are considered category A out-patients (see description of FIG. 3, chrmed1i.dbf). For those out-patients with that B diagnosis but no category A diagnosis and without two other category B diagnosis, they are by definition category B out-patients. If the diagnosis entered is from the category C zone (the letter C is first of the six digits), those out-patients with that diagnosis and two others from category C are considered from Category B. If any of those patients with that category C chronic diagnosis also have a category A diagnosis then they will be considered a category A out-patient and if any of them have a category B chronic diagnosis they will then be considered a category B out-patient. If any out-patient with that category C chronic diagnosis has at most only one other category C diagnosis, that out-patient is a category C out-patient.

It is this 'weighted' type of valuation, where not only the highest level diagnosis determines the diagnostic category but the total number of diagnosis from any one category that can also determine the diagnostic category classification of the out-patients, for the purpose of group specific data processing.

After the total out-patient count is computed and then any further breakdown into separate diagnostic categories for non-category A chronic diagnosis entered, a separate additional count is made on the doctor entered to determine first what percentage of all those out-patients with that diagnosis are under the care of that doctor and then the percentage distribution by diagnostic category for non-category A diagnosis within the total for that doctor.

In summary, caseload.prg generates two types of counts. One totalling those out-patients on the database with that chronic diagnosis entered and expressed as a percentage. In cases were the diagnosis entered is non-category A, then a breakdown into separate diagnostic categories depending upon any other diagnosis any of those out-patients may have is also done and is expressed as a percentage. The second type of count, what percentage of those out-patients with that diagnosis are under the care of the database doctor entered, is specifically for determining if there is any maldistribution or imbalance between the incidence of a diagnosis and any of the database doctors; is there either an overamount of patients with any given diagnosis currently under the care of a particular doctor or of equal concern a serious underamount of patients with a diagnosis or several diagnoses that are under the care of any particular doctor.

After the percentages are determined for both types of counts, a subroutine is called entitled print4.prg that screen displays them in a percentage format.

Referring to FIG. 35, a subroutine entitled print4.prg called by caseload.prg after it generates the count data. It organizes and formats the data for expression into percentages and integers for both the chronic diagnosis and the doctor entered, along with any breakdown into categorys for both, and then routes it to the screen for display.

As is seen in step 1900, the subroutine first tests to see if any out-patients at all have the chronic diagnosis entered and therefore resulted in the passage of data from caseload.prg. If there isn't any, an appropriate message is displayed the program pauses for the user and then returns to the main program for another entry or quits. If there are out-patients on the database with that chronic diagnosis entered at the prompt then, as in steps 1906 or 1907 or 1908, depending upon what diagnostic category it is in, that information is then displayed. Then the total number of out-patients on the database with that chronic diagnosis are displayed as both an integer or absolute number and as a fraction of the total out-patient's. If the doctor who was entered at the prompt does not have any patients with that diagnosis, that information is also displayed. If the doctor does, the usual case, then a number appears alongside the doctor name indicating the number of patients who do that are under that doctor's care, and what fraction of the total out-patient population on the database does that number of patients represent.

That last fraction is very important for determining if there is an imbalance anywhere between any particular doctor and the number of patients that doctor has or doesn't have with a particular diagnosis. If there were many doctors yet its found that over 50% of the out-patients with a particular dx are under the care of only one of them, that would be cause for concern.

As is also illustrated, for any B or C category diagnosis the possibility naturally exists that it may not co-exist with a higher diagnostic category diagnosis in a patient (see page 24) or with two other chronic diagnoses from the same category which would then make that diagnosis alone the sole determinant of what diagnostic category that out-patient is in for the purpose of group-specific data processing.

After displaying the above data, the program pauses to allow the user time to review and then return to the main program, caseload.prg, is made to allow the user another query or to quit the routine.

Referring to FIG. 36, another pre-written query routine entitled meditoxi.prg for generating narrowly formulated, summary type clinical data. It serves a surveillance function by monitoring for impending, early or actual medication-induced toxicity by reporting out the results of patient lab tests known to reflect the potential side effects of certain drugs. For any out-patient on a given medication and under the care of a given doctor, all the results for a given lab test in chronological order are generated and displayed for the purpose of indicating any early, impending or actual medication-induced tissue damage as reflected by abnormalities in the results of certain lab tests.

As in step 2001, the program begins with an explanatory or orientation message. Then a prompt appears for entering both medication name and doctor name. A search is then made on the system's medicine inventory table (see FIG. 12, med_list.dbf) by use of the medication name entered and on that basis its corresponding 5 digit code is accessed. As in step 2007, the out-patient master medical file arranged by doctor is then searched for those out-patients under the care of that doctor who are currently on that medication. If there aren't any such out-patients i.e. none under the care of that doctor who are taking that medication, then a message to that effect is displayed and the program returns to the top to allow for another entry by the user. If there are, then the amount of that medication that each of those out-patients are taking (which may vary even widely from patient to patient) are accessed from their respective records from the master medical file (medical.dbf) and saved temporarily. As is seen in step 2009, a list of all those patients of that doctor who are currently on that medication is then displayed by both name and out-patient I.D. number, and the system laboratory file is opened in preparation for a search.

The user then decides what out-patient is to be monitored and then selects that patient by the I.D. number next to that patients name. Then the system's 14 lab tests are displayed for selection, the assumption being that the user, presumably a doctor, knows what lab tests are most specific for detecting any tissue damage caused by any particular medication (some drugs damage the kidney, some the blood cells, etc.). Upon selection of a lab test, all the numeric data and test dates for that lab test that are on file for that out-patient just selected are displayed.

After a review of the results the user then returns to that previous list of out-patients of that doctor initially entered and who are currently on that medication also initially entered, along with the amounts of that med those patients are currently taking. The user can make another patient selection or quit the program.

As is evident, there is no subroutine with this program.

Referring to FIG. 37, another pre-written query routine that generates summary type, narrowly formulated clinical data. It is entitled Heartmed.prg and produces for screen display both physical and medication data from office visits of out-patients who have chronic cardiac disease and who were seriously symptomatic at the time of the visit.

The program processing is triggered by and the out-patient group is selected by the name of a database doctor selected and entered, that is all that's required.

The program begins with a message and then a prompt appears for the entry of the name of a database doctor (correctly spelled). The system's office visit file, encounte.dbf, is then searched on that name and for each of that doctor'records a test is done to see if that record meets certain criteria for inclusion in the further data processing. That criteria includes a clinical status of 3 indicating a lot of symptoms and very active disease, the main reason for the visit is a chronic heart disease diagnosis of a variety of types (the second character in the condition code field has an 'H' indicating heart disease, while the first character indicates the diagnostic category of the diagnosis), medication activity of some type occured during that visit and the visits themselves occuring no more than two weeks from the date of program run.

As in step 2106, any physical data found in the records are accessed and saved. Then the 5 digit codes from the records representing the signs and symptoms that constitute said physical data are used to search upon their respective tables (see findings.dbf FIG. 10 and CC_list.dbf, FIG. 11) and access from them the literal text of each sign and symptom found in encoded form in that office visit record. As in step 2117, and in order to find and access separately the medication data from that office visit, a subroutine medget.prg is called for that purpose. Upon return, a detail line is printed identifying the visit and patient and then beneath that the physical data consisting of any signs and symptoms documented during that visit. At that point, as in step 2111, the medication data passed back from medget.prg is then tested for the kind of change that occured, and then each of the three possible medicines involved are accessed individually for name, type or change and amount involved. That data is then formatted and printed below the physical data.

The program next skips to the next office visit record. If it's of the same database doctor, whether or not its from the same out-patient, that record is again tested for the above mentioned criteria and if met the same processing is repeated. Once another doctor's office visit record is encountered, the program returns to the top and pauses to allow the entry of another doctor's name or if the user chooses, quit the routine.

Referring to FIG. 38, a subroutine entitled medget.prg called from the previous main program heartmed.prg for the purpose of finding, accessing and passing back the medication activity data generated during the office visit currently being processed.

It begins by opening the system's 'transactional' medication file (see FIG. 9, medicine.dbf) and uses the current office visit invoice to search for the medicine record linked to the current office visit record in order to access the medication activity data. Up to three medications may be found in that linked medicine record and for each found the corresponding 5 digit code is accessed. That is then used to search on the system's medication inventory file (med_list.dbf) to obtain the text or generic name of that medication. That linked medicine record is re-accessed and for each of the 3 fields holding data, both the type of activity (addition,change,etc.) and the amount involved. At this point all the necessary elements are accessed; medication name, type of activity and amount for each of the three possible medications involved. They are then stored to a single variable for passage back to heartmed.prg.

Back in heartmed.prg each of the medication data present are individually accessed from the passed variable, then formatted and printed for screen display.

Referring to FIG. 39, the main calling program entitled labfirst.prg for out-patient lab record creation and test data entry. During the course of this type of processing several lower-level programs are called at various times for executing specialized functions.

This program initiates the processing by first prompting the user for out-patient I.D. no., date of test(s) and for indicating if test(s) were ordered during an office visit (as opossed to emergency room). A search is then made on the lab file for a prior lab record of that out-patient. If not found the operator may re-check the I.D. no. and/or continue with program processing since it may well be that out-patient's first lab record. As in step 2308, if the tests were ordered during an office visit the last (most recent) record for that patient is found and that office visit invoice is accessed. If it's indicated that the tests were ordered during an emergency room visit the emergency room file is processed in the same way.

In either case, a prior source record, whether it's an office visit or an emergency room visit, must be on file in order to obtain the source invoice that will provide the cross-link between the source and the lab record storing the results of the tests ordered during that source visit. If neither record can be found the processing for that out-patient is aborted and the program returns to the top for another out-patient data entry. Once an originating source invoice is found the lab file invoice is incremented automatically in a separate step in preparation for a new lab record creation. The next level program, labentry.prg, is then called.

Referring to FIG. 40, a main subroutine entitled labentry.prg called by labfirst and which serves as a central control and access point for functions necessary in obtaining information about prior results from various aspects for each lab test result, both abnormal and normal, and how to load the various types of data, both actual and encoded, during the data entry process.

It begins with an orientation message for user guide. At this point a new lab record is created and appended, then loaded with the identifying data already obtained; out-patient I.D. No., date of test(s). new lab record invoice and source invoice(either office or e.r.). The lab file, abn__ lab.dbf, is then closed with the record pointer value saved for later access back to the newly created lab record for loading test results, etc.

As is seen in step 2404, the user is then presented with options as to what general action to take; access prior information of each lab test whose result is present and to be loaded, access the program's Help file for assistance in encoding the various historical and comparative results of each lab test into a compilation of prior results called 'Parameter' data that are placed in the segment of the lab test field next to the actual results, and finally the option to activate a customized data entry screen for use in data loading.

Normally, the user would, as in step 2407, first select accessing prior types of information for each test result present. If that selection is made, as in step 2410, a list of all the 14 lab tests are displayed with each assigned a unique number for individual access. Then, after any lab test is selected, a list of options are displayed for obtaining several types or perspectives of prior information of that particular lab test, a kind of 'track record' of that lab test. These prior aspects consist of 4 options presented on the screen but exist as two groups of two each, as seen in steps 2412 and 2414, and each group of two functions, as seen in steps 2413 and 2415, requires accessing the same of two subroutines in which two of the four aspects of prior information may be obtained. (to be discussed in detail later). After such a composite of prior information for each test is obtained, the help file can be accessed. This will assist the user in choosing from amongst a number of possibilities the appropriate 3 single letters that together constitute a retrospective 'composite' and is referred to as 'parameter' data for each lab test result, being loaded along with it into a segment of the same lab test field. The three parameter codes are; duration of abnormal result(how long has that test been abnormal), intensity of the abnormality and comparison to any most recent result for that test. These codes are only for loading with an abnormal test result. For each normal lab test result a letter indication in the first field position for indicating 'normal' result and then one of 3 possible letters in the fourth position of that lab test field depending upon an abnormal prior result, normal prior result or no prior result on file for that test.

After obtaining prior information from the several aspects for each of the test results present for data entry, as indicted by steps 2412 and 2414, and then selecting the appropriate parameter codes depending upon the prior information or 'track record' of that lab test, the customized data entry screen is then activated and the actual results along with the parameter data are loaded into each of the lab test fields of that out-patient's newly created lab test record. And as has been discussed for each lab test present for loading there are two types of information to be loaded; the actual result both normal and abnormal and the parameter data that encodes prior information about that out-patient's lab test from several aspects.

With abnormal test results, the numeric or quantitative result occupy the last 4 positions of the field while the first 3 are occupied by the parameter codes. In the case of normal results, only an indicator in the first position and one of 3 in the fourth position(as a parameter code) for indicating any most recent result for that test.

The discussions beginning on the next page elaborate upon the two subroutines already mentioned here and called by labentry.prg that are used to access prior historical and comparative information for any out-patient lab test.

It's important to keep in mind that just prior to choosing what aspect of prior information on that lab test to look for the lab test itself must be selected first. That's made possible by listing them first in this subroutine with numbers alongside the name of each of the 14 lab tests, and by selecting one first by that associated number, that is the particular lab test searched for, accessed etc. when the selection of prior result from one of several aspects is made just after that.

Referring to FIG. 41, a lower-level subroutine entitled findout1.prg called by the main subroutine labentry.prg just discussed, and is for the purpose of finding and accessing prior information on any of the system's 14 lab tests from 2 perspectives that were selected for in the higher level subroutine labentry.prg that called it. In this subroutine those two prior aspects are; the date and value of the last abnormality for any lab test and the date and value of the first anormality(at least for the current file). The data is routed to the screen and thereby enables the user to interpret the information and then determine which of several possible single letters to choose from in order to encode for those two prior aspects as part of the parameter segment of the lab test field.

The subroutine begins by first opening the lab file(abn_lab.dbf) and positions the record pointer to that out-patient's newly created lab record. As is seen in step 2503, it then skips back one record and if that isn't a record for that out-patient a message is displayed informing the user that a search on that out-patient's prior lab tests is not possible-(because there aren't any). If there are earlier records on that out-patient present in the lab file the most recent record is accessed and the date of those tests are displayed for user orientation. At that point, and as is seen in step 2506, the record pointer is then moved to that out-patient's first lab record(earliest one on file) in order to begin the search. If the selection called 'first abnormality and date' was made in labentry.prg, then beginning with the first previous lab test record for that out-patient. the first abnormal result on the lab test selected for by number back in labentry.prg that is found is accessed and the numeric data as well as the date of the tests ordered are formatted and displayed along with the lab test name and as a reminder to the user/operator the nature of the data accessed, i.e. date and value of first abnormality, etc.. After a pause the user returns to the main subroutine, labentry.prg, and can then choose and access other kinds of prior information on that lab test or another lab test for the purpose of determining the proper parameter coding.

If the user/operator then selects 'date and value of last abnormality' for that lab test, this subroutine (findout1.prg) is again entered. Initially the same steps are involved until step 2513 is entered. Now, whenever a lab record for that out-patient is encountered in which abnormal data in that lab test field is present the numeric values and the data are saved. That is repeated for each successive later lab record in which results for that lab test are found for that out-patient including and until the last record(most recent) is found. At that point and if there were more than one previous abnormal result for that lab test, the values present now represent the last abnormal value and the associated date since all previous values were written over and therefore replaced by all later ones as the record pointer skipped forward from that out-patient's first lab record. And once again, in addition to the numeric and date data displayed, a brief message reminding the user of the kind of prior information being accessed is displayed also. And as in the option whereby date and value of first abnormality is searched for, if there isn't any abnormal results for this particular lab test in any of that out-patient's lab records that are at least currently on file, then a 'lab test normal' message is displayed. If it isn't on file at all, i.e. this is the first time that lab test has been done for that out-patient, then that type of message is also displayed.

Once again, the subroutine pauses for the user to review the data on that lab test's prior results and then returns to the main subroutine, labentry.prg., for another type of selection for the same or another lab test, loading of test results through the customized data entry screen, access the help file for instructions on how to code the parameter data obtained by choosing the 4 options while in the labentry.prg subroutine, or returning to the beginning to start another out-patient or to quit the routine.

Once again, the parameter data are three single letter codes placed in the same field as the test results and represent 3 types of information regarding that lab test. The first or most leftward letter is for indicating the length of an abnormality; recent onset, medium duration or chronically abnormal. The second position is for indicating the intensity of the abnormality and the third or right-most position is for indicating what this result is in comparison to any most recent result for that test. Since it requires accessing prior information on any test from several aspects in order to code for the first and last positions of the 'parameter data', the resultant data reflects a composite of prior results and therefore is spoken of as being compiled.

Referring to FIG. 42, the other subroutine containing two main functions that is called by labentry.prg. This is entitled findout2.prg and like findout1.prg this also searches and accesses aspects of prior results of any lab test. In this routine the nature of the information obtained are of two other types from that in findout1.prg; consistency of a lab test result and the result of its most recent test.

As is seen in step 2601, it begins by positioning the lab file to that out-patient's newly created lab record and then skips back one to see if it isn't the first for that out-patient. If it is, that kind of message would be displayed to notify the user to end any prior search. Otherwise, the record pointer is positioned to that out-patient's first, earliest lab record on file and the type of further processing will depend on which of the two above mentioned aspects of prior lab results and information was selected in labentry.prg.

If 'most recent result' was selected then, as in step 2627, a search begins on that lab test field of that out-patient's lab records. At the first indication of any results at all on that test, a flag is set indicating it was at least done before. For each subsequent lab record for that out-patient in which results on that test are found, the value (numeric) and date are saved and then are over-written by any subsequent results found for that test amongst any later lab records for that out-patient, until that out-patient's last record. At that point and as in step 2630 the fact of a prior result, its value and date of test are saved. The data is then tested and either one of three possibilities as to the result, as illustrated in steps 2621 or 2623 or 2625, is displayed as a message.

If 'consistency of results' was selected in labentry.prg the same initial processing occurs. However, and as seen in steps 2613 and 2611, for each record in which test result data is present in that lab test field, either one of two counters are set and incremented each time depending upon whether the result is normal or not. At the end of the lab records for that out-patient, the condition of the two counters are tested and depending upon whether or not both are zero, non zero or just one is zero, the appropriate message is displayed along with any last test date, see steps 2626, 2620, 2618, 2616.

Once again, the subroutine pauses for user review of the displayed data and then will return to labentry.prg for another selection for the same test, another test, etc. The options regarding what the user can do are identical to the previous subroutine, findout1.prg., at this point.

Referring to FIG. 43, a main calling program entitled Doctorpg.prg that calls other lower-level subroutines for the purpose of accessing and displaying lab test results of individual out-patients from more than one perspective and in the context of other clinical data documented at the time the tests were ordered from office visits. The program and its subroutines are built upon and represent a variation of the multi-level program beginning with labfirst.prg responsible with creating and loading out-patient lab test results. But since this program is designed for querying or inquirying into patient lab data intead of data entry, it lacks a record creation and loading routine but includes a process for cross-linking a lab record with its 'parent' office visit(record) from which the test(s) were ordered.

There are two different ways of viewing the data depending upon user preference; Either by all lab test results done from the same office visit or by individual lab test results for an out-patient from several prior aspects (as in findout1.prg and findout2.prg).

The program begins by displaying an orientation message for the user. Then either of the two above options are selected. As in step 2704, the out-patient's last name and at least the first initial is entered. Then, and again regardless of the selection, that out-patient's master medical record is then accessed and from it are obtained patient identifying and background data for later use in viewing with lab test results.

If the above selection was to display all test results from a given office visit, the user then enters what he or she thinks or knows to be the date of an office visit during which those lab tests of interest were ordered. The office visit file (encounte.dbf) is then searched on the out-patient I.D.No. obtained when the master medical file (medical.dbf) was searched on the patient name entered at the top of the program. The office visit file is also searched on date in order to find and access the exact office visit (record) the user has in mind. If the office visit record from that date for that out-patient isn't found the program is designed to allow the user to enter another date ad infinitum until any record is found, presumably the one the user originally had in mind. Or, after a few trys the user may return to the beginning and view data from a different perspective or quit the routine or choose another out-patient.

If or when the 'correct' date is entered and the desirable office visit (record) is found, the invoice is saved. Now, as in step 2716, by taking advantage of the dualed invoice nature of the lab record (see abn_lab.dbf), that invoice is used to find the lab record storing lab test results ordered from that office visit. At that point a call is made to subroutine digout2a.prg (identical to subroutine digout2 of FIG. 33, so not shown) for stepping through that lab record and accessing those test results present. Another call is then made immediately to subroutine print3b.prg (which is with minor modification identical to print3.prg of FIG. 32, so not shown) which will access, format and print the detail lines for each lab test result in conjunction with other out-patient office visit data. After review the user returns to the top to review test results by the same or other method for the same or another out-patient or quit the routine.

If the user selected instead to review individual lab tests for that out-patient then the entry of a date is by-passed and a main subroutine, selectpg.prg, is called that is virtually identical to labentry.prg of FIG. 40. And as in that subroutine, allows for and controls both the selection of individual lab test results for viewing and from what prior aspect of results for that test; first and last abnormality and dates, consistency of result and most recent result, etc. And upon return of control from the main subroutine selectpg.prg the user may return to the top to select another method of viewing different data for the same out-patient or another out-patient or quit, etc.

Referring to FIG. 44, a subroutine entitled selectpg.prg that is called by the highest level program doctorpg.prg discussed just previously. It is activated if the user, while in doctorpg.prg, has chosen to view the results of individual lab tests and from several prior aspects, as has been defined before except for an additional aspect of prior results developed specially for this inquiry type of routine. In here and unlike before, the largest and smallest abnormal result for any lab test and thier respective dates are determined, accessed and then displayed as another option for the user to select.

The subroutine begins by listing all 14 numbered lab tests available for selection. Then, as before in labentry.prg (FIG. 40), the user first selects a lab test and is then presented with a menu or list of options as to prior aspects of results for that lab test of that out-patient. If the prior aspect of results involving the 'largest and smallest abnormal result' is selected then program control remains in selectpg.prg and a standard 'bubble sort' is executed, as is seen in steps 2825–2832. Then as in step 2820 data from both the largest value and the smallest value variable are displayed with their respective dates. If on the other hand an abnormal result for that test isn't found for that out-patient, that message is displayed shortly after the selection. If however there is only one abnormal result on file it will be displayed as both largest and smallest but since the dates are shown as well there shouldn't be any confusion.

The program then pauses to allow the user to review and then a return is made back to the top with a complete listing of all the numbered lab tests. The user can then view another prior aspect of results for that lab test or choose another lab test for that out-patient, or return back to the top of the main calling program, doctorpg.prg, for another out-patient or to quit.

If the user chooses any of the four other options regarding prior aspects of any lab test result that were described and illustrated before in labentry.prg, either the subroutine finda1.prg or finda2.prg are called and entered. However, since they are virtually identical in function and design to findout1 and findout2 already discussed (see FIGS. 41 and 42) in connection to the lab record creation and data loading, there isn't any need to show them in the same way except to of course mention them as existing and in connection to what particular routine.

Referring to FIG. 45, an upper-most calling program entitled addencrc.prg that controls, through calls to separate lower-level subprograms, the creation and data loading of the office visit record (encounte.dbf)

It begins by collecting the out-patient I.D. No. and then having the user indicate whether or not an acute, temporary 'new problem' was the main reason for that office visit (i.e. the 6 digit condition code is from the short term diagnosis table, er_list.dbf). As in step 2902, a search is then made on the office visit file, using the patient I.D. entered, for a prior record of that out-patient.

If a previous record for that out-patient is found the program then displays guidelines as to what clinical status may be entered depending upon what the most recent status for that patient's office visit was. If there is a conflict the user may return to the top to enter another patient or quit the routine. If there isn't a conflict the status value for that office visit is entered and then a call to the first lower-level subprogram, part1.prg, is made for the actual record creation and more data loading (more of this later). Upon completion of processing in part1.prg, control is returned to this highest level program. If there are any physical data present for loading then another subprogram call is made from addencrc.prg to part2.prg for the entry of encoded physical symptoms data. And if any physical signs data are present for loading then another call is made to part3.prg when control is returned back to addencrc.prg from part2.prg At each point subsequent to the part1.prg call, and as seen in 2908 and 2911, the determination of any need to call further subprograms is made in this most upper level program, either into a lower-level subroutine or, as in steps 2909 and and 2912, back to the beginning for another out-patient record or to quit.

If a prior office visit record for that out-patient doesn't exist, i.e. a first time office visit for a new database patient or the wrong I.D. NO., the user will resolve that. If it represents a new out-patient record then the subprogram for a new out-patient, first time record creation, is entered, named addnewrc.prg. This program will then in that case act like this one, addencrc.prg, as the controlling program for calls to the same lower level subprograms just like this one. Upon completion of a first office visit record, control once again returns here first as in step 2922, and then back to the top for another record, step 2901, or the user may quit.

As in steps 2914, 2915 and 2916, if this main calling program has been executed beyond part3.prg a data check is made to ensure that in any non-status 1 records there are at least one physical data item present. That at least either one sign or symptom in encoded form be present for entry. That is a requirement since the clinical status of the out-patient at the time of the visit is by definition of an unstable nature, i.e. something is clinically wrong and there is some disease activity of some type. Therefore, the requirement that for every non-status 1 record at least one sign or symptom be documented during that visit and then transcribed for the purpose of data entry during this program. And if that isn't the case then that record is deleted for that out-patient and control is returned to the top for another out-patient record creation or quit the routine.

Referring to FIG. 46, a main subroutine entitled addnewrc.prg, called by the main program addencrc.prg just discussed, for the creation and loading of a new out-patient office visit record (first time). And as mentioned it acts like a main calling program by calling on lower level programs depending upon how much data is present for loading into a new patient office visit record (it depends of course on what is found and what the doctor did).

After receiving control from addencrc.prg, a message is displayed reminding the user this is the first record to be placed on file for this new out-patient. The clinical status number is entered and then control is passed to part1.prg for actual record creation and partial data loading. Then with each passage of control back it determines if a need for further calls into lower level subprograms are necessary for physical data entry. As in steps 3005, 3008 and 3013, at the point where all the data for that first record has been entered it will then prompt the user to indicate if any additional records are to be done. And upon that basis on return to addencrc.prg, it will either set up for another record creation and entry or quit the routine.

As in step 3011 and like addencrc.prg, if a non-status 1 office visit record is created but there are no physical data at all present for entry it is disallowed and the new patient record is deleted prior to returning to addencrc.prg.

Referring to FIG. 47, a main subroutine entitled part1.prg that is called by add encrc.prg (or addnewrc.prg for a first time record) for the actual creation and loading it with the essential core of out-patient data that are the most difficult to access. During processing of the new office visit record there is also simultaneous updating of that out-patient's master medical record (and tracking) for any changes to any of that out-patient's chronic long term diagnosis.

It begins by opening the office visit file, positioning to the last record and then incrementing the invoice by one for later inclusion into the new record. Then, as in step 3104, up to 3 4-digit codes, each representing the 'numeric' segments (last 4 digits) of a chronic long-term diagnosis (see FIG. 3, chrmedli.dbf), are present for entry at the designated prompts on the screen.

The master medical file is then searched on that patient I.D. No. If this is a first time record creation for a new out-patient and one doesn't exist, a new master medical record will be created and the I.D. No. for that patient is written to it. At that point, from step 3110 to step 3130, the processing involves interaction with or cross-file processing between the newly created office visit record and that out-patient's master medical record for the purpose of updating any changes to that out-patient's diagnoses's. As in steps 3110 and 3111, if a primary diagnosis (the highest level diagnosis) is entered, that 4 digit code is compared against the last 4 digits of the primary diagnosis in that out-patient's master medical record (both records must have at least a primary diagnosis). If it is the same then the full six digit code in that master medical record field is stored to a variable for later writing to the corresponding position in the newly created office visit record, i.e. cross-file processing. If there is a difference and a 4 digit code has been entered, the chronic diagnosis table is then searched on that 4 digit code and the full 6 digit diagnosis is accessed and because of the mismatch with that position in the master medical record, the six digit diagnosis is written to that diagnostic position in order to update that out-patient's master medical record during loading of the new office visit record (i.e. cross-file processing). In order to indicate a change in that patient's diagnosis and to keep historical track of such changes, the following takes place in each of the three fields associated with each chronic diagnosis field of the master medical record; the new office visit invoice is written to one, a flag is set in another and the current date is written to another.

If a 4 digit code isn't entered at a chronic diagnosis position (field), the corresponding field in the master medical record storing a diagnosis is stored to a variable for later writing to that same field in the new office visit record. That step corrects for any ommission during data entry of an active, current chronic diagnosis, and naturally applies to all three fields.

Beginning at step 3132 the condition code or main reason for the office visit is then accessed from the appropriate table for loading to the new record. If the new problem flag had been set during the data entry at the top of the program at addencrc.prg, then the 4 digit code representing the primary reason for that office visit is used to search on the short-term, acute diagnosis table (er_list.dbf) and the corresponding full 6 digit diagnosis code is accessed from the table and saved for later writing to the newly created office visit record at the condition code field. Alternately, if the new-problem indicator wasn't set, that same 4 digit code is instead used to access the chronic, long term diagnosis table since the condition code field or the main, primary reason for the office visit represents a chronic diagnosis as opposed to a short term one. Then, as in step 3138, the new office visit record is actually created (i.e. appended) and then all the basic data elements that have been written to variables are now written to thier appropriate fields in that new record which includes; the 6 digit condition code, up to three 6 digit codes to each chronic diagnosis field, the new office visit invoice, patient I.D. No., and the clinical status of the patient during that office visit. As in steps 3115, 3113 and 3114, whenever a search by a 4 digit code is unsuccessful, a message is displayed and the user may return to either the start of this subroutine or to the start of the main program.

If the search useing the 4 digit codes are successful in finding and accessing from the appropriate table the corresponding full 6 digit diagnosis and there are no other problems, control is returned to addencrc.prg (or addnewrc.prg for a first time record) and a flag will be set to allow passage to the next lower level subroutine, part2.prg, for the entry of any physical data present.

Referring to FIG. 48, a lower-level subroutine entitled part2.prg called by addencrc:prg (or addnewrc for a first time out-patient record) for the entry of any symptoms or complaints data to the office visit record. (signs or findings data are entered during part3.prg) This subprogram is called after part1.prg and from within addencrc.prg or addnewrc.prg depending upon prior processing of that out-patient's record data.

The extent of processing within this subprogram is naturally dependent upon the presence of any physical symptom data for entry and if there is, it then employs two separate methods for entering that data depending upon the way in which the source document was prepared.

It begins by displaying an orientation message about how to use the routine depending upon the way the data was transposed to the data entry source document from the medical department. At step 3203 another check is made to exclude from the office visit file the addition of any non-status 1 records that don't have any physical data for entry (either it wasn't documented during the visit or it was lost during the transposition to a data entry source document). Beginning at step 3204 and depending upon how the data for entry has been prepared, either a 3 digit code for up to two complaints is entered by directly taking it off the source document or alternately the clinical group indicator of that complaint (what organ system its from, i.e. cough=lung) alone is entered.

As is seen in step 3213, the former case is quicker since it involves less steps. The complaints or symptoms table (see FIG. 11, cc_list.dbf) is opened and searched on that 3 digit code in order to access that physical complaint's full 5 digit code. As a non-binding check on data consistency, the single letter group indicator of the 5 digit complaint code is compared to that of the 6 digit condition code that was already loaded in part1.prg, since it should be identical assumeing both a diagnosis of any problem and any symptoms that result from said problem involve and emanate from the same organ system. If not identical then a brief message is displayed about that non-match but the program will still write the 5 digit complaint code to the new record. As mentioned, the system and program provides for two physical complaints to be entered into the office visit record. At step 3219 the user may return to the top of this subroutine for entry of the second complaint if present, by either the same method or the alternate method to be discussed below, or return to addencrc.prg..

If the clinical-group indicator method is used, there are two main steps involved. First, upon entry of the single letter for indicating the group, a listing is generated for display that includes all complaints from that group. The complaints that are displayed are represented as an entire table entry, i.e. both the 5 digit entry and the literal text (i.e. 'chest pain') contained in a 25 character field. In that way the user can visually search the displayed list in order to find a match between one of the text's displayed and that appearing on the source document in written form and associated with that single letter for indicating clinical group (see FIG. 50). Once a match is made between that complaint within the group originally listed on the screen by entering that single letter and that written on the source document used for data entry, the last 3 digits of that 5 digit code associated with the literal text of the complaint that has been matched is taken off the screen by the user and then entered at the prompt. At this point the same processing then occurs as with the direct method because now that 3 digit segment is used to search on the system's complaints or symptoms table (CC_list.dbf) for accessing the full 5 digit complaint code and write it into the appropriate field position of the new office visit record. The user may then return to the top of this subprogram to enter another complaint for that out-patient documented during that office visit or return to the top program addencrc.prg for another out-patient office visit record creation.

It should be noted that complaints and symptoms are the same thing and findings and signs are the same thing.

Referring to FIG. 49, a subroutine entitled part3.prg called by addencrc.prg (or addnewrc.prg) for the entry of any physical signs (findings) documented during the office visit whose record is currently under creation and loading.

Except for the fact that these data items are clinical findings such as 'tenderness' as opposed to a clinical complaint of 'pain in the stomach' and therefore another type of table is used (i.e. findings.dbf, see FIG. 10) everything else is exactly the same as to the structure of data types, alternate types of access as described in FIG. 48 and method of processing as discussed in part2.prg.

Also, as in part2.prg, upon completion of the data entry control is passed back to addencrc.prg or addnewrc.prg for either creating another out-patient record or terminating the routine.

Except for what is represented by the data types, complaints or symptoms vs, findings or signs, part3.prg is virtually identical to part2.prg.

Referring to FIG. 50, a model source document used in loading a central core of office visit data during the record creation subprogram previously discussed and as represented by the previous FIGS. 45–49. Only those data items involving the greatest complexity in locating, accessing and over-all processing were selected for illustration, while the rest can be transcribed directly.

As mentioned at several places before, the newproblem field is for indicating if an acute, temporary and as yet not fully characterized problem was the main, primary reason for the office visit. In effect, was it the chief complaint as opposed to one of that out-patient's chronic, established diagnosis? Then, if the field is set to true indicating that is the case, the table from which the 6 digit condition code is obtained is the acute diagnosis as opposed to the chronic diagnosis table. The clinical status field contains a single digit number from 1–5 and is for indicating whether or not there is any significant disease activity and to what relative extent. (see FIG. 4, encounte.dbf). The three fields mcode1, mcode2 and mcode3 are for the three possible chronic diagnoses any out-patient may have with mcode1 being the primary diagnosis since it is from the upper-most position of the Chronic Diagnosis table relative to any of the other two (see FIG. 3, chrmedli.dbf and how it is arranged in ascending order of urgency or clinical priority).

That aspect of any diagnosis that is transposed to the source document for data entry is the last 4 'numeric' digits of the full 6 digit diagnostic code and which is, as an inspection of the chronic diagnosis table (chrmedli.dbf) shows, the most unique aspect of each encoded diagnosis. Similarly, the condition code field, whether acute or chronic, is entered as a 4 digit code whereupon the full 6 digit code is then accessed as discussed before. And as mentioned here if the new problem field is set to yes or true then the 4 digit code present in the condition code field of the source document will be directed by the program to search on the acute, short term diagnosis table to obtain the full 6 digit diagnosis code (see FIG. 8, er_list.dbf)

As already shown, the physical data (signs and symptoms) may be represented on the source document in two different ways reflecting two different methods of entry. The most direct method is the one labeled 'first method' and in which the last three digits of either the complaints (symptoms) or the signs (findings) are entered directly and used to search for the full 5 digit physical data item because it is the most unique encoded aspect of it. The alternate or indirect second method involves both a single letter as the clinical group indicator and the presence of the full literal text of that sign or symptom exactly as it exists internally within the two physical data tables (see cc_list.dbf and findings.dbf FIGS. 10 and 11).

All of the above data found on that source document would be prepared by a trained medical staff familiar with and trained to locate those physical data items by either a frequently used hard copy in which those data items are sorted or arranged on a medically logical basis or ready access to a computer based listing of data from the relevant tables.

At the end of a normal day these source documents would be collected from the offices of each primary care physician and all transmitted together to the data entry personnel for transcription and other data entry operations.

Referring to FIG. 51 a main computer program entitled addmedrc.prg for the creation and loading, i.e. data entry, of the out-patient master medical record. As in the office visit record creation routine, only those data items most difficult to locate, access and over-all process have been included in this data entry process as well.

It begins with an orientation message for the user. A counter is then set to remind the user of the current total of chronic diagnosis entered by screen. Then, as in addencrc.prg, depending upon the way in which a source document has been prepared the user may enter a diagnosis in two different ways. It may be either a 4 digit code as the direct method or in the indirect method 2 single letters; one defining the diagnostic category and the other the clinicopathological group of the chronic diagnosis to be entered. In this latter case the purpose is to generate the narrowest possible list of chronic diagnoses's for making it easier for the user to identify one amongst that list as a visual match with that present on the source document. It is for facilitating a visual search until a match is made between two diagnosis's, one on the screen and the other present on the source document.

Briefly, and as in step 3504, when the first or direct method of chronic diagnosis entry is used, the 4 digit code is used to search on the Chronic diagnosis table and if found the full 6 digit diagnostic code is accessed and temporarily stored. The program's diagnosis counter is then incremented and the number of diagnosis already entered is displayed. Return is then made to the top for another chronic diagnosis entry or to quit.

As in step 3505, if the second, indirect method is used, the clinico-pathological group letter must be used while the diagnostic category letter is optional, although by useing that too the list generated for the visual search will be smaller by a factor of three since there are 3 diagnostic categorys. As in step 3521, the user visually searches for a match between the written diagnosis on the source document present with the single letter indicators for the two groups and that from amongst the list generated on the screen by program processing when each letter from the two groups were entered. When a match is found the last 4 digits of the 6 digit code is copied from the screen by the user, entered, and as in the first method the chronic diagnosis table is searched, the full 6 digit code is accessed and written to a variable for temporary storage.

Regardless of the method of entry used, each time a diagnosis is entered the program counter is incremented and when all the ones on the source document have been entered and before the user can by-pass that entry step the program will check to see if at least one diagnosis has been entered. If not a message is displayed and the user must return to the top. If the diagnosis check is o.k. the program still pauses to allow the user opportunity to check what has been entered against the source document, etc. If everything is o.k. the out-patient's name and I.D. No. are entered. The master medical file is then opened and a search on that I.D. No. is made. If found a message 'patient record already on file' is displayed and processing on that out-patient ends, there is no record creation. If not found then a new master medical record is created (appended) and both name and I.D. No. along with all the chronic diagnoses's previously entered (up to three) are then written to the new record.

At that point a subroutine is called, checkrec.prg, to ensure that in cases in which more that one diagnosis was entered, they are sequenced in relation to each other according to their relative position in the chronic diagnosis table; primary dx highest, secondary dx next highest, etc.

Upon return from that subroutine, control is passed to step 3509 for another try, another out-patient, or terminate the routine.

Figure 52:
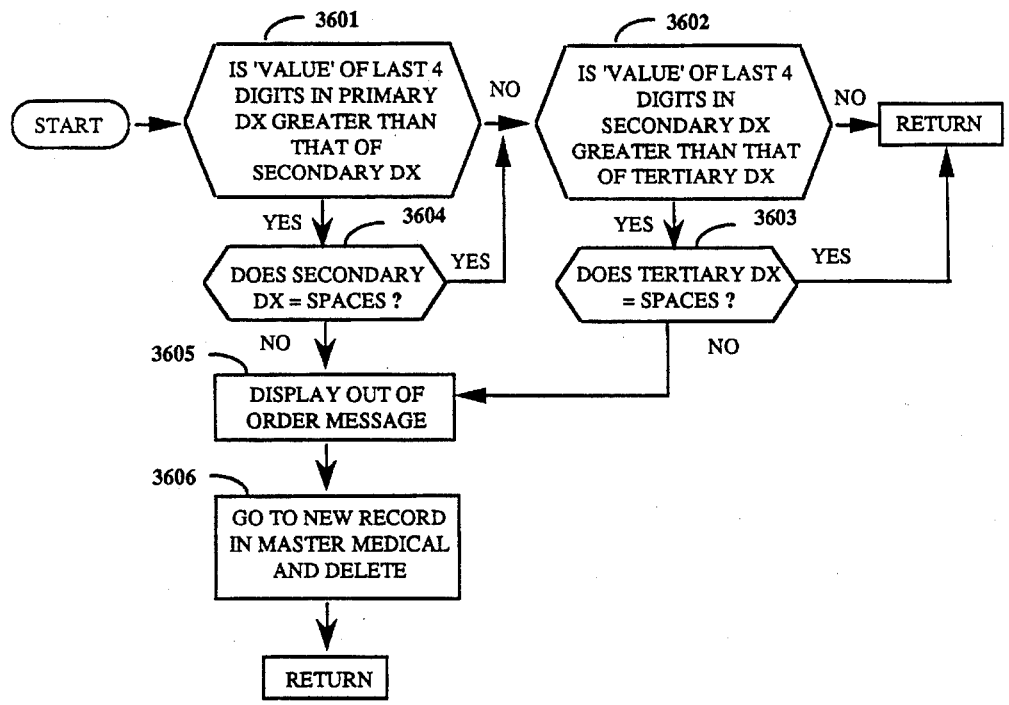

Referring to FIG. 52, a subroutine entitled checkrec.prg called by addmedrc.prg to check on the data integrity of the chronic diagnosis data entry of that main program. It ensures that the proper ordering or ranking of the chronic diagnosis as they were entered into the new master medical record was observed during addmedrc.prg, i.e. the dx from the highest position in the chronic dx table relative to any of the others is in the primary position and the second highest is in the secondary position, etc.

In order to test for the above and as step 3601 shows, the value of the last 4 digits of the primary dx diagnosis is compared against that in the same position of the secondary dx field. If it isn't greater then a comparison is made between that secondary dx's last 4 digits and that in the identical position of the tertiary dx field. If that value also isn't greater then it is assumed there are three entered and they are sequenced properly in relation to each other based upon their relative positions in the chronic diagnosis table. If the value of the 4 digits from a higher level dx is found to be higher than that from a lower one AND it isn't due to blank spaces, an error message is displayed, that new master medical record, loaded incorrectly, is deleted and control is returned to addmedrc.prg for another try, another out-patient or exit the routine.

Referring to FIG. 53 a model source document for use in the data entry routine of addmedrc.prg, the out-patient master medical record. Only those data items most difficult to locate, access and over-all process for are included in the routine for the purpose of illustration as to the feasibility and utility of such a method and process.

As in the source document used with the office visit record routine, both methods for entering the chronic diagnosis's are illustrated. On the left is the direct, quickest method with samples in each of the three diagnostic positions. Note that as before it is the last 4 digits of the 6 digit diagnostic code that is used in this method of direct entry and also how the 'numeric' value becomes progressively higher going from primary to tertiary.

The second or indirect method is on the right. Those samples represent the other segment of the full 6 digit diagnostic code since the diagnostic category and the clinical group indicator as single letters are found. The other aspect of the indirect method is the literal text of that chronic diagnosis for use in the visual search and match, which is located just beneath the two letters. Note that 'compulsory' refers to the clinico-pathological group and the letter representing that must be entered and first. The letter indicating the diagnostic category of that chronic diagnosis is optional but if used will naturally restrict further the number of diagnosis displayed when the list is generated and therefore make the visual search for that diagnosis matching the one written on the source document much easier.

The field for the out-patient I.D. is not shown but as was seen in addmedrc.prg that data was transcribed (entered) directly at the prompt.

Since there was a full explanation of how both methods of entry operate during discussion of addmedrc.prg, that won't be repeated here.

Referring to FIG. 54, a main print program entitled overdrawn.prg for detecting and monitoring overuse of any office based laboratory tests. It reports out in coupled format the results of the same lab tests ordered from separate office visits for any out-patient along with the same salient clinical data from both. In this way, by comparing previous results and conditions with current ones for that out-patient, one can determine the legitimacy of lab work ordered during an otherwise uneventful and unremarkable office visit. Was there a precedent basis or reason for drawing blood work when the clinical condition of the out-patient at the time the tests were drawn would not seem to necessitate it?

Program specific processing isn't triggered until a 'special' type of office visit record is encountered; a status 1 (normal, baseline or asymptomatic) and scheduled visit, a chronic dx as the main, primary reason for the office visit (condition code field=chronic diagnosis) and yet lab work during that office visit was ordered and drawn despite an unremarkable visit. In the face of that was there any justification for drawing blood and consuming expensive resources?

Upon that identification for any office visit record and as in steps 3807, 3808, 3809, 3810, 3811 and 3825, cross-linkage between that office visit and the out-patient's master medical record is established for printing heading and background data once per page. At that point a call is made to a subroutine named digoutod.-prg that accesses all lab test results from the current office visit just identified as being of 'special' type. Then for each lab test result present, that out-patient's from whatever prior lab record of that out-patient it may be in (see discussion for FIG. 55, digoutod-.prg).

Upon return from the called subroutine, the heading data for that office visit is printed then, for each lab test result present in the variable passed from the subroutine, a detail line is printed that includes date of test and invoice of the lab record. At that point, for comparison with previous and identical lab tests of that out-patient along with identical types of other clinical data from those separate office visits for that out-patient as well, the two groups of data from different office visits are printed in coupled format as well for easier comparisons in order to assess justification for the current blood work.

In summary, each most recent lab test result that corresponds to each drawn during that office visit of special type (as defined earlier) is also accessed and as a result different prior lab records for that out-patient may need to be accessed. The same applies to each prior office visit for that out-patient during which each of those most recent lab tests were ordered, i.e. accessing different prior ones. And once again, each lab test result is coupled with its most recent result, if available, and the coupling of printed data also includes the same salient clinical data from different office visits of that out-patient.

In cases where any prior lab tests were ordered during an emergency room visit by that out-patient there is no access of prior lab data and no attempt to compare past with current results, etc. That is because it is assumed any lab test ordered during any office visit type for the purpose of following up on one ordered during an emergency room visit is probably justification in itself.

After all the data, coupled and combined, stemming from any office visit record meeting the previously defined criteria has been printed the resultant detail lines that were generated are separated by a broken line and the program then skips to the next record. If another of the same, special type is encountered and identified and it is the same out-patient, the resultant detail lines are printed below the previous ones. If it is another out-patient then the program skips to the next page, prints heading and background data and repeats each detail line for each lab test result. Processing continues until end of office visit file is encountered.

Referring to FIG. 55, a subroutine entitled digoutod.prg called overdraw.prg for accessing both the lab test results from the current office visit being processed and the most recent result for each of those currently present. In addition, it takes advantage of the dual invoice nature of the lab records. By storing the invoice from the parent office visit (or in the case were blood work was ordered from the emergency room, then the ER invoice no.) it becomes possible to locate and access the office visit (record) from which those 'most recent, prior' lab tests were ordered. In that way the same salient clinical data in addition to just lab test results from the two separate office visits for that out-patient can be coupled for comparison too and in that way obtain a better idea of just why those lab tests from the office visit currently being processed were drawn, i.e. was there a valid reason based upon either a prior lab test result or some other clinical condition.

It begins, as in step 3901, by searching the lab file for that record linked to the current office visit identified as meeting the 'special type' criteria outlined in the discussion of overdraw.prg. Each field of that lab record is then tested for data (lab results). For each result found, the test name and, for abnormal results, the quantitative data is stored. A test is then made on a single letter on the parameter code segment of that lab test field and if it indicates a prior test done then a search is made for that lab record storing the most recent result of that lab test for that out-patient. But, before accessing the data of that most recent lab test the first character of the invoice is tested. If it is from the emergency room as opposed to an office visit then an access of the results from that lab record is not done since the prior lab test was drawn in the atmosphere of acute care, etc. and it will be assumed that any lab test drawn during the office visit currently being processed was justified as a follow-up of a test made previously but during a potentially unstable clinical situation (i.e. ER). And as a result a flag is also set to indicate that for use in the main program during printing. However, if it is derived from a previous office visit for that out-patient then the results and test date are accessed and temporarily stored.

For normal current test results, normal prior test results and no prior test is available, the appropriate flags are set as indicators for interpretation and resolution back in overdraw.prg prior to printing.

After the processing of that lab test result, the subroutine moves (increments) to the next lab test field of that current office visit based lab record. If data is found then repeat of the above processing until the last (14th) field of that lab record, linked to the current 'special' office visit record, has been tested. Then the variables storing all the accessed data, current and prior results and appropriate flag settings, are passed back to overdraw.prg for resolution, formatting and printing.

As in previous subroutines that access lab test data the method used here is virtually the same. The use of several 'dedicated' variables that are for storing either separate aspects of each lab test result or the equivalent in blank spaces, and the position of any test result in relation to other test results is the same as thier relative positions in the lab record. If there are actual results in any lab test field then each of the variables are filled by a fixed amount of characters that are identical for each test but vary for each variable due to the differences in what data they store Back in the main program, overdraw.prg, each of the variables are stepped through together when tested for the presence of data for each lab test. When ever a test result is found each of the passed variable are accessed at the same relative position for the several aspects of each result and one detail line is then printed, with the number of detail lines dependent upon the amount of lab tests done during that triggering office visit (record).

```
public                acondition,aconfirm,mPT_ID,acode
store ctod("  /   ") to mdate1,mdate2
select 1
use encount1 index encountn
append from encount1 for substr(PRIM_DX,1,1) = "A" .or. substr(TERT_DX,1,1) = "B"
go top
  do while .not. eof()
    store DOCTOR to mdoctor
    do while DOCTOR = mdoctor .and. .not. eof()
      store PT_ID to mPT_ID
      store 0 to acount
      do while PT_ID = mPT_ID .and. DOCTOR = mdoctor .and. .not. eof()
        store INVOICE to minvoice
        do while INVOICE = minvoice .and. PT_ID = mPT_ID .and. DOCTOR = mdoctor .and. .not. eof()
        if STATUS = "_" .and. TYPE = "S" .and. .not. MED_CHANGE .and. .not. LAB_WORK .and. .not. NEW_MED .and. .not. CONSULT .and. .not. NE
WPROBLEM .and. .not. INJECTION
            store acount + 1 to acount
            if acount = _
             store DATE to mdate1
             skip&&next record for same patient
            else
             store DATE to mdate2
             store CONDITION to acondition
              if mdate2 - mdate1 < 28
               store DOCTOR to doc
               store PT_ID to patient
               store INVOICE to numb
               there = recno()
               do search
                select 1
                use encount1 index encountn
                goto there
                select 2
                use notify
                append blank
                replace CATEGORY with "SA"
                replace DOCTOR with doc
                replace PT_ID with patient
                replace INVOICE with numb
                replace DATE with mdate2
                replace CONDITION with acondition
                if acode = "t"
                 replace CODE with "t"
                endif
                if "E" $ aconfirm
                 replace EINVOICE with substr(aconfirm,at("E",aconfirm),6)
                endif
                if "H" $ aconfirm
                 replace HINVOICE with substr(aconfirm,at("H",aconfirm),6)
                endif
                if "T" $ aconfirm
                 replace TINVOICE with substr(aconfirm,at("T",aconfirm),6)
                endif
                if "L" $ aconfirm
                 replace LINVOICE with substr(aconfirm,at("L",aconfirm),6)
                endif
                select 3
                use surglink index surglink
                seek mPT_ID
                if found()
```

AP2  Schedul1.Prg (cont.)

```
    aconfirm = space(6)
    do while PT_ID = aPT_ID
     if DATE >= adate1 .and. DATE <= adate2
      store "t" to mcode
      store INVOICE to aconfirm
      exit
     endif
     if substr(SURGCODE,1,1) = "A" .and. adate1 - DATE <= 90
      store "t" to mcode
      store INVOICE to aconfirm
      exit
     endif
     if substr(SURGCODE,1,1) = "B" .and. adate1 - DATE <= 60
      store "t" to mcode
      store INVOICE to aconfirm
      exit
     endif
     if substr(SURGCODE,1,1) = "C" .and. adate1 - DATE <= 60
      store INVOICE to aconfirm
      if substr(SURGCODE,2,1) = substr(acondition,1,1) .or. substr(SURGCODE,2,1) = substr(acondition,2,1)
       store "t" to mcode
       exit
      else
       skip
       if eof()
        exit
       endif
      endif
     else
       skip
       if eof()
        exit
       endif
     endif
    enddo
   endif
    select 2
    if "X" $ aconfirm
     replace KINVOICE with aconfirm
     if CODE () "t"
      if mcode = "t"
       replace CODE with "t"
      else
       replace CODE with "f"
      endif
     endif
    else
     if CODE () "t"
      replace CODE with "f"
     endif
    endif
    select 1
    store adate2 to adate1
    store 1 to mcount
    skip
   else
    store 1 to mcount
    store adate2 to adate1
    skip
   endif
  endif&& this is nonfunctional
 else&& start from scratch
  store 0 to mcount
  skip
 endif
```

```
   store 0 to acount
   skip
  endif
 enddo
 enddo&& end of patient,same doctor
 enddo&& end of doctor
enddo
close databases
return
```

AP3

```
public mdate1,mdate2,mcondition,mconfirm,mPT_ID,mcode
store ctod(" /  / ") to mdate1,mdate2,mdate
use encount1 index encountn
append from encountu for substr(PRIM_DX,1,1) = "A" .or. substr(TERT_DX,1,1) = "B"
go top
do while .not. eof()
 store DOCTOR to adoctor
  do while DOCTOR = mdoctor .and. .not. eof()
    store PT_ID to mPT_ID
    store 0 to mcount
    do while PT_ID = mPT_ID .and. DOCTOR = mdoctor .and. .not. eof()
     store INVOICE to minvoice
     do while INVOICE =minvoice .and. PT_ID = mPT_ID .and. DOCTOR = mdoctor .and. .not. eof()
      if type = "U"
       store DATE to mdate1
       store mcount + 1 to mcount
       if mcount >= 2
        there = recno()
        store DOCTOR to doc
        store PT_ID to patient
        store DATE to mdate
        store INVOICE to numb
        store CONDITION to mcondition
        use notify
        append blank
        replace CATEGORY with "AU" + str(mcount,1)
        replace PT_ID with patient
        replace DOCTOR with doc
        replace DATE with mdate
        replace INVOICE with numb
        replace CONDITION with mcondition
        replace CODE with "C" && for consecutive
        use encount1 index encountn
        goto there
       endif
       if STATUS = "1" .and. .not. MED_CHANGE .and. .not. LAB_WORK .and. .not. NEW_MED .and. .not. CONSULT .and. .not. NEWPROBLEM .and.
.not. INJECTION
        skip
       if PT_ID = mPT_ID
        if TYPE = "S"
         if STATUS = "1" .and. .not. NEW_MED .and. .not. LAB_WORK   .and. .not. CONSULT .and. .not. MED_CHANGE .and. .not. NEWPROBLEM  .
and. .not. INJECTION
          store DATE to mdate2
          if mdate2 - mdate1 < 28
           there = recno()
           store DOCTOR to doc
           store PT_ID to patient
           store INVOICE to numb
           store DATE to mdate
           store CONDITION to mcondition
           do searchv
           do surgfind
           use notify
           append blank
           replace CATEGORY with "AU"
           replace PT_ID with patient
           replace DOCTOR with doc
```

```
    replace INVOICE with numb
    replace CONDITION with mcondition
    if mcode = "t"
    replace CODE with "t"
    endif
    if "E" $ mconfirm
    replace EINVOICE with substr(mconfirm,at("E",mconfirm),6)
    endif
    if "H" $ mconfirm
    replace HINVOICE with substr(mconfirm,at("H",mconfirm),6)
    endif
    if "T" $ mconfirm
    replace TINVOICE with substr(mconfirm,at("T",mconfirm),6)
    endif
    if "L" $ mconfirm
    replace LINVOICE with substr(mconfirm,at("L",mconfirm),6)
    endif
    if "K" $ mconfirm
      replace KINVOICE with substr(mconfirm,at("K",mconfirm),6)
    endif
    use encounti index encountn
    goto there
    store 0 to mcount
    skip
   else
    store 0 to mcount
    skip
   endif
   else
    store 0 to mcount
    skip   && and leave count alone
   endif
   else
    exit
   endif
  else
    exit
  endif
 else
   skip
 endif
 else
  skip
  store 0 to mcount
 endif
enddo
enddo
enddo
enddo
return
```

APS

```
public mconfirm,mPT_ID,mcondition,mdate1,mdate2,mcode
store "" to mconfirm
store "      " to mvar
store " " to mcode
   do while .t.
     use ER_ROOM index erindex
     seek mPT_ID
        if found()
           do while PT_ID = mPT_ID
             if DATE >= mdate1 .and. DATE <= mdate2
                store INVOICE to mvar
                if STATUS = "1" .or. STATUS = "3"
                   if DIAGNOSIS = mcondition
                      store "t" to mcode
                      store mconfirm + mvar to mconfirm
                      exit
                   else
                      skip
                      if eof()
                      exit
                      endif
                   endif
                else
                   skip
                   if eof()
                     exit
                   endif
                endif
              else
               skip
               if eof()
                 exit
               endif
              endif
            enddo
            if mcode <> "t"
             if mvar <> space(6)
             store mvar + mconfirm to mconfirm
             endif
            endif
         endif
     use PT_HOSP index hspindex
        store space(6) to mvar
        seek mPT_ID
         if found()
            do while PT_ID = mPT_ID
              if DAT_ADM >= mdate1 .and. DAT_ADM <= mdate2
                 store INVOICE to mvar
                  if DISCH_DX = mcondition
                    store "t" to mcode
                    exit
                  else
                    skip
                    if eof()
                      exit
                    endif
```

```
        else
         skip
         if eof()
          exit
         endif
        endif
      enddo
  if avar <> space(6)
   store aconfirm + avar to aconfirm
  endif
 endif use TREATMEN index trtindex
  store space(6) to avar
   seek aPT_ID
    if found()
       do while PT_ID = aPT_ID
          if DATE >= adate1 .and. DATE <= adate2
           store INVOICE to avar
            if STATUS = "2" .or. STATUS = "4"
             store "t" to acode
             exit
            else
             skip
             if eof()
              exit
             endif
             loop
            endif
          else
           skip
           if eof()
            exit
           endif
           loop
          endif
       enddo
       if avar <> space(6)
        store aconfirm + avar to aconfirm
       endif
    endif use ABN_LAB index labindex
  store space(6) to avar
   seek aPT_ID
    if found()
       store .f. to gotit
       do while PT_ID = aPT_ID
          if DATE >= adate1 .and. DATE <= adate2
             store INVOICE to avar
             store 6 to afield
             do while afield <= 19
               store field(afield) to var
               store &var to var1
               if asc(var1) = 32 .or. asc(var1) = 78 .or. asc(var1) = 84
                store afield + 1 to afield
               else
                if field(afield) = "EKG".or. field(afield) = "CXR"
                  if substr(var1,1,1) <> "C" .or. substr(var1,3,1) <> "U"
                     store "t" to acode
                     store .t. to gotit
                     exit
                  else
                     store afield + 1 to afield
                     loop
```

AP7

AP8    SearchV.Prq(cont.)

```
     else
       if substr(var1,1,1) <> "C" .or. substr(var1,3,1) <> "U" .or. (substr(var1,2,1) <> "2") .and. (substr(var1,2,1) <> "4
         store "t" to acode
         store .t. to gotit
         exit
       else
         store afield + 1 to afield
       endif
     endif
    endif
   enddo
   if gotit
     exit
   endif
   skip
     if eof()
       exit
     endif
  else
   skip
    if eof()
      exit
    endif
  endif
 enddo && end of patient
  if avar <> space(6)
   store aconfirm + avar to aconfirm
  endif
   if eof()
     exit
   endif
endif && no find
```

 AP9   AStatusB.Prg

```
public there,here,mcat,there1
store 0 to there,there1
store "" to mcat
store "       " to condition
store ctod("  /  /  ") to  mdate
select 1
use encount1 index encountn
append from encountb for substr(PRIM_DX,1,1) = "A" .or. substr(TERT_DX,1,1) = "B
"
goto top
do while .not. eof()
 store DOCTOR to mdoctor
 do while DOCTOR = mdoctor .and. .not. eof()
  store PT_ID to mPT_ID
  store 0 to mcount
  do while PT_ID = mPT_ID .and. DOCTOR = mdoctor .and. .not. eof()
   store INVOICE to minvoice
   do while INVOICE = minvoice .and. PT_ID = mPT_ID .and. DOCTOR = mdoctor .and.
 .not. eof()
    if STATUS = "2" .or. STATUS = "4" .and. CONDITION = PRIM_DX .or. STATUS = "2
" .or. STATUS = "4" .and. CONDITION = SEC_DX .or. STATUS = "2" .or. STATUS = "4"
 .and. CONDITION = TERT_DX
       store mcount + 1 to mcount
       if mcount = 1
        store CONDITION to mcondition
       endif
       if mcount = 2
        if CONDITION <> mcondition
          store 0 to mcount
          skip
        endif
       endif
       if mcount > 3
        if CONDITION <> mcondition
          store 0 to mcount
          skip
        else
        there = recno()
        store mcat + "AB" to mcat
        do binary
        use encount1 index encountn
        goto there
        store DOCTOR to doc
        store PT_ID to patient
        store DATE to mdate
        store INVOICE to numb
        use notify
        goto here
        replace DOCTOR with doc
        replace PT_ID with patient
        replace INVOICE with numb
        replace DATE with mdate
        replace CONDITION with mcondition
        use encount1 index encountn
        goto there
        skip
       endif
       else
        if mcount = 3 && when 3 consecutive status 2,4's
         if CONDITION <> mcondition
           store 0 to mcount
           skip
         else
```

```
      skip -2 && back to first status 2 or 4
      there = recno() && hold the place
      do while mcount >= 1 && quit when 0
        store mcat + "AB" to mcat
        do binary
        use encount1 index encountn
        goto there
        store DOCTOR to doc
        store PT_ID to patient
        store INVOICE to numb
        store DATE to mdate
        use notify
        goto here
        replace DOCTOR with doc
        replace PT_ID with patient
        replace INVOICE with numb
        replace DATE with mdate
        replace CONDITION with mcondition
        use encount1 index encountn
        goto there && now still on first status 2
        store mcount - 1 to mcount
        skip && now to second status 2
        there = recno()
      enddo
      store 3 to mcount
     endif
    else
     skip
     exit && to avoid next skip
    endif
   endif
  else
   store 0 to mcount
   skip
  endif
 enddo
 enddo
 enddo
return
```

```
public there1,here,mcat,there,mcondition,mstatus.
store " " to mcode
store "" to mcat
store " " to mstatus
store ctod(" / / ") to mdate
store "    " to mcondition
store "f" to mcode
use encount1 index encount1,encountn
append from encount3 for substr(PRIM_DX,1,1) = "A" .or. substr(TERT_DX,1,1) = "B"
goto top
do while .not. eof()
   store PT_ID to mPT_ID
     do while PT_ID = mPT_ID
      store INVOICE to minvoice
       do while INVOICE = minvoice .and. PT_ID = mPT_ID
       if STATUS = "3"
         store CONDITION to mcondition
         there = recno()
         store there to there1
         store mcat + "A3" to mcat
         do binary
         use encount1 index encount1
         goto there1
         store DOCTOR to doc
         store PT_ID to patient
         store DATE to mdate
         store INVOICE to numb
         use notify
         goto here
         replace DOCTOR with doc
         replace PT_ID with patient
         replace INVOICE with numb
         replace DATE with mdate
         replace CONDITION with mcondition
         use encount1 index encount1
         goto there1
         if mcode = "f"
          skip -1
          there1 = recno()
         else
          skip
          there1 = recno()
         endif
         do while .t.
         if STATUS <> "1" .and. STATUS <> "3" .and. PT_ID = mPT_ID .and. .not. bof() .and. .not. eof()
           store "" to mcat
           store mcat + "A3" to mcat
           do binary
           use encount1 index encount1
           goto there1
           store DOCTOR to doc
           store PT_ID to patient
           store DATE to mdate
           store INVOICE to numb
           use notify
           goto here
           replace DOCTOR with doc
           replace PT_ID with patient
           replace INVOICE with numb
           replace DATE with mdate
           replace CONDITION with mcondition
```

```
use accountl index accountl
goto therel
if mcode = "f"
  skip -1
  therel = recno()
else
  skip
  therel = recno()
endif
else
if STATUS = "1" .and. mcode = "f" .and. PT_ID = mPT_ID
   goto there
   skip
   therel = recno()
   if STATUS = "3"
     store "t" to mcode
   else
     store "f" to mcode
   endif
   if PT_ID = mPT_ID
   if STATUS = "4" .or. STATUS = "2" .or. STATUS = "5"
     store "t" to mcode
     loop && back to inner loop(only here)
   endif
   endif
   exit
endif
if STATUS = "1" .and. mcode = "t" .and. PT_ID = mPT_ID
   skip
   if STATUS = "3"
     store "t" to mcode
   else
     store "f" to mcode
   endif
   exit
endif
if STATUS = "3" .and. mcode = "f" .and. PT_ID = mPT_ID
   store "t" to mcode
   exit
endif
if STATUS = "3" .and. mcode = "t" .and. PT_ID = mPT_ID
  exit
endif
if PT_ID <> mPT_ID
 if PT_ID < mPT_ID
  goto there
  skip
  therel = recno()
  if PT_ID = mPT_ID
   if STATUS = "4" .or. STATUS = "2" .or. STATUS = "5"
     store "t" to mcode
     loop
   endif
  endif
 else
  if STATUS = "3"
    store "t" to mcode
  else
    store "f" to mcode
  endif
  exit
 endif
endif
if bof()
  goto there
  skip
```

AP12

```
      there1 = recno()
      if STATUS = "3"
        store "t" to mcode
      else
        store "f" to mcode
      endif
      if PT_ID = mPT_ID
        if STATUS = "4" .or. STATUS = "2" .or. STATUS = "5"
          store "t" to mcode
          loop
        endif
      endif
      exit
    endif
   endif
  enddo
 else
    skip && don't reset mcode
 endif
 enddo
 enddo
enddo
return
```

AP13

```
public mcondition,mpt_id,here,there,mcategory,mcat
store .f. to mflag
store ctod("  /  /  ") to mdate
use encount1 index encountn
append from encounte for (substr(PRIM_DX,1,1) = "A" .or. SUBSTR(TERT_DX,1,1) = "B") .and. (CONDITION = PRIM_DX .or. CONDITION = SEC_DX .o
r. CONDITION = TERT_DX)
goto top
do while .not. eof()
 store DOCTOR to mdoctor
  do while DOCTOR = mdoctor .and. .not. eof()
  store PT_ID to mpt_id
  mcat = ""
  do while PT_ID = mpt_id .and. DOCTOR = mdoctor .and. .not. eof()
   store INVOICE to minvoice
    do while INVOICE = minvoice .and. PT_ID = mpt_id .and. DOCTOR = mdoctor .and. .not. eof()
    if STATUS = "1"
      skip
      if eof()
       return
      endif
    else
     skip - 1
       if PT_ID <> mpt_id .or. bof()
         skip
       endif
       store mcat + "AE" to mcat
       store PT_ID to patient
       store DATE to mdate
       store INVOICE to minv
       store CONDITION to mcondition
       there = recno()
       use
       do binary
       use notify
       goto here
       replace CONDITION with mcondition
       replace DATE with mdate
       replace INVOICE with minv
       replace PT_ID with mpt_id
       use encount1 index encountn
       goto there
       skip
        do while STATUS <> "1" .and. PT_ID = mpt_id .and. .not. eof()
         store "" to mcat
         store mcat + "AE" to mcat
         store PT_ID to mpt_id
         store DATE to mdate
         store INVOICE to minv
         store CONDITION to mcondition
         there = recno()
         do binary
         use notify
         goto here
         replace PT_ID with patient
         replace INVOICE with minv
         replace DATE with mdate
         replace CONDITION with mcondition
```

```
    use encount1 index encountn
    goto there
    skip
  enddo
  if eof()
   use notify
   goto here
   replace CATEGORY with stuff(CATEGORY,7,1,"u")
   use
   return
  endif
  there = recno()
  store STATUS to mstat
  store PT_ID To mpt
  use notify
  goto here
  if mpt_id = mpt
     replace CATEGORY with stuff(CATEGORY,7,1,"r")
  else
    replace CATEGORY with stuff(CATEGORY,7,1,"u")
  endif
  use encount1 index encountn
  goto there
  loop
 endif
 enddo
 enddo
 enddo
 enddo
close databases
return
```

AP15

```
public there,here,mcat,there1,
store 0 to first,second,third,fourth
store "       " to msinv
store " " to mdumb
use encount1 index encountn,encount1
if substr(mcat,2,1) = "B" .or. substr(mcat,2,1) = "E"
  goto there
else
  set order to 2
  goto there1
endif
store mcat + STATUS to mcat
if TYPE = "S"
  store mcat + "S" to mcat
else
  store mcat + "U" to mcat
endif
store COMPLAINT1 to mcomp1
store COMPLAINT2 to mcomp2
store FINDING1 to mfind1
store FINDING2 to mfind2
if MED_CHANGE
   first = 1
endif
if NEWPROBLEM
  store "t" to mdumb
else
  store "f" to mdumb
endif
if NEW_MED
   second = 2
endif
if LAB_WORK
   third = 4
endif
if CONSULT
  store INVOICE to minvoice
  use specalst index specinvf
  seek minvoice
  if found()
  store INVOICE to msinv
  fourth = 8
  else
  fourth = 0
  endif
  use encount1 index encountn,encount1
```

```
       goto there
     else
       set order to 2                                      AP 17      Binary.Prg (cont.)
       goto there1
     endif
   endif
   if INJECTION
     store .f. to mflag
     store INVOICE to minvoice
     use MEDICINE index medinv
     seek minvoice
     if found()
       if (ACTION1 = "I" .or. ACTION2 = "I" .or. ACTION3 = "I" ).and.(ACTION1 = "M" .
  or. ACTION2 = "M" .or. ACTION3 = "M")
         store mcat + "B" to mcat
         store .t. to mflag
       else
         if ACTION1 = "I" .or. ACTION2 = "I" .or. ACTION3 = "I"
           store mcat + "I" to mcat
           store .t. to mflag
         endif
         if ACTION1 = "M" .or. ACTION2 = "M" .or. ACTION3 = "M"
           store mcat + "M" to mcat
           store .t. to mflag
         endif
       endif
       if .not. mflag
         store mcat + " " to mcat
       else
         store .t. to mflag
       endif
     else
       store mcat + "E" to mcat
     endif
   else
     store mcat + " " to mcat
   endif
   use
   store 0 to mamount
   store first + second + third + fourth to mamount
     DO CASE
       case mamount = 15
         store mcat + "P" to mcat
       case mamount = 14
         store mcat + "O" to mcat
       case mamount = 13
         store mcat + "N" to mcat
       case mamount = 12
         store mcat + "M" to mcat
       case mamount = 11
         store mcat + "L" to mcat
       case mamount = 10
         store mcat + "K" to mcat
       case mamount = 9
         store mcat + "J" to mcat
       case mamount = 8
         store mcat + "I" to mcat
       case mamount = 7
         store mcat + "H" to mcat
       case mamount = 6
         store mcat + "G" to mcat
       case mamount = 5
         store mcat + "F" to mcat
       case mamount = 4
         store mcat + "E" to mcat
```

```
    case mamount = 3
      store mcat + "D" to mcat
    case mamount = 2
      store mcat + "C" to mcat
    case mamount = 1
      store mcat + "B" to mcat
    case mamount = 0
      store mcat + "A" to mcat
endcase
use notify
append blank
replace CATEGORY with mcat
replace CODE with mdumb
replace COMPLAINT1 with mcomp1
replace COMPLAINT2 with mcomp2
replace FINDING1 with mfind1
replace FINDING2 with mfind2
if msinv <> "           "
  replace SINVOICE with msinv
endif
here = recno()
use && close notify
store "" to mcat
return
```

```
msysdate = ctod("03/01/87")
store ctod("  /  /  ") to mdate
mtitle = "NEWPROBLEM SUMMARY BY PATIENT (physical data)"
store " " to msyst,mdiast
store .f. to m1
set device to print
select a
use medical index medpt_id
select b
use notify1 index notify1
append from notify for msysdate - DATE >= 14 .and. CODE = "t"
goto top
set relation to PT_ID into medical
do while .not. eof()
@ 1,(85 - len(mtitle))/2 say mtitle
@ 2,0 say "PATIENT ID: " + PT_ID + "LAST NAME " + a->LNAME + "BIRTH DATE " + dtoc(a->DOB)
if a->SEX = "M"
  @ 2,66 say " MALE"
else
  @ 2,66 say " FEMALE"
endif
store a->LNAME to mlname
@ 3,0 say "PRIMARY DIAGNOSIS " + a->DIAGNOSIS1
@ 3,45 say "LAST HOSPITALIZATION " + dtoc(a->LAST_HOSP)
if a->DIAGNOSIS2 <> " "
  @ 4,0 say "SECONDARY DIAGNOSIS: " + a->DIAGNOSIS2
  @ 5,0 say replicate("=",80)
  store 6 to mline
else
  @ 4,0 say replicate("=",80)
  store 5 to mline
endif
  store PT_ID to mPT_ID
    do while PT_ID = mPT_ID
      store INVOICE to minvoice
        do while PT_ID = mPT_ID .and. INVOICE = minvoice .and. (condition <> a->code1 .and. condition <> a->code2 .and. condition <> a->code3)
          store CONDITION to mcondition
          store DATE to mdate
          select c
          use er_list index er_list
          seek mcondition
          store DESCRIPT to merlist
          use
          if substr(mcondition,1,1) $ "HVN" .or. substr(a->code1,2,1) $ "HVN" .or. substr(a->code2,2,1) $ "HVN" .or. substr(a->code3,2,1) $ "HVN"
            select d
            use encounte index encptinv
            seek mPT_ID + minvoice
            store SYSTOLIC to msyst
            store DIASTOLIC to mdiast
            use
          endif
          select b
          store COMPLAINT1 to mcomp1
          store COMPLAINT2 to mcomp2
          store FINDING1 to mfind1
          store FINDING2 to mfind2 select e
          use cc_list index cc_list
          if mcomp1 <> " "
```

AP20     Print1.Prq (cont.)

```
      seek mcomp1
      store DESCRIPT to mdes1
     endif
     if mcomp2 <> " "
      goto top
      seek mcomp2
      store DESCRIPT to mdes2
     endif
     use
     select f
     use FINDINGS index findings
     if mfind1 <> " "
     seek mfind1
     store DESCRIPT to mdesfnd1
     endif
     if mfind2 <> " "
      goto top
      seek mfind2
      store DESCRIPT to mdesfnd2
     endif
     use
     @ mline + 1,1 say "INVOICE NO.:" + minvoice + "DATE " + dtoc(mdate) + "
CONDITION " + merlist
     if msyst <> " "
      @ mline + 2,0 say "SYSTOLIC PRESSURE " + msyst + "DIASTOLIC PRESSURE "
+ mdiast
      store "    " to msyst,mdiast
      store mline + 2 to mline
     else
      store mline + 1 to mline
     endif
     if mcomp1 <> " " .and. mcomp2 <> " "
      @ mline + 1,0 say "COMPLAINTS WERE " + rtrim(mdes1) + " and " + mdes2
      store mline + 1 to mline
     endif
     if mcomp1 = " " .and. mcomp2 = " "
      @ mline + 1,0 say "THERE WERE NO SIGNIFICANT COMPAINTS"
      store mline + 1 to mline
      store .t. to m1
     endif
     if mcomp1 = " " .and. mcomp2 <> " "
      @ mline + 1,0 say "COMPLAINT(major) was " + mdes2
      store mline + 1 to mline
     endif
     if mcomp1 <> " " .and. mcomp2 = " "
      @ mline + 1,0 say "COMPLAINT(major) was " + mdes1
      store mline + 1 to mline
     endif
     if mfind2 <> " " .and. mfind2 <> " "
      @ mline + 1,0 say "FINDINGS WERE " + rtrim(mdesfnd1) + " and " + mdes
fnd2
      store mline + 1 to mline
     endif
     if mfind1 = " " .and. mfind2 = " "
      if m1
       @ mline + 1,0 say "DATA ERROR;newproblem record must have physical d
ata"
       store .f. to m1
       store mline + 1 to mline
      else
       @ mline + 1,0 say "there were no significant findings"
       store mline + 1 to mline
      endif
     endif
     if mfind1 <> " " .and. mfind2 = " "
      @ mline + 1,0 say "FINDING major was " + mdesfnd1
```

```
   store mline + 1 to mline
  endif
  if mfind1 = " " .and. mfind2 <> " "
   @ mline + 1,0 say "FINDING major was " + mdesfnd2
   store mline + 1 to mline
  endif
  select b                                    AP21
  skip
  if PT_ID <> mPT_ID
    store .t. to mexit
    exit
  else
    store DATE to mdate
    store INVOICE to minvoice
    @ mline + 2,0 say replicate("=",80)
    store mline + 2 to mline
   endif
   loop
  endif
 enddo
 if mexit
  store .f. to mexit
  exit
 endif
 skip
 enddo
enddo
return
```

Print1.Prg(cont.)

```
public mPT_ID,minvoice,mcategory,mmedchng,mflaga
msysdate = ctod("03/01/87")
store ctod("  /  /  ") to mdate
mtitle = "NEWPROBLEM SUMMARY BY PATIENT(MED. CHANGE DATA)"
set device to print
select a
use medical index medpt_id
select b
use notify1 index notify1
append from notify for msysdate - DATE >= 14 .and. CODE = "t"
goto top
set relation to PT_ID into medical
do while .not. eof()
@ 1,(85 - len(mtitle))/2 say mtitle
@ 2,0 say "PATIENT ID: " + PT_ID + "LAST NAME " + a->LNAME + "BIRTH DATE " + dtoc(a->DOB)
if a->SEX = "M"
 @ 2,66 say " MALE"
else
 @ 2,66 say " FEMALE"
endif
store a->LNAME to mlname
@ 3,0 say "PRIMARY DIAGNOSIS: " + a->DIAGNOSIS1
@ 3,45 say "LAST HOSPITALIZATION " + dtoc(a->LAST_HOSP)
if a->DIAGNOSIS2 <> " "
 @ 4,0 say "SECONDARY DIAGNOSIS: " + a->DIAGNOSIS2
 store .t. to mprint
else
 @ 4,0 say replicate("=",80)
 store .f. to mprint
 store 5 to mline
endif
if mprint
 if a->DIAGNOSIS3 <> " "
  @ 5,0 say "TERTIARY DIAGNOSIS: " + a->DIAGNOSIS3
  @ 6,0 say replicate("=",80)
  store 7 to mline
 else
  @ 5,0 say replicate("=",80)
  store 6 to mline
 endif
endif
 store PT_ID to mPT_ID
  do while PT_ID = mPT_ID
   store INVOICE to minvoice
    do while PT_ID = mPT_ID .and. INVOICE = minvoice
     store DATE to mdate
     store CATEGORY to mcategory
     if substr(CONDITION,2,1) $ "1,2,3"
     select c
     use er_list index er_list
     seek mcondition
     store DESCRIPT to merlist
     use
     else
      store "ERROR,BAD CONDITION CODE" to merlist
     endif
     do digout1
```

AP23  Prints.prg (cont.)

```
if len(mmedchng) > 0 .and. mmedchng <> space(60)
   store 1 to mcounter
   store 1 to mlength
   store .f. to mflag
   do while mcounter <= 3
     if substr(mmedchng,mlength,1) <> " "
       if mline >= 56
         @ 1,0 say "CONTINUATION OF PATIENT:" + mPT_ID + "," + mlname
         @ 2,0 say :INVOICE NO.: + minvoice + "DATE " + dtoc(mdate) + "CONDITION
:" + merlist
         @ 3,0 say replicate("=",80)
         store 5 to mline
       endif
       if .not. mflag
         @ mline + 1,0 say "MED CHANGES FOR INVOICE NO:" + minvoice + " DATE" +
dtoc(mdate) + "CONDITION:" + merlist
         store .t. to mflag
         store mline + 1 to mline
       endif
       store substr(mmedchng,mlength,20) to mvar1
       store left(mvar1,12) to mvara
       store right(mvar1,4) to mvarb
       store substr(mvar1,13,4) to mvarc
       if substr(mvarb,4,1) = "D" .or. substr(mvarc,3,1) = "D"
         store left(mvarb,1) to mvarb1
         store right(mvarb,3) to mvarb2
         store left(mvarc,1) to mvarc1
         store right(mvarc,3) to mvarc2
         @ mline + 1,0 say rtrim(mvara) + " FROM:" + mvarb1 + " "mvarb2 + " TO "
+ mvarc1 + " " + mvarc2
         store mcounter + 1 to mcounter
         store mlength + 20 to mlength
         store mline + 1 to mline
         loop
       else
         @ mline + 1,0 say rtrim(mvara) + " FROM:" + rtrim(mvarb) + "mgm/day" +
" TO:" + rtrim(mvarc) + "mgm/day"
         store mline + 1 to mline
         store mlength + 20 to mlength
         store mcounter + 1 to mcounter
         loop
       endif
     else
       store mlength + 20 to mlength
       store mcounter + 1 to mcounter
       loop
     endif
   enddo
 else
   if mflaga
     @ mline + 1,0 say "DATA ERROR:INVOICE NO:" + minvoice
     store mline + 1 to mline
   else
     @ mline + 1,0 say "NO MED CHANGES FOR INVOICE NO: " + minvoice + " " + dt
oc(mdate) + "CONDITION:" + merlist
     store mline + 1 to mline
   endif
     if mline >= 56
       @ 1,0 say "CONTINUATION OF PATIENT:" + mPT_ID + " " + mlname
       @ 2,0 say replicate("=",80)
       store 3 to mline
     endif
 endif
 select b
 skip
 if PT_ID <> mPT_ID
```

```
        store .t. to mexit
        @ mline + 1,0 say replicate("=",80)
        exit
      else
        store DATE to mdate
        store INVOICE to minvoice
        @ mline + 1,0 say replicate("-",80)
        store mline + 1 to mline
        loop
      endif
    enddo
    if mexit
      exit
    endif
  enddo
enddo
set device to screen
return
```

AP24    Printa.Prq (cont.)

Digout1.Prg
AP25

```
public mPT_ID,minvoice,mcategory,mmedchng,mflaga
store space(5) to mlook1,mlook2,mlook3
store .f. to mflaga
store space(4) to mamount1,mamount2,mamount3
store "" to mmedchng
if substr(mcategory,6,1) $ "BDFHJLNP"
  select d
  use medicine index medicine
  seek mPT_ID + minvoice
if .not. found()
 store .t. to mflaga
 return
endif
  if ACTION1 = "C"
    store MED1 to mlook1
    store AMOUNT1 to mamount1
  else
    store mmedchng + space(20) to mmedchng
  endif
  if ACTION2 = "C"
    store MED2 to mlook2
    store AMOUNT2 to mamount2
  else
    store mmedchng + space(20) to mmedchng
  endif
  if ACTION3 = "C"
    store MED3 to mlook3
    store AMOUNT3 to mamount3
  else
    store mmedchng + space(20) to mmedchng
  endif
  select e
  use firstmed index frpt_id
  seek mPT_ID
  store INVOICE to minv1
  use
  select d
  seek mPT_ID + minv1
  hold1 = recno()
  if mlook1 <> space(5)
  store PT_ID to mPT_ID
  do while PT_ID = mPT_ID
    store INVOICE to minv2
    do while PT_ID = mPT_ID .and. minv2 <> minvoice
    do case
        case mlook1 = MED1 .and. mamount1 <> AMOUNT1 .and. .not. substr(ACTION1,1,
1) $ "IDT"
        store AMOUNT1 to mthe_one
        skip
        store INVOICE to minv2
        loop
        case mlook1 = MED2 .and. mamount1 <> AMOUNT2 .and. .not. substr(ACTION2,1,
1) $ "IDT"
        store AMOUNT2 to mthe_one
        skip
        store INVOICE to minv2
        loop
        case mlook1 = MED3 .and. mamount1 <> AMOUNT3 .and. .not. substr(ACTION3,1,
1) $ "IDT"
        store AMOUNT3 to mthe_one
        skip
```

```
        store INVOICE to minv2
        loop
      otherwise
        skip                           AP26        Digout1.Prg(cont.)
        store INVOICE to minv2
        loop
      endcase
    enddo
    exit
  enddo
endif
if mlook1 <> " "
  select f
  use med_list index codename
  seek mlook1
  store mmedchng + DESCPRIPTN to mmedchng
  store mmedchng + mamount1 to mmedchng
  store mmedchng + mthe_one to mmedchng
  use
endif
select d
goto hold1
if mlook2 <> space(5)
store PT_ID to mPT_ID
do while PT_ID = mPT_ID
  store INVOICE to minv2
    do while PT_ID = mPT_ID .and. minv2 <> minvoice
      do case
        case mlook2 = MED1 .and. mamount2 <> AMOUNT1 .and. .not. substr(ACTION1
,1,1) $ "IDT"
          store AMOUNT1 to mthe_one
          skip
          store INVOICE to minv2
          loop
        case mlook2 = MED2 .and. mamount2 <> AMOUNT2 .and. .not. substr(ACTION2
,1,1) $ "IDT"
          store AMOUNT2 to mthe_one
          skip
          store INVOICE to minv2
          loop
        case mlook2 = MED3 .and. mamount2 <> AMOUNT3 .and. .not. substr(ACTION3
,1,1) $ "IDT"
          store AMOUNT3 to mthe_one
          skip
          store INVOICE to minv2
          loop
      otherwise
        skip
        store INVOICE to minv2
        loop
      endcase
    enddo
    exit
  enddo
  endif
  if mlook2 <> " "
    select f
    use med_list index codename
    seek mlook2
    store mmedchng + DESCPRIPTN to mmedchng
    store mmedchng + mamount2 to mmedchng
    store mmedchng + mthe_one to mmedchng
    use
  endif
  select d
  goto hold1
```

```
     if mlook3 <> space(5)
       store PT_ID to mPT_ID
       do while PT_ID = mPT_ID
         store INVOICE to minv2
         do while PT_ID = mPT_ID .and. minv2 <> minvoice
           if mlook3 <> space(5)
             do case
               case mlook3 = MED1 .and. mamount3 <> AMOUNT1 .and. .not. substr(ACTION1,1,1) $ "IDT"
                 store AMOUNT1 to mthe_one
                 skip
                 store INVOICE to minv2
                 loop
               case mlook3 = MED2 .and. mamount3 <> AMOUNT2 .and. .not. substr(ACTION2,1,1) $ "IDT"
                 store AMOUNT2 to mthe_one
                 skip
                 store INVOICE to minv2
                 loop
               case mlook3 = MED3 .and. mamount3 <> AMOUNT3 .and. .not. substr(ACTION3,1,1) $ "IDT"
                 store AMOUNT3 to mthe_one
                 skip
                 store INVOICE to minv2
                 loop
               otherwise
                 skip
                 store INVOICE to minv2
                 loop
             endcase
           enddo
           exit
         enddo
       endif
       if mlook3 <> " "
         select f
         use med_list index codename
         seek mlook3
         store mmedchng + DESCPRIPTN to mmedchng
         store mmedchng + mamount3 to mmedchng
         store mmedchng + mthe_one to mmedchng
         use
       endif
       use
     endif
     return
```

Digout1.Prg (cont.)

```
public mldate,mlinv,mPT_ID,minvoice,mcategory,mablab1,mablab2,mablab3,mablab4,ma
blab5,mldate1,mlinv1,mflaga,mflagd
msysdate = ctod("02/01/87")
store ctod("  /  /  ") to mdate                          AP28        Print3.Prg
mtitle = "NEWPROBLEM SUMMARY BY PATIENT(LAB VALUES)"
set device to print
select b
use notify1 index notify1
append from notify for msysdate - DATE >= 14 .and. CODE = "t"
goto top
do while .not. eof()
@ 1,(85 - len(mtitle))/2 say mtitle
@ 2,0 say "PATIENT I.D.:" + PT_ID
@ 3,0 say replicate("=",80)
store 3 to mline
store PT_ID to mPT_ID
 do while PT_ID = mPT_ID
  store INVOICE to minvoice
  do while PT_ID = mPT_ID .and. INVOICE = minvoice
     store CONDITION to mcondition
     store DATE to mdate
     store CATEGORY to mcategory
     select c
     use er_list index er_list
     seek mcondition
     store DESCRIPT to merlist
     use
     store .f. to mflaga
     do digout2
     if mablab1 <> space(140) .and. .not. mflaga
      store 1 to mcounter ,ml1,ml2,ml3,ml4,ml5,mld,mlv
      store .f. to mflag
      do while mcounter <= 14
       if substr(mablab1,ml1,1) <> " "
         store substr(mlinv1,mlv,6) to ml
         store substr(mldate1,mld,8) to md
         store substr(mablab1,ml1,10) to m1
         store substr(mablab2,ml2,8) to m2
         store substr(mablab3,ml3,15) to m3
         store substr(mablab4,ml4,14) to m4
         store substr(mablab5,ml5,4) to m5
         if .not. mflag
             @ mline + 1,0 say "LAB VALUES FOR INVOICE NO:" + minvoice + "DATE:" + d
toc(mdate) + " CONDITION:" + merlist
             @ mline + 2,0 say "DATE DRAWN:" + dtoc(mldate) + "LAB INVOICE:" + mlinv
             store .t. to mflag
             store mline + 2 to mline
         endif
         if mcounter <> 13 .or. mcounter <> 14
           if substr(mablab2,ml2,1) = "t"
             do case
               case substr(m2,2,1) = "a"
                 @ mline + 1,0 say "NORMAL TEST FOR" + rtrim(m1) + " AND NORMAL ON:" +
md
               case substr(m2,2,1) = "b"
                 @ mline + 1,0 say "NORMAL TEST FOR " + rtrim(m1) + " AND ABNORMAL ON:"
 + md
               case substr(m2,2,1) = "c"
                 @ mline + 1,0 say "NORMAL TEST FOR " + rtrim(m1) + " NO  PRIOR TESTS O
N RECORD"
               otherwise
                 @ mline + 1,0 say "DATA ENTRY ERROR FOR LAB INVOICE" +  mlinv + "ON "
 + dtoc(mldate)
```

```
          endcase
        else
          @ mline + 1,0 say "ABNORMAL VALUE FOR " + rtrim(m1) + ":"+ m5 + rtrim(
m2) + "," + rtrim(m3) + rtrim(m4)
        endif
        store mline + 1 to mline
      else
        if substr(mablab2,1,1) = "t"
          do case
            case substr(m2,2,1) = "a"
            @ mline + 1,0 say "NORMAL TEST FOR " + rtrim(m1) + " AND NORMAL ON:" +
 md
            case substr(m2,2,1) = "b"
            @ mline + 1,0 say "NORMAL TEST FOR " + rtrim(m1) + " AND ABNORMAL ON:"
 + md
            case substr(m2,2,1) = "c"
            @ mline + 1,0 say "NORMAL TEST FOR " + rtrim(m1) + "AND NO PRIOR TEST
 ON RECORD"
            otherwise
            @ mline + 1,0 say "DATA ENTRY ERROR FOR LAB INVOICE:" +  mlinv + "ON "
 + dtoc(mldate)
          endcase
        else
          @ mline + 1,0 say "ABNORMAL TEST FOR " + rtrim(m1) + ":" + rtrim(m2)
 + "," + rtrim(m3) + rtrim(m4)
        endif
      endif
      store mcounter + 1 to mcounter
      store ml1 + 10 to ml1
      store ml2 + 8 to ml2
      store ml3 + 15 to ml3
      store ml4 + 14 to ml4
      store ml5 + 4 to ml5
      store mld + 8 to mld
      store mlv + 6 to mlv
      loop
    else
      store mcounter + 1 to mcounter
      store ml1 + 10 to ml1
      store ml2 + 8 to ml2
      store ml3 + 15 to ml3
      store ml4 + 14 to ml4
      store ml5 + 4 to ml5
      store mld + 8 to mld
      store mlv + 6 to mlv
      loop
    endif
  enddo
else
  if mflaga
    @ mline + 1,0 say "RECORD NOT FOUND ?DATA ENTRY ERROR FOR INVOICE NO:" + m
invoice + " DATE:" + dtoc(mdate)
    store .f. to mflaga
    store mline + 1 to mline
  endif
  if mflagd
    @ mline + 1,0 say "NO LAB TESTS WERE DRAWN FOR INVOICE NO:" + minvoice + "
DATE:" + dtoc(mdate)
    store .f. to mflagd
    store mline + 1 to mline
  endif
endif
select b
skip
if PT_ID <> mPT_ID
  store .t. to mexit
```

```
    @ mline + 1,0 say replicate("=",80)
    store mline + 1 to mline
    exit
   else
    store DATE to mdate
    store INVOICE to minvoice
    @ mline + 1,0 say replicate("-",80)
    store mline + 1 to mline
    loop
   endif
  enddo
  if mexit
   exit
  endif
 enddo
enddo
set device to screen
return
```

AP 30

Print3.Prg (cont.)

```
public minvoice,mPT_ID,mcategory,mldate,mflaga,mflagd,mldate1,mlinv,mlinv1
store "" to mablab1,mablab2,mablab3,mablab4,mablab5,mldate1,mlinv1
store .f. to mflaga
store .f. to mflagb
store space(6) to minvl
store ctod("  /  /  ") to mldate
if substr(mcategory,6,1) $ "EFGHMNOP"
  select c
  use abn_lab index ablbinvf
  seek mPT_ID + minvoice
  if found()
    store DATE to mldate
    store INVOICE to mlinv
    store 6 to mfield
    do while mfield <= 19
       store field(mfield) to mvar
       store &mvar to mvar1
       if asc(mvar1) = 32
         store mfield + 1 to mfield
         store mablab1 + space(10) to mablab1
         store mablab2 + space(8) to mablab2
         store mablab3 + space(15) to mablab3
         store mablab4 + space(14) to mablab4
         store mablab5 + space(4) to mablab5
         store mldate1 + space(8) to mldate1
         store mlinv1 + space(6) to mlinv1
         loop
       else
         store mablab1 + mvar + space(10 - len(mvar)) to mablab1
         DO CASE
           case substr(mvar1,1,1) = "A"
             store mablab2 + "ACUTE   " to mablab2
           case substr(mvar1,1,1) = "S"
             store mablab2 + "SUBACUTE" to mablab2
           case substr(mvar1,1,1) = "C"
             store mablab2 + "CHRONIC " to mablab2
           case substr(mvar1,1,1) = "T"
             select c
             hold = recno()
             if substr(mvar1,4,1) <> "C"
             skip - 1
             store PT_ID to mPT_ID
             do while PT_ID = mPT_ID
               store INVOICEFRM to minvl
               do while PT_ID = mPT_ID .and. INVOICEFRM = minvl
                 store field(mfield) to mvar2
                 store &mvar2 to mvar3
                   if asc(mvar3) <> 32 .and. asc(mvar3) <> 78
                   store mldate1 + dtoc(DATE) to mldate1
                   store mlinv1 + INVOICE to mlinv1
                     if substr(mvar1,4,1) = "A"
                       store mablab2 + "ta      " to mablab2
                     else
                       store mablab2 + "tb      " to mablab2
                     endif
                   store mablab3 + space(15) to mablab3
                   store mablab4 + space(14) to mablab4
                   store mablab5 + substr(mvar3,4,4) to mablab5
                   store mfield + 1 to mfield
                   goto hold
                   store .t. to mflagb
                   exit
```

```
          else
            skip - 1
          loop
          endif                                    AP 32
        enddo
        if mflagb
          exit
        endif
      enddo
        if .not. mflagb
          store mablab2 + "t         " to mablab2
          store mablab3 + space(15) to mablab3
          store mablab4 + space(14) to mablab4
          store mablab5 + substr(mvar3,4,4) to mablab5
          store mldate1 + space(8) to mldate1
          store mlinv1 + space(6) to mlinv1
          store mfield + 1 to mfield
          goto hold
        endif
        loop
      else
        store mldate1 + space(8) to mldate1
        store mablab2 + "tc        " to mablab2
        store mablab3 + space(15) to mablab3
        store mablab4 + space(14) to mablab4
        store mablab5 + substr(mvar3,4,4) to mablab5
        store mfield + 1 to mfield
        store mlinv1 + space(6) to mlinv1
        goto hold
        loop
      endif
endcase
DO CASE
  case substr(mvar1,2,1) = "1"
    if field(mfield) = "EKG" .or. field(mfield) = "CXR"
      store mablab3 + "VERY ABNORMAL   " to mablab3
    else
      store mablab3 + "VERY HIGH       " to mablab3
    endif
  case substr(mvar1,2,1) = "2"
    if field(mfield) = "EKG" .or. field(mfield) = "CXR"
      store mablab3 + "MILDLY ABNORMAL" to mablab3
    else
      store mablab3 + "MODERATELY HIGH" to mablab3
    endif
  case substr(mvar1,2,1) = "3"
    store mablab3 + "VERY LOW       " to mablab3
  case substr(mvar1,2,1) = "4"
    store mablab3 + "MODERATELY LOW " to mablab3
endcase
DO CASE
  case substr(mvar1,3,1) = "I"
    store mablab4 + " and IMPROVED " to mablab4
  case substr(mvar1,3,1) = "W"
    store mablab4 + " and WORSENED " to mablab4
  case substr(mvar1,3,1) = "U"
    store mablab4 + " and UNCHANGED" to mablab4
  case substr(mvar1,3,1) = "N"
    store mablab4 + " and 1st TIME " to mablab4
  case substr(mvar1,3,1) = "P"
    store mablab4 + " prev. normal " to mablab4
endcase
store mfield + 1 to mfield
store mablab5 + substr(mvar1,4,4) to mablab5
store mlinv1 + space(6) to mlinv1
store mldate1 + space(8) to mldate1
```

Digout2.Prg (Cont.)

```
   endif
  enddo
  use
 else
  store space(140) to mablab1
  store .t. to mflaga
 endif
 use
else
 store space(140) to mablab1
 store .t. to mflagd
endif
return
```

AP 33  Digouta.Prg (Cont.)

```
Record#  CODETYPE  CODE  DESCRIPT
     1   AA        0000  ACUTE MI,V TACH,,CHF
```

AP34        Print1a.prg

```
msysdate = ctod("05/01/87")
store ctod("  /  /  ") to mdate
mtitle = "CHRONIC PROBLEMS BY PATIENT(physical data)"
store " " to msyst,mdiast
set device to print
select a
use medical index medpt_id
select b
use notify1 index notify1
append from notify for msysdate - DATE >= 14 .and. CODE = "f"
goto top
set relation to PT_ID into medical
do while .not. eof()
@ 1,(85 - len(mtitle))/2 say mtitle
@ 2,0 say "PATIENT ID: " + PT_ID + "LAST NAME " + a->LNAME + "BIRTH DATE " + dto
c(a->DOB)
if a->SEX = "M"
 @ 2,66 say " MALE"
else
 @ 2,66 say " FEMALE"
endif
store a->LNAME to mlname
@ 3,0 say "PRIMARY DIAGNOSIS " + a->DIAGNOSIS1
@ 3,45 say "LAST HOSPITALIZATION " + dtoc(a->LAST_HOSP)
if a->DIAGNOSIS2 <> " "
 @ 4,0 say "SECONDARY DIAGNOSIS: " + a->DIAGNOSIS2
 @ 5,0 say replicate ("=",80)
 store 6 to mline
else
 @ 4,0 say replicate("=",80)
 store 5 to mline
endif
   store PT_ID to mPT_ID
     do while PT_ID = mPT_ID
      store INVOICE to minvoice
       do while PT_ID = mPT_ID .and. INVOICE = minvoice
        store CONDITION to mcondition
        store DATE to mdate
        select d
        use chrmedli index diagnose
        seek mcondition
        store DESCRIPT to mdesc
        use
        if substr(mcondition,2,1) $ "HVN"
         select c
         use encounte index encptinv
```

AP 35    Print1a.prg(cont.)

```
                 seek mFT_ID + minvoice
                 store SYSTOLIC to msyst
                 store DIASTOLIC to mdiast
                 use
              endif
              select b
              store COMPLAINT1 to mcomp1
              store COMPLAINT2 to mcomp2
              store FINDING1 to mfind1
              store FINDING2 to mfind2 select e
              use cc_list index cc_list
              if mcomp1 <> " "
              seek mcomp1
              store DESCRIPT to mdes1
              endif
              if mcomp2 <> " "
               goto top
               seek mcomp2
               store DESCRIPT to mdes2
              endif
              use
              select f
              use FINDINGS index findings
              if mfind1 <> " "
              seek mfind1
              store DESCRIPT to mdesfnd1
              endif
              if mfind2 <> " "
               goto top
               seek mfind2
               store DESCRIPT to mdesfnd2
              endif
              use
              @ mline + 1,1 say "INVOICE NO.:" + minvoice + "DATE " + dtoc(mdate) + "
CONDITION " + mdesc
              if msyst <> " "
                @ mline + 2,0 say "SYSTOLIC PRESSURE " + msyst + "DIASTOLIC PRESSURE "
+ mdiast
                 store "    " to msyst,mdiast
                 store mline + 2 to mline
              else
                 store mline + 1 to mline
              endif
                 if mcomp1 <> " " .and. mcomp2 <> " "
                   @ mline + 1,0 say "COMPLAINTS WERE " + rtrim(mdes1) + " and " + mdes2
                   store mline + 1 to mline
                 endif
                 if mcomp1 = " " .and. mcomp2 = " "
                   @ mline + 1,0 say "THERE WERE NO SIGNIFICANT COMPLAINTS"
                   store mline + 1 to mline
                 endif
                 if mcomp1 = " " .and. mcomp2 <> " "
                   @ mline + 1,0 say "COMPLAINT(major) WAS " + mdes2
                   store mline + 1 to mline
                 endif
                 if mcomp1 <> " " .and. mcomp2 = " "
                   @ mline + 1,0 say "COMPLAINT(major)WAS " + mdes1
                   store mline + 1 to mline
                 endif
                 if mfind2 <> " " .and. mfind1 <> " "
                   @ mline + 1,0 say "FINDINGS WERE " + rtrim(mdesfnd1) + " and " + mdes
fnd2
                   store mline + 1 to mline
                 endif
```

AP36

Printza.prg (cont.)

```
if mfind1 = " " .and. mfind2 = " "
  @ mline + 1,0 say "THERE WERE NO SIGNIFICANT FINDINGS"
  store mline + 1 to mline
endif
if mfind1 <> " " .and. mfind2 = " "
  @ mline + 1,0 say "FINDING(major) was " + mdesfnd1
  store mline + 1 to mline
endif
if mfind1 = " " .and. mfind2 <> " "
  @ mline + 1,0 say "FINDING(major) was " + mdesfnd2
  store mline + 1 to mline
endif
select b
if substr(CATEGORY,3,1) = "5"
  @ mline + 1,0 say "patient hospitalized"
  store mline + 1 to mline
endif
if substr(CATEGORY,7,1) = "r"
  @ mline + 1,0 say "problem resolved"
endif
if substr(CATEGORY,7,1) = "u"
  @ mline + 1,0 say "problem unresolved"
endif
skip
if PT_ID <> mPT_ID
  store .t. to mexit
  exit
else
  store DATE to mdate
  store INVOICE to minvoice
  @ mline + 2,0 say replicate("-",80)
  store mline + 2 to mline
  loop
endif
enddo
if mexit
  exit
endif
enddo
enddo
set device to screen
return
```

AP37  Print2a.Prq

```
public mPT_ID,minvoice,mcategory,mmedchng,mflaga
msysdate = ctod("05/01/87")
store ctod("  /  /  ") to mdate
mtitle = "CHRONIC PROBLEM BY PATIENT(MED. CHANGE DATA)"
set device to print
select a
use medical index medpt_id
select b
use notify1 index notify1
append from notify for msysdate - DATE >= 14 .and. CODE = "f"
goto top
set relation to PT_ID into medical
do while .not. eof()
@ 1,(85 - len(mtitle))/2 say mtitle
@ 2,0 say "PATIENT ID: " + PT_ID + "LAST NAME " + a->LNAME + "BIRTH DATE " + dto
c(a->DOB)
if a->SEX = "M"
  @ 2,66 say " MALE"
else
  @ 2,66 say " FEMALE"
endif
store a->LNAME to mlname
@ 3,0 say "PRIMARY DIAGNOSIS: " + a->DIAGNOSIS1
@ 3,45 say "LAST HOSPITALIZATION " + dtoc(a->LAST_HOSP)
if a->DIAGNOSIS2 <> " "
  @ 4,0 say "SECONDARY DIAGNOSIS: " + a->DIAGNOSIS2
  store .t. to mprint
else
  @ 4,0 say replicate("=",80)
  store .f. to mprint
  store 5 to mline
endif
if mprint
  if a->DIAGNOSIS3 <> " "
    @ 5,0 say "TERTIARY DIAGNOSIS: " + a->DIAGNOSIS3
    @ 6,0 say replicate("=",80)
    store 7 to mline
  else
    @ 5,0 say replicate("=",80)
    store 6 to mline
  endif
endif
store PT_ID to mPT_ID
  do while PT_ID = mPT_ID
    store INVOICE to minvoice
    do while PT_ID = mPT_ID .and. INVOICE = minvoice
```

AP 38    Print2a.Prg
         (cont.)

```
store CONDITION to mcondition
store DATE to mdate
store CATEGORY to mcategory
select c
use chrmedli index diagnose
seek mcondition
store DESCRIPT to merlist
use
do digout1
if len(mmedchng) > 0 .and. mmedchng <> space(60)
  store 1 to mcounter
  store 1 to mlength
  store .f. to mflag
  do while mcounter <= 3
    if substr(mmedchng,mlength,1) <> " "
      if mline >= 56
        @ 1,0 say "CONTINUATION OF PATIENT:" + mPT_ID + "," + mlname
        @ 2,0 say "INVOICE NO.: + minvoice + "DATE " + dtoc(mdate) + "CONDITION :" + merlist
        @ 3,0 say replicate("=",80)
        store 5 to mline
      endif
      if .not. mflag
        @ mline + 1,0 say "MED CHANGES FOR INVOICE NO:" + minvoice + " DATE" + dtoc(mdate) + "CONDITION:" + merlist
        store .t. to mflag
        store mline + 1 to mline
      endif
      store substr(mmedchng,mlength,20) to mvar1
      store left(mvar1,12) to mvara
      store right(mvar1,4) to mvarb
      store substr(mvar1,13,4) to mvarc
      if substr(mvarb,4,1) = "D" .or. substr(mvarb,3,1) = "D"
        store left(mvarb,1) to mvarb1
        store right(mvarb,3) to mvarb2
        store left(mvarc,1) to mvarc1
        store right(mvarc,3) to mvarc2
        @ mline + 1,0 say rtrim(mvara) + " FROM:" + mvarb1 + " " + mvarb2 + " TO " + mvarc1 + " " + mvarc2
        store mcounter + 1 to mcounter
        store mlength + 20 to mlength
        store mline + 1 to mline
        loop
      else
        @ mline + 1,0 say rtrim(mvara) + " FROM:" + rtrim(mvarb) + "mgm/day" + " TO:" + rtrim(mvarc) + "mgm/day"
        store mline + 1 to mline
        store mlength + 20 to mlength
        store mcounter + 1 to mcounter
        loop
      endif
    else
      store mlength + 20 to mlength
      store mcounter + 1 to mcounter
      loop
    endif
  enddo
else
  if mflaga
    @ mline + 1,0 say "DATA ERROR FOR INVOICE " + minvoice
    store mline + 1 to mline
  else
    @ mline + 1,0 say "THERE WERE NO MED CHANGES FOR INVOICE NO:" + minvoice + " ON DATE:" + dtoc(mdate)
    store mline + 1 to mline
  endif
```

```
   if mline >= 56
      @ 1,0 say "CONTINUATION OF PATIENT:" + mPT_ID + " " + mlname
      @ 2,0 say replicate("=",80)
      store 3 to mline
   endif
endif
select b
skip
if PT_ID <> mPT_ID
   store .t. to mexit
   @ mline + 1,0 say replicate("=",80)
   exit
else
   store DATE to mdate
   store INVOICE to minvoice
   @ mline + 1,0 say replicate("-",80)
   store mline + 1 to mline
   loop
  endif
 enddo
 if mexit
  exit
 endif
enddo
enddo
set device to screen
return
```

AP39  Print2a.Prg (Cont.)

AP40

Print3a.Prg

```
public mldate,mlinv,mPT_ID,minvoice,mcategory,mablab1,mablab2,mablab3,mablab4,ma
blab5,mldate1,mlinv1,mflaga,mflagd
msysdate = ctod("05/01/87")
store ctod("  /  /  ") to mdate
mtitle = "CHRONIC PROBLEMS BY PATIENT(LAB VALUES)"
set device to print
select b
use notify1 index notify1
append from notify for msysdate - DATE >= 14 .and. CODE = "f"
goto top
do while .not. eof()
@ 1,(85 - len(mtitle))/2 say mtitle
@ 2,0 say "PATIENT I.D.:" + PT_ID
@ 3,0 say replicate("=",80)
store 3 to mline
store PT_ID to mPT_ID
 do while PT_ID = mPT_ID
  store INVOICE to minvoice
  do while PT_ID = mPT_ID .and. INVOICE = minvoice
     store CONDITION to mcondition
     if substr(mcondition,2,1) $ "1,2,3"
       store "ERROR,BAD CONDITION CODE"
     else
      select c
      use chrmedli index diagnose
      seek mcondition
      store DESCRIPT to merlist
      use
     endif
     select b
     store DATE to mdate
     store CATEGORY to mcategory
     store .f. to mflaga
     do digout2
     if mablab1 <> space(140) .and. .not. mflaga
       store 1 to mcounter ,ml1,ml2,ml3,ml4,ml5,mld,mlv
       store .f. to mflag
       do while mcounter <= 14
         if substr(mablab1,ml1,1) <> " "
           store substr(mlinv1,mlv,6) to mi
           store substr(mldate1,mld,8) to md
           store substr(mablab1,ml1,10) to ml
           store substr(mablab2,ml2,8) to m2
           store substr(mablab3,ml3,14) to m3
           store substr(mablab5,ml5,4) to m5
```

AP41 Printsa.Prg (cont.)

```
            @ mline + 1,0 say "LAB VALUES FOR INVOICE NO:" + minvoice + "DATE:" + d
toc(mdate) + " CONDITION:" + merlist
            @ mline + 2,0 say "DATE DRAWN:" + dtoc(mldate) + "LAB INVOICE:" + mlinv
            store .t. to mflag
            store mline + 2 to mline
          endif
          if mcounter <> 13 .or. mcounter <> 14
            if substr(mablab2,m12,1) = "t"
              do case
                case substr(m2,2,1) = "a"
            @ mline + 1,0 say "NORMAL TEST FOR" + rtrim(m1) + " AND NORMAL ON:" +
md
                case substr(m2,2,1) = "b"
            @ mline + 1,0 say "NORMAL TEST FOR " + rtrim(m1) + " AND ABNORMAL ON:"
 + md
                case substr(m2,2,1) = "c"
            @ mline + 1,0 say "NORMAL TEST FOR " + rtrim(m1) + " NO  PRIOR TESTS O
N RECORD"
                otherwise
            @ mline + 1,0 say "DATA ENTRY ERROR FOR LAB INVOICE" +  mlinv + "ON "
 + dtoc(mldate)
              endcase
            else
            @ mline + 1,0 say "ABNORMAL VALUE FOR " + rtrim(m1) + ":"+ m5 + rtrim(
m2) + "," + rtrim(m3) + rtrim(m4)
            endif
            store mline + 1 to mline
          else
            if substr(mablab2,1,1) = "t"
              do case
                case substr(m2,2,1) = "a"
            @ mline + 1,0 say "NORMAL TEST FOR " + rtrim(m1) + " AND NORMAL ON:" +
md
                case substr(m2,2,1) = "b"
            @ mline + 1,0 say "NORMAL TEST FOR " + rtrim(m1) + " AND ABNORMAL ON:"
 + md
                case substr(m2,2,1) = "c"
            @ mline + 1,0 say "NORMAL TEST FOR " + rtrim(m1) + "AND NO PRIOR TEST
ON RECORD"
                otherwise
            @ mline + 1,0 say "DATA ENTRY ERROR FOR LAB INVOICE:" +  mlinv + "ON "
 + dtoc(mldate)
              endcase
            else
            @ mline + 1,0 say "ABNORMAL TEST FOR " + rtrim(m1) + ":" + rtrim(m2)
 + "," + rtrim(m3) + rtrim(m4)
            endif
          endif
          store mcounter + 1 to mcounter
          store m11 + 10 to m11
          store m12 + 8 to m12
          store m13 + 15 to m13
          store m14 + 14 to m14
          store m15 + 4 to m15
          store mld + 8 to mld
          store mlv + 6 to mlv
          loop
        else
          store mcounter + 1 to mcounter
          store m11 + 10 to m11
          store m12 + 8 to m12
          store m13 + 15 to m13
          store m14 + 14 to m14
          store m15 + 4 to m15
          store mld + 8 to mld
```

```
        store mlv + 6 to mlv
        loop
      endif
    enddo
  else
    if mflaga
      @ mline + 1,0 say "RECORD NOT FOUND ?DATA ENTRY ERROR FOR INVOICE NO:" + m
invoice + " DATE:" + dtoc(mdate)
      store .f. to mflaga
      store mline + 1 to mline
    endif
    if mflagd
      @ mline + 1,0 say "NO LAB TESTS WERE DRAWN FOR INVOICE NO:" + minvoice + "
DATE:" + dtoc(mdate)
      store .f. to mflagd
      store mline + 1 to mline
    endif
  endif
  select b
  skip
  if PT_ID <> mPT_ID
    store .t. to mexit
    @ mline + 1,0 say replicate("=",80)
    store mline + 1 to mline
    exit
  else
    store DATE to mdate
    store INVOICE to minvoice
    @ mline + 1,0 say replicate("-",80)
    store mline + 1 to mline
    loop
  endif
 enddo
 if mexit
  exit
 endif
 enddo
enddo
set device to screen
retur
```

AP42

Print3a.Prg (cont.)

AP43    Caseload.Prg

```
public mnumb1,mnumb2,mnumb3,mnum,md,mdoc1,mdoc2,mdoc3,mdoc,mdiag,mcat
set talk off
do while .t.
clear
mdoc = space(20)
mdiag = space(25)
store 0 to mnumb1,mnumb2,mnumb3,mnum,md,mdoc1,mdoc2,mdoc3
@ 1,0 say "this routine generates statistical type data."
@ 2,0 say "For each doctor and system-diagnosis entered,it"
@ 3,0 say "will compute and list the percent of patients"
@ 4,0 say "with that diagnosis who are currently under the"
@ 5,0 say "care of that doctor as compared to the total"
@ 6,0 say "number of patients on the database with that diagnosis."
@ 7,0 say "It will also provide a breakdown of the patients"
@ 8,0 say "with that diagnosis into each of the System Diag-"
@ 9,0 say "nostic Categories and the amount of each for that"
@ 10,0 say "doctor as well(except for category A patients)"
wait
clear
@ 1,0 say "enter the doctor's last name(lower case)"
@ 2,40 get mdoc
@ 3,0 say "enter the diagnosis(from the SYSTEM TABLE)"
@ 4,0 say "then wait 1 min."
@ 4,35 get mdiag
@ 5,0 say "or leave both blank to quit"
read
if mdoc = space(20)
  clear
  return
endif
use chrmedli.dbf index diagname
seek upper(mdiag)
if .not. found()
  clear
  store " " to yesno
  do while .not. upper(yesno) $ "YN"
    @ 1,0 say "probable misspelling(syntax) error"
    @ 2,0 say "press Y/y to re-enter or N/n to quit" get yesno
    read
  enddo
  if upper(yesno) = "Y"
    loop
  else
    clear
    close databases
    return
  endif
endif
store codetype + code to mcode
store substr(mcode,1,1) to mcat
use medicala index doctor
  do case
  case mcat = "A"
    count to mnumb1 for (substr(code1,1,1) = "A") .and. (mcode = code1 .or. mcode
 = code2 .or. mcode = code3)  seek mdoc
    count to mdoc1 while doctor = mdoc for (substr(code1,1,1) = "A") .and. (mcode
 = code1 .or. mcode = code2 .or. mcode = code3)

case mcat = "B"
    count to mnumb1 for (substr(code1,1,1) = "A" .or. (substr(code1,1,1) = "B") .a
nd. (substr(code3,1,1) = "B")) .and. (mcode = code1 .or. mcode = code2 .or. mcod
```

```
e = code3)
  seek mdoc
  count to mdoc1 while doctor = mdoc for (substr(code1,1,1) = "A" .or. (substr(c
ode1,1,1) = "B") .and. (substr(code3,1,1) = "B")) .and. (mcode = code1 .or. mcod
e = code2 .or. mcode = code3)
  goto top
  count to mnumb2 for ((substr(code1,1,1) = "B") .and. (substr(code3,1,1) <> "B"
)) .and. (mcode = code1 .or. mcode = code2)
  seek mdoc
  count to mdoc2 while doctor = mdoc for ((substr(code1,1,1) = "B") .and. (subst
r(code3,1,1) <> "B")) .and. (mcode = code1 .or. mcode = code2)

case mcat = "C"
  count to mnumb1 for (substr(code1,1,1) = "A") .and. (mcode = code2 .or. mcode
= code3)
  seek mdoc
  count to mdoc1 while doctor = mdoc for (substr(code1,1,1) = "A") .and. (mcode
= code2 .or. mcode = code3)
  goto top
  count to mnumb2 for (substr(code1,1,1) = "B" .or. (substr(code1,1,1) = "C") .a
nd. (substr(code3,1,1) = "C")) .and. (mcode = code1 .or. mcode = code2 .or. mcod
e = code3)
  seek mdoc
  count to mdoc2 while doctor = mdoc for (substr(code1,1,1) = "B" .or. (substr(c
ode1,1,1) = "C") .and. (substr(code3,1,1) = "C")) .and. (mcode = code1 .or. mcod
e = code2 .or. mcode = code3)
  goto top
  count to mnumb3 for ((substr(code1,1,1) = "C") .and. (substr(code3,1,1) <> "C"
)) .and. (mcode = code1 .or. mcode = code2)
  seek mdoc
  count to mdoc3 while doctor = mdoc for ((substr(code1,1,1) = "C") .and. (subst
r(code3,1,1) <> "C")) .and. (mcode = code1 .or. mcode = code2)
 endcase
 do print4
mans = space(1)
clear
@ 1,0 say "want to continue?(Y/y) or leave(N/n)" get mans
read
if upper(mans) = "Y"
  loop
else
  close databases
  clear
  return
endif
enddo
```

AP 45  Print4.Prg

```
public mnumb1,mnumb2,mnumb3,mnum,md,mdoc1,mdoc2,mdoc3,mdoc,mdiag,mcat
store 1 to mline
set device to screen
clear
if mcat = "A"
 @ mline,0 say "the diagnosis " + trim(mdiag) + " is from category A"
 if mnumb1 > 0
  @ mline + 1,0 say "the total number with that diagnosis is " + str(mnumb1,2,0)
  if mdoc1 > 0
   @ row() + 1,0 say "DR. " + trim(mdoc) + " has" + str(mdoc1,2,0) + " for " + s
tr((mdoc1/mnumb1)*100,2,0) + "%"
  else
   @ row() + 1,0 say "dr." + trim(mdoc) + " has none"
  endif
 else
  @ mline + 1,0 say "no one on the database at present with " + trim(mdiag)
 endif
 wait
endif
if mcat = "B"
 store mnumb1 + mnumb2 to mnum
 store mdoc1 + mdoc2 to md
 @ mline,0 say "that diagnosis " + trim(mdiag) + " is from category B"
 if mnum > 0
  @ row() + 1,0 say "the total number with that is " + str(mnum,2,0)
  if md = 0
   @ row() + 1,0 say "but there is none for dr." + trim(mdoc)
   wait
   return
  else
   @ row() + 1,0 say "dr." + trim(mdoc) + " has " + str(md,2,0) + " for " + str(
(md/mnum)*100,2,0) + "%"
  endif
  if mnumb1 > 0
   @ row() + 1,0 say "the number in category A is " + str(mnumb1,2,0)
   if mdoc1 > 0
    @ row() + 1,0 say "dr." + trim(mdoc) + " has " + str(mdoc1,2,0)
   else
    @ row() + 1,0 say "dr." + trim(mdoc) + " has none"
   endif
  else
   @ row() + 1,0 say "there are none in category A"
  endif
  if mnumb2 > 0
   @ row() + 1,0 say "the number in category B is " + str(mnumb2,2,0)
   if mdoc2 > 0
    @ row() + 1,0 say "dr." + trim(mdoc) + " has " + str(mdoc2,2,0)
   else
    @ row() + 1,0 say "dr." + trim(mdoc) + " has none"
   endif
  else
   @ row() + 1,0 say "there are none in category B"
  endif
 else
  @ row() + 1,0 say "there are none now with " + trim(mdiag)
 endif
 wait
endif
```

```
  if mcat = "C"
   store mnumb1 + mnumb2 + mnumb3 to mnum                           AP 46
   store mdoc1 + mdoc2 + mdoc3 to md
   @ mline,0 say "the diagnosis " + trim(mdiag) + " is from category C"
    if mnum > 0
     @ row() + 1,0 say "the total number with that is " + str(mnum,2,0)
     if md = 0
      @ row() + 1,0 say "dr." + trim(mdoc) + " has none"
      wait                                                          Print4.Prg(cont.)
      return
     else
      @ row() + 1,0 say "dr." + trim(mdoc) + " has " + str(md,2,0) + " for " + str
((md/mnum)*100,2,0) + "%"
     endif
     if mnumb1 > 0
      @ row() + 1,0 say "the number in category A is " + str(mnumb1,2,0)
      if mdoc1 > 0
       @ row() + 1,0 say "dr." + trim(mdoc) + " has " + str(mdoc1,2,0)
      else
       @ row() + 1,0 say "dr." + trim(mdoc) + " has none"
      endif
     else
      @ row() + 1,0 say "there are none in category A"
     endif
     if mnumb2 > 0
      @ row() + 1,0 say "the number in category B is " + str(mnumb2,2,0)
      if mdoc2 > 0
       @ row() + 1,0 say "dr." + trim(mdoc) + " has " + str(mdoc2,2,0)
      else
       @ row() + 1,0 say "dr." + trim(mdoc) + " has none"
      endif
     else
      @ row() + 1,0 say "there are none in category B"
     endif
     if mnumb3 > 0
      @ row() + 1,0 say "the number in category C is " + str(mnumb3,2,0)
      if mdoc3 > 0
       @ row() + 1,0 say "dr." + trim(mdoc) + " has " + str(mdoc3,2,0)
      else
       @ row() + 1,0 say "dr." + trim(mdoc) + " has none"
      endif
     else
      @ row() + 1,0 say "there are none in category C"
     endif
    else
     @ row() + 1,0 say "no one at present with " + trim(mdiag)
    endif
    wait
  endif
  return
```

AP47   Meditoxi.Prq

```
set talk off
set device to screen
clear
@ 1,0 say "for any doctor entered,this routine will list"
@ 2,0 say "all the patients who are currently on the medication"
@ 3,0 say "also entered.You will then select the patient you"
@ 4,0 say "want,and then any lab test you wish to view to"
@ 5,0 say "determine/assess any drug toxicity"
wait
do while .t.
 set device to screen
 clear
 store 1 to mline
 store .f. to mflag
 store .f. to mflaga
 mtox = ""
 mans = space(1)
 mdoc = space(20)
 mmed = space(12)
 @ 1,0 say "please enter the medication(lower case)" get mmed
 @ 2,0 say "please enter the doctor(last name,lowercase only)" get mdoc
 read
 use med_list index medname
 seek mmed
 if .not. found()
  @ 4,0 say "not found,?incorrect spelling,?try again(Y/y or N/n)" get mans picture "A"
  read
  if upper(mans) = "Y"
   loop
  else
   clear
   return
  endif
 else
  if toxi1 <> space(10)
   store mtox + toxi1 to mtox
  endif
  if toxi2 <> space(10)
   store mtox + toxi2 to mtox
  endif
  if len(mtox) = 20
   @ 4,0 say "the important tests for this medication are:"
   @ 4,46 say rtrim(substr(mtox,1,10)) + " and " + rtrim(substr(mtox,11,10))
  endif
  if len(mtox) = 10
   @ 4,0 say "the important test for the medication is:"
   @ 4,43 say rtrim(mtox)
  endif
  if len(mtox) = 0
   @ 4,0 say "there are no specific tests for this med"
   @ 5,0 say "that are frequently used for toxicity checks"
  endif
  wait
 endif
 store codename to mcode
 use medical index medidoc
 seek mdoc
 clear
```

AP 48    meditoxi.Prg (cont.)

```
do while DOCTOR = mdoc
  if mcode = medone .or. mcode = medtwo .or. mcode = medthree
    store .t. to mflag
    do case
      case mcode = medone
        store amtone to mamt
      case mcode = medtwo
        store amttwo to mamt
      case mcode = medthree
        store amtthree to mamt
    endcase
    @ mline,0 say " " + lname + " " + "patient i.d.:" + PT_ID + " " + "amount:" +
mamt
    store mline + 1 to mline
    skip
    loop
  endif
  skip
enddo
if .not. mflag
  mans = space(1)
  store space(20) to mdoc
  @ mline,0 say "this doctor has no one on that medication"
  @ mline + 1,0 say "try another doctor?(Y/y or N/n)" get mans
  read
  if upper(mans) = "Y"
    clear
    loop
  else
    clear
    return
  endif
endif
mpt_id = space(11)
@ mline,0 say "now enter the patient of interest" get mpt_id picture "999-99-99
99"
read
use abn_laba index patient
seek mpt_id
mnumb = 0
clear
@ 1,0 say "now, choose the lab test you want"
@ 2,0 say "BUN(6),CR(7),HG(8),HCT(9),SED_RATE(10),POTTASIUM(11)"
@ 3,0 say "BLD_SUG(12),PH(13),PO2(14),PCO2(15),WBC(16),"
@ 4,0 say "CALCIUM(17),EKG(18),CXR(19)" get mnumb picture "99"
read
store field(mnumb) to mvar
store 1 to mline
clear
do while PT_ID = mpt_id
  store .f. to mflaga
  store &mvar to mvar1
  if asc(mvar1) <> 32 .and. asc(mvar1) <> 78 .and. asc(mvar1) <> 84
    store .t. to mflaga
    if mnumb = 16
      @ mline,0 say " " + mvar + " " + dtoc(date) + " " + trim(substr(mvar1,4,4)) +
"00"
    else
      @ mline,0 say " " + mvar + " " + dtoc(date) + " " + substr(mvar1,4,4)
    endif
    store mline + 1 to mline
    skip
    loop
  endif
  skip
enddo
```

```
if .not. mrisaga
  clear
  @ 1,0 say "that test not on record for that patient"
  @ 2,0 say "want to view another patient(or medication)? Y/N" get  mans
  read
else
  @ mline + 1,0 say "want to view another patient(or medication)? Y/N" get mans
  read
endif
  if upper(mans) = "Y"
    loop
  else
    exit
  endif
enddo
close databases
clear
return
```

AP49    meditoxi.prg (cont.)

Heart.med.Prg

AP 50

```
public minvoice,medi
set device to screen
set talk off
msysdate = ctod("03/27/87")
clear
@ 1,0 say "For each doctor entered,this routine will list"
@ 2,0 say "pertinent data for each STATUS 3 office visit"
@ 3,0 say "involving chr. cardiac problems that doctor has"
@ 4,0 say "seen within the past two weeks. Please note,"
@ 5,0 say "any one patient may be found to have more than"
@ 6,0 say "one record of this kind"
wait
do while .t.
store .f. to mflag
clear
mdoc = space(20)
mphys = ""
@ 1,0 say "enter doctors last name only(in lower case)" get mdoc
@ 2,0 say "then wait one moment"
@ 3,0 say "if you wish to quit press <return>"
read
if mdoc = space(20)
 clear
 return
endif
use encountf index doctor
seek mdoc
do while DOCTOR = mdoc
 if STATUS = "3" .and. substr(CONDITION,2,1) = "H" .and. .not. NEWPROBLEM .and.
(NEW_MED .or. MED_CHANGE) .and. msysdate - DATE <= 14
   store .t. to mflag
   mphys = ""
   hold1 = recno()
   store PT_ID to mpt_id
   store DATE to mdate
   store INVOICE to minvoice
   store COMPLAINT1 to mcomp1
   store COMPLAINT2 to mcomp2
   store FINDING1 to mfind1
   store FINDING2 to mfind2
    if mcomp1 <> space(5)
     use cc_list index cc_list
     seek mcomp1
     store mphys + descript to mphys
     use
    else
     store mphys + space(25) to mphys
    endif
    if mcomp2 <> space(5)
     use cc_list index cc_list
     seek mcomp2
     store mphys + DESCRIPT to mphys
     use
    else
     store mphys + space(25) to mphys
    endif
    if mfind1 <> space(5)
     use findings index findings
     seek mfind1
```

```
  store mphys + DESCRIPT to mphys
  use
else
  store mphys + space(25) to mphys
endif
if mfind2 <> space(5)
  use findings index findings
  seek mfind2
  store mphys + DESCRIPT to mphys
  use
else
  store mphys + space(25) to mphys
endif
do medget
mline = 1
clear
@ mline,0 say "PATIENT I.D. " + mpt_id + " " + "DATE:" + dtoc(mdate)
store mline + 1 to mline
if substr(mphys,1,1) <> " "
  @ mline,0 say "COMPLAINT:" + substr(mphys,1,25)
  store mline + 1 to mline
endif
if substr(mphys,26,1) <> " "
  @ mline,0 say "COMPLAINT:" + substr(mphys,26,25)
  store mline + 1 to mline
endif
if substr(mphys,51,1) <> " "
  @ mline,0 say "FINDINGS:" + substr(mphys,51,25)
  store mline + 1 to mline
endif
if substr(mphys,76,1) <> " "
  @ mline,0 say "FINDINGS:" + substr(mphys,76,25)
  store mline + 1 to mline
endif
store 1 to mcount
store 1 to mp
store 13 to ml
store 14 to ma
do while mcount <= 3
  if substr(medi,mp,1) <> " "
    do case
      case substr(medi,ml,1) = "A"
        @ mline,0 say "ADDITION:" + substr(medi,mp,12) + substr(medi,ma,4)
        store mline + 1 to mline
      case substr(medi,ml,1) = "C"
        @ mline,0 say "CHANGE:" + substr(medi,mp,12) + substr(medi,ma,4)
        store mline + 1 to mline
      case substr(medi,ml,1) = "D"
        @ mline,0 say "DELETION:" + substr(medi,mp,12) + substr(medi,ma,4)
        store mline + 1 to mline
      case substr(medi,ml,1) = "T"
        @ mline,0 say "TEMPORARY:" + substr(medi,mp,12) + substr(medi,ma,4)
        store mline + 1 to mline
      case substr(medi,ml,1) = "I"
        @ mline,0 say "INTRAVENOUS:" + substr(medi,mp,12) + substr(medi,ma,4)
        store mline + 1 to mline
      case substr(medi,ml,1) = "M"
        @ mline,0 say "INTRAMUSCULAR:" + substr(medi,mp,12) + substr(medi,ma,4)
        store mline + 1 to mline
    endcase
    store mcount + 1 to mcount
    store mp + 17 to mp
    store ml + 17 to ml
    store ma + 17 to ma
  else
    store mcount + 1 to mcount
```

AP51   Heartmed.Prg (cont.)

AP 52    Heartmed.Prg (cont.)

```
        store mp + 17 to mp
        store ml + 17 to ml
        store ma + 17 to ma
      endif
      loop
    enddo
    wait "when ready,press for next record,then wait 1 min."
    use encountf index doctor
    goto hold1
    skip
    loop
   else
    skip
   endif
  enddo
  mans = space(1)
  if .not. mflag
   clear
   @ 1,0 say "no records of that type for that doctor"
   @ 2,0 say "want to search on another(Y/N)?" get mans picture "A"
   read
   if upper(mans) = "Y"
    loop
   else
    exit
   endif
  endif
  @ row() + 1,0 say "that is all for that doctor"
  @ row() + 2,0 say "want to search on another?(Y/y,N/n)" get mans picture "A"
  read
  if upper(mans) = "Y"
   loop
  else
   exit
  endif
 enddo
 clear
 return
```

AP53    medget.prg

```
public minvoice,medi
store "" to medi
use medicinf index medinv
seek minvoice
hold = recno()
store MED1 to m1
store MED2 to m2
store MED3 to m3
if m1 <> " "
  use med_list index codename
  seek m1
  store medi + descpriptn to medi
  use medicine
  goto hold
  store medi + ACTION1 to medi
  store medi + AMOUNT1 to medi
  use
else
  store medi + space(17) to medi
endif
if m2 <> " "
  use med_list index codename
  seek m2
  store medi + descpriptn to medi
  use medicine
  goto hold
  store medi + ACTION2 to medi
  store medi + AMOUNT2 to medi
  use
else
  store medi + space(17) to medi
endif
if m3 <> " "
  use med_list index codename
  seek m3
  store medi + descpriptn to medi
  use medicine
  goto hold
  store medi + ACTION3 to medi
  store medi + AMOUNT3 to medi
  use
else
  store medi + space(17) to medi
endif
close databases
return
```

APS4      Labfirst.Prg

```
public mpt_id,mv,minvoice,mdate
set talk off
do while .t.
padding = "000000"
mv = space(6)
minvoice = "L00000"
mdate = ctod("  /  /  ")
mlab = space(1)
mpt_id = space(11)
clear
@ 1,0 say "THIS IS THE PATIENT LAB RECORD ENTRY AND INQUIRY ROUTINE "
@ 2,0 say " please enter patient i.d. no.(or leave blank to quit) " get mpt_id p
icture "999-99-9999"
@ 3,0 say " please enter date of tests" get mdate
@ 4,0 say "if lab test ordered from office visit,press Y/y"
@ 5,0 say "if not,then press N/n" get mlab picture "A"
read
 if mpt_id <> space(11)
  use abn_lab index abnpatnt
  seek mpt_id
  if .not. found()
   clear
   store " " to mchoice
   @ 1,0 say "either new patient lab record or"
   @ 2,0 say "error in social security no."
   @ 3,0 say "press Y/y to enter another record or try again"
   @ 4,0 say "or press N/n to just continue" get mchoice picture "A"
   read
   if upper(mchoice) = "Y"
    store " " to mchoice
    use
    loop
   endif
  endif
  if upper(mlab) = "Y"
   use encounte index patient
   seek mpt_id
   if .not. found()
    clear
    @ 1,0 say "wrong i.d. no. or patient has no office record"
    @ 2,0 say "you can not continue with this patient"
    wait
    loop
   endif
   do while PT_ID = mpt_id
    skip
```

AP 55　　　Labfirst.prg (cont.)

```
      enddo
      skip - 1
      if lab_work
        store invoice to mv
      else
        clear
        @ 1,0 say "apparently,no tests ordered on that office visit"
        @ 2,0 say "but,the lab record will be created"
        wait
        store invoice to mv
      endif
      use
    else
      use er_room index erindex
      seek mpt_id
      if .not. found()
        clear
        @ 1,0 say "wrong i.d. no. or patient has no er room record"
        @ 2,0 say "the lab test may be from office visit instead"
        @ 3,0 say "you may return for re-entry or another record"
        wait
        loop
      endif
      do while PT_ID = mpt_id
        skip
      enddo
      skip - 1
      if mdate - DATE < 7
        store invoice to mv
      else
        clear
        @ 1,0 say "something is wrong,either lab work WAS"
        @ 2,0 say "ordered from office visit,or check with"
        @ 3,0 say "your supervisor before entering this record"
        wait
        store space(11) to mpt_id
        store space(8) to mdate
        store space(1) to mwhich
        use
        loop
      endif
    endif
    use abn_lab
    goto bottom
    store substr(INVOICE,2,5) to minv
    store val(minv) + 1 to minv
    store stuff(minvoice,2,5, right(padding + ltrim(str(minv,5)),5)) to minvoice
    use
    do labentry
    clear
    store " " to yesno
    @ 1,0 say "if you want to add another record press Y/y"
    @ 2,0 say "or if you want to quit press N/n" get yesno picture "A"
    read
    if upper(yesno) = "Y"
      loop
    else
      exit
    endif
  endif
  exit
enddo
  use abn_lab
  set index to abnpatnt,ablabinv
  reindex
  close databases
```

AP56

Labentry.Prg

```
public mpt_id,mtest,minv1,mchoice,hello,mv,minvoice,mdate
store 0 to mtest
mselect = space(1)
clear
@ 1,0 say "Patient i.d. no. for this record is:" + mpt_id
@ 2,0 say "INVOICE no. for this record is:" + minvoice
@ 3,0 say "lab record will now be initialized for you"
wait "press any key,then wait 1 min."
use abn_lab index ablabinv,abnpatnt
append blank
replace DATE with mdate
replace INVOICE with minvoice
replace INVOICEFRM with mv
replace PT_ID with mpt_id
reindex
seek mpt_id + minvoice
hello = recno()
use DO while .t.
  store " " to mselect
  clear
  @ 1,0 say "SELECT FROM ONE OF THE FOUR CHOICES BELOW BY"
  @ 2,0 say "PRESSING ONE OF THE FOUR LETTERS:A,B,C(or D TO QUIT)"
  @ 3,0 say "THAT ARE ASSOCIATED WITH EACH CHOICE."
  @ 4,0 say replicate ("=",66)
  @ 5,0 say "ARE YOU READY TO ENTER DATA IN ENCODED FORM? (A)"
  @ 6,0 say "WOULD YOU LIKE HELP? (B)"
  @ 7,0 say "DO YOU WISH TO SEARCH PATIENT'S PRIOR LAB DATA FIRST? (C)"
  @ 8,0 say "DO YOU WISH TO LEAVE/QUIT? (D)"
  @ 9,0 say "make your selection here" get mselect
  read
  if upper(mselect) $ "ABCD"
  if upper(mselect) = "A"
   mdone = space(1)
   ret = chr(17)+chr(196)+chr(217)
   clear
   use abn_lab
   goto hello
   set format to abn_lab
   do while .t.
     read save
     if upper(mdone) = "X"
       mselect = space(1)
       exit
     else
```

Ap 57   Lab entry.prg (cont.)

```
      loop
    endif
  enddo
  close format
  use
  clear
  loop
endif
if upper(mselect) = "B"
  do mmessage
  loop
endif
if upper(mselect) = "D"
  clear
  @ 1,0 say "ARE YOU SURE YOU HAVE ENTERED THE DATA ?!"
  @ 2,0 say "if you have forgotten,"
  store " " to yesno
  do while .not. upper(yesno) $ "YN"
    wait "press Y/y to return to menu or N/n to leave" to yesno
  enddo
  if upper(yesno) = "Y"
    loop
  else
    clear
    return
  endif
endif
if upper(mselect) = "C"
  mtest = 0
  mchoice = space(1)
  do while upper(mchoice) <> "5"
  mchoice = space(1)
  clear
  @ 1,0 say "SELECT ONE OF THE FOLLOWING LAB TESTS BY THE"
  @ 2,0 say "NUMBER IN PARENTHESIS ASSOCIATED WITH THE TEST NAME."
  @ 3,0 say replicate("=",66)
  @ 4,0 say "BUN(6)"
  @ 4,7 say "CR(7)"
  @ 4,13 say "HG(8)"
  @ 4,19 say "HCT(9)"
  @ 4,26 say "SEDRATE(10)"
  @ 4,38 say "POTTASIUM(11)"
  @ 4,52 say "BLD SUGAR(12)"
  @ 5,0 say "PH(13)"
  @ 5,7 say "PO2(14)"
  @ 5,15 say "PCO2(15)"
  @ 5,24 say "WBC(16)"
  @ 5,32 say "CALCIUM(17)"
  @ 5,44 say "EKG(18)"
  @ 5,52 say "CXR(19)"
  @ 6,0 say "please select one of the above, or enter 20"
  @ 7,0 say "in order to leave/quit" get mtest picture "@Z 99"
  read
    if mtest = 20
      exit
    endif
    if mtest < 6 .or. mtest > 19
      clear
      @ 1,0 say "wrong key pressed,please repeat"
      wait
      loop
    else
      do while .t.
      store " " to mchoice
      @ 8,0 say "NOW SELECT THE KIND OF PREVIOUS INFORMATION"
      @ 9,0 say "YOU WANT ABOUT THAT LAB VALUE BY SELECTING"
```

```
@ 10,0 say "THE MODIFIED NUMBER IN PARENTHESIS."
@ 11,0 say replicate("=",66)
@ 12,0 say "DATE AND VALUE OF FIRST ABNORMALITY (1)"
@ 13,0 say "DATE AND VALUE OF LAST ABNORMALITY (2)"
@ 14,0 say "IS THE TEST CONSISTENTLY ABNORMAL? (3)"
@ 15,0 say "LATEST ENTRY FOR THAT TEST(normal/abnormal) (4)"
@ 16,0 say "CHOOSE (5) to leave/choose another test"
@ 17,0 say "please make selection here" get mchoice
  read
  if mchoice = "5"
    exit
  endif
  if mchoice $ "1234"
    if mchoice $ "12"
      do findout1
      store " " to mchoice
      loop
    else
      do findout2
      store " " to mchoice
      loop
    endif
  else
    @ 18,0 say "wrong key pressed,press either 1,2,3,4 or 5"
    wait
    loop
  endif
 enddo
 endif
enddo
endif
else
  clear
  @ 1,0 say "wrong key pressed,please repeat"
  wait
  loop
endif
enddo
return
```

AP58

Labentry.Prg (Cont.)

AP59  Findouta.prg

```
public mpt_id,mtest,mchoice,minvoice,hello
clear
mdate = ctod("  /  /  ")
store ctod("  /  /  ") to mdate1,mdate2,mdate4
use abn_lab index ablabinv,abnpatnt
seek mpt_id + minvoice
skip - 1
if bof() .or. PT_ID <> mpt_id
 @ 1,0 say "this is first record!,you can't search"
 wait
 return
else
 store DATE to mdate
 @ 1,0 say "DATE OF LAST RECORD IS:" + dtoc(mdate)
 wait
 set order to 2
 seek mpt_id
endif
 do while .t.
   do case
     case mchoice = "3"
       store .f. to mflag
       store 0 to mcount,mcount1
       do while PT_ID = mpt_id .and. INVOICE <> minvoice
         store field(mtest) to mvar
         store &mvar to mvar1
         if asc(mvar1) <> 32
          if substr(mvar1,1,1) = "T"
            store mcount1 + 1 to mcount1
            store DATE to mdate1
            skip
            if eof()
              exit
            endif
            loop
          endif
          if asc(mvar1) <> 78 .and. substr(mvar1,1,1) <> "T"
            store mcount + 1 to mcount
            if .not. mflag
              store DATE to mdate2
              store .t. to mflag
            endif
            skip
            if eof()
              exit
            endif
```

AP60  Findout2.Prg (cont.)

```
       loop
     else
       skip
       if eof()
         exit
       endif
       loop
     endif
   else
     skip
     if eof()
       exit
     endif
     loop
   endif
 enddo
 if mcount = 0 .and. mcount1 <> 0
   @ 2,0 say rtrim(mvar) + " has never been found abnormal"
   @ 3,0 say "it was last found normal on " + dtoc(mdate1)
   wait
   return
 endif
 if mcount <> 0 .and. mcount1 = 0
   @ 2,0 say rtrim(mvar) + " has been consistently abnormal since " + dtoc(
mdate2)
   wait
   return
 endif
 if mcount <> 0 .and. mcount1 <> 0
   @ 2,0 say rtrim(mvar) + " has been intermittently abnormal"
   @ 3,0 say "the last date it was normal was on:" + dtoc(mdate1)
   wait
   return
 endif
 if mcount = 0 .and. mcount1 = 0
   @ 2,0 say rtrim(mvar) + " has never been drawn"
   wait
   return
 endif case mchoice = "4"
   store .f. to mflag
   do while PT_ID = mpt_id .and. INVOICE <> minvoice
     store field(mtest) to mvar
     store &mvar to mvar1
     if asc(mvar1) <> 32 .and. asc(mvar1) <> 78
       store .t. to mflag
       store DATE to mdate4
       store mvar1 to mvar2
       skip
       if eof()
         exit
       endif
       loop
     else
       skip
       if eof()
         exit
       endif
       loop
     endif
   enddo
   if .not. mflag
     @ 2,0 say "the test" + rtrim(mvar) + " is not on record as normal OR ab
normal"
     wait
```

```
       return
      endif
      if substr(mvar2,1,1) <> "T"
        @ 2,0 say "the latest entry for " + rtrim(mvar) + " was on:" + dtoc(mda
te4)
        if mtest = 18 .or. mtest = 19
          if substr(mvar2,2,1) = "1"
            @ 3,0 say "VALUE OF ABNORMALITY:very abnormal"
          else
            @ 3,0 say "VALUE OF ABNORMALITY:mildly abnormal"
          endif
        else
          @ 3,0 say "the abnormal value was:" + substr(mvar2,4,4)
        endif
        wait
        return
      endif
      if substr(mvar2,1,1) = "T"
        @ 2,0 say "the latest entry was normal on " + dtoc(mdate4)
        wait
        return
      endif
  endcase
enddo
use
return
```

Findout2.prg (cont.)
Af 61

Findout1.Prg

AP62

```
public mpt_id,mtest,mchoice,minvoice,hello
clear
mdate = ctod("  /  /  ")
store ctod("  /  /  ") to mdate1,mdate2,mdate4
use abn_lab index ablabinv,abnpatnt
seek mpt_id + minvoice
skip - 1
if bof() .or. PT_ID <> mpt_id
 @ 1,0 say "this is first record!,you can't search"
 wait
 return
else
 store DATE to mdate
 @ 1,0 say "DATE OF LAST RECORD IS:" + dtoc(mdate)
 wait
 set order to 2
 seek mpt_id
endif
 do while .t.
   do case
     case mchoice = "1"
       store .f. to mflag
       do while PT_ID = mpt_id .and. INVOICE <> minvoice
       store field(mtest) to mvar
       store &mvar to mvar1
        if asc(mvar1) <> 32 .and. substr(mvar1,1,1) <> "T" .and.     asc(mvar1) <>
78
         store .t. to mflag
         store DATE to mdate2
         @ 2,0 say "INQUIRY OF LAB TEST:" + mvar
         @ 3,0 say "DATE OF FIRST ABNORMALITY:" + dtoc(mdate2)
         if mtest = 18 .or. mtest = 19
           if substr(mvar1,2,1) = "1"
             @ 4,0 say "VALUE OF ABNORMALITY:very abnormal"
           else
             @ 4,0 say "VALUE OF ABNORMALITY:mildly abnormal"
           endif
         else
          @ 4,0 say "VALUE OF FIRST ABNORMALITY:" + substr(mvar1,4,4)
         endif
         wait
         exit
       else
        skip
        if eof()
         exit
```

Findout1.prg (cont.)

```
    endif
    loop
   endif
 enddo
 if .not. mflag
   @ 2,0 say "that lab test is not on record as abnormal"   AP63
   wait
   return
 endif
 exit case mchoice = "2"
  store .f. to mflag
  do while PT_ID = mpt_id .and. INVOICE <> minvoice
    store field(mtest) to mvar
    store &mvar to mvar1
    if asc(mvar1) <> 32 .and. asc(mvar1) <> 78 .and. substr(mvar1,1,1) <> "T"
      store mvar1 to mvar2
      store DATE to mdate2
      store .t. to mflag
      skip
      if eof()
        exit
      endif
      loop
    else
      skip
      if eof()
        exit
      endif
      loop
    endif
  enddo
  if mflag
    @ 2,0 say "INQUIRY OF LAB TEST:" + mvar
    @ 3,0 say "DATE OF LATEST ABNORMALITY:" + dtoc(mdate2)
    if mtest = 18 .or. mtest = 19
      if substr(mvar1,2,1) = "1"
        @ 4,0 say "VALUE OF ABNORMALITY:very abnormal"
      else
        @ 4,0 say "VALUE OF ABNORMALITY:mildly abnormal"
      endif
    else
      @ 4,0 say "VALUE OF LATEST ABNORMALITY:" + substr(mvar2,4,4)
    endif
    wait
    return
  else
    @ 1,0 say "LAB TEST " + mvar1 + "is not on file as abnormal"
    wait
    return
  endif
 endcase
enddo
use
return
```

*AP64*  *Abn_Lab.fmt*

*format file for drawing customized data entry screen*

```
@ 1,0 say "DOCTOR "
@ 1,8 get DOCTOR
@ 1,32 say "PATIENT"
@ 1,40 get PT_ID
@ 2,0 say "DATE"
@ 2,6 get DATE
@ 2,16 say "SOURCE INVOICE"
@ 2,31 get INVOICEFRM
@ 2,39 say "LAB INVOICE"
@ 2,52 get INVOICE
@ 4,0 say "BUN"
@ 4,5 get BUN
@ 4,13 say "CR"
@ 4,16 get CR
@ 4,24 say "HG"
@ 4,27 get HG
@ 4,35 say "HCT"
@ 4,39 get HCT
@ 6,0 say "SED-RATE"
@ 6,9 get SED_RATE
@ 6,18 say "POTTASIUM"
@ 6,29 get POTTASIUM
@ 6,36 say "BLD-SUGAR"
@ 6,46 get BLD_SUG
@ 8,0 say "PH"
@ 8,4 get PH
@ 8,12 say "PO2"
@ 8,16 get PO2
@ 8,25 say "PCO2"
@ 8,30 get PCO2
@ 8,38 say "WBC"
@ 8,42 get WBC
@ 10,0 say "CALCIUM"
@ 10,9 get CALCIUM
@ 10,17 say "EKG"
@ 10,21 get EKG
@ 10,29 say "CXR"
@ 10,33 get CXR
@ 12,0 say "Press " +CHR(26)+ " or " +CHR(27)+ " to move within fields"
@ 13,0 say "Press " +CHR(24)+ " or " +CHR(25)+ " to move between fields"
@ 14,0 say "Press " + ret + " to finish data entry and move to next field"
@ 15,0 say "when at last/tiny field,press " + ret + " to REMAIN/RECHECK"
@ 16,0 say "or press X to leave/quit"
@ 16,26 get mdone
```

AP65  DoctorPg.Prg

```
public mpt_id,hello,minvoice,mdate,mlname,mfname
set talk off
mchoose = " "
mlname = space(12)
mfname = space(5)
mdate = ctod("  /  /  ")
clear
@ 1,0 say "HELLO DOCTOR,this routine will allow you to access "
@ 2,0 say "your patient's lab data in two different ways."
@ 3,0 say "These will be listed first for your selection, "
@ 4,0 say "and then you will be asked some patient information."
wait
mrecord = " "
do while upper(mrecord) <> "C"
 store " " to mrecord
 mlname = space(12)
 mfname = space(5)
 clear
 @ 1,0 say "DO you want to view a particular record?(A/a)"
 @ 2,0 say "or comparative/historical data about a "
 @ 3,0 say "particular lab test or tests?(B/b)"
 @ 4,0 say "if you wish to quit/leave,press C/c" get mrecord Picture "A"
 read
 if upper(mrecord) = "C"
  close databases
  clear
  return
 endif
 do while .t.
  clear
  @ 1,0 say "now enter patient's last name" get mlname
  @ 2,0 say "now enter patient's first name(or initial)" get mfname
  read
  use medical index medname
  seek upper(trim(mlname + mfname))
  if .not. found()
   store " " to yesno
   @ 3,0 say "either not on file or wrong entry/spelling"
   do while .not. upper(yesno) $ "YN"
    wait "press Y/y to try again,or N/n to leave/quit" to yesno
   enddo
   if upper(yesno) = "N"
    clear
    return
   else
    clear
    store space(12) to mlname
    store space(8) to mfname
    loop
   endif
  else
   store PT_ID to mpt_id
```

AP 66    DoctorPg.Prg (cont.)

```
    store DIAGNOSIS1 to mdiag
    close databases
    clear
    exit
  endif
enddo
if upper(mrecord) = "A"
  do while upper(mchoose) <> "Q"
    mchoose = " "
    clear
    @ 1,0 say "now enter the office(or e.r.) visit date"
    @ 2,0 say "you can estimate the date,and the program"
    @ 3,0 say "will prompt you again if you miss" get mdate
    @ 4,0 say "or you can leave that field blank(press key with red no. 6(->)"
    @ 5,0 say "and then press Q/q here to leave/quit" get mchoose picture "A"
    read
    if dtoc(mdate) <> "  /  /  "
      use encounte index encdatpt
      seek dtoc(mdate) + mpt_id
      if .not. found()
        mdate = ctod("  /  /  ")
        clear
        store " " to mchoose
        wait "wrong date,press return to try again,or Q/q to quit" to mchoose
        if upper(mchoose) = "Q"
          exit
        else
          loop
        endif
      else
        clear
        wait "now,press any key and please wait 2 min."
        store INVOICE to minvoice
        close databases
        use abn_lab index invfrm
        seek minvoice
        if .not. found()
          clear
          @ 2,0 say "NO LAB RECORD ON THAT INVOICE:" + minvoice + "and  DATE:" + dtoc(mdate)
          wait "press any key to return"
          exit
        endif
        hello = recno()
        close databases
        do digout2a
        do print3b
        store " " to yesno
        clear
        do while .not. upper(yesno) $ "YN"
          wait "CONTINUE with same/other patient(Y/y) or QUIT(N/n)?" to  yesno
        enddo
        if upper(yesno) = "Y"
          mdate = ctod("  /  /  ")
          exit
        else
          clear
          return
        endif
      endif
    endif
    if upper(mchoose) = "Q"
      exit
    endif
  enddo
  loop
```

```
endif
if upper(mrecord) = "B"
  do selectpg
  loop
endif
enddo
return
```

AP67

DoctorPq.Prq (cont.)

AP 68   SelectPg.prg

```
public mpt_id,mtest,mchoice,hello
store 0 to mtest
store space(6) to minvoice
mlabdate = ctod("  /  /  ")
mselect = space(1)
clear
   mtest = 0
   mchoice = space(1)
   do while upper(mchoice) <> "6"
   mchoice = space(1)
   clear
   @ 1,0 say "SELECT ONE OF THE FOLLOWING LAB TESTS BY THE"
   @ 2,0 say "NUMBER IN PARENTHESIS ASSOCIATED WITH THE TEST NAME."
   @ 3,0 say replicate("=",66)
   @ 4,0 say "BUN(6)"
   @ 4,7 say "CR(7)"
   @ 4,13 say "HG(8)"
   @ 4,19 say "HCT(9)"
   @ 4,26 say "SEDRATE(10)"
   @ 4,38 say "POTTASIUM(11)"
   @ 4,52 say "BLD SUGAR(12)"
   @ 5,0 say "PH(13)"
   @ 5,7 say "PO2(14)"
   @ 5,15 say "PCO2(15)"
   @ 5,24 say "WBC(16)"
   @ 5,32 say "CALCIUM(17)"
   @ 5,44 say "EKG(18)"
   @ 5,52 say "CXR(19)"
   @ 6,0 say "please select one of the above, or enter 20"
   @ 7,0 say "in order to leave/quit" get mtest picture "@Z 99"
   read
     if mtest = 20
      exit
     endif
     if mtest < 6 .or. mtest > 19
        clear
        @ 1,0 say "data entry error,please repeat"
        wait
        loop
     else
       do while .t.
       mchoice = " "
       @ 8,0 say "NOW SELECT THE KIND OF INFORMATION"
       @ 9,0 say "YOU WANT ABOUT THAT LAB VALUE BY SELECTING"
       @ 10,0 say "THE ASSOCIATED NUMBER IN PARENTHESIS."
       @ 11,0 say replicate("=",66)
       @ 12,0 say "DATE AND VALUE OF FIRST ABNORMALITY (1)"
       @ 13,0 say "DATE AND VALUE OF LAST ABNORMALITY (2)"
       @ 14,0 say "IS THE TEST CONSISTENTLY ABNORMAL? (3)"
       @ 15,0 say "LATEST ENTRY FOR THAT TEST(normal/abnormal) (4)"
       @ 16,0 say "HIGHEST and LOWEST ABNORMAL VALUES(except ekg &  cxr)(5)"
       @ 17,0 say "CHOOSE (6) to leave/choose another test"
       @ 18,0 say "please make selection here" get mchoice
       read
       if mchoice = "6"
         exit
       endif
       if mchoice = "5"
```

```
store "0.00" to mbig
use abn_lab index abnpatnt
seek mpt_id                                        AP69    SelectPg.Prg(cont.)
do while PT_ID = mpt_ID
  store field(mtest) to mvar
  if mvar <> "EKG" .or. mvar <> "CXR"
    store &mvar to mvar1
    if asc(mvar1) <> 32 .and. substr(mvar1,1,1) <> "T" .and. asc(mvar1) <> 70
      if val(substr(mvar1,4,4)) >= val(mbig)
        store substr(mvar1,4,4) to mbig
        store DATE to mbigdate
        skip
      else
        skip
        if eof()
          exit
        endif
        loop
      endif
    else
      skip
      if eof()
        exit
      endif
      loop
    endif
  else
    skip
    if eof()
      exit
    endif
    loop
  endif
enddo
use
store "9999" to msmall
use abn_lab index abnpatnt
seek mpt_id
do while PT_ID = mpt_id
  store field(mtest) to mvar
  if mvar <> "EKG" .or. mvar <> "CXR"
    store &mvar to mvar1
    if asc(mvar1) <> 32 .and. substr(mvar1,1,1) <> "T" .and. asc(mvar1) <> 70
      if val(substr(mvar1,4,4)) <= val(msmall)
        store substr(mvar1,4,4) to msmall
        store DATE to msmdate
        skip
      else
        skip
        if eof()
          exit
        endif
        loop
      endif
    else
      skip
      if eof()
        exit
      endif
      loop
    endif
  else
    skip
    if eof()
```

```
      exit
    endif
   loop
  endif
 enddo                                          AP70    Select Pg. Prg (cont.)
 clear
 if mbig = "0.00"
  @ 1,0 say "apparently, that lab test is not on file"
  wait
  loop
 endif
 if .not. mtest = 16
  @ 1,0 say "largest abnormal value is " + mbig + " on date:" + dtoc(mbigda
te)
  @ 2,0 say "smallest abnormal value is " + msmall + " on date:" + dtoc(msmd
ate)
 else
  @ 1,0 say "largest abnormal value is " + mbig + "00" + " on  date:" + dtoc
(mbigdate)
  @ 2,0 say "smallest abnormal value is " + msmall + "00" + "  on date:" + d
toc(msmdate)
 endif
 wait
 use
 loop
 endif
 if mchoice $ "1234"
  if mchoice $ "12"
   do finda1
   loop
  else
   do finda2
   loop
  endif
 else
  @ 18,0 say "wrong key pressed, please start over"
  wait
  loop
 endif
 enddo
 endif
enddo
return
``` finda1.prg

AP71

```
public mpt_id,mtest,mchoice,minvl,hello
clear
mdate = ctod("  /  /  ")
store ctod("  /  /  ") to mdate1,mdate2,mdate4
use abn_lab index abnpatnt
seek mpt_id
hold = recno()
skip 1
if eof() .or. PT_ID <> mpt_id
 @ 1,0 say "this is only record! so just review"
 wait
 return
else
 goto hold
endif
 do while .t.
   do case
     case mchoice = "1"
      store .f. to mflag
      do while PT_ID = mpt_id
      store field(mtest) to mvar
      store &mvar to mvar1
        if asc(mvar1) <> 32 .and. substr(mvar1,1,1) <> "T" .and.    asc(mvar1) <>
78
          store .t. to mflag
          store DATE to mdate2
          @ 2,0 say "INQUIRY OF LAB TEST:" + mvar
          @ 3,0 say "DATE OF FIRST ABNORMALITY:" + dtoc(mdate2)
          if mtest = 18 .or. mtest = 19
            if substr(mvar1,2,1) = "1"
              @ 4,0 say "VALUE OF ABNORMALITY:very abnormal"
            else
              @ 4,0 say "VALUE OF ABNORMALITY:mildly abnormal"
            endif
          else
            @ 4,0 say "VALUE OF FIRST ABNORMALITY:" + substr(mvar1,4,4)
          endif
          wait
          exit
        else
          skip
          if eof()
            exit
          endif
          loop
        endif
      enddo
    if .not. mflag
      @ 2,0 say "that lab test is not on record as abnormal"
```

```
wait
 return
endif
exit case mchoice = "2"
 store .f. to mflag
 do while PT_ID = mpt_id
    store field(mtest) to mvar
    store &mvar to mvar1
    if asc(mvar1) <> 32 .and. asc(mvar1) <> 78 .and. substr(mvar1,1,1) <> "T"
      store mvar1 to mvar2
      store DATE to mdate2
      store .t. to mflag
      skip
      if eof()
       exit
      endif
      loop
    else
      skip
      if eof()
       exit
      endif
      loop
    endif
 enddo
 if mflag
   @ 2,0 say "INQUIRY OF LAB TEST:" + mvar
   @ 3,0 say "DATE OF LATEST ABNORMALITY:" + dtoc(mdate2)
   if mtest = 18 .or. mtest = 19
     if substr(mvar1,2,1) = "1"
      @ 4,0 say "VALUE OF ABNORMALITY:very abnormal"
     else
      @ 4,0 say "VALUE OF ABNORMALITY:mildly abnormal"
     endif
   else
     @ 4,0 say "VALUE OF LATEST ABNORMALITY:" + substr(mvar2,4,4)
   endif
   wait
   return
 else
   @ 1,0 say "LAB TEST " + mvar + "is not on file as abnormal"
   wait
   return
 endif
endcase
enddo
use
return
```

AP72  finda1.Prg (cont.)

AP13 findaz.frq

```
public mpt_id,mtest,mchoice,minv1,hello
clear
mdate = ctod("  /  /  ")
store ctod("  /  /  ") to mdate1,mdate2,mdate4
use abn_lab index abnpatnt
seek mpt_id
hold = recno()
skip 1
if eof() .or. PT_ID <> mpt_id
 @ 1,0 say "this is only record!,so just review"
 wait
 return
else
 goto hold
endif
 do while .t.
   do case
     case mchoice = "3"
       store .f. to mflag
       store 0 to mcount,mcount1
       do while PT_ID = mpt_id
         store field(mtest) to mvar
         store &mvar to mvar1
         if asc(mvar1) <> 32
          if substr(mvar1,1,1) = "T"
            store mcount1 + 1 to mcount1
            store DATE to mdate1
            skip
            if eof()
              exit
            endif
            loop
          endif
          if asc(mvar1) <> 78 .and. substr(mvar1,1,1) <> "T"
            store mcount + 1 to mcount
            if .not. mflag
              store DATE to mdate2
              store .t. to mflag
            endif
            skip
            if eof()
              exit
            endif
            loop
          else
            skip
            if eof()
              exit
            endif
            loop
          endif
         else
          skip
          if eof()
            exit
          endif
          loop
         endif
       enddo
       if mcount = 0 .and. mcount1 <> 0
```

AP74  finda2.prg (cont.)

```
          @ 3,0 say "it was last found normal on " + dtoc(mdate1)
          wait
          return
        endif
        if mcount <> 0 .and. mcount1 = 0
          @ 2,0 say rtrim(mvar) + " has been consistently abnormal since " + dtoc(mdate2) + " " + str(mcount) + " time(s)"
          wait
          return
        endif
        if mcount <> 0 .and. mcount1 <> 0
          @ 2,0 say rtrim(mvar) + " has been intermittently abnormal"
          @ 3,0 say "the last date it was normal was on:" + dtoc(mdate1)
          wait
          return
        endif
        if mcount = 0 .and. mcount1 = 0
          @ 2,0 say rtrim(mvar) + " has never been drawn"
          wait
          return
        endif case mchoice = "4"
        store .f. to mflag
        do while PT_ID = mpt_id
          store field(mtest) to mvar
          store &mvar to mvar1
          if asc(mvar1) <> 32 .and. asc(mvar1) <> 78
            store .t. to mflag
            store DATE to mdate4
            store mvar1 to mvar2
            skip
            if eof()
              exit
            endif
            loop
          else
            skip
            if eof()
              exit
            endif
            loop
          endif
        enddo
        if .not. mflag
          @ 2,0 say "the test" + rtrim(mvar) + " is not on record as abnormal for this patient"
          wait
          return
        endif
        if substr(mvar2,1,1) <> "T"
          @ 2,0 say "the latest entry for " + rtrim(mvar) + " was on:" + dtoc(mdate4)
          if mtest = 18 .or. mtest = 19
            if substr(mvar1,2,1) = "1"
              @ 3,0 say "VALUE OF ABNORMALITY:very abnormal"
            else
              @ 3,0 say "VALUE OF ABNORMALITY:mildly abnormal"
            endif
          else
            @ 3,0 say "the abnormal value was:" + substr(mvar2,4,4)
          endif
          wait
          return
        endif
```

```
    @ 2,0 say "the latest entry was normal on " + dtoc(mdate4)
    wait
    return
   endif
  endcase
 enddo
 use
 return
```

Digout2A.Prg

AP76

```
public minvoice,mPT_ID,mldate,mflaga,mflagd,mldate1,mlinv,mlinv1,hello
store "" to mablab1,mablab2,mablab3,mablab4,mablab5,mldate1,mlinv1
store .f. to mflaga
store .f. to mflagb
store space(6) to minv1
store ctod("  /  /  ") to mldate
   select c
   use abn_lab index invfrm
   goto hello
      store DATE to mldate
      store INVOICE to mlinv
      store 6 to mfield
      do while mfield <= 19
         store field(mfield) to mvar
         store &mvar to mvar1
         if asc(mvar1) = 32
            store mfield + 1 to mfield
            store mablab1 + space(10) to mablab1
            store mablab2 + space(8) to mablab2
            store mablab3 + space(15) to mablab3
            store mablab4 + space(14) to mablab4
            store mablab5 + space(4) to mablab5
            store mldate1 + space(8) to mldate1
            store mlinv1 + space(6) to mlinv1
            loop
         else
            store mablab1 + mvar + space(10 - len(mvar)) to mablab1
         DO CASE
            case substr(mvar1,1,1) = "A"
               store mablab2 + "ACUTE   " to mablab2
            case substr(mvar1,1,1) = "S"
               store mablab2 + "SUBACUTE" to mablab2
            case substr(mvar1,1,1) = "C"
               store mablab2 + "CHRONIC " to mablab2
            case substr(mvar1,1,1) = "T"
               select c
               hold = recno()
               if substr(mvar1,4,1) <> "C"
               skip - 1
               store PT_ID to mPT_ID
               do while PT_ID = mPT_ID
                  store INVOICEFRM to minv1
                  do while PT_ID = mPT_ID .and. INVOICEFRM = minv1
                     store field(mfield) to mvar2
                     store &mvar2 to mvar3
                     if asc(mvar3) <> 32 .and. asc(mvar3) <> 78
                        store mldate1 + dtoc(DATE) to mldate1
                        store mlinv1 + INVOICE to mlinv1
                        if substr(mvar1,4,1) = "A"
                           store mablab2 + "ta      " to mablab2
                        else
                           store mablab2 + "tb      " to mablab2
                        endif
                        store mablab3 + space(15) to mablab3
                        store mablab4 + space(14) to mablab4
                        store mablab5 + substr(mvar3,4,4) to mablab5
                        store mfield + 1 to mfield
```

AP77  Digout2a.Prg (cont.)

```
          goto hold
          store .t. to mflagb
          exit
        else
          skip - 1
          loop
        endif
      enddo
      if mflagb
        exit
      endif
    enddo
    if .not. mflagb
      store mablab2 + "t         " to mablab2
      store mablab3 + space(15) to mablab3
      store mablab4 + space(14) to mablab4
      store mablab5 + substr(mvar3,4,4) to mablab5
      store mldate1 + space(8) to mldate1
      store mlinv1 + space(6) to mlinv1
      store mfield + 1 to mfield
      goto hello
    endif
    loop
  else
    store mldate1 + space(8) to mldate1
    store mablab2 + "tc        " to mablab2
    store mablab3 + space(15) to mablab3
    store mablab4 + space(14) to mablab4
    store mablab5 + substr(mvar3,4,4) to mablab5
    store mfield + 1 to mfield
    store mlinv1 + space(6) to mlinv1
    goto hello
    loop
  endif
endcase
DO CASE
  case substr(mvar1,2,1) = "1"
    if field(mfield) = "EKG" .or. field(mfield) = "CXR"
      store mablab3 + "VERY ABNORMAL  " to mablab3
    else
      store mablab3 + "VERY HIGH      " to mablab3
    endif
  case substr(mvar1,2,1) = "2"
    if field(mfield) = "EKG" .or. field(mfield) = "CXR"
      store mablab3 + "MILDLY ABNORMAL" to mablab3
    else
      store mablab3 + "MODERATELY HIGH" to mablab3
    endif
  case substr(mvar1,2,1) = "3"
    store mablab3 + "VERY LOW       " to mablab3
  case substr(mvar1,2,1) = "4"
    store mablab3 + "MODERATELY LOW " to mablab3
endcase
DO CASE
  case substr(mvar1,3,1) = "I"
    store mablab4 + " and IMPROVED " to mablab4
  case substr(mvar1,3,1) = "W"
    store mablab4 + " and WORSENED " to mablab4
  case substr(mvar1,3,1) = "U"
    store mablab4 + " and UNCHANGED" to mablab4
  case substr(mvar1,3,1) = "N"
    store mablab4 + " and 1st TIME " to mablab4
  case substr(mvar1,3,1) = "P"
    store mablab4 + " prev. normal " to mablab4
endcase
store mfield + 1 to mfield
```

```
   store mlinv1 + space(6) to mlinv1
   store mldate1 + space(8) to mldate1
  endif
enddo
use
if mablab1 = space(140)
store .t. to mflaga
endif
return
```

Af 78

Diqoutaa.Prq (cont.)

Print3b.Prg

AP79

```
clear
public mldate,mlinv,mpt_id,minvoice,mablab1,mablab2,mablab3,mablab4,mablab5,mlda
te1,mlinv1,mflaga,mflagd,mdate,mlname,mfname
mtitle = "PATIENT RECORD REVIEW"
@ 1,(66 - len(mtitle))/2 say mtitle
@ 2,0 say "PATIENT:" + rtrim(mlname) + " " + mfname
@ 2,26 say "PRIMARY DX:" + mdiag
@ 3,0 say replicate("=",66)
store 3 to mline
if mablab1 <> space(140)
store 1 to mcounter ,ml1,ml2,ml3,ml4,ml5,mld,mlv
store .f. to mflag
  do while mcounter <= 14
      if substr(mablab1,ml1,1) <> " "
        store substr(mlinv1,mlv,6) to ml
        store substr(mldate1,mld,8) to md
        store substr(mablab1,ml1,10) to m1
        store substr(mablab2,ml2,8) to m2
        store substr(mablab3,ml3,15) to m3
        store substr(mablab4,ml4,14) to m4
        store substr(mablab5,ml5,4) to m5
      if .not. mflag
        @ mline + 1,0 say "LAB VALUES FOR INVOICE NO:" + minvoice + "DATE:" + d
toc(mdate)
        @ mline + 2,0 say "DATE DRAWN:" + dtoc(mldate) + "LAB INVOICE:" + mlinv
        store .t. to mflag
        store mline + 2 to mline
      endif
      if mcounter <> 13 .or. mcounter <> 14
        if substr(mablab2,ml2,1) = "t"
          do case
            case substr(m2,2,1) = "a"
            @ mline + 1,0 say "NORMAL TEST FOR" + rtrim(m1) + " AND NORMAL ON:" +
 md
            case substr(m2,2,1) = "b"
            @ mline + 1,0 say "NORMAL TEST FOR " + rtrim(m1) + " AND ABNORMAL ON:"
 + md
            case substr(m2,2,1) = "c"
            @ mline + 1,0 say "NORMAL TEST FOR " + rtrim(m1) + " NO  PRIOR TESTS O
N RECORD"
            otherwise
            @ mline + 1,0 say "DATA ENTRY ERROR FOR LAB INVOICE" +  mlinv + "ON "
+ dtoc(mldate)
          endcase
        else
          if mcounter = 11
            @ mline + 1,0 say "ABNORMAL VALUE FOR " + rtrim(m1) + ":" + m5 + "00"
 + rtrim(m2) + "," + rtrim(m3) + rtrim(m4)
          else
            @ mline + 1,0 say "ABNORMAL VALUE FOR " + rtrim(m1) + ":"+ m5 + rtrim
(m2) + "," + rtrim(m3) + rtrim(m4)
          endif
        endif
        store mline + 1 to mline
      else
        if substr(mablab2,1,1) = "t"
          do case
            case substr(m2,2,1) = "a"
            @ mline + 1,0 say "NORMAL TEST FOR " + rtrim(m1) + " AND NORMAL ON:" +
```

```
              case substr(m2,2,1) = "b"
              @ mline + 1,0 say "NORMAL TEST FOR " + rtrim(m1) + " AND ABNORMAL ON:"
+ md
              case substr(m2,2,1) = "c"
              @ mline + 1,0 say "NORMAL TEST FOR " + rtrim(m1) + "AND NO PRIOR TEST
ON RECORD"
              otherwise
              @ mline + 1,0 say "DATA ENTRY ERROR FOR LAB INVOICE:" +  mlinv + "ON "
+ dtoc(mldate)
            endcase
          else
            @ mline + 1,0 say "ABNORMAL TEST FOR " + rtrim(m1) + ":" + rtrim(m2)
+ "," + rtrim(m3) + rtrim(m4)
          endif
        endif
        store mcounter + 1 to mcounter
        store ml1 + 10 to ml1
        store ml2 + 8 to ml2
        store ml3 + 15 to ml3
        store ml4 + 14 to ml4
        store ml5 + 4 to ml5
        store mld + 8 to mld
        store mlv + 6 to mlv
        loop
      else
        store mcounter + 1 to mcounter
        store ml1 + 10 to ml1
        store ml2 + 8 to ml2
        store ml3 + 15 to ml3
        store ml4 + 14 to ml4
        store ml5 + 4 to ml5
        store mld + 8 to mld
        store mlv + 6 to mlv
        loop
      endif
    enddo
  else
    @ mline + 1,0 say "THE RECORD IS EMPTY OF DATA " + "INVOICE   NO:" + minvoi
ce + " DATE:" + dtoc(mdate)
  endif
  wait
  return
```

AP 80    Print3b.prg (cont.)

add newrc.prg

AP81

```
public mpt_id,mstatus,mcomp1,mcomp2,mfind1,mfind2
mstatus = space(1)
clear
@ 1,0 say "this is the new record entry routine for:" + mpt_id
@ 2,0 say "now enter the STATUS for this first record" get mstatus
read
store "Y" to yesno
do while upper(yesno) = "Y"
 do part1
 if upper(mwhat) = "N"
  clear
  @ 1,0 say "add another record?"
  @ 2,0 say "press Y/y if yes,N/n if not" get yesno
  read
  exit
 endif
 do part2
 if upper(mwhat) = "N"
  clear
  @ 1,0 say "add another record?"
  @ 2,0 say "press Y/y if yes,N/n if not" get yesno
  read
  exit
 endif
 do part3
 if mcomp1 = space(3) .and. mcomp2 = space(3) .and. mfind1 = space(3) .and. mfin
d2 = space(3)
  if mstatus <> "1"
   use encounte
   goto bottom
   delete
   pack
   use
   clear
   @ 1,0 say "no physical data for a non-1 status record"
   @ 2,0 say "it has been deleted but you may re-enter"
   wait
  endif
 endif
 clear
 @ 1,0 say "add another record?"
 @ 2,0 say "press Y/y if yes,N/n if not" get yesno
 read
 exit
enddo
return
```

AP82    addencrc.prg

```
public mwhat,mpt_id,yesno,mstatus,mflag,mcomp1,mcomp2,mfind1,mfind2
set talk off
do while .t.
mflag = space(1)
mpt_id = space(11)
mget = space(1)
mstatus = space(1)
clear
@ 1,0 say "THIS IS THE OFFICE VISIT RECORD LOADING ROUTINE"
@ 2,0 say "PLEASE ENTER PATIENT I.D. NO(or leave blank to quit)"  get mpt_id pic
ture "999-99-9999"
@ 3,0 say "if a NEWPROBLEM is checked enter a Y/y,if not,enter N/n" get mflag
read
if mpt_id = space(11)
 clear
 return
endif
use encounte index patient
seek mpt_id
if found()
do while PT_ID = mpt_id
 skip
enddo
skip - 1
@ 4,0 say "this is the STATUS of patient's last record:" + STATUS
@ 5,0 say "there are certain restrictions you must observe"
@ 6,0 say "IF IT IS A ONE,YOU CAN'T ENTER A FOUR TO THIS RECORD"
@ 7,0 say "IF IT IS A THREE,YOU CAN'T ENTER A TWO TO THIS RECORD"
@ 8,0 say "IF IT IS A TWO,YOU CAN'T ENTER A ONE TO THIS RECORD"
@ 9,0 say "THERE MUST BE AN INTERVENING FOUR (IMPROVEMENT)"
@ 10,0 say "BETWEEN BOTH TRANSITIONS. ANY OTHER COMBINATION OF"
@ 11,0 say "SEQUENCES IS PERMISSIBLE. IF YOUR DATA ENTRY SHEET"
@ 12,0 say "DOESN'T CONFLICT PLEASE ENTER STATUS HERE" get mstatus
@ 13,0 say "IF it does conflict,then enter Q/q to either return"
@ 14,0 say "for another record entry or to leave ->" get mget
read
close databases
IF upper(mget) = "Q"
 clear
 loop
ELSE
store "Y" to yesno
do while upper(yesno) = "Y"
 do part1
 if upper(mwhat) = "N"
  clear
``` addencrc.prq (cont.)

```
store " " to yesno
@ 1,0 say "ADD ANOTHER RECORD?"
@ 2,0 say "if yes press Y/y,if not press N/n" get yesno
read
if upper(yesno) = "Y"
  clear
  exit
else
  clear
  return
endif
endif
do part2
if upper(mwhat) = "N"
 clear
 store " " to yesno
 @ 1,0 say "ADD ANOTHER RECORD?"
 @ 2,0 say "if yes,press Y/y,if not press N/n" get yesno
 read
 if upper(yesno) = "Y"
   clear
   exit
 else
   clear
   return
 endif
endif
do part3
if mcomp1 = space(3) .and. mcomp2 = space(3) .and. mfind1 = space(3) .and. mfind2 = space(3)
  if mstatus <> "1"
    use encounte
    goto bottom
    delete
    pack
    use
    clear
    @ 1,0 say "no physical data for a non-1 status record"
    @ 2,0 say "it has been deleted but you may re-enter"
    wait
  endif
endif
if upper(mwhat) = "N"
 store " " to yesno
 clear
 @ 1,0 say "ADD ANOTHER RECORD?"
 @ 2,0 say "if yes,press Y/y,if not press N/n" get yesno
 read
 if upper(yesno) = "Y"
   clear
   exit
 else
   clear
   return
 endif
endif
clear
store " " to yesno
@ 1,0 say "ADD ANOTHER RECORD?"
@ 2,0 say "if you do,press Y/y,if not press N/n" get yesno picture "A"
read
if upper(yesno) = "Y"
  clear
  exit
else
  return
```

AP83

```
  endif
 enddo
 endif
 if upper(yesno) = "Y"
  loop
 else
  exit
 endif
else
 clear
 store " " to mwhat
 @ 3,0 say "WRONG i.d. no. or new record for that patient"
 @ 4,0 say "press Y/y to retry,A/a to add new patient,or N/n to quit" get mwhat
picture "A"
 read
 if upper(mwhat) = "Y"
  loop
 endif
 if upper(mwhat) = "N"
  exit
 endif
 if upper(mwhat) = "A"
  do addnewrc
  if upper(yesno) = "Y"
   loop
  else
   exit
  endif
 endif
endif
enddo
clear
return
```

AP84 addencrc.prq (cont.)

APP5      Part1.Prq

```
public mwhat,mpt_id,mstatus,mflag
set talk off
padding = "000000"
store space(1) to mwhat
minvoice = "000000"
clear
use encounte
goto bottom
store substr(INVOICE,2,5) to mv
store val(mv) + 1 to mv
store stuff(minvoice,2,5,right(padding + ltrim(str(mv,5)),5)) to minvoice
use
do while .t.
clear
store space(4) to mcode1,mcode2,mcode3
store space(6) to mvar1,mvar2,mvar3
store space(4) to mcode
@ 2,0 say "enter the 4 digit diagnostic code(s) from"
@ 3,0 say "your data entry sheet,then wait 1 min."
@ 4,0 say replicate("=",66)
@ 5,0 say "PRIMARY DIAGNOSIS:" get mcode1
@ 6,0 say "SECONDARY DIAGNOSIS(leave blank if absent):" get mcode2
@ 7,0 say "TERTIARY DIAGNOSIS(leave blank if absent):" get mcode3
read
select a
use medical index medptid
seek mpt_id
if .not. found()
 append blank
 replace PT_ID with mpt_id
endif
if mcode1 <> space(4)
 select a
 if substr(CODE1,3,4) <> mcode1
  select b
  use chrmedli index diagnose
  seek mcode1
  if found()
   store CODETYPE + CODE to mvar1
   select a
   replace DIAGNOSIS1 with b->DESCRIPT
   replace CODE1 with mvar1
   replace medflag1 with .t.
   replace medinv1 with minvoice
   replace DATE1 with date()
  else
```

AP86    Part1.Prg (cont.)

```
  mwhat = space(1)
   clear
   @ 1,0 say "invalid code,press Y/y to retry or N/n to quit"
   @ 1,49 get mwhat
   read
   if upper(mwhat) = "Y"
    clear
    loop
   else
    clear
    return
   endif
  endif
 else
  store CODE1 to mvar1
 endif
else
 store CODE1 to mvar1
endif
if mcode2 <> space(4)
 select a
 if substr(CODE2,3,4) <> mcode2
  select b
  use chrmedli index diagnose
  seek mcode2
  if found()
   store CODETYPE + CODE to mvar2
   select a
   replace DATE2 with date()
   replace CODE2 with mvar2
   replace medflag2 with .t.
   replace medinv2 with minvoice
  else
   clear
   store space(1) to mwhat
   @ 1,0 say "invalid code,press Y/y to retry  or N/n to quit"
   @ 1,49 get mwhat
   read
   if upper(mwhat) = "Y"
    clear
    loop
   else
    return
   endif
  endif
 else
  store CODE2 to mvar2
 endif
else
 store CODE2 to mvar2
endif
if mcode3 <> space(4)
 select a
 if substr(CODE3,3,4) <> mcode3
  select b
  use chrmedli index diagnose
  seek mcode3
  if found()
   store CODETYPE + CODE to mvar3
   select a
   replace CODE3 with mvar3
   replace medflag3 with .t.
   replace medinv3 with minvoice
   replace DATE3 with date()
  else
   clear
```

Part.1.Prg (cont.)

```
  store space(1) to mwhat
  @ 1,0 say "invalid code,press Y/y to retry  or N/n to quit"
  @ 1,49 get mwhat
  read
  if upper(mwhat) = "Y"
   clear
   loop
  else
   return
  endif
 endif
 else
  store CODE3 to mvar3
 endif
 else
  store CODE3 to mvar3
 endif
 exit
enddo
close databases
clear
do while .t.
mcondition = space(4)
@ 1,0 say "now enter the CONDITION code(4 digits)"
@ 1,40 get mcondition
read
 if upper(mflag) <> "Y"
 use chrmedli index diagnose
 seek mcondition
 if found()
 store CODETYPE + CODE to mvar
 use encounte
 append blank
 replace STATUS with mstatus
 replace CONDITION with mvar
 replace INVOICE with minvoice
 replace PT_ID with mpt_id
 replace PRIM_DX with mvar1
 replace SEC_DX with mvar2
 replace TERT_DX with mvar3
 use
 else
 store space(1) to mwhat
 @ 1,0 say "invalid code,press Y/y to re-enter or N/n to quit"
 @ 1,51 get mwhat
 read
 if upper(mwhat) = "Y"
  clear
  loop
 else
  clear
  return
 endif
 endif
else
 use er_list index er_list
  seek mcondition
  if found()
   store CODETYPE + CODE TO mvar
   use encounte
   append blank
   replace STATUS with mstatus
   replace CONDITION with mvar
   replace PT_ID with mpt_id
   replace PRIM_DX with mvar1
   replace SEC_DX with mvar2
```

```
   replace TEXT_DX with mvars
   replace NEWPROBLEM with .T.
   replace INVOICE with minvoice
   use
  else
   store space(1) to mwhat
   @ 1,0 say "invalid code,press Y/y to return or N/n to quit"
   @ 1,49 get mwhat
   read
   if upper(mwhat) = "Y"
    clear
    loop
   else
    return
   endif
  endif
 endif
exit
enddo
close databases
return
```

Part1.Prq (Cont.)

AP88

AP 89

Part2.prg

```
public mwhat,mstatus
store space(1) to mwhat
clear
@ 1,0 say "now,if present enter the complaints and physical"
@ 2,0 say "findings to the office visit record.They will"
@ 3,0 say "EITHER be present as 3 digit codes which you"
@ 4,0 say "will enter directly,or as an explicitly transcribed"
@ 5,0 say "entry from which you are to enter the associated"
@ 6,0 say "letter and a grouped list will then appear from"
@ 7,0 say "which you are to locate the matching complaint/finding"
@ 8,0 say "and then copy the associated 3 digit number"
@ 9,0 say "IF both are completely absent,then press N/n to quit"
@ 10,0 say "otherwise press return to enter"
@ 10,33 get mwhat
read
if upper(mwhat) = "N" .and. mstatus <> "1"
  clear
  @ 1,0 say "active problem present,must have some physical data"
  @ 2,0 say "check with medical dept. before continuing with"
  @ 3,0 say "this patient/record,(But,You may add another)"
  wait
  use encounte
  goto bottom
  delete
  pack
  use
  return
endif
if upper(mwhat) = "N" .and. mstatus = "1"
  clear
  return
else
clear
do while .t.
store space(3) to mcomp1,mcomp2
store space(1) to mlet1,mlet2
@ 1,0 say "First enter COMPLAINTS"
@ 2,0 say "if you want to leave now,just move cursor off the screen"
@ 3,0 say "COMPLAINT(1) CODE:(leave blank if absent)" get mcomp1
@ 4,0 say "COMPLAINT(1) LETTER:(leave blank if absent)" get mlet1
@ 5,0 say "COMPLAINT(2) CODE:(leave blank if absent)" get mcomp2
@ 6,0 say "COMPLAINT(2) LETTER:(leave blank if absent)" get mlet2
read
if mcomp1 <> space(3)
 use cc_list index cc_list
 seek mcomp1
```

```
  if found()
    store CODETYPE + CODE to mvar
    use encounte
    goto bottom
    if substr(mvar,1,1) = substr(CONDITION,2,1) .or. substr(mvar,1,1) = substr(con
-dition,1,1)
      replace COMPLAINT1 with mvar
    else
      store " " to mwhat
      clear
      @ 1,0 say "complaint not consistent with condition"
      @ 2,0 say "press Y/y to re-enter or <return> to continue" get mwhat
      read
      if upper(mwhat) = "Y"
        clear
        loop
      else
        replace complaint1 with mvar
        use
      endif
    endif
  else
    store " " to mwhat
    clear
    @ 1,0 say "non-existent code,press Y/y to re-enter or N/n to quit" get mwhat
    read
    if upper(mwhat) = "Y"
      clear
      loop
    else
      clear
      return
    endif
  endif
endif
if mlet1 <> space(1)
  use cc_list index cc_list
  set filter to substr(CODETYPE,1,1) = upper(mlet1)
  goto top
  list
  wait "now copy the matching 3 digit no.,then press any key"
  clear
  @ 1,0 say "now enter the associated 3 digit code"
  @ 2,0 say "from the matching complaint and wait 1 min."
  @ 2,45 get mcomp1
  read
  seek mcomp1
  store CODETYPE + CODE to mvar
  use encounte
  goto bottom
  replace COMPLAINT1 with mvar
  use
endif if mcomp2 <> space(3)
  use cc_list index cc_list
  seek mcomp2
  if found()
    store CODETYPE + CODE to mvar
    use encounte
    goto bottom
    if substr(mvar,1,1) = substr(CONDITION,2,1) .or. substr(mvar,1,1) = substr(CON
DITION,1,1)
      replace COMPLAINT2 with mvar
      use
    else
```

*AP90  Part2.prg (cont.)*

```
    store " " to mwhat
    clear
    @ 1,0 say "complaint not consistent with condition"
    @ 2,0 say "press Y/y to re-enter or <return> to continue" get mwhat
    read
    if upper(mwhat) = "Y"
     clear
     loop
    else
     replace COMPLAINT2 with mvar
     use
    endif
   endif
  else
   store " " to mwhat
   clear
   @ 1,0 say "non-existent code,press Y/y to re-enter or N/n to quit" get mwhat
   read
   if upper(mwhat) = "Y"
    clear
    loop
   else
    clear
    return
   endif
  endif
 endif if mlet2 <> space(1)
  use cc_list index cc_list
  set filter to substr(CODETYPE,1,1) = upper(mlet2)
  goto top
  list
  wait "now copy the matching 3 digit no.,then press any key"
  clear
  @ 1,0 say "now enter the associated 3 digit code from"
  @ 2,0 say "the matching complaint and wait 1 min."
  @ 2,40 get mcomp2
  read
  seek mcomp2
  store CODETYPE + CODE to mvar
  use encounte
  goto bottom
  replace COMPLAINT2 with mvar
  use
 endif
 exit
enddo
endif
close databases
return
```

AP91  Part2.prg (Cont.)

AP 93    Part3.Prg

```
public mwhat,mcomp1,mcomp2,mfind1,mfind2
do while .t.
clear
store "   " to mfind1,mfind2
store " " to mlet3,mlet4,mwhat
@ 1,0 say "now,if present,enter physical findings"
@ 2,0 say "if you wish to leave/quit press N/n"
@ 3,0 say "press any other key to continue" get mwhat
read
if upper(mwhat) = "N"
 clear
 return
else
clear
@ 1,0 say "FINDING(1) CODE(leave blank if absent):" get mfind1
@ 2,0 say "FINDING(1) LETTER(leave blank if absent):" get mlet3
@ 3,0 say "FINDING(2) CODE(leave blank if absent):" get mfind2
@ 4,0 say "FINDING(2) LETTER(leave blank if absent):" get mlet4
read
if mfind1 <> space(3)
 use findings index findings
  seek mfind1
  if found()
   store CODETYPE + CODE to mvar
   use encounte
   goto bottom
   if substr(mvar,1,1) = substr(CONDITION,2,1) .or. substr(mvar,1,1) = substr(CON
DITION,1,1)
    replace FINDING1 with mvar
    use
   else
    store " " to mwhat
    clear
    @ 1,0 say "finding not consistent with condition"
    @ 2,0 say "press Y/y to re-enter or <return> to continue" get mwhat
    read
    if upper(mwhat) = "Y"
     clear
     loop
    else
     replace FINDING1 with mvar
     use
    endif
   endif
   use
  else
```

```
    store " " to mwhat
    clear
    @ 1,0 say "invalid code,press Y/y to re-enter or N/n to quit"
    @ 1,51 get mwhat
    read
    if upper(mwhat) = "Y"
     clear
     loop
    else
     clear
     return
    endif
   endif
  endif
endif
if mlet3 <> space(1)
 use findings index findings
 set filter to substr(CODETYPE,1,1) = upper(mlet3)
 goto top
 list
 wait "now copy the matching 3 digit no.,then press any key"
 clear
 @ 1,0 say "now enter the 3 digit no. and wait 1 min." get mfind1
 read
 seek mfind1
 if .not. found()
  store " " to mwhat
  clear
  @ 1,0 say "invalid code,press Y/y to re-enter,or N/n to quit" get mwhat
  read
  if upper(mwhat) = "Y"
   clear
   loop
  else
   clear
   return
  endif
 else
  store CODETYPE + CODE to mvar
  use encounte
  goto bottom
  replace FINDING1 with mvar
  use
 endif
endif if mfind2 <> space(3)
 use findings index findings
 seek mfind2
 if found()
  store CODETYPE + CODE to mvar
  use encounte
  goto bottom
  if substr(mvar,1,1) = substr(CONDITION,1,1) .or. substr(mvar,1,1) = substr(CONDITION,2,1)
    replace FINDING2 with mvar
    use
  else
    store " " to mwhat
    clear
    @ 1,0 say "findings not consistent with condition"
    @ 2,0 say "press Y/y to re-enter or <return> to continue" get mwhat
    read
    if upper(mwhat) = "Y"
     clear
     loop
    else
```

Part3.prg (Cont.)

AP93

AP94  Part3.Prq (Cont.)

```
          replace FINDING2 with mvar
       use
     endif
   endif
  else
    store " " to mwhat
    clear
    @ 1,0 say "invalid code,press Y/y to re-enter or N/n to quit" get mwhat
    read
    if upper(mwhat) = "Y"
      clear
      loop
    else
      clear
      return
    endif
  endif
  use
endif if mlet4 <> space(1)
  use findings index findings
  set filter to substr(CODETYPE,1,1) = upper(mlet4)
  goto top
  list
  wait "now copy the 3 digit no. of the match,then press any key"
  clear
  @ 1,0 say "now enter that matching 3 digit code and wait 1 min."  get mfind2
  read
  seek mfind2
  if .not. found()
    store " " to mwhat
    clear
    @ 1,0 say "invalid code,press Y/y to re-enter or N/n to quit"  get mwhat
    read
    if upper(mwhat) = "Y"
      clear
      loop
    else
      clear
      return
    endif
  else
    store CODETYPE + CODE to mvar
    use encounte
    goto bottom
    replace FINDING2 with mvar
    use
  endif
endif
endif
exit
enddo
close databases
return
``` addmedrc.prq

AP 95

```
public mcode1,mcode2,mcode3
clear
set talk off
set device to screen
@ 1,0 say "this is the NEW-PATIENT CODED DIAGNOSIS LOADING routine."
@ 2,0 say "First,you will be entering from 1-3 seperate diagnosis"
@ 3,0 say "that are present on your entry sheet in either 1 of 2 methods"
@ 4,0 say "Then,after notification,the program will create the record"
wait
do while .t.
clear
store space(11) to mpt_id
store space(12) to mlname
store space(8) to mfname
store space(25) to mdesc1,mdesc2,mdesc3
store space(6) to mcode1,mcode2,mcode3
store .f. to mflag
use chrmedli index diagnose
  do while .t.
    if mflag
      clear
      @ 1,0 say "you have now entered" + " " + str(mc,1) + " " + "diagnosis"
      @ 2,0 say "if that's all,just leave the entries in BOTH methods BLANK"
      wait
      clear
    endif
    mtype = ""
    mcateg = space(1)
    mq = space(1)
    mcode = space(4)
    msymbol = space(1)
    @ 1,27 say "FIRST METHOD"
    @ 2,0 say "if present,enter the four digit diagnostic number"
    @ 3,0 say "if not,then just press <return>" get mcode
    read
    if mcode = space(4)
      clear
    @ 1,27 say "SECOND METHOD"
    @ 3,0 say "NOW,enter the DIAGNOSTIC CATEGORY if present(A,B,C)"
    @ 3,53 get mcateg picture "!"
    @ 5,0 say "NOW,you must enter the appropriate letter displayed below"
    @ 6,0 say "in parenthesis associated with the pathological group implied"
    @ 7,0 say "by the doctor's diagnosis.The program will then display"
    @ 8,0 say "a list of diagnosis from that group in approximate order"
    @ 9,0 say "of descending clinical severity. You will then"
    @ 10,0 say "COPY the four digit number associated with the diagnosis"
```

```
@ 11,0 say "that most closely matches the one on the data entry sheet"
@ 12,0 say "for input in the next step."
@ 13,0 say "Once you have entered all the diagnosis submitted"
@ 14,0 say "(1-3),just press <RETURN> for the record creation"
@ 15,0 say replicate("=",66)
@ 16,0 say "HEART(H),NEURO(N),BLD.PRESS.(V),CANCER(C),ENDO.(E),INF./FEVER(I)"
@ 17,0 say "BLOOD(P),PULMONARY(L),GI(G),BONES/JOINTS(R),KIDNEY(K)"
@ 17,55 get msymbol picture "!"
read
if upper(msymbol) <> space(1)
  store mtype + msymbol to mtype
  if mcateg <> space(1)
    store mcateg + mtype to mtype
    set filter to CODETYPE = upper(mtype)
    goto top
    list
    wait
  else
    set filter to substr(CODETYPE,2,1) = upper(mtype)
    goto top
    list
    wait
  endif
  clear
  @ 1,0 say "NOW enter the four digit number taken from the screen"
  @ 2,0 say "if there is any problem,then just leave blank"
  @ 2,47 get mcode
  read
 endif
endif
  if mcode <> space(4)
    seek mcode
    if found()
      if mdesc1 = space(25)
        store DESCRIPT to mdesc1
        store CODETYPE + CODE to mcode1
        store .t. to mflag
        store 1 to mc
        loop
      endif
      if mdesc2 = space(25)
        store DESCRIPT to mdesc2
        store CODETYPE + CODE to mcode2
        store 2 to mc
        loop
      endif
      if mdesc3 = space(25)
        store DESCRIPT to mdesc3
        store CODETYPE + CODE to mcode3
        store 3 to mc
        loop
      endif
    else
      clear
      @ 1,0 say "DIAGNOSIS not found,return to re-enter or quit"
      wait
      loop
    endif
  endif
  if mflag
    store " " to mq
    clear
    @ 1,0 say "if there is any problem press Q/q to quit/retry"
    @ 2,0 say "if not,then just press return" get mq picture "!"
    read
    if mq = "Q"
``` addmedrc.Prg (Cont.)

```
    exit
   endif
   clear
   @ 1,0 say "NOW the actual record will be created"
   @ 2,0 say "now enter last name" get mlname picture "!!!!!!!!!!!!"
   @ 3,0 say "enter full first name" get mfname picture "!!!!!"
   @ 4,0 say "enter patient i.d. no." get mpt_id picture "999-99-9999"
   read
   use medical index medptid
   seek mpt_id
   if .not. found()
    append blank
    replace LNAME with mlname
    replace FNAME with mfname
    replace DIAGNOSIS1 with mdesc1
    replace CODE1 with mcode1
    replace DIAGNOSIS2 with mdesc2
    replace CODE2 with mcode2
    replace DIAGNOSIS3 with mdesc3
    replace CODE3 with mcode3
    replace DATE with date()
    reindex
    use
    do checkrec
    exit
   else
    clear
    @ 1,0 say "patient with this i.d. already on file"
    wait
    exit
   endif
  else
   clear
   @ 1,0 say "no records were created"
   wait
   exit
  endif
 enddo
 store " " to yesno
 clear
 @ 1,0 say "if you wish to create another record,enter Y/y"
 @ 2,0 say "or if you want to leave/quit,enter N/n" get yesno picture "A"
 read
 if upper(yesno) = "Y"
  clear
  loop
 else
  exit
 endif
enddo
use
clear
return
``` addmedrc.Prg (cont.)

AP 97

AP98    Checkrec.Prg

```
public mcode1,mcode2,mcode3 if .not. substr(mcode1,3,4) < substr(mcode2,3,4)
   if mcode2 <> space(6)
     clear
     @ 1,0 say "ERROR,second diagnosis must go first"
     @ 2,0 say "this record will be removed,you may start over"
     wait
     use medical
     goto bottom
     delete
     pack
     set index to medptid
     reindex
     use
     return
   endif
endif
if .not. substr(mcode2,3,4) < substr(mcode3,3,4)
   if mcode3 <> space(6)
     clear
     @ 1,0 say "ERROR,third diagnosis must go second(or first?)"
     @ 2,0 say "this record will be removed,you may start over"
     wait
     use medical
     goto bottom
     delete
     pack
     set index to medptid
     reindex
     use
     return
   endif
endif
return
```

```
public mdate,mdate1,mresult,mresult1,mablab,minv1,mpt_id,mflaga,mflagb,minvoice,
mflagc
select a
use chrmedli index chrcode                                      Overdraw.Prg
select b
use medical index patient                                       Ap99
select c
use encountf index encounte,encinv
do while .not. eof()
 store DOCTOR to mdoc
 store .f. to mflagd
 do while DOCTOR = mdoc .and. .not. eof()
   store PT_ID to mpt_id
   store .f. to mflage
   do while PT_ID = mpt_id .and. DOCTOR = mdoc .and. .not. eof()
    store INVOICE to minvoice
   do while INVOICE = minvoice .and. PT_ID = mpt_id .and. DOCTOR = mdoc .and. .n
ot. eof()
     if STATUS = "1" .and. TYPE = "S" .and. LAB_WORK .and. .not. NEWPROBLEM
      high = recno()
      store CONDITION to mcond
      store dtoc(DATE) to moffdate
      select a
      seek mcond
      store descript to mdesc
      select c
      set relation to pt_id into medical
      if .not. mflagd .or. .not. mflage
       store 1 to mline
       @ mline,0 say "DOCTOR " + rtrim(mdoc) + " STATUS 1 LAB WORK"
       @ mline + 1,0 say "PATIENT:" + rtrim(B->LNAME) + " " + "ID:" + mpt_id + "D
OB:" + dtoc(B->DOB)
       @ mline + 2,0 say "PRIMARY DIAGNOSIS:" + rtrim(B->DIAGNOSIS1) + " LAST HOS
P:" + dtoc(B->LAST_HOSP)
       store 3 to mline
       if SEC_DX <> " "
        @ mline + 1,0 say "SECONDARY DIAGNOSIS:" + (B->DIAGNOSIS2)
        store 4 to mline
        store .t. to mcode
       else
        @ mline + 1,0 say replicate("=",80)
        store 4 to mline
        store .f. to mcode
       endif
       if mcode
       if TERT_DX <> " "
        @ mline + 1,0 say "TERTIARY DIAGNOSIS:" + (B->DIAGNOSIS3)
        @ mline + 2,0 say replicate("=",80)
        store 6 to mline
       else
        @ mline + 1,0 say replicate("=",80)
        store 5 to mline
       endif
       endif
       store .t. to mflagd
       store .t. to mflage
      endif
      do digoutod
      @ mline + 1,0 say "LAB VALUES FOR OFFICE VISIT:" + minvoice + "DATE:" + mo
ffdate
      @ mline + 2,0 say "CONDITION:" + rtrim(mdesc) + "DATE DRAWN:" + mdate
      store mline + 2 to mline
      store 1 to m1,m2,m3,m4,m5,mcounter
``` overdraw.prg (cont.)

AP100

```
do while mcounter <= 14
 if substr(mablab,m1,1) <> " "
  store substr(mresult,m2,4) to ma
  store substr(mablab,m1,10) to mb
  store substr(mdate1,m3,8) to mc
  store substr(minv1,m5,6) to me
  store substr(mresult1,m4,4) to md
  if me <> space(6)
   select c
   set order to 2
   seek me
   store condition to mcond1
   store status to mstat
   select a
   seek mcond1
   store descript to mdesc2
   if substr(ma,1,1) = "B"
    if substr(md,1,1) = "T"
     @ mline + 1,0 say rtrim(mb) + " NORMAL and NORMAL ON " + mc
     @ mline + 2,0 say "CONDITION was " + rtrim(mdesc2) + " STATUS " + mst
at
     store mline + 2 to mline
    else
     @ mline + 1,0 say rtrim(mb) + " NORMAL and ABNORMAL ON  " + mc + " "
+ md
     @ mline + 2,0 say "CONDITION was " + rtrim(mdesc2) + "STATUS " + msta
t
     store mline + 2 to mline
    endif
   else
    if substr(md,1,1) = "T"
     @ mline + 1,0 say rtrim(mb) + " ABNORMAL:" + ma + " Normal on " + mc
     @ mline + 2,0 say "CONDITION WAS " + rtrim(mdesc2) + " STATUS " + mst
at
     store mline + 2 to mline
    else
     @ mline + 1,0 say rtrim(mb) + " ABNORMAL:" + ma + " AND  ABNORMAL on
 " + mc + " " + md
     @ mline + 2,0 say "CONDITION WAS " + rtrim(mdesc2) + " STATUS was " +
 mstat
     store mline + 2 to mline
    endif
   endif
  else
   if substr(ma,1,1) = "A"
    @ mline + 1,0 say rtrim(mb) + " NORMAL and NO PRIOR TEST"
    store mline + 1 to mline
   endif
   if substr(md,1,1) = "C"
    @ mline + 1,0 say rtrim(mb) + " ABNORMAL:" + ma + " NO PRIOR TEST"
    store mline + 1 to mline
   endif
   if .not. mflagc .and. (substr(ma,1,1) <> "A" .and. substr(md,1,1) <> "C
")
    if substr(ma,1,1) = "B"
     @ mline + 1,0 say rtrim(mb) + " Normal and prior from ER"
     store mline + 1 to mline
    else
     @ mline + 1,0 say rtrim(mb) + " Abnormal:" + ma + "and prior from ER"
     store mline + 1 to mline
    endif
   endif
  endif
 endif
 store m1 + 10 to m1
 store m2 + 4 to m2
```

```
        store m3 + 3 to m3
        store m4 + 4 to m4
        store m5 + 6 to m5
        store mcounter + 1 to mcounter
      enddo
       @ mline +1,0 say replicate("=",80)
       store mline + 1 to mline
       select c
       set order to 1
       goto high
       skip
      else
       skip
      endif
    enddo
   enddo
  enddo
 enddo
return
```

Overdraw.prg (cont.)

AP 101

```
public mdate,mdate1,mresult,mresult1,mablab,minvoice,mpt_id
mfield = 0
store "" to mdate1,mresult,mresult1,mablab,minv1                    Diqoutad.prq
store .f. to mflaga
store .f. to mflagb
select d                                                            AP162
use abn_laba index ablbinvf,pat_date
seek mpt_id + minvoice
hello = recno()
store dtoc(DATE) to mdate
store 6 to mfield
do while .t.
do while mfield <= 19
  store .f. to mloop
  store field(mfield) to mvar
  store &mvar to mvar1
  if asc(mvar1) = 32 .or. asc(mvar1) = 78
    store mfield + 1 to mfield
    store mablab + space(10) to mablab
    store mdate1 + space(8) to mdate1
    store mresult + space(4) to mresult
    store mresult1 + space(4) to mresult1
    store minv1 + space(6) to minv1
    store .t. to mloop
  else
   store mablab + mvar + space(10 - len(mvar)) to mablab
   if asc(mvar1) = 84
    if substr(mvar1,4,1) = "C"
     store mresult + "A   " to mresult
     store mdate1 + space(8) to mdate1
     store mresult1 + space(4) to mresult1
     store minv1 + space(6) to minv1
     store mfield + 1 to mfield
     store .t. to mloop
    else
    store mresult + "B   " to mresult
    endif
   else
    store mresult + substr(mvar1,4,4) to mresult
   endif
   if substr(mvar1,3,1) = "N"
    store mresult1 + "C   " to mresult1
    store mdate1 + space(8) to mdate1
    store minv1 + space(6) to minv1
    store mfield + 1 to mfield
    store .t. to mloop
   endif
  endif
 if .not. mloop
 set order to 2
 goto hello
 skip - 1
 do while PT_ID = mpt_id
   store field(mfield) to mvar2
   store &mvar2 to mvar3
   store .t. to mflagc
   if asc(mvar3) <> 32 .and. asc(mvar3) <> 78
    if substr(INVOICEFRM,1,1) = "E"
     store .f. to mflagc
     exit
    endif
    store mdate1 + dtoc(DATE) to mdate1
    if asc(mvar3) = 84
```

```
            store mresult1 + " 1     " to mresult1
        store minv1 + INVOICEFRM to minv1
        store mfield + 1 to mfield
        exit
      else
        store mresult1 + substr(mvar3,4,4) to mresult1
        store minv1 + INVOICEFRM to minv1
        store mfield + 1 to mfield
        exit
      endif
     else
      skip - 1
     endif
   enddo
 if .not. mflagc
   store mresult1 + "D   " to mresult1
   store mdate1 + space(8) to mdate1
   store minv1 + space(6) to minv1
   store mfield + 1 to mfield
 endif
 set order to 1
 goto hello
endif
enddo
set order to 1
goto hello
if mfield <= 19
 loop
else
 exit
endif
enddo
return
``` digoutad.prg (cont.)

AP108

I claim:

1. A computerized out-patient primary care medical system for the entry of clinical data stored into a database, said medical system includes;

means for documenting up to three chronic, long term diagnosis in an out-patient office visit record, said record created during said entry of data and said diagnosis represented on a source document by a partial code that consists of the last 4 digits of a full six digit chronic diagnosis code, means for determining the primary reason for an office visit through the use of either of two single letter codes obtained from said source document, said codes representing either a chronic, long term diagnosis or an acute short term diagnosis, means for documenting the primary reason for an office visit, said primary reason represented on a source document as a partial code that consists of the last 4 digits of a full six digit chronic or acute diagnosis code, means for documenting any physical data noted during an office visit, said physical data consisting of signs and symptoms and represented on a source document as partial codes that consist of the last 3 digits of a full 5 digit physical data code, means for documenting office visit type, said type being either scheduled or unscheduled and represented by either of two single letter codes present on a source document, means for documenting the clinical status of an out-patient during said office visit, said status being represented by one of five possible single digits that include a 1 indicating normality or baseline, 2 indicating mild instability, 3 indicating serious instability, 4 indicating improvement from the out-patient's most recent office visit, and 5 indicating that hospitalization was ordered during that office visit, means for checking entry of said clinical status according to a set of requirements listed on a screen during entry, said requirements consisting of entering a clinical status of 4 for any improvement in said clinical status of an out-patient in comparison to that out-patient's most recent visit and the mandatory entering of at least one physical data item for any clinical status other than 1, means for updating a related out-patient record during creation and said entry of office visit record, said updating reflecting any changes in any of an out-patient's chronic diagnosis and said related record is an out-patient master medical record, means for identification of an out-patient master medical record, said identification being by entry of an out-patient last name and full first name present on a master medical record source document, means for dating the creation of a master medical record, means for documenting up to three chronic diagnosis of an out-patient in said master medical record, alternate data sets used by said documenting means consisting of either a partial code that consists of the last 4 digits of a full six digit chronic diagnosis code as a direct entry means or a clinical group indicator and a full diagnostic text of said chronic diagnosis with or without a diagnostic category indicator as an indirect entry means of said documenting, means for identifying an out-patient laboratory test record that will store test results, said identification being a nine digit number, means for documenting the date when laboratory tests were taken, said tests numbering up to fourteen for each out-patient lab test record, means for assigning a special number to said lab test record, said special number being an invoice and the most unique aspect of identification of said lab test record, means for linking said lab test record to either of two related out-patient records, said records being either an office visit record or an emergency room record of said out-patient depending upon the location from which the lab tests were ordered, means for entering parameter or historical data with each current lab test result, said parameter or historical data is in encoded form and represents a compilation of past results of any single lab test including chronicity of abnormality and a most recent result of that test whether normal or abnormal, means for recalling prior test results from different aspects for each current lab test result, said prior aspects include date and value of first abnormality, date and value of last abnormality, consistency of prior results, and the most recent result for a particular test normal or abnormal.

2. The computerized out-patient primary care medical system of claim 1 wherein said entry of clinical data into a database office visit record further includes;

means for entering an out-patient identification number from an office visit source document, said number entered consisting of 9 digits, means for obtaining a special six digit number for said office visit record being created, said number is referred to as an invoice and is said record's most unique aspect of identification, and said means for obtaining includes, means for adding one to a number being stored in a data field of the most recent office visit record created, said most recent record is usually that of another out-patient on the database, means for accessing a full six digit chronic diagnosis code from a chronic long-term diagnosis table, and said means for accessing further includes, means for first entering a 4 digit partial code from said office visit source document, said partial code consisting of the last 4 digits of a full six digit chronic diagnosis code, and further includes means for searching by said 4 digit partial code entered upon said chronic, long-term diagnosis table, means for accessing up to two full 5 digit physical data code from a physical signs table, and said means for accessing includes, means for first entering a 3 digit partial code from said office visit source document, said partial code is the last 3 digits of a full 5 digit physical signs code, and further includes, means for searching by said 3 digit code entered upon a said physical signs table, means for accessing up to two full 5 digit physical symptoms codes from a physical symptoms table, and said means for accessing includes, means for first entering a 3 digit partial code from said office visit source document, and further includes means for searching by said 3 digit number entered upon a said physical symptom table, and means for writing the full 5 digit physical signs and symptoms codes accessed to their appropriate data fields in said office visit record being created, means for writing a full 6 digit chronic diagnosis codes to one of three chronic diagnosis data fields, said field written to depends upon the clinical urgency or prognosis of that chronic diagnosis in relation to any of the other two possible chronic diagnosis of that out-patient that may also be entered, means for accessing the primary reason for an office visit, said accessing means further includes, means for entering a single letter code from said office visit source document, and further includes means for then entering a 4 digit partial code from said source document, said 4 digit partial code present in a data field of said source document that is designated as said office visit primary reason, means for obtaining, if said single letter code entered indicates a chronic diagnosis as said primary reason for said office visit, a full six digit code from a chronic, long-term diagnosis table and means for obtaining, if said single letter code entered indicates a short-term acute diagnosis as the primary reason for said office visit, a full six digit code from an acute diagnosis table, and said means for checking the entry of said office visit clinical status according to a set of requirements listed on a computer screen during said entry of clinical data further includes, means for preventing the entry of a status 2 immediately following a status 3 office visit record of that out-patient or a status 1 immediately following a status 2, said prevention is for ensuring that a status 4 indicating clinical improvement intervenes first in both circumstances and further includes, means for preventing the entry of clinical status other than 1 if there are no physical data partial codes on said office visit source document, and means for preventing the creation of said office visit record if any of the prior said clinical status conditions on said source document exists, means for checking that all of an out-patient's current chronic diagnosis are present on said source document for entry, and said means for checking further includes, means for first testing if any chronic diagnosis data field on said source document is blank by absence of any data entered from said field and the corresponding field of that out-patient's master medical record is also blank, and said checking further includes, means for writing from said master medical record any chronic diagnosis of that out-patient that is present but absent from the corresponsign data field on said source document to the corresponding data field of the new office visit record being created, said writing rectifys any ommission of an out-patient's chronic diagnosis that should be entered but is absent from said source document, and further means for testing if any changes in any of an out-patient's chronic diagnosis are to be made during an office visit record data entry, and prior said testing includes means for comparing a said 6 digit code of a chronic diagnosis accessed for writing to a newly created office visit record to that already present in the corresponding field of that out-patient's master medical record, and further means for writing any differences found between the two said corresponding data fields from the field position of said newly created office visit record to the field position of that out-patient's master medical record, said writing is for updating any changes in an out-patient's chronic diagnosis to that out-patient's master medical record.

3. The computerized out-patient primary care medical system of claim 1 wherein said entry of clinical data into a database master medical record further includes;

means for entering the first and last name of an out-patient from a master medical record source document, means for determining which of two methods, direct or indirect, are to be used for entering up to three chronic diagnosis into said master medical record, said method used depending upon which of two alternate sets of data fields have been filled out on said master medical record source document, and means for direct entry, if above said determining means finds just a 4 digit partial chronic diagnostic code present on said source document, and said means for direct entry further includes, means for accessing by said 4 digit partial code entered a full 6 digit code and its corresponding diagnostic text from a chronic diagnosis table, means for indirect entry, if above said determining means finds a clinical group indicator and a text of the diagnosis to be entered with or without a diagnostic category indicator present instead on said source document, and said means for indirect entry further includes, means for displaying on a computer screen the contents of a group of chronic diagnosis records from said chronic diagnosis table that are restricted according to said clinical group indicator entered from said source document and further restricted by diagnostic category if that single letter indicator is also entered from said source document, said display of record contents consist of both the full six digit code and the text of each chronic diagnosis displayed and means responsive to the restricted display means for selecting from said computer screen only the last 4 digits of the full 6 digit chronic diagnosis code that corresponds to and is associated with the diagnostic text also displayed that matches the one present on said master medical record source document, and means responsive to the selecting means for then entering the said 4 digit partial diagnostic code corresponding to said text of chronic diagnosis code displayed that was found to be identical to that existing on said source document, and means responsive to entering means for accessing both the full 6 digit diagnostic code and its corresponding text from said chronic diagnosis table by the said 4 digit partial code entered, and further means for writing to an appropriate data field of said out-patient master medical record both the said full 6 digit code and the diagnostic text accessed from said chronic diagnosis table by said 4 digit partial code entered, and said writing completes the said indirect method of chronic diagnosis entry, means for determining if a previous master medical record is on file for an out-patient before said record is created and said data entered, means for informing a data entry operator of the current total after each of up to three chronic diagnosis for each out-patient is entered, means for checking the proper ordering by clinical urgency or prognosis the relative data field positions occupied by each of up to three chronic diagnosis entered, and said checking means includes, means for comparing the relative numeric values between the last 4 digits of the full six digits of each chronic diagnosis entered, said value of the last 4 digits of the primary field diagnosis should be less than the last 4 digits of any secondary field diagnosis which in turn should be less than the last 4 digits of any tertiary field diagnosis and, means for re-writing any chronic diagnosis that is out of order in relation to any other chronic diagnosis for that out-patient into its correct relative field position in said master medical record.

4. The computerized out-patient primary care medical system of claim 1 wherein said entry of clinical data into a database lab test result record futher includes;

means for entering an out-patient identification number consisting of 9 digits means for entering the date of when said tests were taken, said date may be as much as two or three days after they were ordered, means for determining the origin of said lab tests, said origin being either an out-patient office visit or an emergency room visit, and said means for determining includes, means for indicating by a single letter code entered whether or not said tests were ordered during an office visit, means for accessing, if said determining means indicates an office visit origin of said lab tests, a 6 digit code that most uniquely identifies that office visit record of said origin, and said origin, and said means for accessing includes means for finding the most recent office visit record for that out-patient, means for accessing, if said determining means indicates an emergency room origin of said lab tests, a 6 digit code that most uniquely identifies that emergency room record of said origin, and said means for accessing includes, means for finding the most recent emergency room record for that out-patient, means for preventing entry of emergency room ordered lab test data in cases of poor patient compliance, and said means for preventing entry includes means for determining if period of time between the emergency room visit and when test were actually taken is more than a specified amount of days following said emergency room visit, means for entering first time lab tests for an out-patient of said database, means for recalling prior lab test results for an out-patient who has current test results present for entry, and said means for recalling includes, means for generating a list of selections on a computer screen, each said selection enables obtaining any prior test result already on file from different, separate aspects that include date and value of last abnormality, date and value of first abnormality, most recent result for that lab test and the pattern or consistency of a lab test's prior results, and said means for recalling further includes, means for displaying on a computer screen the prior result of a lab test according to any of the prior said aspects selected from said list of prior aspects generated, means for compiling said prior aspects of results for any lab test into an encoded form for accompanying the current quantitative abnormal result or a normal result into storage in said lab test result record, said compiled data constitute the parameter or historical data for indicating a combination of past results of any lab test to complement the current result stored to said lab test result record, means for activating a customized data entry screen for each of up to 14 lab tests, said customized screen is for assigning each lab test result to a designated position for entry, means for creating a lab test result record for the entry and storage of up to 14 different lab test results, means for linking said lab test record with either the source office visit record or the source emergency room record, said linkage based upon the dual invoice nature of each lab test result record wherein said lab test record contains both a special 6 digit number unique and inherent to it and the special 6 digit number unique to the source or parent record, whether office visit or emergency room, representing from which said lab tests were ordered, means for assisting a data entry operator in the said compiling of said parameter or historical data into encoded form to accompanying said current results into storage, and said means for assisting further includes, means for instructing a data entry operator on how to select from a number of possibilities 3 single letter codes for indicating, in the case of an abnormal result, the three encoded elements of said parameter data that consist, in the case of an abnormal result, chronicity of that abnormality, intensity of that abnormality and the most recent result for that test while in the case of a normal result just one encoded letter for indicating whether or not the most recent result for that test, if present, is normal, and said means for instructing further includes, means for displaying said instructions including sample selections on a computer screen for data entry operator review during said entry of clinical data.

5. A computerized out-patient primary care medical database system for the processing and reporting of clinical data includes;

means for creating by a set of intermediary routines new, office visit-derived intermediary records for the storage of office based clinical data in compiled form; and said creating means includes, means for detecting by out-patient diagnostic category early and possibly unnecessary scheduled office visits, said diagnostic category established and defined by either an individual chronic diagnosis or the combined value of up to three chronic diagnosis of an out-patient present in a said office visit-derived record in reference to a table of chronic diagnosis sorted in descending order by clinical urgency or prognosis, means for detecting by diagnostic category consecutive unscheduled out-patient office visits, means for determining whether or not said early scheduled office visits were clinically justifiable, said justification being either absolute or tentative, means for detecting by diagnostic category 3 types of protracted illnesses, said illnesses represented by a continuous string of office visit-derived records of an out-patient that all contain a clinical status indicator other than 1 and each of said three types of protracted illnesses differing by initial level of severity, means for determining if any, and type of, physician intervention or action occured during each office visit included in any of 3 said types of protracted illness processing for an out-patient, said types of actions include new medication, medication changes, specialty referrals, lab tests ordered and office injections of medication including by what route, intramuscular or intravenous, and said reporting of clinical data includes, means for printing by said diagnostic category from said office visit-derived records the physical, medication change and laboratory test results separately but from the same office visit, means for printing of clinical data that may reveal the overusage of office visit based lab tests ordering, said overusage because of the absence of any documented problems during those office visits when said tests were ordered, and said reporting of clinical data further includes; means for querying of said out-patient database summary-type and narrowly formulated out-come based clinical data for computer screen display.

6. The computerized medical database system of claim 5 wherein said means for the querying of out-patient clinical data in a narrowly formulated and summary form includes;

means for accessing from several related and linked files different types of clinical data for each out-patient, said data combined to define and focus upon distinct aspects of ambulatory, primary care medicine and includes, means for determining by database doctor if a disproportionate number of database out-patients with a particular chronic diagnosis are assigned to and under the care of particular primary care doctor in relation to other primary care doctors on that database, and said means for determining includes, means for entering a doctor name and the full text of a particular chronic diagnosis, and means for responsive to the entering means for accessing, by said doctor name and diagnosis entered, out-patients on the database who are both under the care of that doctor and who have that particular chronic diagnosis, and said accessing means further includes, means for counting amongst a database file both the number of said patients with that diagnosis, and if any, the number of those patients who are under the care of that doctor whose name was entered, said database file that said count is made on is the master medical record file, and further means for computing the percentage of all database out-patients with that chronic diagnosis, and means for computing what percent of that percentage consists of those out-patients who are also under the care of that doctor whose name was entered, and further means for displaying said computed data on a computer screen, said display consisting of both integers and fractions, and said means for querying out-patient database data further includes, means for reviewing both the medication change activity and the physical data observed amongst out-patients with a chronic cardiac diagnosis during office visits in which they were observed to be very symptomatic, said very symptomatic being indicated by a clinical status of 3 being found in that data field of office visit records, and further includes means for entering just the name of a database doctor, and further means responsive to the entering means for selecting a set of office visit records by both a clinical status of 3 and the presence of a chronic cardiac diagnosis and further means for accessing the literal text corresponding to the encoded physical data stored in said set of office visit records selected, said literal text accessed from a physical signs and symptoms table and said means for accessing includes, means for searching said physical signs and symptoms tables by codes present in physical data fields of an office visit record selected, and means for accessing medication activity from medication activity records linked to said office visit records selected, said linkage is by a special six digit number unique to each office visit record and also present in each said medication activity record linked, and means for combining said physical and medication activity from each said office visit record selected with other salient office visit data, said salient data includes out-patient I.D. number and data of office visit and medication activity reported can include an addition, change, deletion or an injection of medication during said office visit, and means for displaying on a computer screen said clinical data combined from each said office visit record selected first by doctor name entered and then by a clinical status of 3 and the presence of at least one diagnosis that is a chronic cardiac one and, said means for querying out-patient clinical database data further includes, means for obtaining prior lab test results for a database out-patient, said said results can be presented by either individual lab test results from any of several prior aspects or a group of tests ordered during the same office visit, and means for entering an indicator for choosing which of the two above types of presentation of data the user desires and, means for determining which said choice was entered and means for entering, if said group of lab tests from an office visit was selected for viewing, an approximate date for that office visit and further means for re-entering another date if said approximate date previously entered is incorrect until a correct date for the desired office visit is entered and, means for accessing the related lab record linked to the office visit of the correct date entered, and said accessing means includes means for searching an out-patient lab test result file that contains a lab record storing a special six digit number that most uniquely identifies that office visit record it is linked to and also found in said lab record, and means for combining all the lab test results from said office visit along with each's parameter or historical data with other salient data from each office visit, said salient data includes patient name, date of visit and the chronic diagnosis of said out-patient, six digit number identifying that office visit, date lab tests drawn and the six digit number identifying that lab record and further means for selecting one at a time from amongst 14 lab tests if prior said choosing means indicates a desire to view individual test results instead of a group of test results from the same office visit, and further includes means for generating a menu listing several prior aspects from which to view previous results of a particular lab test of an out-patient currently on file, said prior aspects include the date and value of both the first and last abnormal result for that test if present, result of most recent test, consistency of results for that test and both the highest and lowest abnormal value of that particular lab test, and further includes means for obtaining from that out-patient's lab test records any of said 14 lab test results depending upon what selection from said menu listing of prior aspects of results was made, and said means for obtaining include means for searching back on said out-patients lab records arranged in chronological order to access a said record or records according to which said prior aspect of results was said selected from said menu listing, and means for combining said individual test results from any of said prior aspect from said menu listing with other salient data, said salient data includes patient identification, date of test in question, first abnormal result and date as a reference, and further means for displaying said combined data for computer screen review, and said means for querying clinical data from a database further includes, means for documenting if there is any impending or actual medication induced toxicity of any databaseout-patient who is currently on medications, said said toxicity indicated by an abnormal result of a lab test that is known to be an especially sensitive marker for the toxic effects of a particular medicine and the degree of abnormality related to the level of toxicity, and said means for documenting further includes, means for entering both a database doctor name and a medication name, and means for accessing by doctor name and medication name entered those database out-patients who are taking that medication and are under the care of that doctor whose name was entered, and said accessing means includes means for searching on a database file by said doctor name entered, said file is the master medical file that stores both the doctor name and the current medications each out-patient is on along with the dosages, and means for listing by both patient I.D. number and name those out-patients taking that medications, the amounts, who are under the care of that doctor whose name was entered, means for informing an operator if said doctor whose name was entered does not have any patients currently taking that medication entered, means for selecting from alist of 14 lab tests, said lab test selected is one presumed by user to be specific for indicating any existing toxic effects from said medication whose name was entered, and further means for selecting from any of said out-patients listed by name and I.D. no. said selection is by entering the I.D. no. listed alongside any patient name also listed on a computer screen, means for combining all data accessed for that out-patient selected, said data includes all the results of that lab test currently on file for that out-patient selected in chronological order alongside the medication in question and the amount of that medication that out-patient is currently taking, and means for displaying that data on a computer screen for user review, said review for the purpose of monitoring for any medication induced toxicity.

7. The computerized medical database system of claim 5 wherein said means for the data processing of a said intermediary routine for the detection of of an early and possibley unnecessary scheduled office visit by diagnostic category further includes;

means for identifying two consecutive minimal-clinical-activity or uneventful types of office visit records for a same out-patient and whose difference in days or length of time between said consecutive office visits is less than that set for that out-patient's diagnostic category for any two uneventful visits occuring consecutively for an out-patient belonging to said category, and said uneventful or minimal-clinical-activity type, either unscheduled or scheduled, is defined as having a clinical status of 1 indicating a normal or absence of change in baseline clincal condition, a chronic diagnosis as the primary reason for said office visits and total absence of any physician action or intervention during either of said two consecutive office visits, and another said intermediary routine that includes, means for identifying an unscheduled office visit of the minimal-clinical-activity type that is followed by a scheduled office visit by the same out-patient that is also of the minimal-clinical-activity type that occurs within the time interval for minimal-clinical-activity types by that diagnostic category, said scheduled type therefore being early and possibley unnecessary and means for determining if said early and possibley unnecessary scheduled type of uneventful office visit is clinically justifiable, said justification may be absolute or tentative and further includes, means for accessing a set of other related out-patient records in separate files whose data represent distinct but related aspects of out-patient primary care, said other records includes emergency room, lab tests, out-patient treatment hospital and surgery files and further means for identifying in any of other related records of that out-patient with an early scheduled office visit of the minimal-clinical-activity type an indication of activity occuring between the two said consecutive office visits of the minimal-clinical-activity type, said activity or event may serve to justify the second early consecutive office visit of the minimal-clinical-activity type if said actvity or event met certain clinical criteria and further means for determining if any said justification can be found in any of said other related out-patient records and includes, means for finding an interim emergency room record of that out-patient dated within the interval of time between both said consecutive office visit records of the minimal-clinical-activity type and further means responsive to the finding means for obtaining the six digit number identifying said interim emergency room record, said six digit number identifying the source of the potential justification for said early, second office visit of the minimal-clinical-activity and scheduled type, and means responsive to the obtaining means for setting an indicator if there is an indication within said interim emergency room record that either an immediate office visit or a hospitalization was advised at the time of said emergency room visit for that out-patient, said indicator set will establish absolute justification for that outpatient's early, consecutive office visit of the minimal-clinical-activity or uneventful type, and said means for determining actual or tentative, potential justification for an early, consecutive office visit of the uneventful type further includes, means for finding an interim hospitalization record of said out-patient that indicates a stay between said two consecutive office visits of the uneventful type, and further means responsive to the finding means for obtaining a six digit number from said hospital record that at least identifys the source of a potential or tentative clinical justification for said early, second office visit and means responsive to the obtaining means for setting an indicator if the discharge diagnosis of said hospital record is the same as the primary reason for the early, consecutive office visit of the uneventful type for that out-patient, said indicator setting establishing absolute justification for that out-patient's early, scheduled visit of the uneventful type, and said means for determining clinical justification further includes, means for finding an interim lab test record of said out-patient that was dated between the two consecutive visits of the minimal-clinical-activity type and means responsive to the finding means for obtaining a six digit number identifying said interim lab test record, said six digit number representing a potential or tentative source of clinical justification for the said early consecutive office visit of the uneventful or minimal-clinical-activity type and additional means responsive to the obtaining means for setting an indicator if the parameter or historical data that is encoded and accompanies the actual result of that lab test indicates any change from the previous result for that test, said indicator setting establishing absolute justification for an early, second scheduled office visit of the minimal-clinical-activity or uneventful type and said means for determing any clinical justification amongst that out-patient's other related clinical database files further includes, means for finding an interim out-patient treatment record dated between the two said office visit records of the uneventful type and means responsive to the finding means for obtaining the six digit number of that said treatment record, said six digit number identifying that record as at least a potential or tentative source for clinical justification for the early, second office visit of the uneventful type and further means responsive to the obtaining means for setting an indicator if the said treatment record contains an indication by the therapist that the out-patient's condition for said therapy is getting worse, said setting of the indicator establishes absolute justification for said early, second uneventful scheduled office visit, and said means for determining any clinical justification further includes, means for finding a most recent surgery record of that out-patient and means responsive to said finding means for determining the date, category and type of surgery performed on said out-patient, and additional means for obtaining a six digit number uniqely identifying said surgery record if said surgery type is from a major surgical catergory, said six digit number serves as at least potential or tentative justification for the early, second scheduled visit of the minimal-clinical-activity or uneventful type, and further means for setting an indicator if said surgery was dated within a particular time interval from the said second, early uneventful visit of the scheduled type said indicator setting establishing absolute justification and means responsive to said determining means for obtaining a six digit number if said surgery is from the moderate surgical category type, said six digit number establishing a potential or tentative source for clinical justification and additional means responsive to said obtaining means for setting an indicator if said moderate surgery type occured within a time interval from the second, early visit of the uneventful type that is lesser in amount that the time interval for the said major surgical category type, said indicator setting establishing absolute clinical justification, and additional means responsive to said determining means for obtaining a six digit number of said surgery record if said surgery is of a minor category and the date of said minor surgery is within a lesser time interval from the second, early uneventful scheduled office visit than that of the major surgical category type, and means responsive to the obtaining means for setting an indicator if the clinical group indicator of the said minor surgery type is the same as that of the primary reason for the early, second scheduled office visit of the uneventful type for that out-patient, said indicator setting establishing absolute justification on the basis of said past minor surgery because the clinical group or organ system involved in said minor surgery is the same as the primary reason for the said second, early office visit of the scheduled and uneventful type, and additional means for creating a new office visit-derived record in an intermediary file for each early consecutive scheduled office visit that followed either an unscheduled or scheduled uneventful type for the same out-patient, and means responsive to said creating means for writing to said newly created office visit-derived record a variety of pertinent clinical data in coded form, means responsive to said creating means for transferring data from said second, early scheduled uneventful office visit to said newly created office visit-derived intermediary record, said written and transferred data includes I.D. number of out-patient, date of second visit, special six digit number identifying said visit, data indicating a potential or actual clinical justification of said visit, the diagnostic category of the out-patient and an indicator for encoding the name of the intermediary routine that processed said out-patient records, and means for identifying every successive unscheduled office visit by an out-patient that follows a first one identified, means responsive to prior said identifying means for creating a new office visit-derived intermediary record for each successive unscheduled office visit record of an out-patient that is found beyond that out-patient's first one, and means for writing to said newly created office visit-derived intermediary record a variety of pertinent data in coded form, and means for transferring data from each of said successive, unscheduled office visit record to the said newly created office visit-derived record, said written and transferred data includes what number in succession each unscheduled visit represents, out-patient I.D. no., date of visit, special six digit number most uniquely identifying that office visit, encoded name of intermediary routine that processed said record and diagnostic category of that out-patient.

8. The computerized medical database system of claim 5 wherein said means for the detection, by diagnostic category, of three types of protracted out-patient illnesses that differ by initial level of severity further includes, means for detecting a minimum number of consecutive office visit records of an out-patient that represent only a mild, fluctuating illness in which the clinical condition of said out-patient has not returned to normal or baseline but hasn't yet become serious, said clinical condition reflected by a clinical status of 2 with any one of the contiguous office visit records of that out-patient within said minimum number being possibley a 4 indicating an improvement from the previous visit and said minimum number of records being 3, and means responsive to the detecting means for further detecting all additional subsequent office visit records for that out-patient that are also either a 2 or 4 clinical status, means for detecting a first office visit record whose clinical condition indicates a serious, prehospital stage, said condition represented by a clinical status of 3, and further means responsive to prior detecting means for the further detection of all antecedent and subsequent contiguous office visit records of that out-patient in which anything other than a baseline or normal clinical status of 1 is found, means for detecting the first office visit record of any out-patient in which the clinical status is anything other than a 1, and further means responsive to the prior detecting means for determining if a most recent office visit record of that out-patient is present, said most recent record would have a clinical status of 1 and serve as a reference for comparing data with that out-patient's subsequent non-1 clinical status records, and means responsive to prior said determining means for the further detection of all subsequent, contiguous office visit records for that out-patient after said first office visit record of a non-1 clinical status that is also anything other than a 1 clinical status, and means responsive to any of 3 prior said detecting means for the accessing of all said office visit records detected as part of a said protracted, continuous out-patient illness and means responsive to any of 3 said prior detecting means for determining what, if any, physician intervention or action occured during each office visit whose record has been said detected as part of any of 3 said protracted out-patient illness, said types of physician intervention may include new medication, medication change, lab test ordering, specialty referrals and office injections of medications, and means responsive to determining means for computing a decimal number based on which, if any, of 4 fields in said office visit records are set to true, said fields correspond to each of said physician actions except that of medication injection and any said number computed out of 16 possible ones correspond to a particular action or combination of said physician actions including zero which indicates no physician action or intervention at all, and means responsive to the computing means for translating said number computed into one of sixteen possible single letter codes, said single letter is for indicating which, if any, type or combination of types of said physician actions occured during any of said office visits whose records were part of any of 3 said protracted out-patient illnesses, and means for determining if an injection occured during any said office visits, means for creating a new, office visit-derived record in an intermediary file, said new record corresponding to each office visit record detected as part of any of said 3 types of protracted out-patient illnesses, and additional means responsive to the creating means for writing to each new record created a compilation of data derived from an office visit record detected as said part of any of 3 types of protracted out-patient illnesses, said data includes out-patient identification, date of visit, office visit identification, a single letter for indicating which of 3 said types of protracted illnesses that office visit record was detected as part of, a single letter for indicating what, if any, type or types of physician actions occured during said visit, and any medication injection that may have occured and by what route during that visit.

9. The computerized medical database system of claim 5 wherein said means for the separate printing of physical, medication and laboratory test data from the same office visit further includes, means for selecting an intermediary file of office visit-derived records by out-patient diagnostic category, primary reason for an office visit and a cut-off date, said records derived from office visit records detected as part of any of 3 said types of protracted out-patient illnesses and said primary reason being either an acute, short-term or a chronic, long-term diagnosis, and said means for the printing of office visit based physical data includes, means for accessing from said selected office visit derived records up to physical data codes reflecting up to 2 signs and two symptoms, said codes consisting of 5 digits with the first indicating the clinico-pathological group or organ system of those signs and symptoms with the last three digits being its most unique aspect of identification, and further means for accessing from physical signs and symptoms tables the literal text corresponding to said codes by the last three digits of said 5 digit codes present in said office visit-derived records, and means for accessing a master medical record belonging to that out-patient of said office visit-derived records said selected, said master medical record is linked to any of said office visit-derived records by out-patient I.D. no.

means for printing out background data for each out-patient whose office visit-derived records were said selected, said data is heading data that appears once for each out-patient whose physical data is for printing and includes up to three chronic diagnosis for that out-patient, date of birth, date of last hospitalization and full name, and means for printing the literal text of up to four physical data elements, said elements consist of said literal text of signs and symptoms from each said office visit-derived record selected, and means for printing a message if any said office visit-derived record that was selected did not contain any physical signs, symptoms or both, and means for printing other clinical data from each office visit-derived record to accompany the literal text of said physical signs and symptoms, said other data includes date of visit, six digit number most uniquely identifying said visit, and the text of the primary reason for said visit, and means for printing, in the case of a chronic diagnosis as the primary reason for said visit, the blood pressure reading from said visit in addition to the physical data, said blood pressure printing is restricted to those out-patients who have either a cardiac, neurological or a vascular basis for that chronic diagnosis that served as the primary reason for said visit, and means for printing, in the case of a chronic diagnosis as the primary reason for an office visit, additional data with each out-patient's last office visit derived record that has been selected for said printing, said additional data is for indicating whether or not that particular protracted illness has been terminated and that out-patient has returned to a normal or baseline clinical status of 1 and whether or not a hospitalization has occured by the time of said cut-off date, and said means for the reporting of office based laboratory data includes, means for determining if laboratory tests were ordered during an office visit whose record was detected as part of any of 3 said types of protracted out-patient illnesses, and said means for determining further includes, means for testing in an office visit-derived record for the presence of one several possible single letter codes, said codes for indicating if lab tests, alone or in combination with other types of physician actions, were ordered during that visit, and means responsive to said testing means, if said means indicates the ordering of lab tests, for accessing a six digit number from that office visit-derived record, said six digit number most uniquely identifies that office visit and is also found in a lab record linked to that office visit-derived record, and means for accessing from said linked lab record all test results present along with each lab result's encoded parameter, said encoded parameter data reflects and is derived from that lab test's track record of past results for that out-patient and includes duration of an abnormality, intensity of the current abnormality and most recent result if present, and means for accessing a master medical record for each out-patient included in said office visit-derived record selection, and means for printing background data once for each out-patient whose office visit-derived records were said selected for said lab test result reporting, means for printing the results of said lab tests along with the literal text of each of the three encoded elements of the parameter data that accompanies each test result, means for printing the normal results of any lab test along with a remark about the most recent result, if present, for that test, means for printing other clinical data from that office visit to accompany the lab test data from that visit, said data includes date of visit, six digit number most uniquely identifying that visit, date lab tests done and the primary reason for that visit, acute or chronic diagnosis, in text form, and said means for the reporting of office based medication data includes, means for determining if an oral medication dosage change occured during an office visit whose record was detected as part of any of 3 prior said protracted out-patient illnesses, and said means for determining includes, means for testing in an office visit-derived record for the pressure of one of several possible single letter codes, said codes are for indicating if medication dosage changes, alone or in combination with other said types of physician actions, were done during said office visit, and further means for accessing, if prior determining means indicates a medication dosage change, that out-patient's first medicine activity record on file, and means responsive to prior said accessing means for locating that out-patient's most recent medicine activity record on file, and said records may store up to three medications which may all have undergone a dosage change during said office visit, and means for testing each of three data fields in said most recent medicine activity record for an indication that a dosage change had been made for any of three medicines that may be stored, and means for finding for each medicine that was found to have undergone a said dosage change in said most recent medicine activity record the most recent prior amount of that medicine that out-patient was on whether or not it was also an amount changed to or a first amount as a new medication, said prior amounts for any of up to three medicines that underwent said change may be found in up to three different prior medicine activity records for that out-patient, and means responsive to the previously said prior amount finding means for accessing both current amount or amount changed to and the most previous amount or the amount changed from for each of up to three medications that may have been found to have undergone said dosage change during said office visit and are now present in said latest medicine activity record, and further means for accessing from said latest medicine activity record a 5 digit code, said code associated with each medication that underwent said dosage change, and further includes, means for searching a medicine inventory table by said 5 digit code to obtain the generic name text of each medication found to have undergone said change in said latest medicine activity record, means for accessing a master medical record for each out-patient whose office visit-derived records were said selected, and means for printing background data once for each out-patient as heading for said medication data reporting, and means for printing up to three medication dosage changes, both amounts changed to amounts changed from and expressed in either grams or tablets per day, and further, means for printing other data from each office visit with said medication change data, said other data includes six digit number identifying said office visit, date of office visit and primary reason for that office visit, and means for determining if any data errors are present, said error might be in the absence of a medicine activity record associated with that office visit even though a said single letter code is present for indicating medication activity during that office visit, and means for printing a message indicating said error is present, and means for printing if no medication activity occured during any office visit.

10. The computerized medical database system of claim 5 wherein said means for the printing of clinical data that may show the overusage of office visit based lab tests further includes, means for selecting a set of out-patient office visit records according to four clinical criterion, said criterion consists of a normal or baseline clinical status of 1 indicating an absence of any disease activity or change in an out-patient's usual condition, a chronic diagnosis as the primary reason for that office visit, the office visit is of the scheduled type and yet, despite these 3 mentioned criteria that indicate an otherwise unremarkable clinical situation, the ordering of lab tests was still done as the fourth criteria, and means for accessing from an office visit record selected by prior said criterion data that links that record to a laboratory record storing the results of said lab tests ordered, said linking data is a six digit number that most uniquely identifies that office visit record selected and is also found in that lab record linked, and means responsive to said accessing means for obtaining all of said test results ordered during those office visits whose records were said selected, said lab tests ordered from said selected office visit records are herein referred to as a first set of lab tests, and further means for determining if there are any prior results on file for that out-patient for each of the first set of lab test results, said prior test results that correspond to each of the said first set of test results may each be found in different prior lab records for that out-patient and said prior test results for each of said first set of test results are herein referred to as the second set of lab test results, and means responsive to prior said determining means for searching back on that out-patient's previous lab records until any most recent prior result of that test for that out-patient is found for each of said first set of lab test results from each of said office visit records selected, and further means for obtaining, if present, a most prior test result for each of said first set of test results ordered during said visit whose records were said selected, and said prior lab test results for each of said first set of results ordered from an office visit whose record was said selected are herein referred to as second set of lab test results but each of which may have been obtained from a different prior lab record since any of said prior or second set of lab test results may have been ordered during a different prior office visit for any out-patient, and means for preventing said accessing of any of the said second set of test results if any of those prior test results were ordered during an emergency room visit by that out-patient, said emergency room visit is, by its very nature and unlike an office visit of the said selected type, is automatically considered significant enough to obviate the need to justify any lab test ordered during even an office visit of said selected type as long as that prior test was ordered during an emergency room visit, and said means for preventing access further includes, means for testing if the first character in a field of a lab test record that is storing any of said most prior or second set of lab test results begins with an E instead of an O, said character E indicating that said tests were ordered during an emergency room visit and not an office one, means for accessing a master medical record for each out-patient whose office visit records were selected by said criterion, and means responsive to said accessing means for printing once for each out-patient whose office visit records were selected salient data as heading, said salient data includes last name of the out-patient doctor, a code indicating the name of the processing routine, last name and I.D. no. of the out-patient date of birth of out-patient, the primary chronic diagnosis of that out-patient and date of last hospitalization, and means for printing with each office visit record selected for an out-patient some identifying data, said data includes the six digit office visit I.D. no, primary reason for that office visit, date of office visit and date lab tests drawn that were ordered from said office visit, and means for accessing for each of said second set of prior lab tests that prior office visit during which each of said second set of tests were ordered, said prior tests may be from different prior office visits of that out-patient means for printing together in coupled form both the first set of lab tests from selected set of office visit records and the second set of the same lab test results for an out-patient, and further means for printing other data from each prior office visit during which each of the second set of prior lab tests for that out-patient were ordered, said data includes primary reason during each office visit and the clinical status of the out-patient during that office visit in order to enable determining the clinical need for ordering said tests from said selected office visit records by comparing the data printed together in coupled form.

11. For use in a computerized out-patient primary care medical database system means for the automatic classification of out-patients into one of three chronic diagnosis-based clinical diagnosis categories through the use of a predefined consensus-based reference table of chronic diagnosis arranged according to the relative prognosis or clinical urgency of each, said reference table divided into three diagnostic categories with each ranked hierarchically in relation to the other two and for classifying said out-patients depending upon the diagnostic category location of up to three chronic diagnosis any out-patient may have in relation to said reference table, and said means for the automatic classification further includes, means for creating an out-patient master medical or first office visit record, said record creation occuring during a data entry routine for either of said record type which then immediately confers upon an out-patient of that record the attribute of classification into one of said diagnostic categories, and means for recognizing said classification of each out-patient by said database system during the execution of data processing instructions, said instructions identify each out-patient record, master medical or office visit, as belonging to one of three said diagnostic categories depending upon the combined value of up to three chronic diagnosis found in said record types determined by thier relative position in said reference table of chronic diagnosis, and said recognizing means includes, means for checking by said data processing instructions an encoded letter present in each chronic diagnosis that is present in any out-patient record of prior said types, said encoded letter present in a fixed position in each chronic diagnosis and for indicating to which of three said diagnostic categorys of said chronic diagnosis reference table that chronic diagnosis belongs to.

* * * * *